US008987431B2

(12) United States Patent
Reeves et al.

(10) Patent No.: US 8,987,431 B2
(45) Date of Patent: Mar. 24, 2015

(54) ESSENTIAL GENES ENCODING CONSERVED METABOLIC PATHWAY FUNCTION IN AUTOTROPHIC SOLVENTOGENIC CLOSTRIDIAL SPECIES

(75) Inventors: Andrew Reeves, Chicago, IL (US); Fenglin Yin, Naperville, IL (US)

(73) Assignee: Coskata, Inc., Warrenville, IL (US)

( * ) Notice: Subject to any disclaimer, the term of this patent is extended or adjusted under 35 U.S.C. 154(b) by 963 days.

(21) Appl. No.: 12/803,710

(22) Filed: Jul. 1, 2010

(65) Prior Publication Data
US 2012/0003652 A1 Jan. 5, 2012

(51) Int. Cl.
*C07H 21/02* (2006.01)
*C07H 21/04* (2006.01)
*C07H 19/00* (2006.01)
*C07H 21/00* (2006.01)
*C12P 1/00* (2006.01)
*C12P 7/06* (2006.01)
*C12N 15/52* (2006.01)

(52) U.S. Cl.
CPC ............ *C12P 7/065* (2013.01); *C12N 15/52* (2013.01); *Y02E 50/17* (2013.01)
USPC ............ 536/23.1; 536/22.1; 435/41; 435/161

(58) Field of Classification Search
None
See application file for complete search history.

(56) References Cited

U.S. PATENT DOCUMENTS

| | | | |
|---|---|---|---|
| 5,908,924 | A | 6/1999 | Burdette et al. |
| 7,105,329 | B2 | 9/2006 | Zeikus et al. |
| 7,163,812 | B2 | 1/2007 | Zeikus et al. |
| 7,195,918 | B2 | 3/2007 | Zeikus et al. |

FOREIGN PATENT DOCUMENTS

WO    WO 2008/028055 A2    3/2008

OTHER PUBLICATIONS

Hoppner (Horm Re. 2002, 58 Suppl. 3:7-15).*
Abrini, J, Naveau, H., and E-J., Nyns. 1994, *Clostridium autoethanogenum*, sp. nov. An anaerobic bacterium that produces ethanol from carbon monoxide. Arch. Microbiol. 161: 345-351.
Burdette, D. and G. Zeikus. 1994. Purification of acetaldehyde dehydrogenase and alcohol dehydrogenase from *Thermoanaerobacter ethanolicus* 39E and characterization of the secondary-alcohol dehydrogenase (2O Adh) as a bifunctional alcohol dehydrogenase-acetyl-CoA reductive thioesterase. Biochem. J. 302: 163-170.
Liou, J.S.C., Balkwill, D.L., Drake, G.R., and Tanner R.S. 2005. *Clostridium carboxidivorans* sp. nov., a solvent-producing *Clostridium* isolated from an agricultural settling lagoon, and reclassification of *Clostridium scatalogenes* strain SL1 as *Clostridium drakei* sp. nov. International Journal of Systematic and Evolutionary Microbiology. 55:2085-2091.
Barik, S, Prieto, S., Harrison, S.B., Clausen, E.C. and Gaddy, JL. 1988. Biological production of alcohols from coal through indirect liquefaction. Applied Biochemistry and Biotechnology. 18:363-378.
Hensgens CM, Hagen WR, Hansen TA. 1995. Purification and characterization of a benzylviologen-linked, tungsten-containing aldehyde oxidoreductase from *Desulfovibrio gigas*. J Bacteriol. 177:6195-6200.
Vega, J.L., Prieto, S., Elmore, B.B., Clausen, E.C. and Gaddy, J. L. 1989. The biological production of ethanol from synthesis gas. Appl. Biochem. And Biotech. 20/21: 781-797.
Ragsdale, S.W. 2004. Life with carbon monoxide. Critical Reviews in Biochemistry and Molecular Biology. 39: 165-195.
Rothstein, D.M. 1986. *Clostridium thermosaccharolyticum* strain deficient in acetate production. J. Bacteriol. 165: 319-320.
Stephen F. Altschul, Thomas L. Madden, Alejandro A. Schäffer1, Jinghui Zhang, Zheng Zhang2, Webb Miller2 and David J. Lipman. 1997. Gapped BLAST and PSI-BLAST: a new generation of protein database search programs. Nucleic Acids Research, 25: 3389-3340.
Sipma, J., Henstra, A.M., Parshina, S.N., Lens, P.N.L, Lettinga, G., and Stams A. J. M. 2006. Microbial CO conversions with applications in synthesis gas purification and bio-desulfurization. Critical Reviews in Biotechnology. 26: 41-65.
Tanner, R.S., L.M. Miller and Yang, D. 1993. *Clostridium ljungdahlii* sp. nov. an acetogenic species in clostridial rRNA homology group I. Int. J. Syst. Bacterol. 43: 232-236.
Zeikus, JG. 1980. Chemical and fuel production by anaerobic bacteria. Annu. Rev. Microbiol. 34:423-464.
Green, E. M. Boynton, Z. L., Harris, L. M., Rudolph, F.B., Papoutsakis, E. T., and Bennett, G. N. 1996. Genetic manipulation of acid formation pathways by gene inactivation in *Clostridium acetobutylicum* ATCC 824. Microbiology. 142: 2079-2086.
Weisblum, B., Graham, M. Y., Gryczan, T., and Dubnau, D. 1979. Plasmid copy number control: Isoaltion and Characterization of High-copy number mutants of plasmid pE194. J. Bacteriol. 137: 635-643.
Williams, D.R., Young, D. I., and young, M. 1990. Conjugative plasmid transfer from *Escherichia coli* to *Clostridium acetobutylicum*. J. Gen. Microbiol. 136: 819-826.
Liu, X., Zhu, Y., and Yang, S-T. 2006. Construction and characterization of ack deleted mutant of *Clostridium tyrobutyricum* for enhanced butyric acid and hydrogen production. Biotech. Prog. 22:1265-1275.
Lefrancois, J, and Sicard, A. M. 1997. electrotransformation of *Streptococcus pneumoniae*: evidence for restriction of DNA on entry. Microbiology. 143: 523-526.
Allen, S. P. and Blaschek, H. P. 1990. Factors involved in the electroporation-induced trarnsformation of *Clostridium perfringens*. FEMS Microbiol. Lett. 70: 217-220.

(Continued)

*Primary Examiner* — Gary Nichol
*Assistant Examiner* — Lakia Tongue
(74) *Attorney, Agent, or Firm* — McDonnell Boehnen Hulbert & Berghoff LLP

(57) ABSTRACT

Essential genes coding for the metabolic pathway of solventogenic autotrophic *Clostridia* were sequenced, and functionality was confirmed. The present invention utilizes a comparative inter-species approach to develop the minimum set of essential genes for metabolic function and estimate productivity in species of suspected solventogenic capability.

2 Claims, 3 Drawing Sheets

(56) References Cited

OTHER PUBLICATIONS

Tyurin, M., Padda, R., Huang, K-X, Wardwell, S., caprette, D., and Bennett, G. N. 2001. electrotransformation of *Clostridium acetobutylicum* ATCC 824 using high-voltage radio frequency modulated square pulses. J. Appl. Microbiol. 88: 220-227.

Tyurin, M.V., Desai, S. G., and Lynd, L. R. 2004. Electrotransformation of *Clostridium thermocellum*. Appl. Environ. Microbiol. 70: 883-890.

Lin, Y-L., and Blaschek, H. P. 1984. Transformation of heat-treated *Clostridium acetobutylicum* protoplasts with pUB110 plasmid DNA. Appl. Environ. Microbiol. 48: 737-742.

Reid, S. J., Allcock, E. R., Jones, D. T., and Woods, D. Transformation of *Clostridium acetobutylicum* protoplasts with bacteriophage DNA. Appl. Environ. Microbiol. 45: 305-307, 1983.

Lyras, D., and Rood, J. 1998. Conjugative transfer of RP4-oriT shuttle vectors from *Escherichia coli* to *Clostridium perfingens*. Plasmid. 39: 160-164.

Parke, D. Construction of mobilizable vectors derived from plasmids RP4, pUC18, and pUC19. Gene. 93: 135-137, 1990.

Monod, M., Denoya, C. And Dubnau, D. 1986. Sequence and properties of pIM13, a macrolide-Lincosamide-Streptogramin B resistance plasmid from *Bacillus subtilis*. J. Bacteriol. 167: 138-147.

Drake, HL, K. Kusel, and C. Matthies. 2006. Acetogenic Prokaryotes. In: The Prokaryotes, vol. 2. M. Dworkin, S. Falkow, E. Rosenberg, et al., Eds.: 354-420. New York: Springer-Verlag.

Young DI, Evans, V.J., Jeffries, J. R., Jennert, K. C. B., Phillips, Z. E. V. Ravagnani, A., and Young, M. Genetic Methods in Clostridia. Methods Microbiology. 1999, 29: 191-207.

Ferry, J. 1995. CO dehydrogenase. Annu. Rev. Microbiol. 49:305-333.

\* cited by examiner

ESSENTIAL GENES ENCODING CONSERVED METABOLIC PATHWAY FUNCTION IN AUTOTROPHIC SOLVENTOGENIC CLOSTRIDIAL SPECIES

FIELD OF THE INVENTION

This invention relates to the cloning and expression of novel genetic sequences of microorganisms used in the biological conversion of CO, $H_2$, and mixtures comprising CO and/or $H_2$ to biofuel products, and functional characterization thereof. Further, this invention relates to a method of pre-screening autotrophic homoacetogenic microorganisms for the ability to produce high ethanol titers from syngas components.

BACKGROUND

Synthesis gas (syngas) is a mixture of carbon monoxide (CO) gas, carbon dioxide ($CO_2$) gas, and hydrogen ($H_2$) gas, and other volatile gases such as $CH_4$, $N_2$, $NH_3$, $H_2S$ and other trace gases. Syngas is produced by gasification of various organic materials including biomass, organic waste, coal, petroleum, plastics, or other carbon containing materials, or reformed natural gas.

Acetogenic Clostridial microorganisms grown in an atmosphere containing syngas are capable of absorbing the syngas components CO, $CO_2$, and $H_2$ and producing aliphatic $C_2$-$C_6$ alcohols and aliphatic $C_2$-$C_6$ organic acids. These syngas components activate Wood-Ljungdahl metabolic pathway 100, as shown in FIG. 1, which leads to the formation of acetyl coenzyme A 102, a key intermediate in the pathway. Under autotrophic fermentation conditions, the enzymes activating Wood-Ljundahl pathway 200, as shown in FIG. 2, are carbon monoxide dehydrogenase (CODH) 104 and hydrogenase ($H_2$ase) 106. These enzymes capture the electrons from the CO and $H_2$ in the syngas and transfer them to ferredoxin 108, an iron-sulfur (FeS) electron carrier protein. Ferredoxin 108 is the main electron carrier in metabolic pathway 100 in acetogenic Clostridia, primarily because the redox potential during syngas fermentation is very low (usually between –400 and –500 mV). Upon electron transfer, ferredoxin 108 changes its electronic state from $Fe^{3+}$ to $Fe^{2+}$. Ferredoxin-bound electrons are then transferred to cofactors $NAD^+$ 110 and $NADP^+$ 112 through the activity of ferredoxin oxidoreductases 114 (FORs). The reduced nucleotide cofactors ($NAD^+$ and $NADP^+$) are used for the generation of intermediate compounds in Wood-Ljungdahl pathway 100 leading to acetyl-CoA 102 formation.

The FOR-mediated ferredoxin reduction reaction additionally feeds an Rnf complex that maintains a proton-motive force (PMF) to generate ATP through interconnectivity of the electron-motive force (EMF) with the PMF since under autotrophic growth conditions homoacetogenic cells are generating net ATP through a PMF via an F1F0 type ATP synthase consisting of seven genes (see Table 1, Gene ID Nos. 50-57). The net ATP generated through operation of the Rnf complex is then consumed for cell growth or maintenance.

Acetyl-CoA 102 formation through Wood-Ljungdahl pathway 100 is shown in greater detail in FIG. 2. Either $CO_2$ 202 or CO 208 provide substrates for the pathway. The carbon from $CO_2$ 202 is reduced to a methyl group through successive reductions first to formate, by formate dehydrogenase (FDH) enzyme 204, and then is further reduced to methyl tetrahydrofolate intermediate 206. The carbon from CO 208 is reduced to carbonyl group 210 by carbon monoxide dehydrogenase (CODH) 104 through a second branch of the pathway. The two carbon moieties are then condensed to acetyl-CoA 102 through the action of acetyl-CoA synthase (ACS) 212, which is part of a carbon monoxide dehydrogenase (CODH/ACS) complex. Acetyl-CoA 102 is the central metabolite in the production of $C_2$-$C_6$ alcohols and acids in acetogenic Clostridia.

Ethanol production from Acetyl CoA 102 is achieved via one of two possible paths. Aldehyde dehydrogenase facilitates the production of acetaldehyde, which is then reduced to ethanol by the action of primary alcohol dehydrogenases. In the alternative, in some homoacetogenic microorganisms, a bifunctional NADPH-dependent ADH/acetyl CoA reductase ("AR") thioesterase facilitates the production of ethanol directly from acetyl CoA.

Wood-Ljungdahl pathway 100 is neutral with respect to ATP production when acetate 214 is produced (FIG. 2). When ethanol 216 is produced, one ATP is consumed in a step involving the reduction of methylene tetrahydrafolate to methyl tetrahydrofolate 206 by a reductase, and the process is therefore net negative by one ATP. The pathway is balanced when acetyl-$PO_4$ 218 is converted to acetate 214.

Acetogenic Clostridia organisms generate cellular energy by ion gradient-driven phosphorylation. When grown in a CO atmosphere, a transmembrane electrical and chemical potential is generated and used to synthesize ATP from ADP. Enzymes mediating the process include hydrogenase, NADH dehydrogenases, carbon monoxide dehydrogenase, and methylene tetrahydrofolate reductase. Membrane carriers that have been shown to be likely involved in the ATP generation steps include quinone, menaquinone, and cytochromes.

The acetogenic Clostridia produce a mixture of $C_2$-$C_6$ alcohols and acids, such as ethanol, n-butanol, hexanol, acetic acid, and butyric acid, that are of commercial interest through Wood-Ljungdahl pathway 100. For example, acetate and ethanol are produced by C. ragsdalei in variable proportions depending in part on fermentation conditions. However, the cost of producing the desired product, an alcohol such as ethanol, for example, can be lowered significantly if the production is maximized by reducing or eliminating production of the corresponding acid, in this example acetate. It is therefore desirable to metabolically engineer acetogenic Clostridia for improved production of selected $C_2$-$C_6$ alcohols or acids through Wood-Ljungdahl pathway 100 by modulating enzymatic activities of key enzymes in the pathway.

Acetogenesis as described above is a general metabolic trait that is not phylogenetically conserved. Therefore, production of liquid fuels via biocatalyst is the result of a unique collection of genes and functional protein activities that are expressed when grown in the presence of syngas under desirable growth conditions. Not all organisms that have the Wood-Ljungdahl pathway make ethanol, since some lack alcohol dehydrogenases or other genes to convert acetate to ethanol. Thus, the ability to convert syngas components to high ethanol titers is embodied in the unique collection of conserved genes described below.

SUMMARY OF THE INVENTION

The present invention is directed to an isolated and purified sequence encoding a series of polypeptides encoding polynucleotides which express the minimum set of required genes to maintain ethanologenic function, and which more particularly express the minimum set of required genes to maintain Acetyl-CoA to ethanol function and the minimum set of required genes to maintain Rnf complex function.

The present invention is additionally directed to a method of producing ethanol comprising: isolating and purifying anaerobic, ethanologenic microorganisms carrying the polynucleotides described above; fermenting syngas with said microorganisms in a fermentation bioreactor.

Further, the present invention is directed to a method of confirming high titer autotrophic solventogenesis function of a potentially commercially viable microorganism, said method comprising: sequencing the genome of said potentially commercially viable microorganism; comparing a resulting sequence of the genome of the microorganism to SEQ ID NO. 1.

Finally, the present invention is directed to a method of prescreening natural isolates with suspected autotrophic solventogenesis function for high ethanol titer potential, said method comprising: isolating and enriching a sample containing said natural isolates; subjecting said sample to a polymerase chain reaction using at least one set of degenerate primers capable of hybridizing to one or more of the genes of SEQ ID NO. 1; separating the amplified product of the polymerase chain reaction based on size; and determining the presence of said genes based on the results of said separation.

DETAILED DESCRIPTION

The present invention is directed to novel genetic sequences coding for acetogenic Clostridial microorganisms that produce ethanol and acids from syngas comprising CO, CO2, H2, or mixtures thereof, and functional characterizations thereof.

Specifically, the present invention is directed to a minimum set of metabolic pathway genes of biocatalysts involved in conversion of syngas to ethanol under autotrophic growth conditions. Further, the present invention is directed to a process for prescreening autotrophic homoacetogenic microorganisms for the ability to produce high ethanol titers from syngas components.

Several species of acetogenic *Clostridia* that produce $C_2$-$C_6$ alcohols and acids via the Wood-Ljungdahl pathway have been characterized: *C. ragsdahlei*, *C. ljungdahlii*, *C. carboxydivorans*, and *C. autoethanogenum*. The genomes of four of these microorganisms were sequenced in order to locate and characterize the portions of the genome that code for the functions of interest, and that are conserved within the group of known organisms that produce high titers of ethanol when grown autotrophically on syngas.

Figure 1:
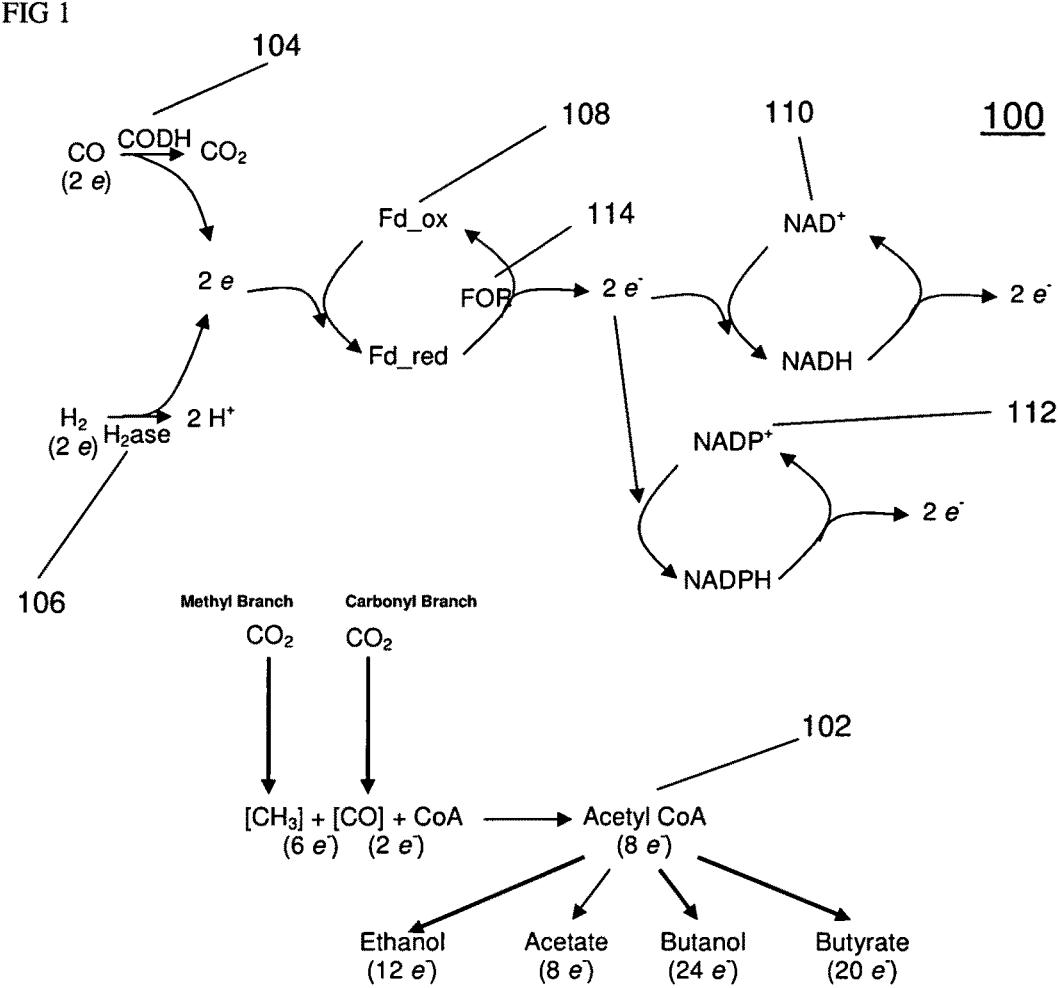
FIG. 1 is a diagram illustrating the electron flow pathway during syngas fermentation in acetogenic *Clostridia* including some of the key enzymes involved in the process.
Figure 2:
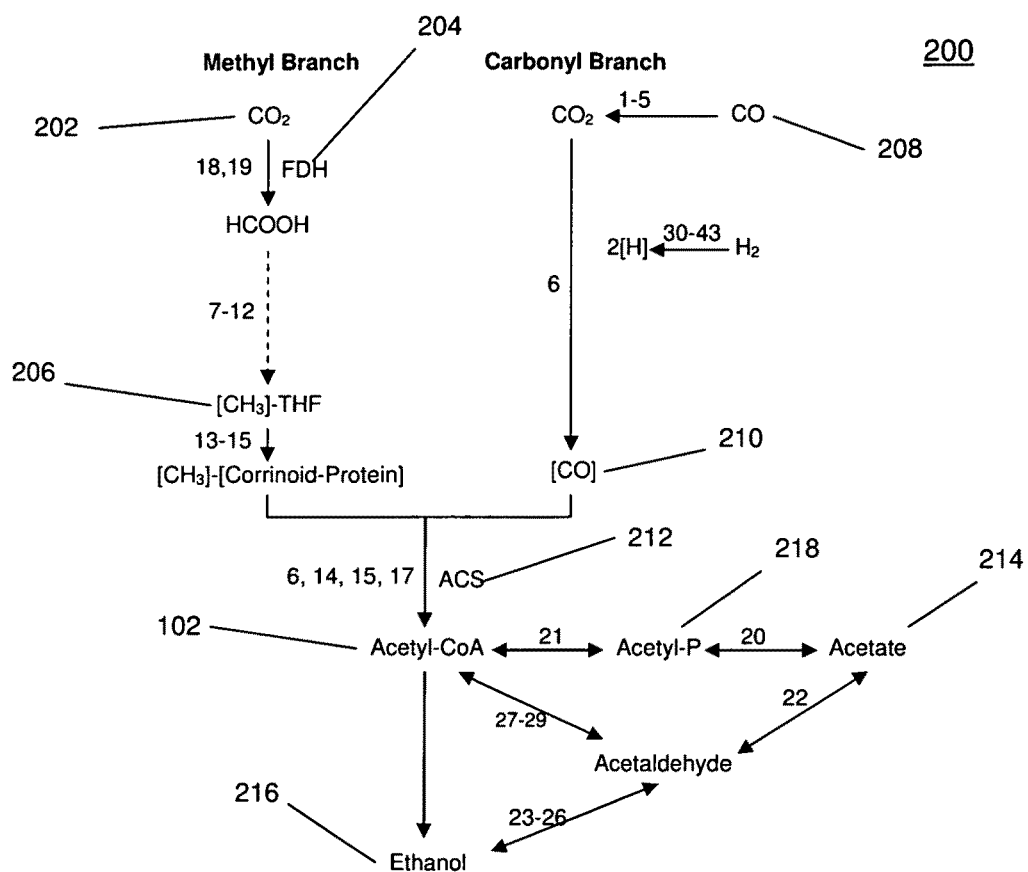
FIG. 2 is a diagram illustrating the Wood-Ljungdahl ($C_1$) pathway for acetyl-CoA production and the enzymatic conversion of acetyl-CoA to acetate and ethanol.
Figure 3:
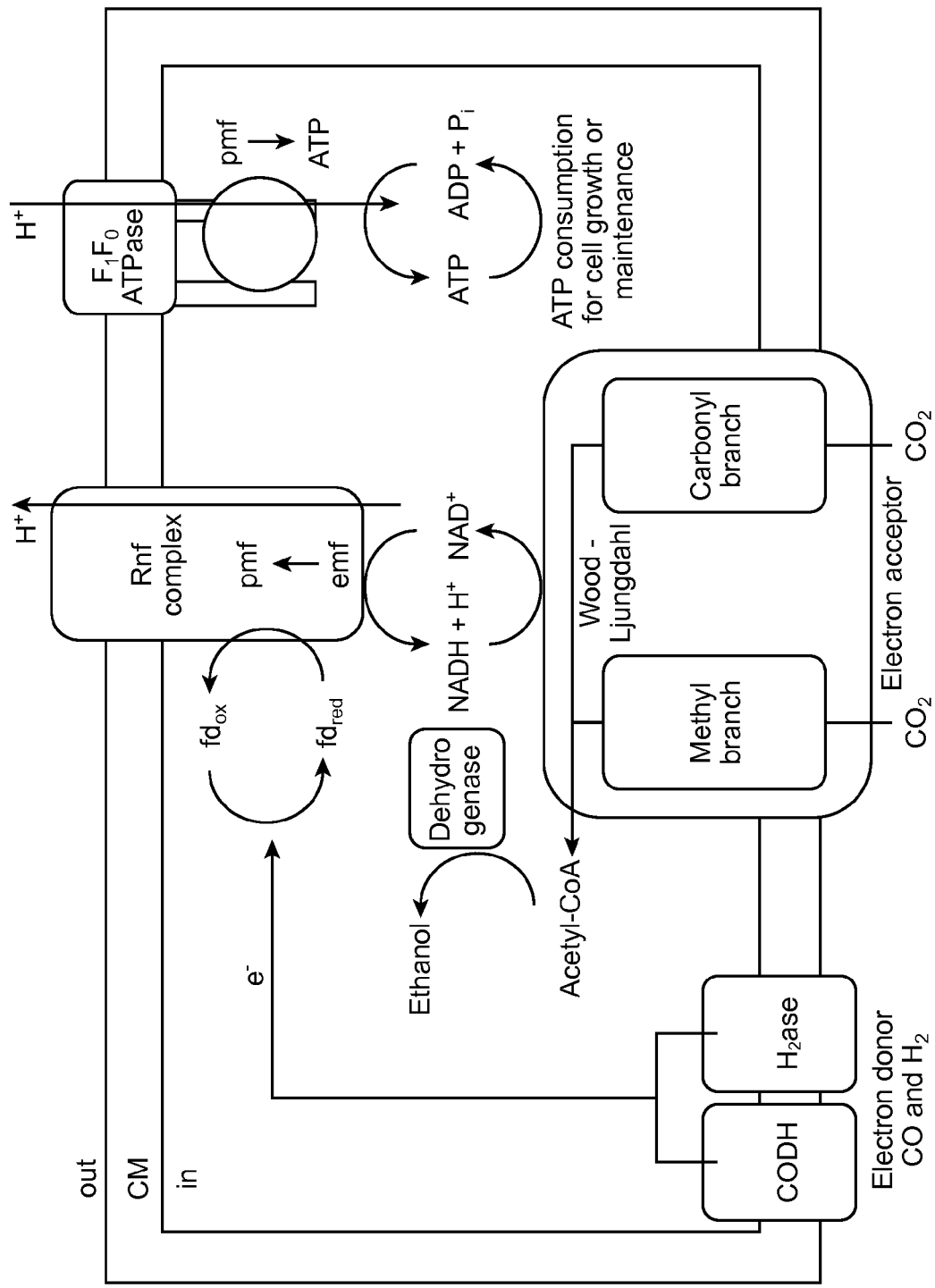
FIG. 3 is a diagram illustrating the metabolic pathway utilized by acetogenic *clostridia*. The pathway is understood to consist of all the electron transfer reactions involved in the extraction of electrons from CO an H2 to carriers which feed into the Wood-Ljungdahl pathway to form acetyl-CoA and eventually on to ethanol biosynthesis. Also integral to the whole process is the maintenance of a proton-motive force (PMF) to generate ATP and the interconnectivity of the electron-motive force (EMF) with the PMF since under autotrophic growth conditions cells are generating net ATP through a PMF.

The genes that code for the minimum set of metabolic pathway enzymes (including (1) electron transfer genes; (2) Wood-Ljungdahl pathway genes; (3) ethanol and acetate biosynthetic genes; and (4) energy [ATP] generation genes) are presented in Table 1. The first column identifies the broadly-categorized pathway associated with each gene. The gene identification numbers indicated in the second column correspond to the numbers representing the enzymes involved in the metabolic reactions in the pathway shown in FIG. 1. Any inclusion in an operon is noted in the fifth column.

TABLE 1

| Pathway | Gene ID | Gene Name | EC number | Operon | Minimum Set | Description |
|---|---|---|---|---|---|---|
| Monofunctional CODH | 1 | Carbon Monoxide Dehydrogenase | 1.2.2.4 | CODH | RCCC01175 | CO oxidation |
| | 2 | | | | RCCC02026 | CO oxidation |
| | 3 | | | | RCCC02027 | |
| | 4 | | | | RCCC02028 | |
| Wood Ljungdahl | 5 | | | CODH/ACS | RCCC03874 | acsA |
| | 6 | Carbon monoxide dehydrogenase accessory protein cooC | | | RCCC03873 | cooC |
| | 7 | Formyltetrahydrofolate Synthase | 6.3.4.3 | | RCCC03872 | Methyl branch carbon fixation, fhs |
| | 8 | Formimidotetrahydrofolate cyclodeaminase | 4.3.1.4 | | RCCC03871 | ftcd |
| | 9 | Methenyltetrahydrofolate cyclohydrolase/ Methylenetetrahydrofolate dehydrogenase | 3.5.4.9/ 1.5.1.5 | | RCCC03870 | Methyl branch carbon fixation, fold |
| | 10 | Zinc finger protein | | | RCCC03869 | unknown function |
| | 11 | Methylenetetrahydrofolate reductase | 1.5.1.20 | | RCCC03868 | Methyl branch carbon fixation, metF |
| | 12 | Dihydrolipoamide dehydrogenase | 1.8.1.4 | | RCCC03867 | acoL |
| | 13 | Carbon monoxide dehydrogenase accessory protein, ACS chaperone | | | RCCC03866 | acsF, similar to cooC |
| | 14 | Corrinoid/Iron-sulfur protein | 1.2.99.2 | | RCCC03865 | Part of CODH/ACS |

TABLE 1-continued

| Pathway | Gene ID | Gene Name | EC number | Operon | Minimum Set | Description |
|---|---|---|---|---|---|---|
| | 15 | Corrinoid/Iron-sulfur protein | 1.2.99.2 | | RCCC03864 | complex, Small subunit, acsD Part of CODH/ACS complex, Large subunit, acsC |
| | 16 | Methyltransferase | 2.1.1.13 | | RCCC03863 | Methyl branch carbon fixation, acsE |
| | 17 | Carbon Monoxide Dehydrogenase/Acetyl-CoA Synthase | 1.2.99.2 | | RCCC03862 | bifunctional CODH/ACS enzyme, carbon fixation, acsB |
| | 18 | Formate Dehydrogenase | 1.2.1.2 | | RCCC00874 | Methyl branch carbon fixation |
| | 19 | | | | RCCC03324 | |
| Ethanol and acetate production | 20 | Acetate Kinase | 2.7.2.1 | | RCCC01717 | Acetate production |
| | 21 | Phospho-transacetylase | 2.3.1.8 | | RCCC01718 | Acetate production |
| | 22 | Tungsten-containing aldehyde ferredoxin oxidoreductase | 1.2.7.5 | | RCCC00020 | Reduction of acetate to acetaldehyde |
| | 23 | Alcohol Dehydrogenase | 1.1.1.1 | | RCCC01356 | two pfam domain: FeADH and ALDH, AdhE |
| | 24 | | 1.1.1.1 | | RCCC03300 | one pfam domain: FeADH |
| | 25 | | 1.—.—.— | | RCCC01567 | short chain ADH, multiple copy |
| | 26 | | 1.—.—.— | | RCCC02765 | short chain ADH, multiple copy |
| | 27 | Aldehyde Dehydrogenase | 1.2.1.10 | | RCCC03290 | Acetylating |
| | 28 | | 1.2.1.10 | | RCCC04101 | Acetylating |
| | 29 | | 1.2.1.10 | | RCCC04114 | Acetylating |
| Hydrogenase | 30 | Hydrogenase | 1.12.7.2 | | RCCC00038 | Fe only, H2 production |
| | 31 | | 1.6.5.3 | H2ase 1 | RCCC00878 | NADH-quinone oxidoreductase chain E |
| | 32 | | 1.6.5.3 | | RCCC00879 | NADH-quinone oxidoreductase chain F |
| | 33 | | 1.6.5.3 | | RCCC00880 | NADH-quinone oxidoreductase chain G |
| | 34 | | | | RCCC00881 | Electron transport protein hydN, Fe—S-cluster-containing hydrogenase components 1 |
| | 35 | | 1.12.7.2 | | RCCC00882 | Fe only, large subunit, H2 production |
| | 36 | | | | RCCC00884 | Electron transport protein hydN, Fe—S-cluster-containing hydrogenase components 2 |
| | 37 | | 1.6.5.3 | H2ase 2 | RCCC01502 | NADH-quinone oxidoreductase chain E |
| | 38 | | 1.6.5.3 | | RCCC01503 | NADH-quinone oxidoreductase chain F |
| | 39 | | 1.12.7.2 | | RCCC01504 | Fe only, H2 production |

TABLE 1-continued

| Pathway | Gene ID | Gene Name | EC number | Operon | Minimum Set | Description |
|---|---|---|---|---|---|---|
| | 40 | | 1.12.5.1 | H2ase 3 | RCCC02998 | Ni—Fe small subunit, H2 oxidation |
| | 41 | | 1.12.5.1 | | RCCC02997 | Ni—Fe large subunit, H2 oxidation |
| | 42 | | 3.4.24.— | | RCCC02996 | Hydrogenase maturation protease |
| | 43 | | | | RCCC02995 | Hypothetical protein |
| Electron transfer | 44 | rnf Complex | | rnf | RCCC01825 | rnf B |
| | 45 | | | | RCCC01826 | rnf A |
| | 46 | | | | RCCC01827 | rnf E |
| | 47 | | | | RCCC01828 | rnf G |
| | 48 | | | | RCCC01829 | rnf D |
| | 49 | | | | RCCC01830 | rnf C |
| Energetics | 50 | F0F1 type ATP synthase | 3.6.3.14 | ATPase | RCCC00393 | ATP synthase A chain |
| | 51 | | | | RCCC00394 | ATP synthase C chain |
| | 52 | | | | RCCC00395 | ATP synthase B chain |
| | 53 | | | | RCCC00396 | ATP synthase delta chain |
| | 54 | | | | RCCC00397 | ATP synthase alpha chain |
| | 55 | | | | RCCC00398 | ATP synthase gamma chain |
| | 56 | | | | RCCC00399 | ATP synthase beta chain |
| | 57 | | | | RCCC00400 | ATP synthase epsilon chain |
| Electron carriers | 58 | Ferredoxin | | | RCCC00086 | Ferredoxin |
| | 59 | | | | RCCC00301 | Ferredoxin |
| | 60 | | | | RCCC00336 | Ferredoxin |
| | 61 | | | | RCCC01168 | Ferredoxin |
| | 62 | | | | RCCC02435 | Ferredoxin |
| | 63 | | | | RCCC02890 | Ferredoxin |
| | 64 | | | | RCCC03063 | Ferredoxin |

The results of the sequence analysis and the creation of the minimum set of functional genes for the four primary functions inherent in metabolic function of homoacetogenic *Clostridia* (electron transfer, Wood-Ljungdahl pathway, ethanol and acetate biosynthesis, and ATP generation) indicate that certain Clostridial strains (i.e. those with a low G+C) can be categorized according to their ability to make ethanol from different substrates and that organisms characterized by high ethanol titers must contain at a minimum the genes contained in the minimum set to maintain function and autotrophic ethanol production from syngas.

The comparison and creation of the minimum set additionally indicates that the key differences between high ethanol producing strains and strains producing no ethanol or low levels of ethanol (i.e. "smears") lies in the electron transfer reactions and the large collection of alcohol dehydrogenases.

Two operons coding for CODH function were identified as members of the minimum set (see Table 1), indicating that both are essential for proper metabolic pathway function in any acetogenic *Clostridia*. One operon (Gene ID Nos. 2-4) codes for a monofunctional CODH which transfers electrons from a reduced CO to ferredoxin carriers. The two carbon moieties are then condensed to acetyl-CoA 102 through the action of acetyl-CoA synthase (ACS) 212, which is part of a carbon monoxide dehydrogenase (CODH/ACS) complex, and makes up the second CODH operon, which codes for Wood-Ljungdahl function (Gene ID Nos. 5-18) that is conserved across known species of acetogenic *Clostridia*. The CODH/ACS operon is also responsible for reducing the carbon from CO2 208 to a carbonyl group 210.

Additionally, there are three further genes that do not reside in an operon that have been identified as members of the minimum set for Wood-Ljungdahl function: A fourth CODH gene and two formate dehydrogenase genes complete the minimum set.

Ten genes coding for ethanol and acetate production enzymes (Gene ID Nos. 20-29) have been identified as the minimum set for proper production by acetogenic *Clostridia*. These ten genes code for acetate kinase, phosphotransacetylase, tungsten-containing aldehyde FOR, and alcohol and aldehyde dehydrogenases, all of which are required for ethanol and aldehyde production from the primary metabolite in autotrophic acetogenic microorganisms, acetyl CoA. Aldehyde dehydrogenase facilitates the production of acetaldehyde, which is then reduced to ethanol by the action of primary alcohol dehydrogenases.

Two operons, one consisting of six genes (Gene ID Nos. 44-49) and coding for electron transfer function, and the other consisting of eight genes and coding for ATP generation were found to be conserved across all known autotrophic acetogenic *Clostridia*. Electron transfer function in acetogenic microorganisms is ultimately controlled by an Rnf complex which mediates EMF/PMF function. The Rnf complex maintains a PMF to generate ATP through interconnectivity of the EMF with the PMF since under autotrophic growth conditions homoacetogenic cells are generating net ATP through a PMF via an F1F0 type ATP synthase consisting of seven genes (see Table 1, Gene ID Nos. 50-57). The net ATP generated through operation of the Rnf complex is then consumed for cell growth or maintenance.

Key genes to promote production of ethanol in solventogenic *Clostridia* include:

SEQ ID NO 1 (Gene ID Nos. 1-64, Table 1), the minimum set of genes required to maintain function of the metabolic pathway of acetogenic *Clostridia*, including the experimentally determined promoter regions for all monocistronic genes and the promoter regions for the first gene in all operons.

SEQ ID NO 2 (Gene ID Nos. 20-29, Table 1), the minimum set of genes required to maintain function of the Acetyl-CoA to ethanol step of the Clostridial metabolic process, including the experimentally determined promoter regions for all monocistronic genes and the promoter regions for the first gene in all operons;

SEQ ID NO 3 (Gene ID Nos. 44-64, Table 1), the minimum set of genes required to maintain function of the Rnf complex and corresponding PMF to ATP step of the Clostridial metabolic process, including the experimentally determined promoter regions for all monocistronic genes and the promoter regions for the first gene in all operons;

TABLE 1

Sequence Listing
Minimum set sequences

>SEQ ID NO. 1: (cooS, cooF, NADH:
Ferredoxin Oxidoreductase operon (includes STOP)
>GENE ID NO. 1:
RCCC01175 Contig0001_4148927_4150588
CACGATTCTGTGGAAGAAATGCTTAAAAGAATCAGGGAAGATGGTATGTC
AAACGTATTTGACAGATGGTCCTCTCAAGAAAAAATTAGATGTAAGTTTT
GCCTAGAAGGATTAAGCTGTCAATTGTGTTCTCAAGGTCCCTGCAGAATT
AATCTTAAAGGAGAACAGAAAAAGGTGTTTGTGGTATTGGCCCAGATGCC
ATGGCAATGCGAAATATGTTACTTAAAAACATAATGGGAGCTGGTACATA
TAGCCATCACGCATATGAAGCCTTTAGAACATTAAGAGAAACTGGAGAAG
GCAAGACTCCATTTACAATTAAAGATGTGGATAAACTCAAATGGATGTGC
CAGAAAGTCGGAATTAATACAAGCGGAGATACCAATAAAATGGCAGTGAA
TCTGGCAAATTTTTTGGAAGCTGAGATGGGTAAAGATGTAGAAGAACCTA
GTGTTATGGTAGATGTGTTTTCACCAAGAAAGAGAAAAAAAGTTTGGAAA
GATCTTGGAATTTATCCTTCAGGAGTAGTTCACGAAGAGCAAAATGCAGT
AGCAAGTTGTTTAACAAATGTTGATGGGGATTATGTATCATTAGCTAAAA
AAGCGCTGCGGCTAGGTCTGTCAACTATCTATACAGCACAAATAGGACTT
GAAATGGCTCAGGATATACTTTTTGGCACGCCTACACCCCATGAGGTAAA
TGTGGACTTAGGAATTATGGATCCAGAGTATATAAATATTGTATTTAATG
GACATCAACCTTGGGCTGGTGTTGCTACTATTCAAAAGGCAAAGATGCAG
CAGATACAGGAAAGAGCAAAGGCAGCTGGTGCAAAAGGGCTTAGAATAGT
TGGGTCAATTGAAACAGGACAGGAATTATTACAAAGATTTGAGGTAGATG
ATGTATTTGTAGGTTTAATGGGAGATTGGCTATCTATAGAACCACTTCTT
GCTACAGGTACAGTTGATGTTCTTGCAATGGAAGAAAACTGTTCTCCACC
TGCAATAGATCATTATGCTGAAAAGTATCAGGTAACTTTAGTAGGTGTAA
GTACTATTATAGGTATTCCGGGGTTAAATCATATGATTCCATATAATCCT
GAAAAAGTGGGTGAAATGGCTGATAAATTGATTGATTTGGCCATTGAAAA
TTTTAAAAAGAGAAAGGATAACATTACACCAAAGGTTCCTAAAATAACAC
AGAAAGCAATAGCAGGGTTTTCTACTGAAGCAGTTTTAAAAGCTTTAGGA
AATAAGCTTGATCCACTTGTTGATGTTATTAAGGCAGGGAAGATTAAAGG
AATTGTGGCTTTGGCAAATTGTTCAACTCTAAGAAATGGTCCTCAAGATT
GGAATACAGTTAACCTGGTAAAGGAATTGATTAAAAAGGATATTTAGTT
GTGGCTGGTGGGTGCGGCAATCATGCTCTTGAAGTAGCAGGGCTGTGCAA
CCTAGATGCAATAAACATGGCTGGCCAAGGACTAAAAGAAGAATATGCAATA
TGCTAAAGATTCCTCCAGTTCTAAGCTTTGGAACTTGTACAGATACGGGA
AGAATATCCATGCTTGTTACAGAACTTGCTAATTACCTTGATGTAGATAT
ACCAGATCTTCCTATTGCTGTAACGGCTCCTGAGTGGATGGAACAAAAAG
CTACTATAGATGGTTTATTTGCAGTAGCCTATGGAACATATACACATTTA
TCTCCAACTCCATTTCTAACAGGCGCAGAACAGCTTGTAAAGCTTCTTAC
TGAGGATGTAGAGAGCTTAACAGGAGGTAAAGTTGCATTAGGAGATAATC
CAAAAGAGGCAGCTGATAATATTGAAGCACATATATTAAGTAAAAGAAAG
GGTTTGGAGTTATAA >Gene ID No. 2:
RCCC02026 Contig0001_3297939_3296062
CAATTATTTTTTAGTTAGTTGTACTTGTAAATAAATAGTATTAATTAATA
CTATTAAACTATTACAGTTTTTGATTCTTAGTATAAGTATTCTTAGTATC TABLE 1-continued Sequence Listing
Minimum set sequences TTTAGCACTTAGAATACGTTATCCTTTAGGAGAATAATCCTAATCAGTAA
TTTTAATAATTTAATAGTATACTTAAATAGTATAGTTTGGAGGTTTTATT
ATGTCAAATAACAAAATTTGTAAGTCAGCAGATAAGGTACTTGAAAAGTT
TATAGGTTCTCTAGATGGTGTAGAAACTTCTCATCATAGGGTAGAAAGCC
AAAGTGTTAAATGTGGTTTTGGTCAGCTAGGAGTCTGCTGTAGACTCTGT
GCAAACGGTCCCTGCAGAATAACACCTAAAGCTCCAAGAGGAGTATGTGG
TGCTAGTGCTGATACCATGGTTGCAAGAAACTTTCTTAGAGCTGTAGCTG
CCGGCAGTGGATGTTATATCCATATAGTCGAAAATACAGCTAGAAACGTA
AAATCAGTAGGTGAAACCGGCGGAGAGATAAAAGGAATGAATGCTCTCAA
CACCCTAGCAGAAAAACTTGGTATAACAGAATCTGACCCACATAAAAAAG
CTGTACTAGTAGCTGATGCCGTATTAAAGGACTTATACAAACCAAAATTC
GAAAAAATGGAAGTTATAAATAAATTAGCTTATGCACCTAGACTAGAAAA
TTGGAACAAATTAAATATAATGCCTGGCGGTGCAAAATCAGAAGTTTTTG
ATGGTGTAGTAAAAACTTCTACAAATCTAAACAGCGACCCTGTAGATATG
CTTCTAAATTGTTTAAAACTTGGAATATCCACTGGGATTTACGGACTTAC
CCTTACAAATTTATTAAATGACATAATTTTAGGTGAACCTGCTATAAGAC
CTGCAAAAGTTGGTTTTAAAGTTGTAGATACGGATTATATAAATTTGATG
ATAACAGGCCACCAGCACTCCATGATTGCCCACCTTCAAGAAGAACTTGT
AAAACCTGAAGCTGTAAAAAAAGCCCAAGCAGTTGGTGCTAAAGGATTCA
AACTAGTTGGATGTACCTGTGTCGGACAGGATTTACAGTTAAGAGGTAAA
TACTATACTGATGTTTTCTCCGGTCATGCAGGAAATAACTTTACAAGTGA
AGCCTTAATAGCAACTGGAGGTATAGATGCAATAGTATCTGAATTTAACT
GTACTCTTCCTGGCATCGAGCCAATAGCTGATAAGTTCATGGTTAAAATG
ATATGCCTAGATGACGTTTCTAAAAAATCAAATGCAGAATATGTAGAATA
CTCTTTTAAAGATAGAGAAAAATAAGCAACCATGTTATAGATACGGCTA
TTGAAAGTTATAAGGAAAGAAGATCTAAAGTTACAATGAATATTCCTAAA
AACCATGGCTTTGATGACGTCATAACAGGTGTAAGTGAAGGTTCCTTAAA
ATCCTTCTTAGGCGGAAGTTGGAAACCTCTTGTAGACTTAATTGCTGCTG
GAAAAATTAAAGGTGTTGCTGGAATAGTAGGTTGTTCAAACTTAACTGCC
AAAGGTCACGATGTATTTACAGTAGAACTTACAAAAGAACTCATAAAGAG
AAATATAATTGTACTTTCTGCAGGTTGTTCAAGTGGTGGACTTGAAAATG
TAGGACTTATGTCTCCAGGAGCTGCTGAACTTGCAGGAGATAGCTTAAAA
GAAGTATGTAAGAGCCTAGGTATACCACCTGTACTAAATTTTGGTCCATG
TCTTGCTATTGGAAGATTGGAAATTGTAGCAAAAGAACTAGCAGAATACC
TAAAAATAGATATTCCACAGCTTCCACTTGTCTTTCTGCACCTCAATGG
CTTGAAGAACAAGCATTGGCAGATGGAAGTTTTGGTCTTGCCCTTGGATT
ACCACTTCACCTTGCTATATCTCCTTTCATTGGTGGAAGCAAAGTGGTAA
CAAAAGTTTTATGTGAAGATATGGAAAATCTAACAGGCGGCAAGCTTATA
ATAGAAGCGATGTAATAAAAGCTGCAGATAAATTAGAAGAAACCATACT
TGCAAGAAGGAAAAGCTTAGGTCTTAATTAA >Gene ID No. 3:
RCCC02027 Contig0001_3296040_3295588
ATGAAAAGAATAATGATAAATAAGGATTTATGTACCGGATGCTTAAATTG
TACTTTAGCTTGTATGGCAGAACACAATGAAAATGGGAAATCTTTTTATG
ATCTGGATCTCAGCAATAAATTTCTTGAAAGTAGAAATCATATATCTAAA
GATGATAATGGAAACAAGCTTCCTATATTTTTGCCGTCACTGTGACGAACC
TGAGTGCGTAATGACATGTATGAGCGGTGCCATGACTAAAGATCCTGAAA
CTGGTATAGTATCCTATGATGAGCATAAATGTGCCAGCTGCTTTATGTGC
GTCATGTCCTGTCCTTATGGAGTATTGAAACCAGATACTCAGACCAAAAG
TAAAGTAGTTAAATGTGACCTGTGTGGTGACAGAGATACACCTAGATGCG
TTGAAAATTGTCCAACAGAAGCAATTTATATTGAAAAGGAGGCAGATCTC
CTATGA >Gene ID No. 4:
RCCC02028 Contig0001_3295588_3294329
ATGAGTGGTTTAACAATAAAAATATTTTTCACACAAAATATGTAATAAT
AGGAGCCAGTGCTGCTGGAATAAATGCTGCTAAAACTTTAAGAAAGTTAG
ATAAATCCTCCAAAATAACTATTATTTCAAAGGATGATGCAGTTTATTCA
AGATGTATACTCCACAAAGTACTTGAGGGAAGTAGAAATTTAGATACCAT
AAATTTTGTAGATTCTGATTTCTTTGAAAAAAATAATATAGAATGGATAA
AAGATGCAGATGTAAGCAATATTGATATTGACAAGAAAAAGTCTTACTT
CAAGACAACAGCAGCTTCAAATTTGACAAGCTCCTTATAGCTTCTGGTGC
TTCCTCCTTTATTCCCCCAGTTAAAAAATTAAGAGAAGCTAAAGGAGTGT
ACTCCCTTAGAAATTTTGAAGATGTAACTGCTATACAAGACAAACTTAAA
AACGCAAAACAAGTGGTAATACTTGGTGCAGGTCTTGTAGGAATTGATGC
ACTTTTAGGTCTTATGGTGAAAAATATAAAGATTTCAGTTGTAGAAATGG
GAGATAGGATTCTCCCCCTTCAACCTTACTGGACAAAACTGCATCCACTATAT
GAAAAGTTGTTAAAAGAAAAAGGTATAGATGTCTTTACTTCAGTTAAATT
GGAAGAGGTAGTTTTAAATAAAGACGGAACTGTAAGTAAAGCAGTACTAT
CAAATTCAACTTCTATAGATTGCGATATGATAATAGTTGCTGCTGGTGTT
AGACCAAATGTAAGCTTTATAAAAAGACAGCAGGATAAAAGTTGAAAAGG
CATTGTCATAGACAAACATTGTAAAACCACTGTAGATAATATATATGCTG
CAGGAGATGTTACTTTTACTGCTCCTATATGGCCTATAGCTGTAAAGCAG
GGAATAACTGCTGCTTACAACATGGTAGGTATAAATAGAGAATTACATGA
CACTTTTGGCATGAAGAACTCAATGAATTTATTTAACCTTCCATGCGTAT
CCCTTGGTAATGTAAATATAGCAGATGAAAGTTATGCTGTTGATACATTA TABLE 1-continued Sequence Listing
Minimum set sequences GAAGGAGATGGAGTTTATCAAAAAATAGTTCACAAAGATGGAGTAATCTA
CGGTGCACTTCTAGTTGGAGATATATCTTACTGCGGCGTACTAGGATATC
TCATAAAAAATAAAGTAAATATAAGCAATATCCATAAAAATATTTTTGAC
ATAGATTATTCTGATTTTTACAATGTTGAAGAAGATGGACAATATAGTTA
TCAATTGAGGTAA >Gene ID No. 5:
RCCC03874 Contig0001_1807911_1806019
TTATACTTAAATGGATGTTTATTTTTTAACATTTTTTATGGTAAATATAT
TTATTTTATGTAGTAAAAAGGTTATAATTATAATTGTATTTATTACAATT
AATTAAAATAAAAAAATAGGGTTTTAGGTAAAATTAAGTTATTTTAAGAA
GTAATTACAACAAAAATTGAAGTTATTCTTTAAGGAGGGAATTATTAAA
ATGGAAGAAAAGGCAAAGTCAATTGATCAAGCTACTTTACAATTATTGGA
CAAGGCAAAAAAAGATGGGGTTGAAACTGCTTTTAGATAGGAAAGCAGACA
TGAAGGTACAGTGTGGATTTGGGTCAGCAGGAGTTTGCTGTAGAAATTGC
AGCATGGGTCCTTGTAGAGTAAGTCCAGTGCCAGGAAAAGGCGTTGAAAG
AGGTATATGTGGTGCTACAGCAGATGTAATTGTATCTAGAAATTTTGCAA
GAATGGTTGTAGGCGGAGCTGCTGCCACATTCAGATCATGGTAGAAGTATA
GCACTTAGCTTATACCACTCCAGCAAAGATGGAGATATAAAAGTTAAAGA
TGAAAATAAATTGAAAGAAGTTGCAAAATATATGATGTAGAAACTGAAG
GAAGAGACATATATGATATAGCTCATGATGTAGCTAAAAGAGGATTAGAT
GATTATGGTAGACAAATGGGAGAAGTTAAACTTCCACCGTCCCTTCCACC
AAAGAGAAAGGAAATATGGATAAACTTGACATAGTTCCAAGGGCAATTG
ATAGAGAAATAGCTGCAGTTTATGCACTCAACACATATAGGATGTAATGCA
GATGCAGAAGCTATGATTAAAATGGCTATGAGATGTTCGCTAGGTGATGG
ATGGCTAGGATCATATATGGACTACAGATTTAGAGATATAAATGTTTGGAA
CACCTAAGTCAATTGAGACAGAAGCAAATCTTGGAGTACTTGAAAAGAAT
TCTGTAAATGTAGTTTTACACGGACATGAACCTCTTCTTTCAGATATGAT
AGTAGAAGCAGCATCAGATCCAGAACTAGTTGAACTTGCTAAATCAGTAG
GTGCTGATGGAATAAACTTATGCGGAATGTGCTGTACTGGAAATGAAGTT
TCCATGATACATGGCATCAAAATAGCAGGAAATCTTTATGCAGCAGGAATT
GGCTGTAGTTACAGGAGCAGTAGATGGACTTATAGTTGATGTACAGTGTA
TAATGCCAGCATTAGCAAAATTGACTAAGTCATATCATACTAAGTTTATA
ACGACTTCACCAAAGGCACATATCACAGATTCAACTTATATTGAATTTGA
TGAAGAACATCCACTTGATTCTGCTAAACAGATTTTAAAGGAAGCAATAT
TAAATTTTAAAAATAGAGATAACAGTAAAGTAATGATTCCTGAATTGAAA
TCAAAGGGAATTGTAGGATATAGTGTTGAAGAAGTAATAAACAAATTGGA
CAAAGTTGTTAATACACAAATAGGACCAATGCAAACTGTAAAGCCTTTAG
CAGATGTTTTAGTATCAGGAGTATTAAGAGGTGCCGCAGGTGTAGTTGGT
TGTAACAATCCTAAAGTTACTCATAATTCTGCACATATTGAAACTATAAA
GGGATTAATAAAGAATGATGTAATAGTTGTTGCTACAGGTTGTGCAGCTC
AAGCAGCAGCAGAATATGGATTAATGCAATTAGAAGCAGCAGAAAAATAT
GCAGGACCAGGACTAGCTACTGTATGTAAGCCGTATATTAGACTTAGTTG
ACTTCATATGGGTTCTTGTGTTGATATAAGCCGTATATTAGACTTAGTTG
GTAGAGTAGCTAATTTCTTAGGTACAGATATGAGTGATCTTCCAGTTGTA
GGTGTAGCACCTGAATGGATGTCAGAAAAAGCTGTTTCTATAGGTACTTA
TGTAGTAACTTCAGGTATAGATATTGGCTTGGAGTGACACCTCCAGTAA
CAGGCGGTCCAGAAGTTGTAGATATTCTTACTAATAAGATGGAAGACTGG
GTAGGAGCTAAATTCTTTATAGAAACAGATCCTCATAAAGCAGTTGAACA
AATGGTTAATAGGATGAATGAAAACGTAAAAAATTAGGTATCTAA >Gene ID No. 6:
RCCC03873 Contig0001_1805723_1804944
TCAAAGTGATATGAAGTCAAGATTACATATCATTTTGAGAAGAATTTTAA
TTTATAGATGGTATAATGTAGAATAAAATTTATAATTTATCTACAAATAA
ATAAATTATAAGGGAATATATTTGTAGATAAAAGTATATATTAAGTTTGT
ATTTTAAATAAATTATATAAAATGGTTGTTCAAAATGGGAGGGACTACAT
ATGAAAATGAAAATGGCTATAACAGGTAAAGGTGGTGTAGGTAAAACTAC
ATTTTCAGCGATAATGAGTAGAATATATGCAGAAGAAGGATATAATGTTT
TAGCTGTGGATGCAGATCCTGATCCCAATTTGGCATTAGCATTAGGATTT
CCAAAAGAGATAGCAGATGAGATTGTTCCAATTTCAGAAATGAAAAGTT
AGTAGCAGAGAGAACAAATTCTACTCCAGGATCCTTTGGAAAATGTTTA
AAATAAATCCTAAAGTTGATGATATACCAGAAAGATATTGCAAGGAATAC
AAAGGTGTAAGCATTTTAACTATGGGAACAGTTGATCAGGCGGAACAGG
TTGTTTCTGCCCGGAAATGTTTTGCTTAAAAAACTCACGTCACATTTAA
TGCTCCAAAACAAAGATCGTCATAATGGATATGGAAGCAGGTATTGAA
CATTTGGGAAGGGAACAGCGCAAGGTGTAGATGTATTTATTGTTGTTGT
AGAACCTGGAATAAGAGTATACAGCGTTCAAGCATGTTAAAAATTAG
CTAAGGATATAGGAATAGAAAAGATATTTGTGTAGCAAATAAAATTAGA
AATAAGAAGGACGAAGAATTTGTATTGGAAAATGTAGATGAAAAAGAATG
TCTTGGATTTATACATTATAGTGACACAGTTGGAAGTTCTGATAGAGTCA
ATCAATCTCCTTACGATTCCAATGAGGAAACTGTTAAGGAGGTAAAAAT
ATAAAACAAAAATTAGAAATGGGGGTTTTTAA >Gene ID No. 7:
RCCC03872 Contig0001_1804940_1803267
ATGACTTATAAATCAGACATCGAAATAGCTCAAGAATGCACAATGAAGGA CATTAAGGAAATTGCAAAGAAATTAAATATTTCCGAAGATGATATTGAAT
TGTATGGTAAATACAAAGCAAAGGTAAATTACAACTTGTTAAAGACTACA
CCTGGAAAGAATGGAAAACTTATATTATGTACAGCTATAAACCCAACACC
TGCTGGAGAAGGAAAAACTACTACAGCAATAGGTGTAGCAGATGCATTAA
ATAGAATGGGAAAATCTGTTGTTGTTGCACTTAGAGAACCATCTATGGGA
CCTGTATTTGGTATAAAAGGTGGAGCTGCCGGTGGTGGATATGCTCAAGT
AGTACCTATGGAAGACATAAACCTACACTTTACAGGTGATATACATGCAC
TCACTGCTGCTAACAATTTACTTGCAGCAATGATAGATAATCATATATAT
CAAGGCAATAAGCTTAACATAGACCCAAGAAGAATTGCTTGGAGAAGATG
CGTAGACATGAACGACAGACAGCTCAGGTTTGTAGTTGATGGATTAGGTG
GAAAAGCCAATGGTACACCTAGAGAAGATGGATTTGATATAACAGTTGCT
TCAGAAATAATGGCTATATTCTGTTTATCAAGTGACATAATTGATTTGAA
GAAGAGAATTGCTAAAATAGTTGTAGGATACACTAGAGATGGCCAGCCTG
TAACAGCTCATGATTTGAAAGCTGAAGGAGCTATGGCAGCACTTCTTAAA
GATGCATTAAAACCAAATCTAGTTCAAACTCTTGAAGGAACACCAGCATT
TGTACACGGCGGACCATTTGCAAATATAGCTCATGGTTGTAACTCAATAA
TGGCTACTAGAATGGCTCTTCACTTTGGTGATTATGTAGTTACGGAGGCA
GGTTTCGGTGCTGACCTGTGAAAAATTCTTAGATATCAAGTGCAG
AATGGCAGGATTAAAACCAGATGCAGTAATAATAGTTGCTACAGTTAGAG
CATTGAAATACAATGGCGGAGTTCCAAAGGCTGACTTAAATAATGAAAAC
TTAGAAGCTCTTGAAAAAGGACTTCCAAATCTATTAAAACATGTAGAGAA
TATAACTAAGGTATATAAATTTACCAGCAGTAGTTGCATTAAATGCATTCC
CTACAGATACACAGGCAGAATTAAAATTAGTAGAAGATAAATGTAAAGAA
TTAGGTGTAAATGTAAGATTATCAGAAGTTTGGGCTAAAGGCGGCAAGG
TGGACTAGAAGTTGCCAAAGAAGTGCTTAGACTTATAAAAGAAGAGAAAA
ATGACTTCCAGTTTGCTTATGATGAAAAATTACCAATTAGAGATAAAATA
AGAGCAGTAGCTCAAAAGATATATGGTGCTGATGATGTTACTTTCACAAG
TCAGGCAGAAAAAGAAATTGATGAGCTTGAAAAATTAGGATTTGGTAAAA
CACCAGTATGTATAGCAAAGACCCAATACTCCTTAACTGATGACCAGACT
AAACTTGGAGACCAACAGGATTTAATATTACAGTAAGACAGGTTACAAT
TTCTGCTGGGAGCAGGTTTTGTAGTTGCAGTAACTGGTTCAATAATGAAGA
TGCCAGGTCTTGGAAAAGTTCCATCTGCTGAAAAAATAGATGTAGATGAG
AATGGAGTAATAAGCGGATTATTCTAA >Gene ID No. 8:
RCCC03871 Contig0001_1803243_1802614
ATGAAAATTAGCAGATAAAAGTTGCACAGATTTTATAGAAGTTCTTGCATC
TAAAGCTGCAACTCCTGGTGGAGGCGGAGGATCAGCTATTACAGGTGCTA
TAGGAATGGCACTTGGAGGCATGGTATGTAACCTTACAATAGGAAAAGAA
AAGTATGCACAGTATGATGAAAAGGTAAAAGGCATACTTAAAAGATCTGA
TGAGCTTCAAGCAGAGCTTTTAAAGATGATGGATGCAGATGCAGAATGCT
TTCTGCCTCTTTCAAAGGCTTATGGAATGCCAAAAGACACTGAAGAGCAG
AAAAAAATAAAAGAAGAACTCTAGAAAAAGTGTCTAAAGCAAGCATGCAG
TGTTCCAGTAAGCATTGTTAACAAGCTTATGAAGCAATAAAACTCCACG
AGGCACTTGTAGATAACTGCTCCAAACTTGCAATAAGTGATGTTGGTGTA
GGAGTTCAGTGTCAAGAGCTGCTATTATTGGAGCACAGCTTAATGTCAT
AATCAACATTAATTCCATTAAAGATCAGGAATATGTTAAAAAGGTAAAAG
CAGAGACGGAACCTTTAGTTGAAGAAGGCATTAAGATTGCAGATAAGGTA
TATGAAAAAGTAGTTAGTGCACTTTCCAAATAA >Gene ID No. 9:
RCCC03870 Contig0001_1802508_1801657
ATGGGTCAAATAATTAAAGGTAAACCAGTGGCAGATGCTATAAGTGAAGC
TTTAACTAAAGAAGTTAATGATTTAAAGGTAAAGGGTATTACTCCAAAAC
TTACATTAGTAAGAGTTGGAGCAAACGGAAGTGACCTTGCTTATGAAAAA
GGAGCTCTAAAAAAGTGCGAAAAATTGGAATAGAGGCAGTTGTTAAAGA
GCTACCAGCAGATATATCACAAGACAAGTTTATTGAAGAATTGAAAAAAA
TAAATGCGGACAAGACTGTAAATGCAATAATGGTATTCAGACCATTTCCT
AAGCAATTAGATGAAAGCGTTATAAAATATAATAATCGCCCCTGAAAAAGA
TGTAGATTGCTTTAGTCCTGTAAATGTTGCTAAATTGATGAAAAGATA
TGACAGGATTTGCACCTTGTACACCATCTGCTGTTATAGAAATCCTTAAG
CATTATAAAGTTCCTATGAAGGGAAAGAATGCAGTTATAGTAGGAAGATC
TATGGTAGTTGAAAACCAGCGTGCATGCTCCTATTAAATGAAAATGCTA
CAGTTACCGTATGTCATTCAAAAACTACTGATATGCCAAAGGTTTAGTTC
CAGGCAGACATACTGGTAGTAGGCATAGAAAAGCTAAAATGATAGATTC
AAAATATGTAAAAGATGGTGCCGTAGTTATAGATAGGCATAAATGTAG
ATGAAAGTGGAAAGCTATGTGGAGATGTAGATACAGAAGACTGTGAATCA
AAAGCTTCAATGATAACACCTGTTCCTAAAGGAGTAGGCTCTGTTACATC
ATCTATACTTGCACAGCATATTGTAAAGGCCTGTAAGTTACAAAATAACC
TATAA >Gene ID No. 10:
RCCC03869 Contig0001_1801626_1800979
ATGATTATTTCAGAAAAAAATCTTTTGATGAATTATTGGATTACCTTAA
AGACAGTGAAAAGTAATAATCACAGGATGTTCTTTATGCGCAACTACCT
GTAAAGTAGGCGGAGAAGAAGAAGTATTAGCAATGAAAGCCAAGTTAGAA
GAACAAGGCAAAAAAGTTTAGGCTATAAAATACTTGATCCTTCCTGCAA TABLE 1-continued Sequence Listing
Minimum set sequences TCTTTTAAAAACAAGAAAAGATTTAAAGTCCTTAAAAGCTGAATTAAAAG
AAGCAGATGCAGTAGTATCCCTAGCTTGTGGTGATGGAACTCAAACTGTA
GCCAAGTTAGTAAAGATTCCCGTTTATCCAGGTAATAACACTATGTTTAT
AGGCGAAGTAGAAAGAGTTGGACAATATGCAGAAGCTTGTAAAGCTTGTG
GAAATTGCCAGCTTGGATGGACAGGGGGAATATGTCCAATTACAATGTGT
GCAAAGGGACTTTTGAATGGACCTTGCGGTGGTGCAAGAGATGGTAAATG
TGAAGTTGATCCTGAAAATGATTGTGCTTGGATATTAATATACAATAAAT
TAAAAGAACTAGGACAGCTCGATAATTTGACAGAATTAAGAAAGCCAAGA
GATTATCAAATAAGTGCTCATCCTAGAAAAATAAATTTAAATGCTAAGTA
A >Gene ID No. 11:
RCCC03868 Contig0001_1800953_1800075
ATGAGCTTATTGAAGGAAGCTTTTGAAAAGGGAGAGTTTGCAGTTACAGC
TGAAATGGCACCTCCAAAGGGAACGGATCTTTCTCATTTAATTGAATGTG
CCAAAAAGATAAAAGGAAGAGTTCATGGAGTTAATGTAACGATTTTCAG
TCTGCTACGTTAAAAGCTACATCTTTAGCTACTTGTAAAGTGTTAAAAGA
TGCAGGATTAGAACCTGTATTTCAAATAACAGGAAGGATAGAAACAGAA
TAGCAATTCAAGGAGAATTGTTATCTGCAGGTGTTTTTGAAATTGAAAAT
GTTTTAGCTCTTACTGGAGATTATACTGCTACAGGAGATCACCCTGGTGC
AAAGCCAGTTTATGATCTAGATAGTGTTGGAATATTACAGGTGGCAAGCA
TTTTAAATGGCGGAAAAGACATGTGGTTGGAACTGATTTAAAAGGAACCA
GATTTCTTTTTAGGGGCCTGTGTTACACCTGATATGATCCGTTAGAGCT
TCAAGTTATAAAGATGAAGAAGAAAATTAAAGCTGGAGCTAAATTCTTTC
AAACTCAAGCTGTTTATGATATGGAAACTTTAAAGAAATTCAAGAAGAG
ACTAAAGCTCAAGGTGTAGATGCTAAAGTTATGGTAGGCATATACCTTT
AAAGTCAGCTGGTATGGCTAAATACATGAATAAAAACGTGCCTGGTATAT
TCGTACCTGATGAACTTATAGATAGAATGAAAAATGCTGAGGATAAAGTT
CAAGAAGGCATAAAGATAGCAGGAGAATTTATAAAGGCCGTAAAAGAATC
AGGACTTTGCGATGGAGTTCATATAATGGCAATTGGTGCGGAAGAAAATG
TGCCATTAATATTGGACGAAGCAGGATTATAA >Gene ID No. 12:
RCCC03867 Contig0001_1800037_1798658
ATGAAATTAGTTGTAATTGGTGGAGGACCAGGAGGATATGTAGCTGCACT
GCAAGCTGCAATTTTAGGAGCAGATGTTACTGTAGTTGAGAAGAAAGCTG
TAGGAGGAACTTGCTTAAATGTAGGATGTATACCTACAAAAGCACTGCTT
GCTTCCACAGATGTTTAAGTGTAATAAAAGGAGCATCAAAATTTGGAAT
TAATGTTGAAGGTGAAGTAAAACCTGATTTTGATGCAATTATGAAGAGAA
AAGATAAAGTAGTAGATCAACTTGTAAAAGGCATAGAATATATGTTTGAA
CATAGAGGGTAAAGCTTATAAGGGGAACAGGAAAACTTATAAGCAATAA
AGAGGTAGAGGTTACAAAGCAGGATGGATCTAAAGAATCCATAACGGCAG
ATAAAATTATACTTGCTACTGGTTCTGTACCTGTTACACCTGGAGTATTC
AAGTATGATGGTAAAAAGGTTATAACTTCAGATGAAGTTTTGAATTTAGA
GAAACTTCCAAAGTCAATGATACTAGTTGGTGGAGGTCCTATAGGATGTG
AAATAGGATTCTTCTTAAATAGTATGGGAGTAGAAGTTAAGGTAGTTGAA
GCTCTTCCACATCTTGCACCTTGAAGATGAAGATGTTGCAAAACAACT
TCAGAGAATTTTCAAACAGCATAAGATTAAATACTTTGTAGGCGATGGTA
TAACTAGTGTAGAAGTTAAAGGTGATACGGTAACTGCTACATTGGGAAGC
GGAAAAGTTTTAGAGGCTGAAACACTTCTCATAGCAGTTGGAAGAAGAGC
TTATGCTGAAGGTTTAGGTTTGATGATATTGGTATTAAGAAAGATCAAA
AGGAAGAATAATTGTAAATGAATATTTAGAAACTAATGTAGAGGGAGTT
TATGCAATAGGTGATTTAATTCCTACTGCTGCTCTTGCACATGTAGCTGA
AAGAGAAGGTATTGTAGCTGTTCAAAATGCAGTTTTAGATAAAAAGAAGA
AGATGAGTTACAAAGCAGTACCTGGTTGTACATTTGTAGAACCAGAAATA
GCTTCTGTAGGTATGAAAGAGAAAGATGCTGAAAAAGCAGGAATCCAGTA
CAAGGTTGGAAAATTTGACTTTAGGGGGCTTGGAAAAGCTCAAGCTATGG
GTAAATTACAAGGATTTGTAAAGATTATTACAGACGAAAAGGACGTAATA
ATTGGAGCTGCTATTGTAGGTGATAGAGCAACAGATATGATTTCAGAATT
AGGTGTTGCTTGTGAGCTTGGTTTAACAGCAGAACAGTTGGTGAAGTTA
TTCATCCACATCCGACTTTATCTGAGGCAATGATGGAAGCTCTTCATGAT
GTACACAAACAATGTGTTCATTCTGTTGATTAA >Gene ID No. 13:
RCCC03866 Contig0001_1798516_1797746
ATGGGATATAAAATAGCTGTAGCAGGTAAGGGTGGTACCGGCAAAACTAC
TTTGACAGGTCTTTTAATAGATTATTTGACAAAAAAAGGTTCAGGACCTA
TTTTAGCAGTAGATGCTGATGCAAATGCTAATTTAAATAGTTGAAGTACTTGGA
ACAGACATTGAGGGAACTATTGGAGAATAAAAAGAGGACGTAAATAAAAA
ATCACTTGAAGGGGATAATTTTCCTGGAGGTATGATGAAAGCAGATTATT
TAAAGTATAAATTAAATGCATCAGTAGCTGAAGGAGACGGTTATGACCTT
ATTGTTATGGGAAGATCCCAGGGGCCGATGATTGTTGTTAATGAAGTTGA
AATACTTAAAGCACAAGTGGATTCACTTTCTGGTAATTATGATTACATAG
TAGTTGATAATGAAGCAGGAATGGAACACTTAAGTAGAAAACTTATAGAT
CCTATTGATACTCTATTTCTGATAAGCGATTGTTCCAGAAGAGGCATACA
GGCTGTTGGAAGAATAAAACGGTTAGTTGCTGAATTAAAGTTAAAAGTTG
GCCAAATCTTTCTTATCGTAAATAGAGCTCCAGAAGGTAAATTGAATTCA GGAATAAAAGAAGAAATAAAAAAGCAAGAACTGGATTTAGTAGGAGTTGT
GCCGATGGACCAAATGGTCTATCAATTTGATTCAGATGGAAAAGCATTAG
TAGAGCTGCCAGAGGATTCTTCATGCAGAAAAGCATTGAATGAAATACTA
TCAAAAATTCAATTTGAAAATTAA >Gene ID No. 14:
RCCC03865 Contig0001_1797724_1796783
ATGTTCAAAAAACCAACACAAAAATTTTCAGGCAAAATTGGTGAAGTTGA
AATTGGAACAGGAGAAAAAGTATTAAAATTAGGAGGAGAATCAGTATTAC
CATTTTACACTTTTGATGGAGATACAGGAAATAGCCCAAAAGTAGGTATG
GAAATTTTGGATGTATATCCAGAAGACTGGATAGATCCTTTAAAAGACAT
ATACAAGGATGTTGCAAAAGATCCTGTTAAATGGGCACAATTTGTAGAAG
AAAAATATAGTCCAGATTTTATATGCCTAAGACTTATAAGTGCTGATCCA
AACGGTACAGATGCTGCACCAGAAGATTGTCTAAAACAGCTAAAGCAGT
AGTTGAAGCTATAAAAACTCCATTAGTAGTTGCAGGTACAGGAAATCATG
AAAAAAGATGCAAAATTATTTGAAAAAGTTGCTCAGGAAACTGAAGGACAC
AATATACTTTTAATGTCTGCAGTAGAAGATAATTATAAGACAGTAGGAGC
TGCAGGCGTAACTGCCTTATAATGACAAAGTTGTAGCTGAATCTTCAGTTG
ATATAAACCTTGCAAAACAGATAAATATTTTAATGAATCAACTTGGAATA
GACAATACAAAGTTTGTTGACAACGTAGGATGTGCAGCAGGTGGATATGG
TTATGAATATGTTATATCAACTTTAGACAGAGTAAAACTTGCAGCACTTG
GTCAAGATGATAAAACTCTTCAAATTCCTATAATAAGCCCTGTTTCTTTC
GAAGCTTGCAAAGTAAAAGAAGCAATGGATTCAGAAGAAGATTCACCACA
ATGGGGAAGTCAGGAAGCAGAACAGTTTCCATGGAAGTTGCAACAGCAT
CCGGAGTATTAGCATCAGGAACAGATGCTGTAATATTACGTCATCCAAAA
TCTGTAGAAGTAATTAGAAATTTTATTAAGGAATTATTAGGTTAA >Gene ID No. 15:
RCCC03864 Contig0001_1796741_1795392
ATGGCTTTAACAGGATTAAATATATTTAAATTAACACCAAAAAAAGAATTG
TAAGGATTGTGGTTTTCCTACTTGTCTAGCTTTTTCAATGAAAGTAGCAG
CAGGAGCTGTGGAAATAGGAAAATGTCCTCATATGAGTGATGAGGCAATG
GAAAAATTAGCTGAAGCTACTGCACCAATTATGAAGACAATAACTATTGG
TAAGGGAGATAATGAATATAAATTAGGTGGAGAAACTGTTTTATTCCGTC
ATGAAAAAACTTTTGTAAATAGAAAATAGATTTGCAGTTGCATTTTCCGAT
AGTATGGATGATGCAGAAGTAGATGCTAAGATCCAACTATATAAAAGATGT
AGATTATGTTAGAATCGGTGAACAAATGAAAACCGAATTTGCTGCAATAA
AATATGCAGGAAATAAAGACAAATATCTTGCTTTGATAAATAAAATAAAA
GCAAGTGGAGTAAAAGTAGCTTATGCTCTAGTTTGTGAAGATGCAGCAGT
AATGAAAGAAGCTCTTCCACTAGTTAAAGATGAAAATCCATTAGTTTATG
GAGCTAATAAAGATAACTTCAAAGAAATGGTTGAACTTGTAAAAGAAGAT
AAATTAGCTTTAGGTGTAAAGGCAGACGGATTGGAAGCTCTTTATGGTTT
AGTAGAAGAAATACAAAAATTAGGATATAGAACTTAGTACTTGATCCAG
GTGGAAAATCCATTAAAGAAGCTTTTGAAAATACAGTTCAAATTAGAAGA
ATAAATATTGAAAATCAGGATAGAACTTTTGGATATCCTTCTATACTATT
CCTAGATGAACTTACTAAAGCTGATAAATTTATGGAAGTAGCTTTATCTA
CATTATTTACTTTGAAATATGGTTCATTACTTTGTTTTAAGTGATATGGAT
TATGCAAGACACTTCCTCTTTATAGTATAAGACAGAATGTATTTACAGA
TCCACAAAAGCCAATGACAGTTGATTTGGGCATACATGGAATTAACAACC
CAGATGAAAACTCACCAGTATTATGTACTGTTGACTTTGCTCTTACTTAC
TTCCTAGTTTCAGGAGAAGTTAAAGATCTAAAGTTCAGTATGGAATGGT
TATACCAGATGCAGGTGGATATTCTGTTCTTACATCTTGGGCTGCAGGTA
AATTTACTGGTGCTGCAATAGCTGATGAAATAAAGAATGTGGAATATCA
GAGAAGACTAAGAACAGAACTCTTTTAATCCCAGGAAAGGTTGCAGTTTT
GAAAGGCGAATTAGAGGAACTTCTTCCAGACTGGAATATAGTAATTAGTA
GTACGAAGCTATGTTTATTCCTAAGTTATTAAAAGAGTTAACTGCTAAG
TAA >Gene ID No. 16:
RCCC03863 Contig0001_1795278_1794496
ATGGATAAATTTATGATTATAGGCGAAAGAATTCACTGCATATCTCCATC
TATAAGGAAGGCTATTGAGGAGAAATCCTGAACCAATATTTAAAAGAG
CAAAAGAACAATTGGATGCAGGAGCTAATTATCTAGATTTTAATATAGGA
CCAGCAAGAAAAGATGGAGAAGAAATAATGCAGTGGGGTGTTAAGGCTCT
TCAAAGTGAATTTGACAATGTTCCACTAGCACTTGATCAACAAATAAGA
AGGCTATAGAGGCAGGACTTAAAGTTTACAATAGAGAAAAAGGAAAACCT
ATCATAAATTCTGCAGATGCAGGAGAAAGAATTGGAAATATAGATTTAGC
TGCAGAGTATGATGCTATGAGCATAGCTCTTTGTGCAAAAGAGGAATAA
CAAAAGACAATGATGAAAGAATACATATTGTACAGAAATGCTTGAAAAA
GGTATGGGTCTTGAATGGAGCCTACAGATTTACTGTTTGATCCATTATT
TTTAGTAATAAAGGGCATGCAGGATAAACAAAAAGAAGTATTAGAGGCTA
TTAAATTAATAAGTGATATGGGTCTTAGAACTTGCTGTGGATTAAGCAAT
GTTTCAAATGGAGCCACCTAAGGAGAATAAGACCATAATGGATGCAACTTT
TGCAGCTATGGCAATACAATGGTCTTACTTCTGCAATAATGAATCCAT
GTGATAAGAGATTAATGGAGACAATAAAGACTTGTGATGTTGTAAATGGT
GCTGTTTTATATGCAGATTCTTACTTAGAGTTATAA TABLE 1-continued Sequence Listing
Minimum set sequences >Gene ID No. 17:
RCCC03862 Contig0001_1794434_1792311
ATGAATTTATTTCAAACTGTATTCACTGGTTCAAAGCAGGCTTTAGCAGC
TGCTGAAGGCATAGTTAAGCAAGCTGTTGACGAGAAGGGTAGAGACTATA
AAGTAGCATTTCCTGATACTGCATATTCATTATTAGTAATTTTTGCAGCT
ACAGGAAAAAAGATAACTAATGTAGGAGAATTAGAAGGTGCATTAGATAT
AGTAAGAAGTTTGATAGTTGAGGAGGAAATGCTTGATAAGCTTTTAAATT
CAGGACTTGCAACAGCTGTTGCAGCAGAAATTATAGAAGCTGCAAAGTAT
GTCCTTTCAGATGCTCCTTACGCAGAACCATGTGTAGGATTTATCTCAGA
TCCAATAATTAGATCATTTGGAGTACCACTTGTTACAGGTGATGTTCCAG
GTGTAGCAGTTGTACTTGGAGAATTCCCAGATTCTGAAACTGCAGCAAAA
GTAATAAAGGATTACCAATCAAAAGGATTACTTACTTGTTTGGTAGGCAA
AGTAATAGATCAGGCTATAGAAGGCAAAGTTAAGATGGGACTTGACCTCA
GGGTTATTCCACTTGGATATGATGTTACATCCGTAATTCATATTGTAAGT
TTTGCTATAAGAGCTGCACTTATGTTCGGAGGAATTAAGGGCGGACAGTT
AAATGATATATTGAAATATACAGCAGAAAGAGTACCTGCTTTTGTAAATG
CATTTGGACCATTAAGCGAACTTGTAGTTTCAGCAGGTGCAGGAGCTATA
GCACTTGGATTCCCTGTATAACTGATCAGGTTGTACCAGAAGTTCCTAC
ATTGTTGTTAACTCAAAAAGATTACGATAAAGTTGTTAAAACTTCATTAG
AAGCTAGGAATATAAAGATAAAGATAACTGAGATCCCAATTCCAGTTGCT
TTTGCAGCAGCATTTGAAGGTGAAAGAATAAGAAAGAATGATATGCTTGC
AGAGTTTGGTGGAAATAAGACTAAAGCTTGGGAATTAGTTATGTGTGCAA
ATCAGGGAGAAGTTGAAGATCACAAGATAGAAGTTATAGGACXCAGATATA
GATACTATAGATAAGGCTCCTGGAAGAATGCCTCTTGGAATGCTTATTAA
AGTAAGTGGAACAAATATGCAGAAGGATTTTGAGCCAGTGCTTGAAAGAA
GACTTCACTACTTCTTAAACTATATAGAAGGATAATGCTAAATGTTGGTCAG
AGAAATCTTACTTGGGTAAGAATAGGTAAGGAAGCTTTTGAAAAAGGATT
TAGATTGAAACATTTTGGTGAAGTAATATATGCTAAAATGTTAGATGAAT
TTGGTTCAGTTGTAGATAAATGTGAAGTAACTATAATAACTGATCCAGAT
AAGGCTGAAGAATTGGAAGGCAAATATGCTGTACCTAGATATTCAGAAAG
AGATGCAAGACTTGAATCATTAGTTGATGAAAAGTTGATACTTTCTATT
CATGTAATTTGTGTCAATCATTTGCACCTGCACATGTATGTATAGTAACT
CCTGAAAGACTTGGACTTTGCGGTGCAGTTTCATGGCTTGATGCTAAAGC
TACACTTGAATTGAATCCAACAGGACCATGTCAGGCAGTTCCAAAAGAAG
GCGTGGTTGATGAAAATTTAGGTATTTGGGAAAAAGTAAATGAAACTGTT
TCAAAAAATTTCTCAAGGCGCTGTAAAGAGTGTTACATTATACAGTATATT
ACAAGATCCAATGACTTCCTGTGGATGTTTTGAGTGTATTACAGGTATAA
TGCCAGAAGCAAATGGTGTTGTAATGGTAAACAGGGAATTTGGAGCAACA
ACTCCTCTTGGAATGACATTTTGGTGAACTTGCATCTATGACAGGTGGTGG
AGTTCAGACTCCAGGATTTATGGGACATGGACAATTCATAGCTTCAA
AGAAGTTTATGAAAGGTGAAGGTGGACTTGGTAGAATAGTTTGGATGCCA
AAAGAATTAAAAGACTTTGTTGCAGAAAAATTAAATAAGACAGCAAAGGA
ATTATATAATATAGATAATTTGTGAACTTGATATCTGTGATGAAACTATAG
CTACAGAATCTGAAGAAGTATTAAAATTCTTGGAAGAAAAAGGCCATCCT
GCATTAAAGATGGATCCAATAATGTAG >Gene ID No. 18:
RCCC00874 Contig0001_3075295_3076956
AATTGTCACAAATAAAAGAGAAATATGGACCTGATTCTATAATGGGAACA
GGATGTGCTAGGGGTTCTGGAAATGAAGCAAACTACGTAATGCAAAAGTT
TATGAGGGCGGTTATTGGAACCAATAACGTAGATCACTGCTGTGCCAGATT
GACATGCTCCTTCTGTAGCCGGTCTGGCTTACGTTTAGGGAAATGGTGCT
ATGTCAAATGGTATACATGAAATAGATGATACAGATTTACTACTTATTTT
TGGATATAATGGAGCAGCTTCGCATCCAATAGTTGCTAAGAGAATAGTTA
GGGCAAACAAAAAGGTGCAAAGGTAATAGTTGTAGATCCACGTATAACA
GAGTCTGGTAGGATAGCAGATTTATGGCTCCCTATAAAAAATGGAACAAA
TATGGTTCTTGTAAATACTTTTGCCAATATACTTATAAACAAGCAATTTT
ATGACAAACAATATGTAGAAGATCATACTGTTGGTTTTGAAGAATATAAA
TCTATAGTTGAGGATTATACGCCTGAATATGCAGAAAAAGTTACTGGTAT
ACCTGCAGAGGATATAGTAGAAGCTATGAAAATGTACCTCAGTGCTAAAA
ATGCTATGATATTGTACGGATTGGGAGTATGTCAGTTTGCTCAAGCTGTA
GATGTAGTAAAAGGGTTAGCTTCAATAGCTTTATTAACTGGTAATTTTGG
AAGACCTAATGTAGGCATAGGACCTGTAAGAGGCCAGAACAATGTGCAAG
GTGCCTGCGATATAGGGAGCACTTCCTAATGTATACCCAGGTTATCAAGT
GTAACTGACGATGCAATTAGAGAAAAATTTGAAAAAGCTTGGGGAGTTAA
ACTTTCAAACAAGTTGGTTATCACCTGACACGAGTTCCTGAATTAACGC
TTAAAGAGGATAAAATAAAAGCATATTATATAATGGGCGAAGATCCAGCT
CAAAGTGATCCTGATTCTAATAGAGGGGAAACACTTGATAAAGTGA
ACTTGTAATAGTTCAAGATATATTTATGAATAAAACTGCACTCCATGCAG
ATGTAATTTACCTTCTACGTCTTGGGGAGACATGAAGGAGTCTTCAGT
TCTGCTGATAGAGGATTCCAGAGATTTAGAAAAGCTGTAGAACCTAAGGG
CGATGTTAAACAGATTGGGAGTAATTTCAGAAATTGCATGTGCTAAG
GTTATGATATGCATTATAACAATACTGAGGAAATATGGGTGAACTTATA
AATTTATGCCCAAATTTCAAAGGAGCAACTTATAAGAGATTGGATGAATT
AGGAGGAATTCAATGGCCTTGTCCATCTGAAGATCATCCAGGAACTTCTT
ATCTCTACAAAGGAAATAAATTTAATACACCTACTGGAAAAGCAAATTTA
TTTGCAGCAGAATGGAGACCTCCTATAGAAGACAGATGAAGAATATCC ACTTGTTCTTTCTACAGTTAGAGAAGTAGGGCATTACTCCGTAAGAACAA
TGACAGGAAACTGTAGGGCACTCCAGCAGTTAGCTGATGAACCAGGATAT
GTACAAATTAATCCAGTGGATGCAAAGGCTAAAAAAATAATAGATGGTGA
GCTTATGAGAGTAAGTTCACGAAGAGGTTCTGTAGTTGCCCGTGCACTTG
TTACTGAAAGGGCAAATAAAGGAGCAGTTTATATGACCTATCAATGGTGG
GTAGGTGCATGTAATGAGCTTACAGCTAACTAATAATTTAGATCCAGTATCAAA
AACTCCTGAATTAAAGTATTGTGCAGTGAAGGTAGAAGCTATAGAAGATC
AGAAAGAAGCTGAAAAGTTTATAAAAGATCAATATGCTTCAATAAAGAAA
AAGATGAATGTTTAA >Gene ID No. 19:
RCCC03324 Contig0001_1234499_1232313
TATTTTGCAAAGGAGTTCATATTCATATAGGTAAACTATGCCTATTATGA
GTATGATGCTTTTATATTATCAAAATATTTTTAATTTTTATTTTATACAA
AAAATATATAAGTATATTATTACTCAAGTTATTTTTAAAGATACATAGAA
ATTTGAGTGATAATGATTTTTAGTTTCTACCGAGCCCTGAAATAAAAGGG
GTGAGAGTTATGATTACGCCTATTTATAAAAAAGAAGGAGTGGAATTATT
AATGGAAAAAAAGGTATTAACTGATGTCTTATTGCGGTGCTGGATGTC
AACTGTATCTAATTGTTAAAGATGGACAAATAGTAAGAGCAGAACCTGCT
AATGGAAGAACAAATGAAGGAACTCTTTGTCTTAAAGGACGCTATGGTTG
GGATTATCTAAATGATCCTCAACTTCTAACTCCACGTATAAAAAACCTA
TGTTAAGAAAAAATGGTAAATTAGTAGAAGTAACTTGGGATGAAGCTATT
AAGTTTACGTCAGAAAAATTAACAGAAATAAAAAATAAGTATGGTGCTGA
TTCTATAATGACTACAGGCTGTTCTAGAGGTCCTGGAAATGAGACAAATT
ATATAATGCAAAAATTTGCACGTGCTGTAATAGGTACAAACAATGTAGAT
AACTGTGCTAGAGTTTGTCATGGTCCCTCAGTAGCAGGATTAGCTACAGT
ACTTGGAAATGGTGCCATGTCAAATACTATTCCTGAAATTGAAAATGCAG
ATTTGCTTCTTATATTTGGATACAATCCAGCAGAATCTCATCCTATAGTT
GCTAGAAGAGTAGTTAAAGCAAAGGAAAAAGGAGCAAAAATTATAGTTGT
AGATCCTAGGGTCACAGATAAGTTGAGAATATCTGATCTTTGGCTTCAAT
TAAAAGGTGGACAAATATGGCACTTGTAAATGCATTTGCCAATGTACTA
CTTAATGAAAAATTTGTATAACAAAGAATATGTTGCTAATTATACTGAAAA
CTTTGAAGAATATAAATCAATTATACAAAAATATAATCCAGAATATGCAG
GGAAAATAACAAATGTTCCCTGCTGAAGACATAAAAAAAAGCCATGAGAATG
TATGCTAACGCAAAAAATCCAATGATTCTTTATGGTATGGGGGTATTAA
ATTTGGTCAAGCTGTAGATGTAGTTAAAGGTTTAGCTGGCTTAGCGTTAA
TGACAGGAAACTATGGCAGGCCTAGCGTTGGTATAGGTCCTGTAAGAGGA
CAAAATAATGTTCAGGGCGCTTGTGATATGGGTGCTATTCCTAATTGTTA
CCCTGGATATCAAAAGGTTACGGATAAAAATGTTAGAGAAAAATTTGAAA
AGGCTTGGGGAGTAAAGCTTCCTGATAAAGTGGGATATCATTTAACAGAA
GTGCCTGAGTTAGTTTTTAAAAGAAAATAAACTGAAAGCTTATTATATAAT
GGGCGAGGATTGTGTTCAAAGTGACCCAAATGCAAACGATGTAAGAAAAG
CTTTAGATAAATTTGGAACTTGTAAGTTCAAGATATATTTATGAAAA
ACAACTTTACATGCTGATGTAATACTTCCGGCTACTGCTTGGGGAGAACA
TGAAGGTGTATACAGTTCTGCTGATAGAGGTTTTCAAATATTCCGAAAAG
CTGTTGAACCAAAGGGAGATGTTAAACCAGATTGGCAGATAATTTGTGAG
TTAGCTACTGCCATGGGATCTTATGCATTATAATAATACAAAGAAAT
ATGGGATGAAATGAGAAGTCTTTCTCCAAAATTTGCTGGTGCTAGCTATG
AAAGAATGGAAAGTTAGGAGGAATAATTTGGCCTTGTCCTTCTGAAGAT
CATCCTGGAACTCCTGTGCTTTATGAAGGAAACATTTTTAGTACACCAAG
TAAAAAAGGTATTTTATTTGCTGCAGAATGGAGACCTACACAAGAATCTC
CAGATAAAGAATATCCATTAAGTTTATGTACAGTTAGAGAAATAGGTCAC
TACTCTGTAAGAACAATGACTGGTAATTGCCGTGCTCTCAAGGCACTTGA
AGATGAACCAGGTAAAATTCAAATGAGTTTGGAAGATGCTGAAGAACTTG
CTATAAATGATGGAAGCTAGTACGAAGTAAGTTCAAGAAGAGGTTCGTA
ATGTCAAGAGCTTAGTTACAGATAGAGTTCGTAAGGGTAATACTTATAT
GACTTATCAATGGTGGATTGGAGCTTGTAATGACCTTACTGTTGATAACT
TAGATCCTGTATCAAAAACACCTGAATATAAATATTGTGCAGTTAAAGTG
GAGGCAATAAAGGATCAAGATAAAGCTGAAAAATGTTTATTAGAAACATA
CAATGAATTACGTAAAAAAATGGGAGTAAAAAATATGTAG >Gene ID No. 20:
RCCC01717 Contig0001_3590430_3591623
TATAAACTTGTTCAAAGATTTGCAAAAGCTGATGCTATAGGACCTGTATG
CCAGGGATTTGCAAAACCTATAAATGATTTGTCAAGAGGATGTAACTCCG
ATGATAGTAAATGTAGTAGCTGTAACAGCAGTTCAGGCACAAGCTCAA
AAGTAATAACAAAAAGCATAAATGATTCATTTTTAGGAGGAATATTAAAC
ATGAAAATTAGTGTAAACTGTGGAAGTTCATCTTTAAAATATCAACT
TATTGATATGAAAGATGAAAGCGTTGTGGCAAAAGGACTTGTAGAAAGAA
TAGGAGCAGAAGGTTCAGTTTTAACACATAAAGTTAACGGAGAAAAGTTT
GTTACAGAGCAGCCAATGGAAGATCATAAAGTTGCTATACAATTAGTATT
AAATGCTCTTGTAGATAAAAACATGGTGTAATAAAAGATATGTCAAAA
TATCTGCTGTAGGGCATAGAGTTTTGCATGGTGGAAAAAATATGCGGCA
TCCATTCTTATTGATGACAATGTAATGAAAGCAATAGAAGAATGTATTCC
ATTAGGACCATTACATAATCCAGCTAATATAATGGGAATAGATGCTTGTA
AAAAACTAATGCCAAATACTCCAATGGTAGCAGTATTTGATACAGCATTT
CATCAGAACAATGCCAGATTATGCTTATACTTATGCAATACCTTATGATAT TABLE 1-continued Sequence Listing
Minimum set sequences ATCTGAAAAGTATGATATCAGAAAATATGGTTTTCATGGAACTTCTCATA
GATTCGTTTCAATTGAAGCAGCCAAGTTGTTAAAGAAAGATCCAAAAGAT
CTTAAGCTAATAACTTGTCATTTAGGAAATGGAGCTAGTATATGTGCAGT
AAACCAGGGAAAAGCAGTAGATACAACTATGGGACTTACTCCCCTTGCAG
GACTTGTAATGGGAACTAGATGTGGTGATATAGATCCAGCTATAATACCA
TTTGTAATGAAAAGAACAGGTATGTCTGTAGATGAAATGGATACTTTAAT
GAACAAAAGTCAGGAATACTTGGAGTATCAGGAGTAAGCAGCGATTTTA
GAGATGTAGAAGAAGCTGCAAATTCAGGAAATGATAGAGCAAAACTTGCA
TTAAATATGTATTATCACAAAGTTAAATCTTTCATAGGAGCTTATGTTGC
AGTTTTAAATGGAGCAGATGCTATAATATTTACAGCAGGACTTGGAGAA
ATTCAGCTACTAGCAGATCTGCTATATGTAAGGGATTAAGCTATTTTGGA
ATTAAAATAGATGAAGAAAAGAATAAGAAAAGGGGAGAAGCACTAGAAAT
AAGCACACCTGATTCAAAGATAAAAGTATTAGTAATTCCTACAAATGAAG
AACTTATGATAGCTAGGGATACAAAAGAAATAGTTGAAAATAAATAA >Gene ID No. 21:
RCCC01718 Contig0001_3589384_3590382
GATTAAATTTTTACTTATTTGATTTACATTGTATAATATTGAGTAAAGTA
TTGACTAGTAAAATTTTGTGATACTTTAATCTGTGAAATTTCTTAGCAAA
AGTTATATTTTTGAATAATTTTTATTGAAAAATACAACTAAAAAGGATTA
TAGTATAAGTGTGTGTAATTTTGTGTTAAATTTAAAGGGAGGAAATAAAC
ATGAAATTGATGGAAAAAATTTGGAATAAGGCAAAGGAAATGCAAAAAAA
GATTGTCTTAGCTGAAGGAGAAGAAGAAAGAACTCTTCAAGCTTGTGAAA
AATAATTAAAGAAGGTATTGCAAATTTAATCCTTGTAGGGAATGAAAAG
GTAATAGAGGAGAAGGCATCAAAATTAGGCGTAAGTTTAAATGGAGCAGA
AATAGTAGATCCAGAAACCTCGGATAAACTAAAAAAATATGCAGATGCTT
TTTATGAATTGAGAAAGAAGAAGGGAATAACACCAGAAAAAGCGGATAAA
ATAGTAAGAGATCCAATATATTTTGCTACGATGATGGTTAAGCTTGGAGA
TGCAGATGGATTGGTTTCAGGTGCAGTGCATACTACAGGTGATCTTTTGA
GACCAGGACTTCAAATAGTAAAAGACAGCTCCAGGTACATCAGTAGTTTCC
AGCACATTTATAATGGAAGTACCAAATTGTGAATATGGTAGCAATGGTGT
ACTTCTATTTGCTGATTGTGCTGTAAATCCATGCCCAGATAGTGATCAAT
TGGCTTCAATTGCAATAAGTACAGCAGAAACTGCAAAGAACTTATGTGAA
ATGGATCCAAAAGTAGCAATGCTTTCATTTTCTACTAAGGGAAGTGCAAA
ACACGAATTAGTAGATAAAGTTAGAAATGCTGTATGAAAATGCCTAAAAAAG
CTAAACCAGATTTAAGTTTGGACGGAGAATTACAATTAGATGCCTCTATC
GTAGAAAAGGTTGCAAGTTAAAGGCTCCTGAAAGTGAAGTAGCAGGAAA
AGCAAATGTACTTGTATTTCCAGATCTCCAAGCAGGAAATATAGGTTATA
AACTTGTTCAAAGATTTGCAAAAGCTGATGCTATAGGACCTGTATGCAG
GGATTTGCAAAACCTATAAATGATTTGTCAAGAGGATGTAACTCCGATGA
TATAGTAAATGTAGCTGTAACAGCAGTTCAGGCACAAGCTCAAAAGT
AA >Gene ID No. 22:
RCCC00020 Contig0001_19768_21588
GGAGAACTGTATTGCTTATTATTTAAGCATTTTATTATAAAATAAAAAAA
CGTTATTAAATTATTTACTATGAATTCACTTGATAATCAACACATTGCAT
GTAATGTTGATTATTGAGTGTTTTTTTGTAACCATATTTGGCACAATTTA
TGCTCTATAACATTTCTGAAATAAATATATGTATATGAGGAGGAATTTCA
ATGTATGGTTATAATGGTAAAGTATTAAGAATTAATTTAAAAGAAAGAAC
TTGCAAATCAGAAAATTTAGATTTAGATAAAGCTAAAAAGTTTATAGGCT
GTAGGGGACTAGGTGTTAAAACTTTATTTGATGAAATAGATCCTAAAATA
GATGCATTATCACCAGAAATAAATTTATAATTGTAACAGGTCCGTTAAC
TGGAGCTCCAGTTCCAACTAGTGGAAGGTTTATGGTAGTTACTAAAGCAC
CGCTTACAGGAACTATAGGAATTTCAAATTCGGGTGGAAAATGGGAGTA
GACTTGAAAAAAGCTGGCTGGGATATGATAATAGTAGAGGATAAGGCTGA
TTCACCAGTTTACATTGAAATAGTAGATGATAAAGTAGAAATTAAAGATG
CGTCACAGCTTTGGGGAAAAGTTACATCAGAAACTACAAAAGAGTTAGAA
AAGATACTGAGAATAGATCAAAGGTATTATGTATAGGACCTGCTGGTGA
AAGATTGTCCCTTATGGCAGCAGTTATGAATGATGTAGATAGAACTGCAG
CAAGAGGCGGCGTTGGTGCAGTTATGGGATCTAAAAACTTAAAAGCTATT
ACAGTTAAAGGAACTGGAAAAATAGCTTTAGCTGATAAAGAAAAAGTAAA
AAAAGTGTCCGTAGAAAAAATTACAACATTAAAAAATGATCCAGTAGCTG
GTCAGGGAATGCCAACTATGGCAGTACGCTATACTGGTTAATATAATAAAT
GAAAATGGAGTTCATCCTGTAAATAATTTTCAAGAATCTTATACGGATCA
AGCAGATAAATAAGTGGAGAGACTCTTACTGCTAACCAACTAGTAAGGA
AAAATCCTTGTTACAGCTGTCCTATAGGTTGTGGAAGATGGGTTAGACTA
AAAGATGGTACAGAGTGCGGAGGCCGGATGTAGAAAACTGTGGTGTTT
TGGCTCTGACTGTGGTTCATATGATTTAGATGCTATAAATGAAGCTAATA
TGTTATGTAATGAATATGGTATTGATACTATTACCTGTGGTGCAACAATT
GCTGCAGCTATGGAACTTTATCAAAGAGGATATGTAAAAGATGAAGAAAT
AGCCGGAATACTATCTCTCAAGTGGGGAGATACGGCCTGTATGATTG
GCTGGATAAAGAAAATGGTATATAGTGAAGGCTTGGAGCAAAGATGACA
AATGGTTCATATAGGCTTTGTGAAGGTTATGGAGTACCTGAGTATTCTAT
GACAGTTAAAAAACAAGAAATTCCAGCATATGATCCAAGGGGAATACAGG
GACATGGTATTACCTATGCAGTTAATAATAGAGGAGGATGTCATATTAAG
GGATATATGATTAATCCTGAAATATTAGGTTATCCGGAAAAACTTGATAG ATTTGCATTAGATGGTAAAGCAGCCTATGCCAAAATGATGCATGATTTAA
CTGCTGTAATTGATTCTTTAGGATTGTGCATATTCACTACATTTGGGCTT
GGAATACAGGATTATGTAGATATGTATAATGCAGTAGTAGGAGAATCTAC
TTGTGATTCAGATTCACTATTAGAGGCAGGAGATAGAGTATGGACTCTTG
AAAAATTATTTAATCTTGCAGCTGGAATAGACAGCAGCCAGGATACTCTA
CCAAAGAGATTGTTAGAAGAACCTATTCCAGATGGTCCATCAAAGGGACA
CGTTCATAGGCTAGATGTTCTTCTGCCAGAATATTACTCAGTACGAGGAT
GGAGTAAAGAGGGTATACCTACAGAAGAAACATTAAAGAAATTAGGATTA
GATGAATATATAGGTAAGTTCTAG >Gene ID No. 23:
RCCC01356 Contig0001_3966524_3969232
TAAAGAGCAATTATGAATAATAATAACATAGAAACAAACAATAAAAGTGA
GAATCTTGTTTATCCGATGACTACTCGCTCTAATACTCCCACTTCTGCAA
GTGGGAGTAAAGAGCGACTACGTCCCTGGATAACGATTTTTCCTAAAGGA
TAACGTCTTCTAAGTGCTGAAGCACTAAGAATACTGTTAATAAGCATCAG
GTGGAGTTAAAACTCCATCTGATGCCAAGAAATCTGTTTATATTTAACAG
CATGAAAAATAAGAAAGAGGGTGCATTAATGAAGGTAACTAAGGTAACTA
ACGTTGAAGATTAATGAAAAAGTTAGATGAAGTAACGGCTGCTCAAAAA
AAATTCTCTAGTTATAGTCAGGAACAAGTGGATGAGATCTTTAGGCAGGC
AGCTATGGCAGCCAATAGTGCTAGAATAGATCTAGCTAAAATGGCAGTGG
AAGAAAGCGGAATGGGAATTGTAGAAGACAAGGTTATTAAAAATCATTT
GTTTCAGATATATATATAACAAATATAAGGATGAAAAGACCTGTGGAGT
TTTAGAAGAAGACCAAGGTTTTGGTATGGTTAGAATTGCGGAACCTGTAG
GGGTTATAGCAGCAGTAGTTCCAACAACTAATCCAACATCCACAGCAATC
TTTAAATCTTTAATAGCTTTGAAAACTAGAAATGGTATAGTTTTTTCACC
ACATCCAAGAGCAAAAAAATCAACTATTGCAGCAGCTAAGATAGTACTTG
ATGCAGCAGTTAAAGCTGGTGCTCCTGAAGGAATTATAGGATGGATAGAT
GAACCTTCCATTGAACTCTCACAGGTGGTAATGAAAGAAGCAGATTTAAT
TCTTGCAACTGGTGGCCCGGGTATGGTTAAGGCTGCCTATTCTTCAGGAA
AGCCTGCTATAGGAGTTGGCCCAGGTAACACACCTGCTGTAATTGATGAA
AGTGCTGATATTAAAATGGCAGTAAATTCAATACTCCTTTCAAAAACTTT
TGATAATGGTATGATTTGTGCTTCAGAGCAGTCAGTAGTAGTTGTAAGCT
CAATATACGATGAAGTCAAGAAAGAATTTGCAGATAGAGGAGCGTATATA
TTAAGTAAGGATGAAACAGATAAGGTTGGAAAAACAATTATGATTAATGG
CGCTCTAAATGCTGGCATTGTAGGGCAAAGTGCTTTTAAAATAGCACAGA
TGGCAGGAGTGAGTGTACCAGAGGGATGCTAAAGTACTTATAGGAGAAGTT
AAATCAGTAGAACCTGAAGAAGAGCCCTTTGCTCATGAAAAGCTGTCTCC
AGTTTTAGCTATGTACAAAGCAAAAGATTTTGATGAAGCACTTCTAAAGG
CTGGAAGATTAGTTGAACGAGGTGGAATTGGGCATACATCTGTATTATAT
GTAAATTCAATGACGGAAAAAGTAAAAGTAGAAAAGTTCAGAGAAACTAT
GAAGACTGGTAGAACATTGATAAATATGCCTTCAGCACAAGGTGCTATAG
GAGATATATAACTTTAACTAGCTCCTTCTTTGACGCTAGGATGTGGT
TCCTGGGGAGGAAACTCTGTATCAGAAAATGTTGGACCTAAACATTTATT
AAACATAAAAGTGTTGCTGAGAGGAGAGAAAATATGCTTTGGTTTAGAG
TACCTGAAAAAGTTTATTTCAAATATGGTAGTCTTGGAGTTGCATTAAAG
GAATTGAGAACTTTGGAGAAAAAGGCATTTATAGTAACGGATAAGGT
TCTTTATCAATTAGGTTATGTAGATAAAATTACAAAAAATCTCGATGAAT
TAAGAGTTTCATATAAAATATTTACAGATGTAGAACCAGATCCAACCCTT
GCTACAGCTAAAAAAGGTGCATCAGAACTGCTTTCCTATGAACCAGATAC
AATTATAGCAGTTGGTGGTGGTTTCGGCAATGGATGCAGCCAAGATCATGT
GGGTAATGGTAGCATCCAGAAGTAAGATTTGAAGATTTGGCTATGAGA
TTTATGGATATAAGAAAGAGTATATGTTTTCCTAAGATGGGTGAAAA
AGCAATGATGATTTCAGTAGCAACATCCGCAGGAACAGGATCTGAAGTTA
CTCCATTTGCAGTAATTACGGATGATGAAAAGAACAGGAGCTAAATATCCACTG
GCTGATTATGAATTGACTCCAAACATGGCTATAATTGATGCAGAACTTAT
GATGGGAATGCCAAAAGGGCTTACAGCAGCTTCGGGTATAGATGCATTAA
CCCATGCACTGGAGGCGTATGTATCAATAATGGCTTCAGAATATACCAAT
GGATTGGCTCTTGAAGCAACAAGATTAGTATTTAAATATTTGCCAATAGC
TTATACAGAAGGTACAACTAATGTAAAAGGCAAGAGAAAAATGGCTCATG
CTTCAACTATAGCAGGTATGGCTTTTGCCAATGCATTCTTAGGGTATGT
CACTCTATGGCACATAAATTGGGAGCACAGCACCATATACCACATGGAAT
TGCCAATGCGCTTATGATAGATGAAGTTATAAAATTCAATGCTGTAGAGG
CTCCAAGGAACAAGCGGCATTTCCACAATATAAGTACCCAAATGTTAAA
AGAAGATATGCTAGAATAGCTGATTACTTAAATTTAGGAGGAAGCACAGA
TGATGAAAAGTACAATTGCTAATAAATGCTATAGATGACTTAAAAACTA
AGTTAAATATTCCAAAGACTATTAAAGAGGCAGGAGTTTCAGAAGATAAA
TTCTATCTACTTTAGCACACAATGTCAGAACTGGCTTTTGATGATCAAT
TACAGGAGCTAATCCAAGATATCCACTAATAGGAGAAATAAACAAATGT
ATATAAATGCATTTGATCACCCAAAGGCAACTGTGGAGAAGAAAACAAAA
AAGAAAAAATAA >Gene ID No. 24:
RCCC03300 Contig0001_1213196_1212027
TGTAAAATAAAATCAGAAATTAGTTAAATATTTAAAATAAAATAAAAATT
TATACAATGATGTATGAAAAAGCGATGAAGCTTCTAAAAGAATATTTATA
TTCTTAGGAAGCTTTTTTTATTTTATTGGTAGCTATCAAAAAATTACAAA TABLE 1-continued Sequence Listing
Minimum set sequences ATTTAATATGACTAATGTGAAGTTTCATAGATATTTTATTAAATTGGAGT
ATGATTATTGTGAAAAATTTTAATGTTAAACCAAAGGTTTATTTTGGTAC
TGATGCTTTAAATCATTTGTGTGAATTAAAATGTAAGAAAGCTTTAATCG
CTGCAGATCCATTTATGGTTAAGTCATCAACGGTTGATAAAATTACTGAA
CAGCTTGATAAGGCACATATAGAGTATGATATATTTTCAGATATAGTACC
AGATCCTCCTGTTGAAGTTATTATAAAAGGAGTGCAGGAAGCTGTTAAAT
TTAAACCTGATGTACTTATAGCACTTGGAGGAGGATCAGCTATTGATTCT
GCAAAAGGAATAAGGTATTTTTGTCAGTATGTAAATAATGAATTGAATAA
CGAAATGAAAGAGCCCCTGTTTATAGCAATTCCGACAACAAGTGGTACAG
GCTCTGAGGTTACTAACTTTTGTATTGTAACTGATAAGCAAAAAGGAGTC
AAATATGCTCTTGTTGATGACAATTTGACGCCGGATCAGGCGGTACTTGA
TATTGAACTTGTAAATCAGTGCCAAAAGCTACCACATCAGAAACAGGAA
TAGACGTACTTACACATGGAATTGAAGCATATGTTTCTACAAATAGATCA
GATTATTCTGATGCACTGGCAGAAAAATCAATAAAAATGGTATTTAAATA
CTTGTTAGCCGCATATGAAAATGGAGATGATGAAGAAGCTAGAACGAAGA
TGCATAATGCATCCTGCATAGCAGGTATGGCATTTACAAATGCTTCCCTT
GGACTTAACCATGGCATGGCTCATGCACTTGGTGAAAAATTCATATACC
GCATGGAAGAGCAAATGGCTACTTCTTCCATACGTAATAGAGTATAATG
CAAACCTTAAAAACTTACAAGGAAAGATAAACCATTCTAGTGCAGCATAT
AGGTATACTGAAATATCAAAATTCTTGGGACTTCCAGCATCTAACCAATT
TGAAGGTGTTAGGAGTTTGATTGCAGCAGTTAAGATACTGATGAATAAAC
TTAACTTACCTAAATGTATTAATAAATTGTGAAGTTTTATGTGAAAATTTG
GATAATGAGATTCATGAGTTATCGATAACTGCCCTAAATGATAGATGTAC
AAAAACAAATCCGAGAATTCCTGAAATAAAGGATGTTGAAAATTTGTTTA
AGAGGGTTTTTTCTAAAGAATAA >Gene ID No. 25:
RCCC01567 Contig0001_3730455_3731297
CATAAAAGAAGAGCATGCAATTAGTTTTAAATTATTAGATAGTGTAAAGC
GTTATAAACAATTTCTTGATACATACCCTGATTTGGAAGAACGTGTTAAG
CAGTGTTATATTGCATCCTATTTAGGAATAACTCCTGTGTCTCTTAGCAG
AATAAGAAGAAAATTAAATCTTAACAAATGATAATGCAATAAATCTCTAG
GTGATTTATGATGTAGTTAATTTTTATTACTGGAGGTTAATTGTTATGAA
AAATGAAATAGTTGTTTAATTACTGGATGTTCTACAGGGATTGGAAGAG
AGCTTTGTAGTATATTGTTTCACAAAGGATGTACGGTTGTTGCAACAGCA
AGAAATGTAGAAACTTTAAAAGATTTATCTGCGTCCTTAAGATTACCACT
GGATGTTACCCAAAAGAGTCTATTAACGATACAATAAATGAGTTGTAT
CAAAATTTCATAAAATTGATATTCTTATAAATAACGCAGGCTATTCAATT
AGAGGAGCTTTAGAAGAAATTGATTTAAATAGTGCTAAAAGTATGTTTGA
TGTAAATGTATTTGGTATTATTAACATGATTCAGGCAGTTATTCCAGAAA
TGCGTAAAAAACAATTTGGTAAGATTATAAATATTGGCTCCATTTCAGGG
AAATTTGTTCAATCCATCAATGGAGCGTATTGTGCATCAAAATTTGCAGT
TGAGGCACTAAGTGACACACTTCGTTTAGAATTACACAGCTACAATATTC
AGAGCACCGTCATTGAGCCAGGTCCCATGAAAACCAACTTTTTTAAGGCA
TTAGTGGATAATTCAGGCGATGTTATAAAAATGAAAATTCTTGTTATTC
ACATTTTTATAAATCAGATGATGAATATAGAAAAAGCAAAAACAAGCTG
ATCCTAAAGTAGCAGCACAAGCTATTAGTAGTATAATTTTGAAAAAACGA
CTTAATGCTCGTTATAAAGTTGCTGTTCCATTTACATATAAGATGGTTAC
ATATTTTCCTGATTTTCTAAGAATACTTTATGAAAAAAGATAG >Gene ID No. 26:
RCCC02765 Contig0001_686363_687232
TAGTTGATATATAACTTTTTAGTCGTACAAATACGAAATATATTTTATCA
TACTTGCATGTAAAATGCTATACAGCTTATACTTCTAAAGTTTGTTTATA
TTAGTTCACAGGGTTTCAAAATTGTAGTTTATAATCACATATATTTTCG
AAATTCATATATTAAATAGAAGTACTTTACAATATTGGAGGAACTACTAT
ATGTGTTCAAATCATATTGGATGCAAATTTCCACGCTTTTTTCCACCCCA
ACATCAGCCACATCAACCTGGTATTGAATATATTATGACACCTAGACCAG
TTTTCGAACCACCATTATGTGCAACAATATCAAACGACAAAAAGATTATTA
AACAAAGTAGCTTTAATAACAGGAGGAGACAGCGGTATTGGGCGTGCTGT
AGCATGTGCTTATCAAAGAAGGAGCTGATATTGCCATTGTCTATCTAA
ATGAACATGTAGATGCAGAGGGAACAAAATCTAGAATAAAAAAATTGGGG
CGAAGATGTTTAACCATTCCAATTAACATAGGAGTCGAAGAGAATAGTAA
AATTATAATTCAAGAAGTTATGAATCATTTTGGTAAATTAGATATTCTTG
TAAATAATGCTGCAGTACTTTATTACAATAATTCTATAGAAGAAGTATCT
AGCAAACAATTAGAATGGACTTTTCGTATAAATGTATTTTCTTATTTCTA
CTTAACTAAAGCAGCTCTACCTTATATGAAACCAGGCGGTTCTATCATCA
ATACTTCTTCAATAGTTGCTTTTAAATCCTCCTTATGGGATATCTTTAGAT
TATGAAGCTTCAAAAGGTGCCATTGCTAATTTCACTATAAATTTAGCCCG
AAGTTTGGTTTCAAGAGGAATACGTGTAAATGGTGTAGCTCCAGGTGAAA
CCTGGACACCCTTTAATTCCAGCAGGATTACCTGCAGATAAAGTTGCCGTT
TGGGGTTCAAAAACACCAATGGGAAGAGCTGCTCAACCATTTGAAATTGC
TCCAGCCTATGTATTCTTAGCTTCCAATGAATCAAGCTATATGTCAGGAC
AAACAATCCATATGTATTCTTAA >Gene ID No. 27:
RCCC03290 Contig0001_1203895_1202426
GAGTAAAAGTTGATGAGGAGAGAAAATCAGGGTCACTTCTCGAAATAAAA
CAAAAACTTGAAAGAATGAAAGTTATTGAACTCAGAAATATGGCTAGAAA
AATGAATTTAAGTTCATTGACTAAGAAGGACATTAAATTTGGCAAGAAAA
AGCAGCTGATTAAAGCAATTTTAGAGTACTATACAAGGAGGTTAAAGTAA
ATGGAAATATAGATAGGGATTTACAATCTATACAAGATGTAAGGCGGCT
TGTTGAAAAGGCAAGACAAGCTCAACAAGAATATTGTAAATTCAGTCAGG
AAAAGATGAATAAAATTATTGAGCATGTAGCGGAATCTGCTGGCTTACAA
GCTGAAAGATTAGCAAACTTGCTGTAGAAGAAACAACTTTTGGAAATTT
ACCTGATAAGATAATTAAAAATAAGTTTGCTAGTGAAATAGTGTATGAAA
ATATAAAGGACATGAAGTTAGTAGGTATTTTAAGAGATGACAAAGATAGA
AAAGTATTAGAGATAGGTTCACCTGTAGGTATTATTGCAGGGCTTGTACC
ATCAACTAATCCTACTTCTACTGTTATATATAAAAGTCTTATAGCTTTAA
AATCGGGAAATGCAATTGTATTTAGTCCTCATCCAAAGGCAAGACATTGC
ATTGCAGAAGCTATAAAGGTTGTAAGTGATGCAGCTGTTGAGGCAGGAGC
ACCTTTAGGAATGGTTTCCGGAATGAGTATACTTACTATGGAAGGAACTC
ATGAGCTTTATGAAAAACGTTGATCTCATCATAGCAACAGGTGGATCAGCT
ATGGTAAAGGCAGCATACAGTTCAGGAACTCCGGCTATAGGAGTTGGACC
TGGAAATGGACCTGCTTTTATTGAAAAAACAGCAAATATAAAACTTGCAG
TAAAAAGAATAATGGATAGTAAACATTTTGACAATGGGGTAATATGTGCT
TCAGAACAGTCCATAGTAGTTGAAAAATGTATAAAAGATGAAGTTGTAGA
TGAGCTTAAACGCCAAGGAGCATACTTCTTATCTAAAGAACAATCAGAAA
AAGTAGCAAAGTTTATATTGAGAGCAAATGGTACTATGAATCCTCAAATT
GTAGGAAAATCAGCTCAGAAAATAGCTGAAATGGCAGGTATAACTGTAGA
TCCAAATGCAAGAATATTGATTTCAGAGCAGACGACAGTTGGAAAAGATA
ACCCATTTTCAAGGGAAAAAGCTTACAACGATTTTAGCATTCACTGTGAA
GAAAATTGGGAAAAAGCTTGCGAGAGATGCATTGAGCTTTTAAATAATGA
AGGTATAGGACATACTCTCATAATACATTCAAATAATGAAGAAAATAGTAA
AAGAATTTGGACTTAAAAAACCTGTATCCAGAATACTTGTAAACACGCCA
GGATCACTTGGAGGAATAGGAGCTACTACAAATCTAGTGCCTGCACTTAC
ACTTGGATGCGGAGCAGTTGGAGGAAGTGCAACTTCTGATAATGTAGGAC
CTAGGAATCTTATAAATATAAGAAGAGTTGCCTATGGAGTAAAGGAAATA
GAAGATATAAAAAATTTTGTAAGTAATTGTAGTGACAGAGAAACCTCACA
CACTGTTTTGGATATTTCTGATCAGTACATTGAACTTATAACTAAAAAAAA
TAGCTGAAAAGCTTAGTTTGTAA >Gene ID No. 28:
RCCC04101 Contig0001_2040462_2038897
ATGGTTTAGAAAAAGCTATTGAGATTTTAAGTAAGTTTAAGGTAATAGAG
CTTCGAAATCTCGCTCGTAAATATAAGAACTTTGGTATCAAAGGAAGGTC
CATTTCTAAAGCAGACAAGAAGTTGCTGCTTATAGAGTTCAAAAAATATT
ATGGGCATAATTAGCCAGCTATAAAAATTAAAATATAAATAATAAACA
ATGGAGGGAACACAATTGGAAAATTTTGATAAAGACTTACGCTCTATACA
AGAAGCAAGAGATCTTGCACGTTTAGGAAAAATTGCAGCATGTGAAATTG
CTGATTATACTGAAGAACAAATTGATAAAATCCTATGTAATATGTTAGG
GTAGCAGAGGAAAATGCAGTTTGCCTTGGTAAAATGGCTGCAGAAGAAAC
TGGTTTTGGAAAAGCTGAAGATAAGGCTTATAAGAACCATATGGCTGCTA
CTACAGTATATAATTATATCAAGGATATGAAGACTATTGGTGTTATAAAA
GAAGATAAAGTCAAGGTGTAATTGAATTTGCTGAACCAGTTGGTTTATT
AATGGGTATTGTACCATCTACAAATCCAACATCTACTGTTATCTATAAAT
CAATCATTGCAATTAAATCAAGAAATGCAATTGTATTCTCACCACACCCA
GCTGCATTAAAATGTTCAACAAAAGCAATAGAACTTATGCGTGATGCAGC
AGTAGCAGCAGGAGCTCCTGCAAATGTAATTGGCGGTATTGTTACACCAT
CTATACAAGCTACAAATGAACTTATGAAAGCTAAAGAAGTTGCTATGATA
ATTGCCACTGGAGGCCCTGGAATGGTAAAGGCTGCTTATAGTTCAGGAAC
ACCTGCAATAGGCGTTGGTGCTGGTAACTCTCCATCTTATATAGAAAGAA
CTGCTGATGTTCATCAATCAGTTAAAGATATAATTGCTAGTAAGAGTTTT
GACTATGGTACTATTTGTGCATCTGAGCAATCAATAATTGTTGAAGATATG
CAACCATGATGAAGTAATAGCTGAGTTGAAGAAACAAGGCGGATATTTCA
TGACAGCTGAAGAACTGCAAAAGTTTGCAGTATACTTTTTAAGCCTGGT
ACACACAGTATGAGTGCTAAGTTTGTAGGAAGAGCTCCTCAGGTTATAGC
AGCAGCTGCAGGTTTTCTCAGTTCCAGAAGGAAACAAAAGTTTTAGTAGGAG
AACAAGGCGGAGTTGGTAATGTTACCCTCTATCTTATGAGAAACTTACA
ACAGTACTTGCTTTCTATACAGTTAAAGATTGGCATGAAGCATGTGATCT
TAGTATAAGATTACTTCAAAATGGTCTTGGACATACTATGAACATTCATA
CAAATGACAGAGACCTTAGTAATGAAGTTTGCTAAAAAACCAGCATCCGT
CTATATTAGTTAATACTGGTGGAAGCCAAGGAGGTACTGGTCAAGCACAGG
ATTAGCACCTGCATTTACATTAGGTTGTGGTACATGGGAGGAAGCTCTG
TTTCCGAAAATGTTACTCCATTACATTTAATCAATATAAAGAGAGTTGCA
TATGGTCTTAAAGATTGTTCTACATTAGCTGCAGATAGACAACCTGTTTAT
TCATCCTGAACTTTGTGGAAGCAAAAATGACTTAGGATGCTGTGCTACAA
GCCCTGCAGAATTTGCAGCAAATAGCAATTGTGCTAGCACTGCTGCGGAT
ACTACTGATAATGATAAACTTGCTAGACTCGTAAGTGAATTAGTAGCTGC
AATGAAGGGAGCTAACTAA TABLE 1-continued Sequence Listing
Minimum set sequences >Gene ID No. 29:
RCCC04114 Contig0001_2051568_2050075
AAGCTGTAACAGATATGGGCGCTGAAGTTTATAGTTCAGTTGTTATTGCA
AGTCCACATCCGGATCTTCAGAAAATCACCAAACGTTATACAATTGAAAA
TTTACTTCCTTAATATGTGGATGATATGATACCACCACATAATAATAAA
AGTACAGAAGTACAGTACTTAGTTAGTAAAAATGAAAGGGAGAGTTAGAA
ATGAATATTATTGATAATGATTTGCTCTCCATCCAAGAATCCCGAATCCT
TGTGGAAATGCTGCACGAGCACAAAAAATGTTAGCAACTTTTCCGCAAG
AAAAGTTAGATGAGATTGTTGAACGTATGGCTGAAGAAATCGGAAAACAT
ACCCGAGAGCTTGCTGTAATGTCACAGGATGAAACTGGTTATGGAAATG
GCAGGATAAATGCATCAAAAACCGATTTGCCTGTGAATATTTGCCAGCTA
AGCTTAGAGGAATGCGATGTGTAGGTATTATTAACGAAATGGTCAGGAT
AAGACCATGGATGTAGGTGTACCTATGGGTGTAATTATTGCATTATGTCC
TGCAACTAGTCCGGTTTCTACTACCATATATAAGGCATTAATTGCAATTA
AGTCTGGTAATGCAATTATCTTTTCTCCACATCCTAGAGCAAAGGAGACA
ATTTGTAAGGCGCTTGACATCATGATTCGTGCAGCTGAAGGATATGGGCT
GCCAGAAGGAGCTCTTGCATACTTACATACTGTGACGCCTAGTGGAACAA
TCGAATTGATGAACCATGAGGCGACTTCTTTGATTATGAATACAGGCGTT
CCCGGGATGCTTAAAGCGTCATATAGATCTGGAAAACCTGTGATCTATGG
AGGAACTGGTAATGGACCAGCATTTATTGAACGTACAGCTGACATCAAGC
AGGCGGTAAGAGATATTATTGCTAGTAAGACCTTTGATAACGGAATAGTA
CCATCATCTGAACATCTATTGTTGTAGATAGCTGTGTTGCATCTGATGT
TAAACGTGAGTTGCAAAATAGTGGTGCATATTTCATGACAGAGGAGGAAG
CACAAAAACTGGGTTCTCTCTTTTTCCGTTCTGATGGTAGTATGGATTCA
GAAATGGTTGGCAAATCCGCACAGAGATTGGCTAAGAAAGCAGGTTTCAG
TATTCCTGAAAGTAGCACAGGTCTAATTTCAGAGCAGAAATATGTTTCCT
AAGATAATCCTTATTCCAAGGAGAAACTTTGTCCGGTACTAGCTTACTAC
ATTGAAGATGATTGGATGCATGCATGTGAAAAGTGTATTGAGCTGCTATT
AAGTGAGAGACATGGTCACACTCTTGTTATACATTCAAAAGACGAAGATG
TAATTCGCCAGTTTGCATTAAAAAAACCTGTAGGCAGGATATGTTGTTAAT
ACGCCTGCTTCCTTTGGTAGTATGGGTGCTACAAGTAATTTATTTCCTGC
TTTAACTTTAGGTAGTGGATCGGCAGGTAAAGGTATTACCTCCGATAATG
TTTCACCAATGAATCTTATTTACGTCCGTAAAGTCGGATATGGCGTACGG
AATGTAGAAGAGATTATTAATACTAATGGATTGTTTACAGAAGAAAAAAG
TGATTTGAGTGGTATGACAAAGCAGTCAGACTATAATCCAGAGGATATAC
AAATGTTGCAGCATATTTTGAAAAAAGCTATGGAAAAAATTAAATAG >Gene ID No. 30:
RCCC00038 Contig0001_43778_45121
AAATGAATATTTATTGCTGCAGTACTATATTCCACTGGTTGAATAGTGTA
CTTAAATGCTCCTTTAGGTTTAGCAAAAATTTGTGATTATTATCCTTTAG
ATAAGGAAAGTATATTAGTTATTAGAAGCTATTGAATTAGAGAAAATTAA
TTGTAATGAGCAAGTTTTTGATGAACGGTTAAGGAGAGTATGTAGTGTAAA
TTGAGAGATGATTATAGGAATCTATTTAAATTCATAATAAAGGCATATTA
TAGTGGAAACTTTGAAGAAGAAGTGATGTCATTTTTATTAGAGTCTAAAA
TGGATAAACAGGAATTGTGTAAGATTATATCTACATTGTGCGGTACTAAT
GTAGATTACAGCTCTAACTTTATAGAAAATTTAAAAAAAGCAAGAAAGTC
TTATAAACAAGATGGTAAAGTAGTCAATAAAGTTAAAGACTGTTCCATGG
AATGTGTGGATGAAAAAGGTGAGATACTATGTCAAAAAACATGTCCTTTT
GATGCAATTTTTATAGACAATAAGAAAAATTGTGCTTACATAGATAAAGA
AAAGTGTACCGATTGTGGTTTGTGTGTAGATGTTTGCCCTACTGGGGGAA
TAATGGATAAAGTTCAGTTCATTCCTATTTTGGATATTTTAAAAAGTAAA
TCTCCAGTTGTGGCTATAGTGGCTCCTGCCATAATAGGACAGTTTGGGGA
AGATGTTACTATGGATCAACTTAGGACCGCTTTTAAAAAACTGGGATTTA
CTGATATGATTGAAGCTGCATTTTTTGCAGATATGCTTACTTTAAATGAA
TCTATTGAATTTGACAATCATGTAAAAGATGAAAAAGATTTTATGATAAC
TTCCTGCTGTTGTCCTATGTGGGTGGCTATGGTAAAAAAGGTATACAGTA
ACTTGGTTAAACATGTATCTCCCTCTGTATCTCCGATGGTTGCAGGAGGA
AGAGTACTTAAAAAGTTAAGTCCTTACTGCAAGGTAGTGTTTATAGGCCC
ATGTATTGCTAAAAAATCTGAGGCAAAGGAAGAAGGAAATGAGAAAAACA
TAGATTTTGTACTTACTTTTGAAGAATTAAGAGATATATTTGATGCTTTT
CATATAGTTCCATCTAAACTTGAAGGAGATTTTCATCTAAATATGCTTC
TAGAGGTGGAAGATTATATGCCCGTACAGGTGGAGTTTCTATTGCAGTAA
GCGAAGCTGTGGAAAAGATTTTTCTGAAAAGCAAAATCTTTAGTTAGTGCA
ATTCAGGCAAATGGCATTAGAGAATGTAAAGAAATGCTTACCAAGGTGCA
AAATGGAGAAATAAAAGCTAATTTTATTGAAGGAATGGGCTGTATTGGTG
GATGTGTAGGTGGTCCCAAAGCAATTGCATCTAAGGATGAAGGTAGGGAT
CGAGTAAATAAATTTGCACAAGATTCTGAAAAGCAAAAGTTGCTGTAGATAG
TGAATGTATGCATGGAGTATTACATGCTTTGGATATACATTCTATAGATG
ATTTTAAGGATGAGAAAAAATAGAACTGTTAGAACGAGAATTTTAA >Gene ID No. 31:
RCCC00878 Contig0001_3079817_3080311
ATAATTAGTTCTTAATTAAATAGGACTAAATTTATATTTAATTTTTAAA
TAAGGTAATTAAAATAATTTTAAATTAAATATGTTATATGTTTTAAAATT
ATTTCTTAAGCATAGAGGCTCAAATCTTTGATTTAGAGCTAATACTTTAT
TCCTTCTAATATTTTAAGGGGAAATCAATTATAAATATTCAAATGGGAGG
GTGAAGTATTTAATGTTAACTAAACAGCAAAATGAAGACCTGTCTGGACA
AGATGTAATTGAAAAATATCCTAAAGAGCAGAGATTTACTCTTGCTATAC
TACAGGATATACAGAGAAAGTACAAATATATACCCAGAGAAGCACTGGAG
AATTTAGCTAAGTATTTGGACACGCCTGTAAGTAGACTGTATGGTATGGC
TACTTTTTTATAAGGCATTGAGCCTTACTCCAAAAGGGGAAAACATAATAA
CTGTATGTGATGGAACCGCTTGCCATGTTGCTGGTTCTATGGTTGTAATG
GATGAACTTGAAAAGGCAATAGGAATTAAACCAGGTGAAACTACAGAAGA
TCTTAAATTTTCAATAAATACAGTTAACTGTATAGGATGCTGTGCAATAG
CTCCTGTCATGATGATAAATGACAAATATTTTGGAAATTTAACACCTAAA
CTGGTTGAAGAAATTCTTAGTGAGTATAGGAGTGAAAGCCATGAGTGA >Gene ID No. 32:
RCCC00879 Contig0001_3080271_3082103
TTGAAGAAATTCTTAGTGAGTATAGGAGTGAAAGCCATGAGTGATAAAAA
AATTGTCAATATATGTTGTGGAACAGGTTGCTTAGCTAAAGGCAGCAAGG
AAGTATATGAAGAAATGAAGGCACAAATAGCTAAATTAGGGGCAAATGCA
GAAGTAAATGTTAAATTAAAAGCAACAGGTTGCGATGGATTGTGTGAGAA
AGGTCCTGCTACTGAAAATATATCCAGATGACATTGCTATATTTTAAAGTTA
AAGTAGAAGATGTAGAAGACGTAGTAAAAAGACAATTGATGAATGGGGAA
ATAATTGAAAAATTATTATATTTTGAAACTGCTACAAAACAGAGATTAAG
AAATCATAAAGAAAGTGAATTTTGTAAAAGACAATACAAAATTGCTCTCA
GAAATGTTTGGTGAAATAGATCCAATAAGTTTGGAAGATTATGTTGAAAGA
GGCGGATATAAAGCTCTTAAAAAAGCAATAAGCAGCATGAAACCTGAAGA
TGTGCTTGAAGAAATAACAAAATCAGGTCTTAGAGGAAGAGGTGGAGCAG
GATTCCCAACAGGACGTAAATGGAAAACTGCTGCAGATATTGATACATCA
CCTATATATGTAGTAGCAATGGTGATGAGGGAGATCCTGGAGCATTTAT
GGATAGAAGTATAATGGAGGGAGATCCTAACAGTGTTATAGAAGGTATGA
CATTGTGTGCCTATGCAGTAGGAGGTACAAACGGCTTTGCTTATATAAGA
GATGAATATGGACTTGCTGTAGAAAATATGCAGAAAGCTATTAATAAAGC
AAAAGATGAAATATTTAGGTAATATATTAGGAACTGACTTTTCCT
TCGATATACAGATAGTAAGAGGTGGAGGAGTCTTTTGTATGTGGTGAGTCT
ACTGCACTTATGTCATCTATAGAAGGTATGGTAGGAGAACCTAGAGCTAA
ATATATACACACTACAGAAAAAGGATTGTGGGGACAACCTACTGTTTTAA
ATAATGTAGAAACTTGGGCCAATGTACCTATAATAATTGAAAAAGGTGGA
GATTGGTATCATGCTATAGGAACTATGGAGAAGATAAGGGAACAAAAGT
ATTCTCATTAGTTGGAAAAGTTAAGAATACTGGACTTGTAGAAGTACCTA
TGGGAACTACTCTTAGAGAAATAATATATGATATTGGCGGTGGAGTATTA
AACGACAGAAAGTTTAAGGCAGTTCAAATAGGTGGACCTTCAGGAGGATG
TTTACCATCTGAATATTTAGACTTTGCAGTAGATTATGATACTTTGGTTA
AAGCGGATTCTATGATGGGTTCCGGCGGAATGATCGTAATGGATGATAGA
ACCTGTATGGTAGATGTAACTAGATATTACTTGAGTTTCTTAGCTGAAGA
ATCTTGTGGAAAGTGTGTACCTTGTAGAGAAGGCGTAAAGAGAATGCTTG
AAATACTCACTGATATGTCAATGGTGATGAAAAGAAGGAGACATAGAA
GAGCTTCTTGAAATATGTTCCATGACAAGCAAGGCATCTCTGTGCAGTCT
TGGTAAGAGTGCTCCAAATCCAGTAAAAGCAGCTATAAGATATTTTAGAG
ATGAATTTGAAGAACATATAAAGAATAAGAGATGTAGAGCAGGAGTTTGT
AAGAAACTTACTACATTTGGTATAGCATCAAGATAAATGTAAGGGATGCGA
TATGTGTAAAAGAATTGTCCAGCTGATTGTATAACAGGGGAAATTAAGA
AACCACATCAATAGATGTCCGATAAGTGCTTGAGATGCGGGTAACTCATG
AACATCTGTAAGTTTGATGCTGTTAAGGTTTTATAG >Gene ID No. 33:
RCCC00880 Contig0001_3082084_3082875
TTGATGCTGTTAAGGTTTTATAGGGAGGTGAATGTAGATATGAAAATTAC
AATAGATGAAAGCTTGTGAAGCTTACTGAAGGAGAATTCATATTACAAA
TAGCAAGAAGAAATAATATATATATACCTACACTGTGCCACAGTGATGCA
TTGCCTGGGCTTGCTAGCTGTAGACTGTGTATAGTTAAAGTAGTAGATAG
GGGACGTGCAAAGATAGTAACTTCCTGTATATTCCCTGTAAGTAAGGAAG
TAGAAGTTATAACTAATGACGATGAAATAAAGAGAATGAGAAAAAACATA
GTTATCGTTTAAAAGTAAGATGCCCTGAAAAATAAAGAAGTAAATGAATT
AGCTAAAGCCTTTGGAGTAGAGGAAAAGAGAGTAAAGAGGTTCAAATTGG
ATCCAGAACAAAATTGTGTTTTGTGCGGACTTTGTCAAAAGCTTGCAAG
GAATTAGGTACTGGAGCAATCTCAACAGTTAATAGGGGTATGTATAAAGA
AGTAGCAACTCCATATCCAACTTCTCACCAGATGTATAGGATGTGCTT
CCTGTGCAAATGTTTGTCCAACTAATGCAATAAAAGTTGTGGATAAAGAT
GGAGAAAGAGAATATGGGCAAAAATTCAAGATGGTTAAATGTGATTT
GTGCGGAGAATATTTCTACAGAAGAACACGTAAAATATGCTTACAATA
GGCTTGGAAAAGAGCAGCCAGAAAAGCTTATGTGCAGCAGCTGCAAGAAG
AAAGTTACAGCCAAAGATGTCAAAAATATTTTTGAGAACGTGTGA >Gene ID No. 34:
RCCC00881 Contig0001_3082905_3083456
ATGAAAACAGAGTTTAATTCTTTTGTAATAGCCGATCCTGACAAGTGCAT
AGGCTGTAGATCTTGTGAGATTGCCTGTGCTGCAAAACATAGAGAAGATA
CTCAAGGAAAAACTATTGGAACTATGAATAATAAAGTTACTCCAAGGTTA
TTCTTTGTTAAAAATAAAGGAAATGTAATGCCGGTACAATGCAGACATTG
TGAGGATGCACCATGTCTAAATGCCTGCCCAGTTAATGCTATAGTTGAAA TABLE 1-continued Sequence Listing
Minimum set sequences AAGATGGAAGTATCATTATAAATGAAAGTGCATGTATAGGGTGTCAGACC
TGTACAATAGTATGTCCGGTAGGTGCTGTAAGTTTACTTCCTAGAACTCA
AGGTAAAGTAGTTACAGGAGGAATTCAGGTTAAAGTAAGAGCAGCAGCTT
ATAAATGTGATTTATGTAAGGAAGAGGGAGGAGAACCTGCCTGCGTCAAA
GAATGTCCAAAAGAGGCCTTAAGGTTAGTAGATCCTAGAGAAGATAAAAA
AGATCGTAGTGTGAAAGCTGCTATGGAACTGTTAAATATAAACGCAAATC
TCTAA >Gene ID No. 35:
RCCC00882 Contig0001_3083493_3084479
ATGTTAAATATGCCAACTAGTACTTCTATGATAAATATAGATGAAGAATT
ATGTACAGGCTGCAGACGATGTGCGGATGTCTGCCCTGTAGATGCTATAG
AAGGTGAACAGGGTAAACCTCAGAAGATAAATACTGAAAAGTGTGTTATG
TGCGGACAATGCATTCAAGTTTGTAAAGGCTATCAATCTGTATACGATGA
TATTCCTACTCCAGTTAGCAAAAGGTTATTTGATAGAGGATTGTTAAAGG
AAGTAGATGAACCATTATTTGCAGCATATAATAAAGGTCAGGCAAAGAGA
GTTAAAGAAATTTTACAAAACAAAGATGTATTTAAAATTGTGCAATGTGC
ACCTGCTGTAAGAGTTGCTATAGGAGAGGATTTTGGAATGCCTCTTGGAA
CTTTAAGTGAAGGAAAAATGGCAGCTGCACTCAGAGAATTAGGATTTGAC
AAAGTATATGATACAAACTTTGGTGCAGATCTTACTATAATGGAAGAAGG
TAGTGAGTTACTAAAAAGAGTAGCTGAAGGTGGAGTTTTGCCAATGTTTA
CTTCTTGTTGTCCAGCATGGGTAAAATATGCAGAACAAACATATCCAGAA
CTTTTACCTCATCTTTCAAGTTGTAAGTCTCCAAATCAGATGGCTGGAGC
TATATTTAAAACTTATGGAGCAGAGATAAATAAGGTTAATCCGGCTAAAA
TTTATAATGTATCTGTTATGCCATGTACATGCAAGGAATTTGAAAGTGAA
AGAGAAGAAATGCATGACAGTGGACACAGAGATGTAGATGCAGTTATAAC
TACAAGGGAATTAGCACAACTGTTCAAAGATGCTAATATAGATTTTAATA
CTATTGAAGAAGAACAGTTTGATACTCCTCTTGGTATGTATACTGGTGCA
GGAACTATATTTGGTGCTACAGGTGGAGTTATGGAAGCAGCACTTAGAAC
TGGATATGAACTTTATACTAAAAAACTATTCCAAGTATAG >Gene ID No. 36:
RCCC00884 Contig0001_3084843_3085457
ATGAATTATTGCACACTAAATATATCTCAAGAAAAAAGGAGAGTTAATAA
AATGAAGAATTGCCTCGTAGTAGCAGATGCTAATAAATGCATAGGAGTA
GGACTTGTGAAGCAGCTTGTGGTATTGCACATTCAGGAGGGGACTTTTTT
AATACAAATGTATCCAAAATTAATTTTAATCCTCGCTTAAATGTGATAAA
AACTGCTAAAGTAAGTGCTCCTGTTCAATGCAGACAATGCGAAGATGCAC
CTTGTGGTAAAGCTTGTCCAGTTAACGCTATTTCAATAGAGAGTGGTTAT
GTTAGTGTAGATAAAGATGTATGTGTTGGATGTAAAATCTGCATGTTAGC
TTGTCCTTTTGGAGCTATTGAATTAGCTTCTCAATATAAGGATGGAGAAG
TTGTAGACCAAAAGGGACTTAAGATGAGTGAGGAAGGTAATCCTACTGTA
AATGGAAAAGGAAGAGTGGTAGCAAATAAGTGTGATCTTTGCCAGGATAG
GGATGGAGGACCTGCTTGCATAGAAGTTTGTCCTACAAAATCTCTCAAAT
TAGTTACTTATGATGACAATAATAATAGTTGAAAAAAAAGATGACGAC
GAACGTGAAGTAGGCTAA >Gene ID No. 37:
RCCC01502 Contig0001_3809248_3808769
CTATATGTATCCATAAAAATTTTCCTCCATTAGTCAATATATTGTCTAAT
TATAGTTTAATGATATTTTTATATTTGTCAATACATTGTCTATTATTTT
ATCCGATGACTATATAATAAAAAACTCCCATACTACCAATACTATCTTAA
GAATATAAAATGAAAGATGGTGAAAAAACTGCGGCACAGCAGGAAATATT
ATGGATGTATGCAAATTAGATAACGAAAAACTAAAAGAACTATCTTCCTA
TATAGATAGTTTGGAGAAAAAGAAGGTTCACTTATAAGTGTACTTCACA
GAGCTCAGGATATATTTGGATACCTTCCTGAAGAATTACAAACATTTATT
GCAAATAAACTTGACATTAGTGCAGCAAAAGTATTTGGCGTAGTTACTTT
CTATTCATACTTTACAATGAAGCCCAAGGTAAACATGTAATAAGCATAT
GCATGGGTACAGCTTGTTTGTTAAGGGTGCAGAAAACATTTTAGAAGAA
TTTAGGAATCAGCTTAAAGTAAAAGATGGATTTACCACAGAAGACGGATT
GTTCACTATAGATATTTAAGATGTGTTGGAGCTTGCGGCCTTGCACCAG
TAGTTGTAGTTGACGGAACAGTCCATGGAAAAGTAAAGGTCGAAGATGTT
AAAGGAATATTAAGTCAATATACCTTAAAATAA >Gene ID No. 38:
RCCC01503 Contig0001_3808736_3806859
ATGGATAAGATAAAATCCTTTGAAGATTTAAAAGCTTTAAGAGAAAAGTA
TAAAGCTAAGATAGCAAACGCTACTTATGATAATGCAGATAAAAATATAA
AAAAAACTTACTTGTATGCGGTGGAACAGGATGTCGTGCTTCAAGAAGC
TTAGATAGTCAATATACTTAAAACTGAAATTAAAAACGCAGGTCTAGA
AAATACAGTTGATGTCATTTCTACAGGATGTTTTGGATTTGTGAGAAAG
GACCTATCGTCAAAGTTGTACTGAATAATATTTTATGTGAAGTTAAT
ACCGAGAGAGCAAAGCTAATTGTGTATGAACATATGCCAAAATACAGT
AGTTGAGGAAGCTTATATAGATAGCCTATCACTAAAGAAAAAATATCAA
ATCAAACGGATATTCCATTTTATAAAAATCAAAAAGAATTGCTCTTAGA
AACTGCGGCCTTTTAAACCCTGAAGATATTACAGAATACATAGCAATGAA
TGGGTACGAAGCTTTAGGCAGAGTTCTAACACAAATGACACCTGACAGCA TABLE 1-continued Sequence Listing
Minimum set sequences CAATTGATGAAATTAAAAAAAGCGGCCTCAGAGGCAGAGGGGGCGGCGGC
TTCCCTACAGGCGTAAATGGGAAATGACAAGAAAATCCAAATCTGATAC
AAAGTTTATGATCTGTAATGCTGATGAAGGTGATCCCGGTGCCTTTATGG
ATAGAAGCATACTTGAGGGAGATCCAAATTCTGTACTTGAAGCTATGGCT
ATTGCAGGTTACTGCATAGGTGCAATAAGGGTTATATTTATATCAGAGC
TGAATATCCTCTTGCAATAAACAGATTAAAAATTGCTTTAAAGCAAGCTT
ATGATTTAGGTTTACTGGGTGATAATATTTAGGTACTGATTTTTCCTTT
CATATAGATTTAAAATATGGTGCCGGAGCTTTCATCTGTGGTGAGGAAAC
TGCACTCATAAATTCCATAGAAGGCGGACGTGGAGAGCCTACCGTAAAAC
CTCCTTTTCCTTCCCAAATAGGTCTCTGGAAAAAACCAACTAATATAAAT
AATGTAGAAACTCTGGCAAACATCCCCCCTATTATATTAAAAGGCTCTAA
GTGGTTTAGTTCTATAGGAACTGAAAAGAGTAAAGGAACCAAAGTTTTTG
CCTTAGCAGGCAAGATCAATAATGTTGGCCTTGTTGAGGTACCTATGGGT
ATAACCTTGCGGGAAATAATATATAATTTAGGCGGAGGTATTCGCGGTGG
TAAAAATTTAAGGCTGTTCAAACTGGCGGTCCTTCTGGCGGGTGCATTC
CTGCAGATCATTTAGATACTGCCATTGATTACGAAAGTCTTACTGAAATA
GGCTCCATGATGGGTTCTGGTGGAATGATAGTTATGGATGAAGATAATTG
TATGGTGAATATAGCCAAATTCTATCTCCAATTTAGTGTAGATGAATCCT
GTGGAAAGTGCACTGCCTGCAGAATCGGGAATAAAAGACTTTTAGAAATT
TTAGAGGATATCACTAAAGGAAAAGGTACCATGGAACACTCTTGAAGGATT
AAAAGATTTATCCTATGTAATAAAGGATTCAGCCCTATGTGGTCTTGGTC
AACATCACCTAATCCAATTATAAGTACAATGAAATTTTTTTGGGATGAA
TATATAGCCCACGTAAAAGATAAAGCTGTCCTGCTGGAGTTTGCACTGC
ACTTTTAAAATACAATATAAATTCTGAAAAATGTATTGGCTGCACAGCCT
GTACAAAGGTATGCCCTAAAGGAGCTATTTCCGGAGAAATAAAAAAGTCA
CATGTAATAGATAAGTCAAATGTATAAATTGTGGTGCATGTAGTAGTAT
TTGTAAGTTTTCTGCTATTACGAAAGAATAA >Gene ID No. 39:
RCCC01504 Contig0001_3806829_3805096
ATGGTAAATTTAACTATAAACGATATAAAGGTTTCTGTCCCAGAAGGCAC
TACAATTTTAAACGCTGCAAAAAAGTAAACATAAATATACCTACTCTCT
GCTATCTTGATCTTCACGATATAAAAATGGTAAATAGGACTTCCTCCTGC
AGAGTCTGCCTTGTTGAAATTGAAGGCAGGCGAAATCTTGCACCTTCATG
TTCTACAGAAGCTTTCGAAGGTATGATAGTTAGAACAAATAGTGCCAGA
CTATAAAAGCAAGGCGTACTATGGTAGAATTTTTATTATCAGATCATCCT
ACCGACTGCCTTGTATGTGAAAAGAATACTCAATGTCAACTTCAATTAAT
CGCTGCTGAATTAGGTATAAGAAAATAAGATATAAAGGTGCTATGTCTA
ATTACATAAAGGATTCATCAAGTGGTGCTATATATAGAAATCTTGATAAA
TGTATAATGTGCAGACGATGTGAAACCATGTGCAATGAAGTTCAAACCTG
TCAGGTTTACTCTGCAGTAGATAGAGGCTTCGAAACTGTAGTATCCCCTG
CATTTGGTCGTCCCATGGTTGACACGCAATGCACATTTTGCGGTCAATGT
GTATCCGTATGCCCACCTGCTGCATTAACTCAAGTTAGTAATGTGCTAA
GGTATGGGAAGTACTAACTGATCCTGATAAATATGTAGTAGTTCAAACTG
CCCCTGCTATAAGAGTTACTTTAGGTGAAAAATTCGGTATGGAACCTGGA
ACTATTGTAACTGGCAAAATGGTATCTGCTCTTAGAAGATTGGGCTTTGA
TAAGGTATGTAATACCGATTTTGCAGCAGATGTAACTATTTTAGAAGAAG
CTCATGAATTTATAGATAGCTTCAAAACGGCGGAAGACTTCCAATACTC
ACAAGCTGCTGTCCCAGCTGGGTTAAATTTATAGAACATCAATTTCCTGA
TCTTTTTAGATATACCTTCAACTTGTAAGTCTCCACACATAATGTTTGGTA
CTTTAGCTAAAACATATGGCAGAAAATTAAATATTGATCCATCTAAA
ATTGTAATAGTTTCAGTTATGCCATGTATTGCAAAAAATATGAAGTAAG
CAGAAAAGAACTTCAATATGAAGGTCATAAAAATGTTGATCTTGTAGTTA
CCACAAGAGAGCTTGCAGATATGATAATGGAAGCAGGAATAGATTTTAAT
AAACTTCCTGATGAAGACTTTGATAAACCTTTTGGAGAATCCACAGGTGC
TTCTGTAATATTTGGAACTACCGGCGGTGTAATTGAAGCAGCTCTTAGAA
CTGCTTATGAATGGATTACTGGAGAGACTTTAAAAGAAGTAGAATTTCAT
GGTGTAAGAGGACTTGATGGACTTAAAGAAGCCAGTATAAATATTGGTGG
TAAAGAAATAAACATTGGCGTAGCTCACGGTCTTGGCAACGCAAGAAAAC
TTCTTGCAGATAGAAGATCTGGTGAATCAAAATATCACGCTATAGAAATA
ATGGCATGTCCTGGAGGATGTATTGACGGAGGAGGTCAGCCGTATCATTT
TGGAGATTTAGATATTGTAAAGAAAGAATGGACGCTTTATATAGAGAAG
ATAGAAACAAACCTCTCAGAAAATCTCATGAGAATCCTGAAGTTCAAGCT
CTATATAAAGAATTTATTGGAGATGTAGGCGGAAAAAAAGCTCATGATCT
CCTTCACACTCATTATATAAAAAGGCAAAAGTTATAA >Gene ID No. 40:
RCCC02998 Contig0001_914271_913393
GGTATGTATAATTCCCTTAGACGTGAATTTAATATGCTATAAGTATACAA
GCTTAAGAAGAATATATTAGAAATGATTTAAAAGATAAAGCTACTTTAAA
AAATAAGGTGGTTTATTTTTTGTATAAATACACGTTATATTAATTGTC
TTTTAATTATAATAATATAGAAAATTAAAGAGCAGAGTGATAAGTAA
ATGAATGTTCGAAACAAGGGTATATGTCCTTTAATCGTAGATAAGGAACG
CAGTTCAAAGGCTTTTACTAGTGAAGCTATAGATTTAATTAAAAGGGGAA
AGACGAAAAATTAAATGCTATATGGCTTGAAGTAACAGGATGTTCAGGA
AATATTATTTCTTTTTTAAAAGTAGTGAAAATCCTGGACTCGATTATATTTT
AGAAAAACTCATTAATTTAAAAATACAACAATACTCTAATGACTTCAGAAG TABLE 1-continued Sequence Listing
Minimum set sequences GTGAGTATGCTTTTAAACAATTCTTAGATACATTGGATACTGAATTTATA
CTACTAGTAGATGGAGCGGTATCTACTGCTCAAAATGGTTTTTATAATAT
TGTTGCCAATTATGAAGGAAAACCTGTTACTGCACTTGAAGCTGTAAAAA
TGGCAGGAGAAAAGCAAAGTATGTTCTCTGTGTAGGAACTTGTGCATCC
TATGGTGGAATTTCTGCCGCCAGGCCAAACCCATCAGAAAGCAAAAGTGT
TAAAGAAATACTAAATCGTGAAGTCATAAGACTTCCAGGCTGTCCATGCC
ATCCGGATTGGGTAGTTGGAACTTTAGCACATTTAGTTGCTTTTGGCAAA
CCGCAATTGGATGAAGATGAAGACCTCTTCTTTTTTATGGAATTACCAT
TCATGATAGGTGTACAAGAAGGGGATTTTTTGATAACAGAATTTTTGCAA
AAAAATTTGGAGAAGATGGATGTATGTTTAAACTTGGATGCAGGGGGCCT
GTAACTAAAACAGATTGTCCTAGGAGAAAGTGGAATGGATATGTGAACTG
GCCTGTTGAAGACAATACCAACTGTATAGGATGTGCAAATTCTAGATTTC
CAGATGGTATGGAACCATTTGTAAGGTATTAG >Gene ID No. 41:
RCCC02997 Contig0001_913376_911994
ATGAAAAAGAAAATTACCATTGATCCAATTACGAGAATAAGTGGTTTTTT
GGAAACTAAAGTGCAAGTAGAAAAAAATATTATAGTAGATGCTGAAACTA
GTGGATTGCTTTTTAGAGGATTTGAAAAAATGTTAAAAACAGACAGCCG
CTGGATGCAGTATATTTTACAGAAAGAATTTGTGGGATATGTTCAACAGC
TCATGCTGTGGCAGCTGCTACAGCTCTTGAAGATGCTTTGAAGATAAAAA
TTAGTGTAAATGATTCGTATATGCGTAATTTAATACATGGTTTTGAATTT
ATACAAAATCATATAAGACATTTTTATAATTTGACTATACCAAGTTATGT
GAAGATGCCCAATATAAATCCTCTTTTTTCAGATCAATATGAAGATTATA
GATTACCTTATAACTTAAATAAAAAGATAAGTGAAGATTATATTGAAAGT
ATTAAATACAGTAGGTTAGCCCATGAAGGATTGGCTACTCTTGGAGGAAA
GGCTCCCCATAATCACGGAATTTTTGTTGGAGGAGTTACCATAAATATAG
ATCCATATAAACTTACAAAAGTTAAATCTATTATTTCTCAAATTAATGAA
TTCGTAAGTAGTGTTATGTTAGAGGACATGAACATAATTTCAAAATACTA
TGCTGATTATTTTAAAATGGGAAAAGCCTATGGAAACTTTATGACTATG
GAATTTTTGATAAGTATGCTGATCCTGAGATAAGTTATGTAGGACCTTCT
GTCTTAATAAATGGACAAAAGCATAACTTTAATAGTAATAAAATTACAGA
GAATATACTTTACACCTGGTACATGAATGATGATGAAACAATAAATTTAT
CTAAAGAAACAGGTTACAGCTTTATAAAATCGCCAACTTATGATGATCTAT
TCTATGGAAGTAGGACCTCTAGCAAGATTGATACTTTCAGGTGAGTATAC
TGGTGGAAGTTCATGTATGGACAGAAATGTTGCCAGAGTACTTGAAACAA
AAAAGATTTAGAAATTATGCAAGGACTTGCAGATAGAATTAAGCTTATT
CCAGCAGAACAAAGAATATATGAAATCCCAGATAAAGCATTTGGTGCAGG
ATTAATTGACACAACTAGAGGATCCTTGGGACACTGGATAAGTATAGAAG
ATAAATTTATAAAGCATTACAATATTATAACTCCTACAGTGTGGAACATG
GGGCCAAGAAATCAATCAGGTGCGCTTGGAATTGGAGAAAAATCTTTACT
TGGAACGAAAATAAAAGATATAAAGCAGCCTATAGAAGTTGGGAGAATTA
TGAGGTCCTTTGATCCTTGTGTTTCCTGTGCAACTCATTTGATAAGTGAT
GCATATGAACCAGTGGACGTACAGGTTATAGTATGA >Gene ID No. 42:
RCCC02996 Contig0001_911994_911533
ATGAAAGCAAAAGTTATTGCTCTAGGGAAATATATTAATGGAAGACGATGG
CATTGGAATTAAGATCCTGGAAAATATAAAGAGGAACTTGCACATAACC
ATATTCAATCTATAATAGGAGAAACAGATGTGGAATACTGCATTTCCCAA
GTAAAAGATGGTGATTTTATATTTATAATAGATGCTTCTTAATAAGTGAAA
AGTTCCAGGTACGATAACAGTTGCCAGCTTACAAGATTATAAGTGCAAAA
ACAAATATTATACCCAGCACAGCTATAGCTTCATAGACATTATAGGAGTT
TACTACAAATCATTAACTGGGTTTATTATTGAAATTGAAGCAGCTAGTGT
AAGCTTTAAATTGGGACTTAGCCATAATTTACAAAGTAAGCTTAAGGATA
TTTCAAAAGATGTATTGAAAAAATATTTTTCTGAGATTGAATGATAGAGCA
GAGGAGGAAAAATAG >Gene ID No. 43:
RCCC02995 Contig0001_911529_911119
TTGGATTTTTATTTAATGAAAAGTTGAAGATAATTAGGCGAAAAATAAC
TTTTTATAAAAAAGTAGTATGTTTGCTGTATGCCCTTTTATAAAAAGCT
ATTATGGACATCTCATGAATATTCAAATAGGGGAATTAGAAAAACTAATG
AATACAATGAACAAAGATATGATAACAGGAAAACAATTTACTTTGA
AGAACTTTCAAAATACAATGGTGCTGGTGGCTCTCCGGCTGTATGTTGCTG
TAAATGGAATAGTGTATGTGTGAGTTTGTCTCCTGTATGGGGTGGAGGG
ACGCATTTTGGTCTGTATGCTGGAAAAGACTTAACTTTACAATTTAGGGC
ATGTCACAGTGGAGAAATAAAGATATTTAATGGTCTACCTAAAGTGGGAG
AGTTAAAATTTAA >Gene ID No. 44:
RCCC01825 Contig0001_3489615_3490466
ATGAATACTGTAATTATGATTTAGTTGTAATGACTGTTATAGGTCTTAT
ATTTGGACTTGTTTAGCCTATGTAAATAAAAGATTTGCAATGGAAGTAA
ATCCACTTGTGGACTTAGTAGAAGATGTACTTCCAAAAGGCCAATGTGGA
GGGTGTGGATTTGCAGGATGTAAAGCTTATGCAGAAGCTGTTGTTTTAGA
TGAGAGTGTACCTCCAAATCTTTGTGTACCTGGAAAAGCAGCAGTTGCAG >Gene ID No. 45:
RCCC01826 Contig0001_3489018_3489596
ATGGCATCTTACCTTACTCTTTTTATAAGTGCAGTAGTTGTAAATAACTA
TGTTTTAACAAGGTTTTTGGGACTTTCTGTATATTCTTTGGTGTTTCTAAGA
ATTTAAATGCTTCTGTAGGTATGGGTATGGCTGTTACTTCTGTTATTACT
ATGAGTTCAATATTGGCCTGGGTAGTATATCATTTTGTACTTATACCATT
TAATTTAACTTTCTTGAAGACAGTAGTTTTTGTACTTCTTATTGCTAGTT
TTGTACAGCTTTTGGAGACTATTATTAAAAAGCAGGCACCAGCCCTATAA
AATATGTGGGAATATACCTTCTTTTAATAGCTACAAACTGTATAGTACT
TGCTGTACCTATATAAATGCTGATTCTAACTTTAATTTTTTACAGAGTG
TTGTTAATGCGATAGGATCTCGGGCTAGGCTTTGCTATGGCTATAATTTTG
ATGGCAAGCCTTAGAGAAAATTGAGATTAGCAGATGTACCTAAACCTTT
AGAAGGTCTTGGAGTAGCTTTTATTTAGCAGGAATGTTAGCCCTAGCTT
TCCTTGGTTTTCAGGTATGATTTCTATGTAG >Gene ID No. 46:
RCCC01827 Contig0001_3488377_3489015
ATGAAGAATTTGTGGAATATATTTAAAAAAGGATTGATTGCAGAAAACCC
CATATTCGTACTTGCACTTAGTTTGTGTCCAGCACTGGCAACTACAAGTA
CAGCTGTAAATGGATTTACCATGGGGCTCTGCGTGCTATTTGTTATAACT
TGTAATAATACTGTGGTTTCTATAATTAAAGAATTTTGTAAATCCTAAGGT
ACGTGTACCTGTATATATCACTTGTATAGCAACTATAGTTACAGTAGTGG
AACTTGTTATGCAGGCTTATGCACCTCTATTATAAGCAATTGGGAATT
TATTTAGCATTGGTAGTTGTATTTGCTATAATACTTGCCCGTGCAGAGAC
ATTTGCATCTAAAATCCTGTAGTTCCTTCTTCTTTGATGGACTTGGAA
TGGGATGTGGATTTACTTTGGCACTTACTATAATAGGAATGATACGTGAA
TTATTTGGATCTGGAGCTATATTTGGTTTTAATGTATTTGGGCTTCATA
TAATCCAGCTTTGATTATGATACTTCCACCTGGAGGATTCATACTTATAG
GATATTTAGTTGCTATAGTAAAGTTTATAACCAACATATGGAGAAAATT
AAAATGCAAAAATTAGAACAAGCAAATGGAGGTGAAGCATAA >Gene ID No. 47:
RCCC01828 Contig0001_3487817_3488371
ATGGCTAAAGATAAAGATCAAAATAGTATTTTTGCAATTACTAAGAACTT
AACCATTACGTGTTTTATATCTGGAATTATAATAGCTGCGGTTTATATG
TAACATCACCAGTGGCAGCACAAAAACAAGTTCAAATACAAAATGATACC
ATGAAAGTTTGATTCAATGATGCTGATAAATTTAATAAAGTAAATTGTAA
AAAGGATTGGTATGCAGCTCAAAAAGGAAACAAGACAATTGCATATGTTG
TACCTGCAGAGAGTAAAGGTTACGGTGGAGCTATAGAGCTATTGGTAGCT
GTTACTCCAGATGGAAAAGTAATAGATTTCAGCATTGTATCTCATAATGA
AACTCCAGGACTTGGAGCAAATGCTTCAAAGGATTCTTTTAGGGGACAGT
TTAAGGATAAAAGCGGATGCCTTAACAGTTGTAAAAGATAAGTCTAAC
ACTAAAACATTCAAGCTATGACAGGAGCTACAATTACGTCAAAAGCTGT
AACTAAAGGAGTTAAAGAAGCTGTTGGGCAAGTTACTACGTTTACGGGAG
GTAAGTAA >Gene ID No. 48:
RCCC01829 Contig0001_3486815_3487807
ATGGCGGAAGCACAGATAAAGAAAAATATTTTACTATTTCGTCATCACC
TCATGTCGTTGTGATGAATCTGTTTCTAAGATAATGTGGAGTGTCTGTT
TAGCACTAACTCCAGCTGCGATTTTGGCGTATTTAATTTTGGAATTCAT
GCTTTAGAAGTAATTATAACAGGAATTTATAGCTGCTGTAGTTACAGAGTA
CCTTGTAGAAAAGTTAGAAATAAACCTATAACTATTACAGATGGAAGTG
CTTTTTTAACAGGACTTTTACTTCTATGTGTTTACCTCCTGATATTCCA
CCTTATATGGTAGCTATAGGATCTTTTATAGCAATAGCTAAACA
TTCTATGGGAGGACTTGGTCAGAACATATTTAATCCAGCTCATATTGGAA
GGGCTGCACTAATGGTTTCCTGGCCTGTAGCAATGACAACATGGTCAAAA
TTAATGCCAGTGGTTGAAGCATTCGTAACCACAGCAACTCCTCTTGGAAT
TTTAAAGCTTCAAGGTATTCAAAATTACTTGGACTTTTGGAGGTCAAG
GTGCACTTTACAAGGCAATGTTCTTAGGTACTAGAAATGGAAGTATAGGA
GAAACTTCTACAATATTACTTGTTTTAGGTGGACTTTATCTAATATAAA
AAAATATATTAACTGGCAGATTCCAGTAGTAATGATCGGTACTGTAGGAA
TACTTACCTGGGCTTTTGGAGGAACTACGGGACTTTTTACAGGAGATCCT GTATTTCATATGATGGCAGGCGGACTTGTAATTGGAGCTTTCTTTATGGC
TACTGATATGGTAACAATTCCTATGACTATTAAAGGACAGGTTATTTTTG
CATTAGGTGCAGGTGCGCTTACATCACTTATAAGATTAAAAGGTGGTTAT
CCAGAAGGCGTATGTTATTCAATATTACTTATGAATGCAGTTACTCCTCT
AATAGATAAGTTTACACAGCCAGTTAAATTTGGGACAAGGAGGTAA >Gene ID No. 49:
RCCC01830 Contig0001_3485423_3486793
AACTTTAATTAATAAGAGTATCTTTTAAAGTTAACTGACATTTAATAGAT
AAATTGTCATTATATATTATTTCCTATAGTATATAATTTTATAACGGATT
ATGGAAAATTCTATAATCTGTTATAAAAATTATGTTTATATTTATTTTGC
AGTTTCGTTATATACATGCTGTAAAAATTATTGAAAGAGGTGTTTAAGA
GTGTTAAAAAGTTTTCGAGGTGGAGTACACCCGGATGATAGCAAAAGTA
CACAGCTAATAAACCTATAGAAATAGCACCTATACCAGACAAGGTGTTTA
TTCCCGTTAGACAGCATATAGGTGCTCCTACATCTCCTGTAGTACAAAAA
GGAGATGAGGTAAAAAGGGACAACTTATTGCGAAGAGTGATGCTTTTGT
TTCAGCCAATATATATGCATCTACTTCTGGAAAGGTTGTAGATATAGGAG
ATTACCCACATCCTGGTTTTGGAAAGTGTCAAGCTATAGTTATTGAAAAA
GATGGAAAAGATGAGTGGGTGGAAGGAATACCAACTTCACGTAATTGGAA
AGAGCTAAGTGCAAAAGAAATGCTTGGAATAATAAGAGAAGCAGGCATTG
TAGGAATGGGAGGCGCAACTTTTCCTGTTCATGTTAAACTTGCACCACCA
CCAGATAAAAAAGTAGATGTTTTTATTTTGAATGGTGCTGAGTGTGAACC
TTATTTAACTGCAGATTATAGGTCCATGTTGGAAAAATCAGATAAGGTAG
TTGCTGGAGTTCAAATAATTTATGAAAATCCTCAATGTGGAAAAAGCATTT
GTAGGTATTGAAGATAATAAACCAGATGCCATAGAAGCTATGAAAAAAGC
TTTTGAAGGTACAAAAGTACAAGTAGTAGGCCTTCCTACTAAGTATCCTC
AGGGTGCTGAAAAATGCTTATAAATGTTTTGACAGGTAGAGAAGTTCCA
TCAGGTGGATTGCCTGCAGATGTAGGTGCGGTTGTTCAAAATGTAGGTAC
ATGCATAGCAATAAGCGATGCAGTGGAGAGAGGAATTCCACTTATACAGA
GAGTTACAACTATAAGTGGAGGTGCTATTAAAGAGCCTAAAAATATATTA
GTTAGAATTGGAACTACATTTAAAGATGCCATTGATTTTTGTGGAGGATT
TAAGGAAGAACCAGTTAAAATAATTTCAGGTGGACCTATGATGGGATTTG
CCCAATCAAATTTGGATATTCCAATAATGAAGGGTTCATCAGGAATACTT
GGTTTAACTAAAAATGATGTAAATGATGGAAAAGAATCTTCTTGCATTAG
ATGTGGCAGATGTCTAAAAGCCTGTCCTATGCACTTGAATCCAAGTATGT
TAAGTATTCTTGGACAAAAAGATTTATATCAAGAAGCTAAGGAAGAATAT
AATCTTTTGGACTGCGTAGAATGCGGCAGCTGTGTATATACATGTCCTGC
TAAACGAAGAATTGTACAGTATATTAGATATTTAAAATCAGAAAATAGAG
CTGCAGGGGCAAGGGAAAAGGCTAAAGCAGAAAAGGCTAAAGAAAAGAAA
GAAAAAGAAGAGGTCTTAAAATAA >Gene ID No. 50:
RCCC00393 Contig0001_2563153_2563626
GCTTTTTCACCATTGTTTTAATACATCTGGGAGCATTTCAAATTCCAAT
AACTTCCAGTGTCATTGTACAATGGGCCATTATTATAATTTTAGCTATAT
TGGCAAAATTTTTTACATCTAGTATGAAAAAATACCGGATAAAAAACAAA
GTGTTATTGAAATTATTGTTGAAGCAGTAAGAAATTTAGTTACTGAAATA
ATGGGAAAAGAGTATGTATCATTTATACCATATTGTAGGAACGCTTGCCAT
ATACATTTTAGTAATGAACATTGCTCCAGTGATGATAGGAGTAAGGGCAC
CAACGGAAGATCTAAGTGTTGCAGTTGGATTGGCATTAATAACTTTTGTA
TTAGTCCAATTTAATTCAATTAAAAAAAAATGGTTTAGTGCGTTATTTTGG
AGCATATACTAAGCCAGTAGTACCGCTATTGCCAATTAATATTATAGAAA
GGCTAGTTCTTCCAGTTTCCCTAAGTCTACGACTTTTTGGTAATTTGACA
GCAGGAGCTGTAATTATCGGTATGGTATATAAAGGATTAGGTAGTATGGC
ATGGTTTTCTCAATTGTTAATACCAATTCCTTTACACGCTTTCTTTGATT
TATTTGATGGTTCAATCCAAATGATAGTATTTGTTATGTTAACAATAATG
AATATAAAAGTTATAGCTGAAGACTAA >Gene ID No. 51:
RCCC00394 Contig0001_2563672_2563914
ATGAATTTAGATGCACATTCATTTATATCAGGTATGGCAGCAATAGGTGC
AGGTTTAGCTGCTATAGGATGTTTAGGAGGAGGTATTGGAGTTGGAAATG
CTGCTGGTAAGGCAGTTGAAGGAGTATCAAGACAGCCAGAAGCAAGTGGT
AAAATACTAAGTACATTCTTTGTAAGTGCAGCTTTATCAGAGGTAACAGC
TATTTACTCTCTATTAATAGCTCTTATTTTAGTATTTAAAGTTTGA >Gene ID No. 52:
RCCC00395 Contig0001_2563964_2564452
TTGGAATTTAATATGCAAATTGATTGGACTACAGTCGTTATAACAATAAT
AAATTTTATCATATTGTATTTCATTCTAAAGCATTTCTTTTTTAAACCTG
TCAATAACACTATTACAAATAGGCAGCAAGAAATTGACAATAAAATAAGA
ACTGCTGATGAAATGAAAAGAAGTCTAAACAATTAGTAACTCAACATCA
AGAGTTGTTAAAGAATTCAAAACAAGAAGGAAAAGCTATTGTTGAAGACT
ATAAAAATAAAGCCGATAAAGTTTCCGAAAACATAGTAAATGATGCCCAG
AAAGAAGCTCAACTAATATTAGATAGGGCAAAAGTTGAAGCTGAAAGAGA
AAGAGAAAAAGCAAAAGACGATATAAAAAATCAAGTGGTAGATTTAGCAC
TTTTAGTATCATCAAAAAGCTTTAGAGGGATCTATTAATGAGCAGCAGCAT
AGGAAACTTATTGAGGACTTTATAGCTAAGGTAGGTATTTAA >Gene ID No. 53:
RCCC00396 Contig0001_2564458_2565000
ATGCATGAGTATTTAGATAGAAGATATGCCCTTGCACTCTATAAAATTGG
AGAAGAAAAAGGAAAAGTTAAAGAATACCTAGAAGAATTAAGGCAGGTTG
TAGCCGCTATAAAAGGTAATTCTAAATTTTTGGAAATCATGGAACATCCA
GAAGTAAGTACATCAGAGAAGAAAAAAATGTTTACTGAAATCTTTAAAGA
TAAGGTGAATGAAGACATACTTTCATTCTTATTAGTTCTTATAGAGAANA
ATAGAATTAATGAAATTGATGGAAAACTTAGGGAAATGGAAAATATATAT
CTTGAGAGTAATAATACTGTTAAGGCAAAAGTAAAAACAGTTATTGCTTT
GAATGATGATGAGAGAAACACTTTAATTGAAAAGCTAGAAAAGAAATTTA
AGGAAAGTTTTGATTGAAGAAAGAATAGATCCTAGTATAATAGGTGGG
GTTTATGTTGAGGTAAATAATGAAGTTATTGATGGTAGTATAAGGTCAAA
ACTTTCTGAAATGAAAAAAATAATGCTTAAGGGAGAACAGAGGTGA >Gene ID No 54:
RCCC00397 Contig0001_2565008_2566519
ATGAACATAAAACCTGAAGAAATAACTTCAATTATAAAAGATGAAATACA
GAAATATGAAAAGAAAATAGAAACAGTTGATTCAGGTACAATAATTCAAA
TCGGTGATGGTATTGCTAGAGTTTATGGCCTTAATCAATGTATGGCAAAT
GAACTCTTAGAGTTTCCAAATGATGTTTATGGTATGGCTTTAAACCTTGA
ACAGGATAATGTAGGTTGTGTTCTTTGGGTTCCCAGAAGGGAATAAAAG
AAGGAGATACAGTTAAAGAACAGGTAGAGTTGTAGAAGTACCAGTAGGT
GAAGCTATTGTTGGAGAAGGTTGTAAATTCACTTGGACAGCCTATTGATGG
GAAAGGTCCTATAAAGACATCAGAAACTAGGCCTGTAGATCTTGTAGCTC
CAGGAGTTATAACAAGACAGTCAGTTAAAGAACCACTGCAAACCGGGTTA
AAGGCTATAGATTCAATGATACCAATTGGAAAAGGACAAAGGGAATTAAT
AATAGGAGACAGGCAAACAAGGTAAGACTGCTATTGCCATGGATACTATA
TAAATCAAAAAGGAAAAGATGTAATATGCATATATATGTAGCTATAGGTCAG
AAGCAGTCTACTGTAGCTCATATAGTAAATGACTTAACAGAAGCAGGTGC
TATGGACTATAGCATAATAGTATCTGCATCAGCATCTGAGTCAGCACCAC
TTCAGTATATTGCTCCTTATGCAGGATGTTCCATGGGTGAATATTTTATG
AATAAGGGAAAAGATGTACTTATAGTGTATGATGATTTATCAAGCATGC
GGTTGCCTATAGAGAAATGTCATTATTACTCCGTAGACCACCAGGAAGAG
AAGCATATCCTGGAGATGTATTCTATCTGCATTCAAGATTACTTGAAAGA
GCAGCAAAGCTTTCTGATAAGTTAGGTGGAGGCTCACTTACAGCACTTCC
TATAATAGAAACTATGGCAGGAGATGTTACTGCATATATACCAACAAATG
TTATTTCTATAACGATGGTCAGATATTCCTTGAATCAGAGCTTTTCTAT
GCGGGTCAAAGACCAGCTATAAATGCAGGTATATCCGTATCCAGAGTTGG
TGGTAATGCACAAATTAAAGCAATGAAGCAGGTAGCAGGTACTCTTAGAT
TGGATTTAGCACAGTATAGAGAACTTGCATCATTTGCTCAATTTGGATCA
GACCTTGATAAAGAATCTATGAAAAGGCTTGAAAAAGGTAAGAGATTAAC
AGAAAATATTAAAACAACCTCAATACAAAACCAATGCCTGTAGAAAATCAGG
TAATGATACTGTTTGCAGCTGGTAGAGAGTATATAATGGATGTACCGGTT
GAAAAAGTTGTAGAATTTGAAGGAGAATTCCTTGATTATATGAGTGATCA
TCATAAAGAATAGGTGATGAAATAAAAATAAAAAATTTATATCCGATG
AATTAAGTGATAAACTTGGAAATGCTATAGAGGAATTCAAAAAAATATTT
TTAGCAGAGGCATAG >Gene ID No. 55:
RCCC00398 Contig0001_2566545_2567393
ATGGCAGGGGCAGGACTTGTTACAATAAAAAGAAGAATTAGATCAATAAC
CAGTACTCAAAAAATAACAAATGCCATGGGACTCATTGCCACCTCTAAAC
TTAGAAAAGTTAGAAAAAGACTTGAGGCAAATAATAAATATTGTGAACTA
TTTAGTTCCCTTATGAATGAATTTGTTTTAGGAGCAGAGGGAAGAAACAT
TTATATACATGGTAATAAAAGCAATAAGAAACTCTACATAGCTTTAAATT
CAGATACAGGATTATGCGGAGGCTTTAATGGCAGTGTAGTAAATGAAGCA
GATGCTGCAATGTCAAAAAATAAAGAAAATTGCCTTTTGATATCTGTGG
ACAAAAAGGAAGAACGTATTTTAAAAGGCTTAAGTATAGTACAGAAGCAG
AATACGTGGATATTTCAGATGTTCCTACTATAAAGTAAGCAGATACCATA
GTATATAAGGCTCTAGACCTTTATAGAAGTGGCGAGGTTGGAGAAGTTAA
TATAGTATATACTAAGTTTATTTCAACAGTTAGACAAAAAGTAGTTGTTG
AAAAATTACTTCCATTGGAAGCTGATAAAGAAGAAAAAACAAATTTATCTT
GTTAAATTTGAACCATCAATAGATGAAATGATGGATGAAGTAGTACTTTT
ACACTTAAAGCAAAAGTACTTAACTGTATGATAAATTCAAAAGTAAGTG
AACAGGCTTCCAGATACAGCAATGACAGGTGGGCAACTAAAAATCAAAATG
GATTACTGATAAATTGAATCTTAAATACAATAGAGAGAGACAATCTGC
TATTACACAGGAAATAACTGAAATAGTTGGAGGAGCAGAAGCTCTTAAGT
AA >Gene ID No. 56:
RCCC00399 Contig0001_2567406_2568800
TTGATGCCAAATATAGGCAAAGTTGTTCAGGTTATAGGACCTGTAGTAGA
TATAAAGTTTGATACAGAAAACCTTCCTAATATATATAATGCCATAGATA
TAAAATCAGGTGATAAAAAAATTATTACAGAAGTTGCACAACATTTGGGT TABLE 1-continued Sequence Listing
Minimum set sequences GATGATGTAGTAAGAACTATATCCATGGAGAGTACGGATGGATTAATGAG
AGGTATGGATGCAGAAGATACAGGATCTCCTATATCTGTACCTGTAGGTG
AGCCAGTTTAGGAAGACTTTTTAATATGCTAGGACAGCCAATTGATGAA
AATGGAGAAGTAAAGGCAGAACAATACTATCCTATTCATAGACAGGCGCC
AAGTTTTGAAGATCAATCTGTTAAGCCTGAAATGTTTGAAACTGGTATTA
AAGTTATAGATCTTCTTGCACCCATACCAAAGAGGCGGAAAGATAGGACTG
TTTGGTGGAGCTGGTGTTGGTAAAACAGTTCTTATACAGGAACTTATAAA
CAATATAGCAAAAGAACACGGTGGATTATCAGTATTTACAGGTGTTGGAG
AAAGAACAAGAGAAGGAAATGACCTATATTATGAAATGCAGGAATCAGGA
GTTATAAAGAAGACTGCTTTGGTATTTGGTCAGATGAATGAGCCACCTGG
AGCAAGAATGAGAGTTGCACTTACAGGACTTACTATGGCAGAATATTTTA
GAGATAAAGGTCAGGATGTACTTTTATTTATAGATAATATATTCAGATTT
ACTCAGGCAGGATCCGAAGTTTCAGCGTTACTTGGTAGAATACCTAGTGC
TGTTGGTTACCAGCCAACTCTTGCAACTGAAATGGGTGCTCTTCAAGAAA
GAATAACATCCACAAAACAGGGGTCTATTACATCTGTTCAGGCAGTATAT
GTTCCAGCAGATGACTTGACTGACCCGGCACCATCTACGACATTTACGCA
TCTTGATGCAACTACAGTTCTTTCTAGATCTATATCAGAAATTGGTATAT
ATCCTGCTGTTGATCCACTGGCATCCACTTCAAGAATATTGGATCCAAGG
ATTGTAGGAGAGGATCATTATAAAGTAGCATCAGATGTTAAACATATACT
TGAAAGATACAGTGAACTTCAAGATATTATAGCAATACTTGGTAGATG
AGCTTTCAGAAGATGATAGATTAGTAGTTATTAGAGCTAGAAGAATTCAA
AGATTTTTATCACAACCATTTTCTGTTGCAGAACAATTTACAGGATATCA
GGGTAAAATATGTTCAAATAAAGGAAACTATAAGAGGTTTTAAAGAAATTC
TTGAAGGTAAATATGATGATTTGCCAGAAACTGCTTTCTTATTTAAAGGA
AGTATAGATGAAGTGGTTGAAGCAGCTAAAAATATGGGAAAAAATTAA >Gene ID No. 57:
RCCC00400 Contig0001_2568870_2569265
ATGTCAGAAGTTTTAAAATTAACTATCCTTACTCCCGATAGAGAATTCTA
TGAAGGAGAAGTAGTAGAAGTAATAACGGAAGTATTCAAGGCGACATAG
CAATTCTTCCAGACCATATGCCTTTAGTTACCACTTTAAAACCTGCAGAT
ACCGAAATCGTTCAAAAAGATGGCAAAAAATTAAAGGCATTTACATCAAC
CGGAGTACTGGAAGTAATAAATAATGAGCTAAAAATTTTATGTGATTCTT
GTGAATGGCCAGATGAAATAGACATAGATAGAGCAAAAGCTGCTAAAGAT
AGAGCTGAAAAAAGATTATCTAGTCAGAAAGACGGAGTCGATGTGAAAAG
AGCAGAAATGGCATTGGCTAGGGCACTGGCGAGAATTAATCTGAAATAA >Gene ID No. 58:
RCCC00086 Contig0001_2233162_2232383
ATATAAGAGAAACTATACTTGCAGGAGCTAATGCTATATAGCTTTTACGCCT
CCTACTTCGGCTGAAATTTTAAGACAAATTATGAATGAACATAGGAAAAA
ATATAAAAAATAGAAGACCAGAATAAATATTTACAGTATATTATAGGGAGA
GGAGTAACTACTTTTATTTTAATTATTTAAAAATAAAGATTAGATTAGT
ATGAAAGGTATTTTATATTATTTTAGCGGTACTGGAAATACCAAGTGGGT
GGCGGATAGGTTTAAGGAAAAATTTCAGCTTTATAATGTAGATATAGACT
TAGCATATATTCAATCTCTAGAAGAGAGGAAAATAAAAAAATATGATTTC
ATAATCATTGGCTTTCCTGTCCATTGGAAATTACCACCTAAAATTGTAAC
AAATTTTTTAAATAGACTGAATAATACAAAAGAAAATACAAGGGTTATAG
TATATTCTACACAAGGTGCTTCATCATCTTCAGCTTCTTGTTTTGTTGCA
GGATGTTTAAAGAAGAAAGGATATGTACCATCTATACAGATTAGCATAAA
AATGCCTAATAATTTTTACTTCTTTATAGGTAAAAAATATAATGAAATAG
GAAAGTTTTATAAAGGGGAGGATTGTAAAAGAATCTAATTCTTTAATAAG
GCTTCAATTTAGTAAAGTACTGAATAACGTGTTCAAAGGTAGGGTACCTA
AATTATCTAGAAATATATCATCAACTAAAGATTGTGTTAAATGTGGATTA
TGCCTTAGAAATTGTCCTCAAGGTAATAATAACATTTGAAAATGGACATGC
AGTTTTTCATAGCAAATGTATTTTATGTTTGAGATGTATACATATATGTC
CAATAAATGCAATAAGATATAGAGGTAAGAAAATAGATCAAACTCAAAAA
GATATTATCAGGTATTAGATCTGAATAAATAA >Gene ID No. 59:
RCCC00301 Contig0001_2468464_2468646
GAAATTGTTATCCAGGGACATAGCCACTCTTTGCTCACACTTGGAAAAGT
GTAAGTATTAGATGGGTAGTCATCCGATAAAAAATATTCGTCGCATCTT
TGACTTGTTATTTTCTTTCAAATGCCTAAATTATCTTTTAAAATTATAA
CAAATGTGATAAAATACAGGGGATGAAAACATTATCTAAAAGTTAAGGAG
GTGTTACATAAGATGGCATATAAAATTACAGAAGAGTGTGTAAGTTGTGG
TTCAGTCTGCTTCAGAATGTCCAGCTGATGCTATAAGCCAAGGAGATAGTC
AATTTGTAATAGATCCAGAAAATGTATAGAATGTGAAACTGTGCTAAT
GTTTGTCCAGTAGGAGCACCAGTTGAAGAAAACTAA >Gene ID No. 60:
RCCC00336 Contig0001_2498650_2498835
ATATGGAAGCTAAAAAGGCAGAAGAATACATATCAAACTCATTGGAATAT
AATGATTTGCTTAATAACTTTATAAAAAAATTAAAATAGAAATTAAATTA
TTTAATAAGCATTATTTTGGAATAATAAAGTGTACTTTAAAGTAAC
TAATTATATAGCGAGGAGTGAAAACTTGTTATTAATAACAGGAAAATAGT ATGAAAGCTGTAGTTGATAAAGACACTTGTATAGGATGTGGGTTATGTCC
AAGTATATGTCCAGAGGTTTTTCAGATGGATGATGATGAAAAAGCTAAGG
CAATTGAAGATAATGTCCCAGGAGAAGCAGAGGACACTGCGAAGGAAGCA
GAGGACAGTTGTCCTGTTTGTGCTATTAAGGTAAGCTAA >Gene ID No. 61:
RCCC01168 Contig0001_4158324_4159373
GTTGAAACATTTCCAATTTTCGAAATTGTCCTATAGTGTACATAAAAAC
CTCCTAATATTTATTTCCTTCGAAGTGATTAATTATATTTTAAACTTTAC
CATAATGTCAAAGTCAATAGAGATAGAGTCAAAAATTGAATTATGGGATT
TGCTGGGTAAACTATGCTCTATAATTTTTAGTAGAATAAAAAATTTAATTTA
TTGCTGGAGGTTTATTCTATGAAAAAAGTTTATTTTAAGGCTATTGATTC
ATACTCCAAAACAGAAGAGATAAGTGATGCTGCTGGCAAACTCTTAAGAA
AAGTAGTGGAAGAGGAGCATATAAGTCTTGAAAAATTCATACCTCTCAAG
GTTCATTTTGGAGAAAAGGGTAATAATACTTTTATACAATCAAAAAATTT
TGTTGGTATAATAAATTATTTAAAGGAAAATAACATAGATAGTGCATTTA
TAGAGACGAATGTTCTCTATAGAGGTGAAAGAACTACAAGAGAAAAGCAT
TTGAAACTAGCAAAAGATCATGGGTTTACGGAACTCCCTATAATAATAGC
CGATGGTGAACATGGAGAGATTTTGAGGAGATTGAAATCAGTAAAAAGA
ATTTTAACAAATGTAAGGTAGGAAAACAAATTGCAAACAAAAAACAGCTT
ATTGTCCTAAGTCACTTTAAAGGTCATATACTTGCTGGTTTTGGAGGTGC
CATAAAACAACTTGGAATGGGATGTGCATCAAGAGGAGGAAAGCTTGCCC
AGCATGCAAATTCTACACCTAAAATTAACTTTTTTAAGTGTAAAGGCTGC
AGCGCTTGTGCAAAAAAGTGCCCTCAAAATGCCATAACTGTAAATAGAAA
GGCAAAGATCAATAAAGACAAGTGTATTGGATGTGCCTCTTGTATGGCAA
TATGTCCACAGGGAGCTATTTACCACAGCTGGATTGATCATAGCCAAA
TCTTTTAATGAAAGACTTGCAGAATATGCTTATGCTGCAGCAAAGGAAAA
AAATAATATTTATATAACCTTTGCTTTTAATATAACTAAAAATTGTGACT
GTGAAGGACACAATATGAAATCAATAGCAAATGATATTGGAGTTTTTGCT
TCAACGGATCCTGTACTGCTATTGAAAAGCATGCCTTGATGTTCTTGATAA
AAATAATGATAGAATTGTATTTAAAAGGGGCAGGTATACTCTTGATTATG
CAGAAAAAATAGGCTTGGGTAGTAAAAAATATGAACTTGTTGAAATAAAT
TAG >Gene ID No. 62:
RCCC02435 Contig0001_320737_320336
ATCTGATGGCTACCTACTGTAACACTCCCACGCACACAGCGAAAGCGACT
ATCACCCAAATCAAAGATTTGGGATATCTGCTTTTCCCACTAAGTAAGATT
CGTTGATATAAACCAAAATAATAGGCATAAAATTTGCGGTATTGATATAT
ACCTTATATATTTGTATAATTAAGATATATGTACAAAGTATATATAAATA
ATGTTTAAAGGGGAATGTATTATGAAAAAATTAGTTGTTAAAGATAAGTC
TTTATGTATGTCTTGTTTAAGTTGTGAAATGGCTTGTTCCGAGGCATTTT
ACAAAACCTACGGCCAATTCTTGATTAAGATTGATGAAGGAAAAGATGGA
TCTGTAGATTTAAAAGTATGCAATCAATGTGGAGTGTGTGCTAAAAAATG
TCCTGAAGAGGCAATTAAACAAAATGCTAAGGGAATATATATGATAGATA
AAAAAGCTTGTACTGGCTGTGGTACATGTGTAGAAGCCTGTCCAAAAGGT
ATTATTGTAAAAGTAGAAGACAAGCCTAATCCAAGTAAGTGTATGGCATG
TGGTATTTGTGTTAAAGCTTGTCCTATGGGAGTACTTGAAATTCAAGAAG
ATTAA >Gene ID No. 63:
RCCC02890 Contig0001_794294_793599
ATTGTTATGTTGCGGTTGTGGATGCAGATAATTGTACAATAAGTAGTAGA
GAAGGAAACGAAATTTTCGTTTCCTTTTCTCTATTTAAAGAAAGATATTG
TTATCTGTTATGTACTCTTTAGACTTAGTAACATATGTTACGGATTTTGT
GACTGCATTTTATTATAATATAGACAGTAAAATAAGGAGGAGAAAATATT
ATGATAAGAAAATTGTTAATATAAATAAAGAGAAATGCAATGGATGTGG
ACTTTGCGTAAATGCATGTCATGAAGGTGCTATTGAACTTGTAAAGGGAA
AAGCTGAACTTATAAGTGATGAGTACTGTGACGGACTTGGTGACTGTCTT
CCTGAATGTCCTACAGGAGCTATAAGTATAATTGAAAGAGAAAGCAAGGA
TTATGATGAGGAACTAGTTGCTAAAAAGGCTAAAGAAAAAGGAAGAAGTTA
TGCCTTGTGGATGTCCAGGTACAGCAGCTAGAAGAATAGAGAGAGCTTCA
GATAAAAATGCGTATACAGATAAAAAGAATTCGGAAGATTTTAGTGCCGC
TTCTGACTTAACACAGTGGCCTGTTCAATTGAGACTTATAAATACAAATG
CACCTTATCTTAAGAATGCGAAGTTACTTGTAGCTGCTGATTGTACTGCA
TATGCCTGTGGAGATTTTCACAAAAAATTTATAAAGGATCACATTACAGT
AATAGGGTGTCCTAAGTTAGACGACATTAATATATTATGAAGATAAATTAA
CTGAAATTATAGAAAAAATAATTTGAAAAGTATAACTGTAGTGAAATG
GAAGTACCATGCTGCTCAGGCATTGTAAATGCAGTGAAAAATGCAATGCT
TAGGGCAAAGACAATAATTCCTTATGAGGAAGTTATAATATCAATTTAA >Gene ID No. 64:
RCCC03063 Contig0001_983504_982689
AAGAATGGTGTTTATAATATGCTTAATATGCTGCTGGATTCCCTAGAAG
GTGATATGAATGGGGATGAACGAAGAAATGTGGTAAGATTTGCGTTTAAA
TACAATTATGATGGATTTAAAAGATTACTTACAGAATACACTAAGTAAAA
TTGTGAATGGGAAAGTGTAGAATTACATTGAAAAAGGAGTAAAAACTTT TABLE 1-continued Sequence Listing
Minimum set sequences ATGATGAATGTAAATAGTGAAAAGTGTATAGGATGCGGACAATGTGTTAA
AGATTGTTTTGCAAGAGACATAGAGATAATAAATGGTAAAGCTAAAATTA
ATAATATTACTTGCATAAAGTGCGGGCACTGTATTGCAGTGTGCCCTAAA
AATGCAGTATCAACGGACGAATATAACATGGAAGATGTAAAAGAATATAA
TAAAGAATATTTTTCCATAGATGCTGATACTTTATTAAATTCTATTAAGT
TTAGAAGAACTATAAGGCAGTTTAAAGACAAAGAAGTAGAGAAGGAAAAA
CTGCTTAAAATTATAGAAGCTGGAAGGTTTACTCAAACAGCAAGTAATAT
GCAGGATGTATCTTATACAGTTGTAAGAGATGGAATACAGGATTTAAGAA
AATTAATAATTGAAAGTTTAAATCAAATTGGAGAAAAAATACTTAAAGAT
ACAAATGCGAAAAATATACTTTATCAAAGATATGCTAAAATATGGATTGA
TATGTATAAGGAATATAAAGAAAACCCTAAAAATGATAGATTGTTTTTA
ATGCTCCAGTAGTAATAGTTGTTACAGCAAGACAGGAAGTAAATGGAGCT
TTAGCATCTTCAAATATGGAACTTATGATTAATTCTTTAGGACTTGGAAC
GTTGTTTAGTGGTTTTTCTGTTGCGGCTGCCCAAATGGATGAAAAAATAA
GTAAGTTTCTTGGAGTTAAGAAAGGAAGAAAGGTTGTAACTTTCATGATA
GTTGGATATCCTAATGTGAAATATCTAAGAACTGTACCAAGGAGAAAAGC
AGATATACGCTGGAAGTAA SEQ ID NO. 2
>Gene ID No. 20:
RCCC01717 Contig0001_3590430_3591623
TATAAACTTGTTCAAAGATTTGCAAAAGCTGATGCTATAAGGACCTGTATG
CCAGGGATTTGCAAAACCTATAAATGATTTGTCAAGAGGATGTAACTCCG
ATGATATAGTAAATGTAGTAGCTGTAACAGCAGTTCAGGCACAAGCTCAA
AAGTAATAACAAAAAGCATAAATGATTCATTTTTAGGAGGAATATTAAAC
ATGAAAATATTAGTAGTAAACTGTGGAAGTTCATCTTTTAAAATATCACT
TATTGTATATGAAAGATGAAAGCGTTGTGGCAAAAGGACTTGTAGAAAGAA
TAGGAGCAGAAGGTTCAGTTTTAACACATAAAGTTAACGGAGAAAAGTTT
GTTACAGAGCAGCCAATGGAAGATCATAAAGTTGCTATACAATTAGTATT
AAATGCTCTTGTAGATAAAAACATGGTTGATAATAAAGATATGTCAGAAA
TATCTGCTGTAGGGCATAGAGTTTTGCATGGTGGAAAAAAATATGCGGCA
TCCATTCTTATTGATGACAATGTAATGAAAGCAATAGAAGAATGTATTCC
ATTAGGACCATTACATAATCCAGCTAATATAATGGGAATAGATGCTTGTA
AAAAACTAATGCCAAATACTCCAATGGTAGCAGTATTTGATACAGCATTT
CATCAGACAATGCCAGATTATGCTTATACTTATGCAATACCTTATGATAT
ATCTGAAAAGTATGATATCAGAAAATATGGTTTTCATGGAACTTCTCATA
GATTCGTTTCAATTGAAGCAGCCAAGTTGTTAAAGAAAGATCCAAAAGAT
CTTAAGCTAATAACTTGTCATTTAGGAAATGGAGCTAGTATATGTGCAGT
AAACCAGGGAAAAGCAGTAACTATGGGACTTACTCCCCTTGCAG
GACTTGTAATGGGAACTAGATGTGGTGATATAGATCCAGCTATAATACCA
TTTGTAATGAAAAGAACAGGTATGTCTGTAGATGAAATGGATACTTTAAT
GAACAAAAAGTCAGGAATACTTGGAGTATCAGGAGTAAGCAGCGATTTTA
GAGATGTAGAAGAAGCTGCAAATTCAGGAAATGCAACTATGGACAAAACTTGCA
TTAAATATGTATTATCACAAAGTTAAATCTTTCATAGGAGCTTATGTTGC
AGTTTTAAATGGAGCAGATGCTATAATATTTACAGCAGGACTTGGAGAAA
ATTCAGCTACTAGCAGATCTGCTATATGTAAGGGATTAAGCTATTTTGGA
ATTAAAATAGATGAAGAAAGATAAGAAAAGGGGAGAAGCACTAGAAAT
AAGCACACCTGATTCAAAGATAAAAGTATTAGTAATTCCTACAAATGAAG
AACTTATGATAGCTAGGGATACAAAAGAAATAGTTGAAATAAATAA >Gene ID No. 21:
RCCC01718 Contig0001_3589384_3590382
GATTAAATTTTTACTTATTTGATTTACATTGTATAATATTGAGTAAAGTA
TTGACTAGTAAAATTTTGTGATACTTTAATCTGTGAAATTTCTTAGCAAA
AGTTATATTTTGAATAATTTTATTGAAAAATACAACTAAAAAGGATTA
TAGTATAAGTGTGTGTAATTTTGTGTTAAATTTAAAGGGAGGAAATAAAC
ATGAAATTGATGGAAAAATTTGGAATAAGGCAAAGGAAGACAAAAAAAAA
GATTGTCTTAGCTGAAGGAGAAGAAGAAAGAACTCTTCAAGCTTGTGAAA
AATATTAAAGAAGGTATTGCAAATTTAATCCTTGTAGGGAATGAAAAG
GTAATAGAGGAGAAGGCATCAAAATTAGGCGTAAGTTTAAATGGAGCAGA
AATAGTAGATCCAGATACCTCGGATAGTACTAAAAAAATATGCAGATGCTT
TTTATGAATTGAGAAAAGAAGAAGGGAATAACACCAGAAAAGCGGATAAA
ATAGTAAGAGATCCAATATATTTTGCTACGATGATGGTTAAGCTTGGAGA
TGCAGATGGATTGGTTTCAAGGTGCAGTGCATCTACAGGTGATCTTTTGA
GACCAGGACTTCAAATAGTAAAGACAGCTCCAGGTACATCAGTAGTTTCC
AGCACATTTATAATGGAAGTACCAAATTGTGAATATGGTGACAATGGTGT
ACTTCTATTTGCTGATTGTGCTGTAAATCCATGCCCAGATAGTGATCAAT
TGGCTTCAATTGCAATAAGTACAGCAGAAACTGCAAGAACCTTATGTGAA
ATGGATCCAAAAGTAGCAATGCTTTCATTTTCTACTAAGGGAAGTGCAAA
ACACGAATTAGTAGATAAAGTTAGAAATGCTGTAGAAATTGCCAAAAAAG
CTAAACCAGATTTAAGTTTGGACGGAGAATTACAATTAGATGCCTCTATC
GTAGAAAAGGTTGCAAGTTTAAAGGCTCCTGAAAGTGAAGTTGAAGAAAA
AGCAAATGTACTTGTATTTCCAGATCTCCAAGCAGGAAATATAGGTTATA
AACTTGTTCAAAGATTTGCAAAAGCTGATGCTATAGGACCTGTATGCCAG
GGATTTGCAAAACCTATAAATGATTTTGTCAAGAGGATGTAACTCCGATGA
TATAGTAAATGTAGTAGCTGTAACAGCAGTTCAGGCACAAGCTCAAAAGT
AA >Gene ID No. 22:
RCCC00020 Contig0001_19768_21588
GGAGAACTGTATTGCTTATTATTTAAGCATTTTATTATAAAATAAAAAAA
CGTTATTAAATTATTTACTATGAATTCACTTGATAATCAACACATTGCAT
GTAATGTTGATTATTGAGTGTTTTTTTGTAACCATATTTGGCACAATTTA
TGCTCTATAACATTTCTGAAATAAATATATGTATATGAGGAGGAATTTCA
ATGTATGGTTATAATGGTAAAGTATTAAGAATTAATTTAAAAGAAAGAAC
TTGCAAATCAGAAAATTTGATTTAGATAAAGCTAAAAAGTTTATAGGCT
GTAGGGGACTAGGTGTTAAAACTTTATTTGATGAAATAGATCCTAAAATA
GATGCATTATCACCAGAAAATAAATTTATAATTGTAACAGGTCCGTTAAC
TGGAGCTCCAGTTCCAACTAGTGGAAGGTTTATGGTAGTTACTAAAGCAC
CGCTTACAGGAACTATAGGAATTTCAATTCGGGTGGAAAATGGGGAGTA
GACTTGAAAAAGCTGGCTGGGATATGATAATAGTAGAGGATAAGGCTGA
TTCACCAGTTTACATTGAAATAGTAGATGATAAAGTAGAAATTAAAGATG
CGTCACAGCTTTGGGGAAAAGTTACATCAGAAACTACAAAAGAGTTAGAA
AAGATAACTGAGAATAGATCAAAGGTATTATGTATAGGACCTGCTGGTGA
AAGATTGTCCCTTATGGCAGCAGTTATGACTATGAATGATGTAGATAAGATGCAG
CAAGAGGCGGCGTTGGTGCAGTTATGGGATCTAAAAACTTAAAAGCTATT
ACAGTTAAAGGAACTGGAAAAATAGCTTTAGCTGATAAAGAAAAAGTAAA
AAAAGTGTCCGTAGAAAAAATTACAACATTAAAAAATGATCCAGTAGCTG
GTCAGGGAATGCCAACTTATGGTACAGCTATACTGGTTAATATAATAAT
GAAAATGGAGTTCATCCTGTAAATAATTTTCAAGAATCTTATACGGATCA
AGCAGATAAAATAAGTGGAGAGACTCTTACTGCTAACCAACTAGTAAGGA
AAAATCCTTGTTACAGCTGTCCTATAGGTTGTGGAAGATGGGTTAGACTA
AAAGATGGTACAGAGTGCAGGAGGACCGGAGTATGAAACACTGTGGTGTTT
TGGCTCTGACTGTGGTTCATATGATTTAGATGCTGTATAAATGAAGCTAATA
TGTTATGTAATGAATATGGTATTGATACTATTACCTGTGGTGCAACAATT
GCTGCAGCTATGGAACTTTATCAAAGAGGATATGTAAAAGATGAAGAAAT
AGCCGGAGATAACCTATCTCTCAAGTGGGGAGATACGGAGTCTATGATTG
GCTGATAAAGAAAATGGTATATAGTGAAGGCTTTGGAGCAAAGATGACA
AATGGTTCATATAGGCTTTGTGAAGGTTATGGAGTACCTGAGTATTCTAT
GACAGTTAAAAAACAAGAAATTCCAGCATATGATCCAAGGGGAATACAGG
GACATGGTATTACCTATGCAGTTAATAATAGAGGAGGATGTCATATATAAG
GGATATATGATTAATCCTGAAATATTAGGTTATCCGGAAAAACTTGATAG
ATTTGCATTAGATGGTAAAGCAGCCTATGCCAAAATGATGCATGATTTAA
CTGCTGTAATTGATTCTTTAGGATTGTGCATATTCACTACATTTGGGCTT
GGAATACAGGATTATGTAGATATGTATAATGCAGTAGTAGGAGAATCTAC
TTGTGATTCAGATTCACTATTAGAGGCAGGAGATAGAGTATGGACTCTTG
AAAAATTATTTAATCTTGCAGCTGGAATAGACAGCAGCCAGGATACTCTA
CCAAAGAGATTGTTAGAAGAACCTATTCCAGATGGTCCATCAAAGGGACA
CGTTCATAGGCTAGATGTTCTTGCCAGAATATTACTCAGTACGAGGAT
GGAGTAAAGAGGGTATACCTACAGAAGAAACATTAAAGAAATTAGGATTA
GATGAATATATAGGTAAGTTCTAG >Gene ID No. 23:
RCCC01356 Contig0001_3966524_3969232
TAAAGAGCAATTATGAATAATAACATAGAAACAAACAATAAAAGTGA
GAATCTTGTTTATCCGATGACTACTCGCTCTAATACTCCCACTTCTGCAA
GTGGGAGTAAAGAGCGACTACGTCCCTGGATAACGATTTTTCCTAAAGGA
TAACGTCTTCTAAGTGCTGAAGCACTAAGAATACTGTTAATAAGCATCAG
GTGGAGTTAAAACTCCATCTGATGCCAAGAAATCTGTTTATATTTAACAG
CATGAAAAATAAGAAAGAGGTGTCATTAATGAAGGTAACTAAGGTAACTA
ACGTTGAAGAATTAATGAAAAAGTTAGATGAAGTAACGGCTGCTCAAAAA
AAATTCTCTAGTTATAGCTCAGGAACAAGTGGATAGATCTTTAGGCAGGC
AGCTATGGCAGCCAATAGTGCTAGAATAGATCTAGCTAAAATGGCAGTGG
AAGAAAGCGGAATGGGAATTGTAGAAGACAAGGTTATTAAAATCATTTT
GTTTCAGAATATATATATAACAAATATAAGGATGAAAAGACCTGTGGAGT
TTTAGAAGAAGACCAAGGTTTTGGTATGGTTAGAATTGCGGAACCTGTAG
GGGTTATAGCAGCAGTAGTTCCAACAACTAATCCAACATCCACAGCAATC
TTTAAATCTTTAATAGCTTTGAAAACTAGAAATGGTATAGTTTTTTCACC
ACATCCAAGAGCAAAAAATCAACTATTGCAGCAGCTAAGATAGTACTTG
ATGCAGCAGTTAAAGCTGGTGCTCCTGAAGGAATTATAGGATGGATAGAT
GAAGCCTTCCATTGAACTCTCACAGGTGGTAATGAAAGAACAGATTTAAT
TCTTGCAACTGGTGGCCCGGGTATGGTTAAGGCTGCCTATTCTTCAGGAA
AGCCTGCTATAGGAGTTGGCCCAGGTAACACACCTGCTGTAATTGATGAA
AGTGCTGATATTAAATGCAGTAAATTCAATACTCCTTTCAAAAACTTTT
TGATAATGGTATGATTTGTCTTCAGAGCAGTCAGTAGTAGTTGTAAGCT
CAATATACGATGAGTCAAGAAAGAATTTGCAGATAGAGGAGCGTATATA
TTAAGTAAGGATGAAACAGATAAGGTTGGAAAAACAATTATGATTAATGG
CGCTCTAAATGCTGGCATTGTAGGGCAAAGTGCTTTAAAATAGCACAGA
TGGCAGGAGTGGGTGTACCAGAGGATGCTAAGCTTATTATAGGAGAAGTT
AAATCAGTAGAACCTGAAGAGAGCCCTTTGCTCATGAAAAGCTGTCTCC
AGTTTTAGCTATGTACAAAGCAAAAGATTTTGATGAAGCACTTCTAAAGG
CTGGAAGATTAGTTGAACGAGGTGGAATTGGGCATACAATCTGTATTATAT
GTAAATTCAATGACGGAAAAAGTAAAAGTAGAAAAGTTCAGAGAAACTAT
GAAGACTGGTAGAACATTGATAAATATGCCTTCAGCACAAGGTGCTATAG TABLE 1-continued Sequence Listing
Minimum set sequences GAGATATATATAACTTTAAACTAGCTCCTTCTTTGACGCTAGGATGTGGT
TCCTGGGGAGGAAACTCTGTATCAGAAAATGTTGGACCTAAACATTTATT
AAACATAAAAAGTGTTGCTGAGAGGAGAGAAAATATGCTTTGGTTTAGAG
TACCTGAAAAAGTTTATTTCAAATATGGTAGTCTTGGAGTTGCATTAAAG
GAATTGAGAACTTTGGAGAAGAAAAAGGCATTTATAGTAACGGATAAGGT
TCTTTATCAATTAGGTTATGTAGATAAAATTACAAAAAATCTCGATGAAT
TAAGAGTTTCATATAAAATATTTACAGATGTAGAACCAGATCCAACCCTT
GCTACAGCTAAAAAGGTGCATCAGAACTGCTTTCCTATGAACCAGATAC
AATTATAGCAGTTGGTGGTGGTTCGGCAATGGATGCAGCCAAGATCATGT
GGGTAATGTATGAGCATCCAGAAGTAAGATTTGAAGATTTGGCTATGAGA
TTTATGGATATAAGAAAGAGAGTATATGTTTTCCTAAGATGGGTGAAAA
AGCAATGATGATTTCAGTAGCAACATCCGCAGGAACAGGATCTGAAGTTA
CTCCATTTGCAGTAATTACGGATGAAAGAACAGGAGCTAAATATCCACTG
GCTGATTATGAATTGACTCCAAACATGGCTATAATTGATGCAGAACTTAT
GATGGGAATGCCAAAAGGGCTTACAGCAGCTTCGGGTATAGATGCATTAA
CCCATGCACTGGAGGCGTATGTATCAATAATGGCTTCAGAATATACCAAT
GGATTGGCTCTTGAAGCAACAAGATTAGTATTTAAATATTTGCCAATAGC
TTATACAGAAGGTACAACTAATGTAAAGGCAAGAGAAAAATGGCTCATG
CTTCAACTATAGCAGGTATGGCTTTTGCCAATGCATTCTTAGGGGTATGT
CACTCTATGGCACATAAATTGGGAGCACAGCACCATATACCACATGGAAT
TGCCAATGCGCTTATGATAGATGAAGTTATAAAATTCAATGCTGTAGAGG
CTCCAAGGAAACAAGCGGCATTTCCACAATAAGTACCCAAATGTTAAA
AGAAGATATGCTAGAATAGCTGATTACTTAAATTTAGGAGGAAGCACAGA
TGATGAAAAGTACAATTGCTAATAAATGCTATAGATGACTTAAAAACTA
AGTTAAATATTCCAAAGACTATTAAAGAGGCAGGAGTTTCAGAAGATAAA
TTCTATGCTACTTTAGACACAATGTCAGAACTGGCTTTTGATGATCAATG
TACAGGAGCTAATCCAAGATATCCACTAATAGGAGAAATAAAACAAATGT
ATATAAATGCATTTGATACACCAAAGGCAACTGTGGAGAAGAAAACAAAA
AAGAAAAAATAA >Gene ID No. 24:
RCCC03300 Contig0001_1213196_1212027
TGTAAAATAAAATCAGAAATTAGTTAAATATTTAAAATAAAATAAAAATT
TATACAATGATGTATGAAAAAGCGATGAAGCTTCTAAAAGAATATTTATA
TTCTTAGGAAGCTTTTTTATTTTATTGGTAGCTATCAAAAAATTACAAA
ATTTAATATGACTAATGTGAAGTTTCATAGATATTTTATTAAATTGGAGT
ATGATTATTGTGAAAAATTTTAATGTTAAACCAAAGGTTTATTTGGTAC
TGATGCTTTAAATCATTTGTGTGAATTAAAAATGTAAGAAAGCTTTAATCG
CTGCAGATCCATTTTAGGTTAGTTGTCATCAACGGTTGATAAAATTACTGAA
CAGCTTGATAAGGCACATATAGAGTATGATATATTTTCAGATATAGTACC
AGATCCTCCTGTTGAAGTTATTATAAAAGGAGTGCAGGAAGCTGTTAAAT
TTAAACCTGATGTACTTATAGCACTTGGAGGAGGATCAGCTATTGATTCT
GCAAAAGGAATAAGGTATTTTTGTCAGTATGTAAATAGAATTACTGAA
CGAAATGAAAGAGCCCCTGTTTATAGCAATTCCGACAACAAGTGGTACAG
GCTCTGAGGTTACTAACTTTTGTATTGTAACTGATAAGCAAAAAGGAGTC
AAATATGCTCTTGTTGATGACAATTTGACGCCGGATCAGGCGGTACTTGA
TATTGAACTTGTAAAATCAGTGCCAAAAGCTACCACATCAGAAACGAAA
TAGACGTACTTACACATGGAATTGAAGCATATGTTTCTACAAATAGATCA
GATTATTCTGATGCACTGGCAGAAAATCAATAAAAATGGTATTTAAATA
CTTGTTAGCCGCATATGAAAATGGAGATGATGAAGAAGCTAGAACGAAGA
TGCATAATGCATCCTGCATAGCAGGTATGGCATTTACAAATGCTTCCCTT
GGACTTAACCATGGCATGGCTCATGCACTTGGTGGAAAATTCATATACC
GCATGGAAGAGCAAATGGACTACTTCTTCCATACGTAATAGAGTATAATG
CAAACCTTAAAAACTTACAAGGAAAGATAAACCATTCTAGTGCAGCATAT
AGGTATACTGAAATATCAAAATTCTTGGGACTTCCAGCATCTAACCAATT
TGAAGGTGTTAGGAGTTTGATTGCAGCAGTTAAGATACTGATGAATAAAC
TTAACTTACCTAAATGTATTAATAATTGTGAAGTTTTATGTGAAAATTTG
GATAATGAGATTCATGAGTTATCGATAACTGCCCTAAATGATAGATGTAC
AAAAACAAATCCGAGAATTCCTGAAATAAAGGATGTTGAAAATTGTTTA
AGAGGGTTTTTCTAAAGAATAA >Gene ID No. 25:
RCCC01567 Contig0001_3730455_3731297
CATAAAAGAAGAGCATGCAATTAGTTTTAAATTATTAGATAGTGTAAAGC
GTTATAAACAATTTCTTGATACATACCCTGATTTGGAAGAACGTGTTAAG
CAGTGTTATATTGCATCCTATTTAGGAATAACTCCTGTGTCTCTTAGCAG
AATAAGAAGAAATTAAATCTTAACAAATGATAATGCAATAAATCTCTAG
GTGATTTATGATGAGTTAATTTTTATTACTGGAGGTTAATTGTTATGAA
AAATGAAATAGTTGTTTTAATTACTGGATGTTCTACAGGGATTGGAAGAG
AGCTTTGTAGTATATTGTTTCACAAAGGATGTACGGTTGTTGCAACAGCA
AGAAATGTAGAAACTTTAAAAGATTTATCTGCGTCCTTAAGATTACCACT
GGATGTTACCCAAAAAGAGTCTATTAACGGACTACAATAAATGAGTTGTAT
CAAAATTTCATAAAATTGATATTCTTATAAATACGCAGGCTATTCAATT
AGAGGAGCTTTAGAAGAATTGATTTAAATAGTGCTAAAAGTATGTTTGA
TGTAAATGTATTTGGTATTATTAACATGATTCAGGCAGTTATTCCAGAAA
TGCGTAAAAAACAATTTGGTAAGATTATAAATATTGGCTCCATTTCAGGG
AAATTTGTTCAATCCATCAATGGAGCGTATTGTGCATCAAAATTTGCAGT >Gene ID No. 26:
RCCC02765 Contig0001_686363_687232
TAGTTGATATATAACTTTTTAGTCGTACAAATACGAAATATATTTTATCA
TACTTTGCATGTAAAATGCTATACAGCTTATACTTCTAAAGTTTGTTTATA
TTAGTTCACAGGGTTTCAAAAATTGTAGTTTATAATCACATATATTTCG
AAATTCATATATTAAATAGAGTACTTTACAATATTGGAGGAACTACTAT
ATGTGTTCAAATCATATTGGATGCAAATTTCCACGCTTTTTTTCCACCCCA
ACATCAGCCACATCAACCTGGTATTGAATATATTTATGCACCTAGACCAG
TTTTCGAACCACCATTATGTGCACAATATCAAACGACAAAAAGATTATTA
AACAAAGTAGCTTTAATAACAGGAGGAGACAGCGGTATTGGGCGTGCTGT
AGCATGTGCTTATGCAAAAGAAGGAGCTGATATTGCCATTGTCTATCTAA
ATGAACATGTAGATGCAGAGGGAACAAAATCTAGAATAAAAATTGGGG
CGAAGATGTTTAACCATTCCAATTAACATAGGAGTCGAAGAGAATAGTAA
AATTATAATTCAAGAAGTTATGAATCATTTTGGTAAATTAGATATTTCTTG
TAAATAATGCTGCAGTACTTTATTACAATAATTCTATAGAAGAAGTATCT
AGCAAACAATTAGAATGGACTTTTCGTATAAATGTATTTTCTTATTTCTA
CTTAACTAAAGCAGCTCTACCTTATATGAAACCAGGCGGTTCTATCATCA
ATACTTCTTCAATAGTTGCTTTTAATCCTCCTTTATGGAGATATCTTTAGAT
TATGAAGCTTCAAAAGGTGCCATTGCTGCTAATTTCACTATAAATTTAGCCCG
AAGTTTGGTTTCAAGAGGAATACGTGTAAATGGTGTAGCTCCAGGTGAAA
CCTGGACACCTTTAATTCCAGCAGGATTACCTGCAGATAAAGTTGCCGTT
TGGGGTTCAAAACACCAATGGGAAGAGCTGCTCAACCATTTGAAATTGC
TCCAGCTCCATGTATTCTTAGCTTCCAATGAATCAAGCTATATGTCAGGAC
AAACAATCCATATGTATTCTTAA >Gene ID No. 27:
RCCC03290 Contig0001_1203895_1202426
GAGTAAAAGTTGATGAGGAGAGAAATCAGGGTCACTTCTCGAAATAAAA
CAAAAACTTGAAGAATGAAAGTTATTGAACTCAGAAATATGGCTAGAAA
AATGAATTTAAGTTCATTGACTAAGAAGGACATTAAATTTGGCAAGAAAA
AGCAGCTGATTAAAGCAATTTTAGATACTATACAAGGAGGTTAAAGTAA
ATGGAAAATATAGATAGGGATTTACAATCTATACAAGATGTAAGGCGGCT
TGTTGAAAAGGCAAGACAAGCTCAACAAGAATATTGTAAATTCAGTCAGG
AAAAGATGAATAAAATTATTGAGCATGTAGCGGAATCTGCTGGCTTACAA
GCTGAAAGATTAGCAAACTTGCTGTAGAAGAAACAACTTTTGGAAATTT
ACCTGATAAGATAATTAAAATAAGTTTGCTAGTGAAATAGTGTATGAAA
ATATAAAGGACATGAAGTTAGTAGGTATTTTAAGAGATGACAAAGATAGA
AAAGTATTAGAGATAGGTTCACCTGTAGGTATTATTGCAGGGCTTGTACC
ATCAACTAATCCTACTTCTACTGTTATATATAAAAGTCTTATAGCTTTAA
AATCGGGAAATGCAATTGTATTTAGTCCTCATCCAAAGGCAAGACATTGC
ATTGCAGAAGCTATAAAGGTTGTAAGTGATCAGCTGTTGAGGCAGGAGC
ACCTTTAGGAATGGTTTCCGGAATGAGTATACTTACTATGGAAGGAACTC
ATGAGCTTGATAAGTTTGATCTCATACTAGCAACAGGTGGATGGACCT
ATGGTAAAGGCAGCATACAGTTCAGGAACTCCGGCTATAGGAGTTGGACC
TGGAAATGGACCTGCTTTTATTGAAAAAACAGCAAATATAAAACTTGCAG
TAAAAAGAATAATGGATAGTAAAACTTTTGACAATGGGGTAATATGTGCT
TCAGAACAGTCCATAGTAGTTGAAAAGATGTATAAAAGATGAAGTTGTAGA
TGAGCTTAAACGCCAAGGAGCATACTTCTTATCTAAAGAACAATCAGAAA
AAGTAGCAAAGTTTATATTGAGAGCAAATGGTACTATGAATCCTCAAATT
GTAGGAAAATCAGCTCAGAAAATAGCTGAAATGGCAGGTATAACTGTAGA
TCCAAATGCAAGAAATATTGATTTCAGAGCAGACGACAGTTGGAAAAGATA
ACCCATTTTCAAGGGAAAGCTTACAACGATTTTAGCATTCTTACTGTGAA
GAAAATTGGGAAAAGCTTGCGAGAGATGCATTGAGCTTTTAAATAATGA
AGGTATAGGACATACTCTCATAATACATTCAATAATGAAGAAATAGTAA
AAGAATTTGGACTTAAAAACCTGTATCCAGAATACTTGTAAACACGCCA
GGATACTCTTGGAGGATAGGAGCTACTACAAATCTAGTGCCTGCACTTAC
ACTTGGATGCGGAGCAGTTGGAGGAAGCTGCAACTTCTGATAATGTAGGAC
CTAGGAATCTTATAAATAAGAAGAGTTGCCTATGGAGTAAAGGAAATA
GAAGATATAAAAAATTTTGTAAGTAATTGTAGTGACAGAGAAACCTCACA
CACTGTTTTGGATATTTCTGATCAGTACATTGAACTTATAACTAAAAAAA
TAGCTGAAAAGCTTAGTTTGTAA >Gene ID No. 28:
RCCC04101 Contig0001_2040462_2038897
ATGGTTTAGAAAAGCTATTGAGATTTTAAGTAAGTTTAAGGTAATAGAG
CTTCGAAATCTCGCTCGTAAATATAAGAACTTTGGTATCAAAGGAAGGTC
CATTTCTAAAGCAGACAAGAAGTTGCTGCTTATAGAGTTCAAAAATATT
ATGGGCATAATTAGCCAGCTATAAAAATTAAAATATATAAATAATAAACA
ATGGAGGGAACACAATTGGAAAATTTTGATAAAGACTTACGCTCTATACA TABLE 1-continued Sequence Listing
Minimum set sequences AGAAGCAAGAGATCTTGCACGTTTAGGAAAAATTGCAGCATGTGAAATTG
CTGATTATACTGAAGAACAAATTGATAAAATCCTATGTAATATGGTTAGG
GTAGCAGAGGAAATGCAGTTTGCCTTGGTAAAATGGCTGCAGAAGAAAC
TGGTTTTGGAAAAGCTGAAGATAAGGCTTATAAGAACCATATGGCTGCTA
CTACAGTATATAATTATATCAAGGATATGAAGACTATTGGTGTTATAAAA
GAAGATAAAAGTCAAGGTGTAATTGAATTTGCTGAACCAGTTGGTTTATT
AATGGGTATTGTACCATCTACAAATCCAACATCTACTGTTATCTATAAAT
CAATCATTGCAATTAAATCAAGAAATGCAATTGTATTCTCACCACACCCA
GCTGCATTAAAATGTTCAACAAAAGCAATAGAACTTATGCGTGATGCAGC
AGTAGCAGCAGGAGCTCCTGCAAATGTAATTGGCGGTATTGTTACACCAT
CTATACAAGCTACAAATGAACTTATGAAAGCTAAAGAAGTTGCTATGATA
ATTGCCACTGGAGGCCCTGGAATGGTAAAGGCTGCTTATAGTTCAGGAAC
ACCTGCAATAGGCGTTGGTGCTGGTAACTCTCCATCTTATATAGAAAGAA
CTGCTGATGTTCATCAATCAGTTAAAGATATAATTGCTAGTAAGAGTTTT
GACTATGGTACTATTTGTGCATCTGAGCAATCAATAATTGTTGAAGAATG
CAACCATGATGAAGTAATAGCTGAGTTGAAGAAACAAGGCGGATATTTCA
TGACAGCTGAAGAAACTGCAAAAGTTTGCAGTATACTTTTTAAGCCTGGT
ACACACAGTATGAGTGCTAAGTTTGTAGGAAGAGCTCCTCAGGTTATAGC
AGCAGCTGCAGGTTTCTCAGTTCCAGAAGGAACAAAAGTTTTAGTAGGAG
AACAAGGCGGAGTTGGTAATGGTTACCCTCTATCTTATGAGAAACTTACA
ACAGTACTTGCTTTCTATACAGTTAAAGATTGGCATGAAGCATGTGATCT
TAGTATAAGATTACTTGAAGATAATGGTCTTGGACATACTATGAACATTCATA
CAAATGCAGAGACTTAGTAATGAAGTTTGCTAAAAAACCAGCATCCCGT
ATATTAGTTAATACTGGTGGAAGCCAAGGAGGTACTGGTGCAAGCACAGG
ATTAGCACCTGCATTTACATTAGGTTGTGGTACATGGGGAGGAAGCTCTG
TTTCCGAAAATGTTACTCCATTACATTTAATCAATATAAAGAAGTTGCA
TATGGTCTTAAAGATTGTTCTACATTAGCTGCAGATGATACAACTTTCAA
TCATCCTGAACTTTGTGGAAGCAAAAATGACTTAGGATGCTGTGCTACAA
GCCCTGCAGAATTTGCAGCAAATAGCAATTGTGCTAGCACTGCTGCGGAT
ACTACTGATAATGATAAACTTGCTAGACTCGTAAGTGAATTAGTAGCTGC
AATGAAGGGAGCTAACTAA >Gene ID No. 29:
RCCC04114 Contig0001_2051568_2050075
AAGCTGTAACAGATATGGGCGCTGAAGTTTATAGTTCAGTTGTTATTGCA
AGTCCACATCCGGATCTTCAGAAAATCACCAAACGTTATACAATTGAAAA
TTTACTTCCTTAATATGTGGATGATATGATACCACCACATAAAATGAAAA
AGTACAGAAGTACAGTACTTAGTTAGTAAAAATGAAAGGGAGAGTTAGAA
ATGAAATATTATTGATAATGATTTGCTCTCCATCCAAGAATCCCGAATCT
TGTGGAAAATGCTGCACGAGCACAAAAAATGTTAGCAACTTTTCCGCAAG
AAAAGTTAGATGAGATTGTTGAACGTATGGCTGAAGAAATCGGAAAACAT
ACCCGAGAGCTTGCTGTAATGTCACAGGATGAAACTGGTTATGGAAAATG
GCAGGATAAATGCATCAAAAACCGATTTGCCTGTGAATATTTGCCAGCTA
AGCTTAGAGGAATGCGATGTGTAGGTATTATTAACGAAAATGGTCAGGAT
AAGACCATGGATGTAGGTGTACCTATGGGTGTAATTATTGCATTATGTCC
TGCAACTAGTCCGGTTTCTACTACCATATATAAGGCATTAATTGCAATTA
AGTCTGGTAATGCAATTATCTTTTCTCCACATCCTAGAGCAAAGGAGACA
ATTTGTAAGGCGCTTGACATCATGATTCGTGCAGCTGAAGGATATGGGCT
GCCAGAAGGGAGCTCTTGCATACATTACATACTGTGACGCCTAGTGGAACAA
TCGAATTGATGAACCATGAGGCGACTTCTTTGATTATGAATACAGGCGTT
CCCGGGATGCTTAAAGCGTCATATAGATCTGGAAAACCTGTGATCTATGG
AGGAACTGGTAATGGACCAGCATTTATTGAACGTACAGCTGACATCAAGC
AGGCGGTAAGAGATATTATTGCTAGTAAGACCTTTGATAACGGAATAGTA
CCATCATCTGAACAATCTATTGTTGTAGATAGCTGTGTTGCATCTGATGT
TAAACGTGAGTTGCAAAATAGTGGTGCATATTTCATGACAGAGGAGCAAT
CACAAAAACTGGGTTCTCTCTTTTTCCGTTCTGATGGTAGTATGGATTCA
GAAATGGTTGGCAAATCCGCACAGAGATTGGCTAAGAAAGCAGGTTTCAG
TATTCCTGAAAGTAGCACAGTGCTAATTTCAGAGCAGAAATATGTTTCCC
AAGATAATCCTTATTCCAAGGAGAAACTTTGTCCGGTACTAGCTTACTAC
ATTGAAGATGATTGGATGCATGCATGTGAAAAGTGTATTGAGCTGCTATT
AAGTGAGAGACATGGTCACACTCTTGTTATACATTCAAAAGACGAAGATG
TAATTCGCCAGTTTGCATTAAAAAAACCTGTAGGCAGGATACTTGTTAAT
ACGCCTGCTTCCTTTGGTAGTATGGGTGCTACAAGTAATTTATTTCCTGC
TTTAACTTTAGGTAGTGGATCGGCAGGTAAAGGTATTACCTCCAGTAATG
TTTCACCAATGAATCTTATTTACGTCCGTAAAGTCGGATATGCGTACGG
AATGTAGAAGAGATTATTAATACTAATGGATTGTTTACAGAAGAAAAAAG
TGATTTGAGTGGTATGACAAAGCAGTCAGACTATAATCCAGAGGATATAC
AAATGTTGCAGCATATTTTGAAAAAAGCTATGGAAAAAATTAAATAG SEQ ID NO. 3
>Gene ID No. 44:
RCCC01825 Contig0001_3489615_3490466
ATGAATACTGTAATTATGATTTTAGTTGTAATGACTGTTATAGGTCTTAT
ATTTGGACTTGTTTAGCCTATGTAAATAAAAGATTTGCAATGGAAGTAA
ATCCACTTGTGGACTTAGTAGAAGATGTACTTCCAAAAGGCCAATGTGGA
GGGTGTGGATTTGCAGGATGTAAAGCTTATGCAGAAGCTGTTGTTTTAGA
TGAGAGTGTACCTCCAAATCTTTGTGTACCTGGAAAAGCAGCAGTTGCAG AACAGGTGGCAAAGTTAACGGGTAAATCTGCTCCACCTATTGAACCTAGA
GTTGCACATGTAAGATGTGGTGGAGATTGTACAAAGGCAGTTAAAAATTT
TGAATATGAAGGTATACATGATTGTGTAGCTGCAAATTTACTTGAAGGTG
GACCTAAAGCTTGTAAATATGGATGTCTGGGATTTGGGACATGTGTAAAG
AGCTGTCCTTTTGGACTATGGCAATGGGTTCAAATGGACTTCCAATAAT
TGATACAGATATATGTACAGGTTGTGGTACCTGTGTAAGCGCGTGCCCAA
AACAGGTACTTGGATTAGGCCTGTAGGTTCTAAAGTAATGGTTAATTGT
AATTCTAAAAATAAAGGTGGAGCTGTACGTAAGGCATGTAGTGTAGGATG
TCTTTGGATGTGGATTGTGTGCTGTAAAAATTGTCCAAATGATGCCATTAAAG
TAGAGAACAATCTAGCAGTAGTAGACCAAAGTATTTGTGCGTCATGTAGT
GAAGCTACCTGTCTTGCTAAATGTCCTACAGGAGCTATTAAGGCTATTGT
AAGCGGTACAGACTTACAACAGCAGAGCAAGAATGAAGCTGCTGCAAATT
CATAA >Gene ID No. 45:
RCCC01826 Contig0001_3489018_3489596
ATGGCATCTTACCTTACTCTTTTTATAAGTGCAGTAGTTGTAAATAACTA
TGTTTTAACAAGGTTTTTGGGACTTTGTATATTCTTTGGTGTTTCTAAGA
ATTTAAATGCTTCTGTAGGTATGGGTATGGCTGTTACTTCTGTTATTACT
ATGAGTTCAATATTGGCCTGGGTAGTATATCATTTTGTACTTATACCATT
TAATTTAACTTTCTTGAAGACAGTAGTTTTTGTACTTCTTATTGCTAGTT
TTGTACAGTTTTGGAGACTATTATTAAAAAGCAGGCACCAGCCCTATAA
AATATGTGGGAATATACCTTCTTTTAATAGCTACAAACTGTATAGTACT
TGCTGTACCTATATTAAATGCTGATTCTAACTTTAATTTTTTACAGAGTG
TTGTTAATGCGATAGGATCTGGGCTAGGCTTTGCTATGGCTATAATTTTG
ATGGCAAGCCTTAGAGAAAAATTGAGATTAGCAGATGTACCTAAACCTTT
AGAAGGTCTTGGAGTAGCTTTTATTTTAGCAGGAATGTTAGCCCTAGCTT
TCCTTGGTTTTTCAGGTATGATTTCTATGTAG >Gene ID No. 46:
RCCC01827 Contig0001_3488377_3489015
ATGAAGAATTTGTGGAATATATTTAAAAAAGGATTGATTGCAGAAAACCC
CATATTCGTACTTGCACTTAGTTTGTGTCCAGCACTGGCAACTACAAGTA
CAGCTGTAAATGGATTTACCATGGGGCTCTGCGTGCTATTTGTTATAACT
TGTAATAATACTGTGGTTTCTATAATTAAGAATTTTGTAAATCCTAAGGT
ACGTGTACCTGTATATATCACTTGTATAGCAACTATAGTTACAGTAGTGG
AACTTGTTATGCAGGCTTATGCACCTCTATTATATAAGCAATTGGGAATT
TATTTAGCATTGGTAGTTGTATTTGCTATAATACTTGCCCGTGCAGAGAC
ATTTGCATCTAAAAATCCTGTAGTTCCTTCTTCTTTCTTTGATGGACTTGGAA
TGGGATGTGGATTTACTTTGGCACTTACTATAATAGGAATGATACGTGAA
TTATTTGGATCTGGAGCTATATTTGGTTTAATGTATTTGGGGCTTCATA
TAATCCAGCTTTGATTATGATACTTCCACCTGGAGGATTCATACTTATAG
GATATTTAGTTGCTATAGTAAAAGTTTATAACCAACATATGGAGAAAATT
AAAATGCAAAAATTAGAACAAGCAAATGGAGGTGAAGCATAA >Gene ID No. 47:
RCCC01828 Contig0001_3487817_3488371
ATGGCTAAAATAAAGATCAAATAGTATTTTTGCAATTACTAAGAACTT
AACCATTACGTGTTTTATATCTGGAATTATAATAGCTGCGGTTTATATG
TAACATCACCAGTGGCAGCACAAAACAAGTTCAAATACAAAATGATACC
ATGAAAGTTTTAGTCAATGATGCTGATAAATTTAATAAAGTAAATTGAT
AAAGGATTGGTATGCAGCTCAAAAAGGAAACAAGACAATTGCATATGTTG
TACCTGCAGAGAGTAAAGGTTACGGTGGAGCTATAGAGCTATTGGTAGCT
GTTACTCCAGATGGAAAAGTAATAGATTTCAGCATTGTATCTCATAATGA
AACTCCAGGACTTGGAGCAAATGCTTCAAAGGATTCTTTTAGGGGACAGT
TTAAGGATAAAAAGGCGGATGCCTTAACAGTTGTAAAAGATAAGTCTAAC
ACTAAAAACATTCAAGCTATGACAGGAGCTACAATTACGTCAAAAGCTGT
AACTAAAGGAGTTAAAGAAGCTGTTGGGCAAGTTACTACGTTTACGGGAG
GTAAGTAA >Gene ID No. 48:
RCCC01829 Contig0001_3486815_3487807
ATGGCGGAAGCACAGATAAAGAAAAATATTTTTACTATTTCGTCATCACC
TCATTGTCGTTGTGATGAATCTGTTTCTAAGATAATGTGGAGTGTCTGTT
TAGCACTAACTCCAGCTGCGATTTTTGGCGTATTTAATTTTGGAATTCAT
GCTTTAGAAGTAATTATAACAGGAATTATAGCTGCTGTAGTTACAGAGTA
CCTTGTAGAAAAGTTAGAAATAAACCTATAACTATTACAGATGGAAGTG
CTTTTTTAACAGGACTTTTACTTTCTATGTGTTTACCTCCTGATATTCCA
CCTTATATGGTAGCTATAGGATCTTTTATAGCAATAGCTAAACA
TTCTATGGGAGGACTTGGTCAGAACATATTTAATCCAGCTCATATTGGAA
GGGCTGCACTAATGGTTTCCTGGCCTGTAGCAATGACAACATGGTCAAAA
TTAAGTGCCAGTGGTGAAGGCTGTAACCACAGCAACTCCTCTTGGAAT
TTTAAAGCTTCAAGGTTATTCAAAATTACTTGAGACTTTTGGAGGTCAAG
GTGCACTTTACAAGGCAATGTTCTTAGGTACTAGAAATGGAAGTATAGGA
GAAACTTCTACAATATTACTTGTTTTAGGTGGACTTTATCTAATATATAA
AAAATATTAACTGGCAGATTCCAGTAGTAATGATCGGTACTGTAGGAA
TACTTACCTGGGCTTTTGGAGGAACTACGGGACTTTTTACAGGAGATCCT

TABLE 1-continued

Sequence Listing
Minimum set sequences

```
GTATTTCATATGATGGCAGGCGGACTTGTAATTGGAGCTTTCTTTATGGC
TACTGATATGGTAACAATTCCTATGACTATTAAAGGACAGGTTATTTTG
CATTAGGTGCAGGTGCGCTTACATCACTTATAAGATTAAAAGGTGGTTAT
CCAGAAGGCGTATGTTATTCAATATTACTTATGAATGCAGTTACTCCTCT
AATAGATAAGTTTACACAGCCAGTTAAATTTGGGACAAGGAGGTAA

>Gene ID No. 49:
RCCC01830 Contig0001_3485423_3486793
AACTTTAATTAATAAGAGTATCTTTTAAAGTTAACTGACATTTAATAGAT
AAATTGTCATTATATATTATTTCCTATAGTATATAATTTTATAACGGATT
ATGGAAAATTCTATAATCTGTTATAAAAATTATGTTTATATTTATTTTGC
AGTTTCGTTTATATACATGCTGTAAAAATTATTGAAAGAGGTGTTTAAGA
GTGTTAAAAAGTTTTCGAGGTGGAGTACACCCGGATGATAGCAAAAAGTA
CACAGCTAATAAACCTATAGAAATAGCACCTATACCAGACAAGGTGTTTA
TTCCCGTTAGACAGCATATAGGTGCTCCTACATCTCCTGTAGTACAAAAA
GGAGATGAGGTAAAAAAGGGACAACTTATTGCGAAGAGTGATGCTTTTGT
TTCAGCCAATATATATGCATCTACTTCTGGAAAGGTTGTAGATATAGGAG
ATTACCCACATCCTGGTTTTGGAAAGTGTCAAGCTATAGTTATTGAAAAA
GATGGAAAAGATGAGTGGGTAGAAGGAATACCAACTTCACGTAATTGAA
AGAGCTAAGTGCAAAAGAAATGCTTGGAATAATAAGAGAAGCAGGCATTG
TAGGAATGGGAGGCGCAACTTTTCCTGTTCATGTTAAACTTGCACCACCA
CCAGATAAAAAAGTAGATGTTTTTATTTTGAATGGTGCTGAGTGTGAACC
TTATTTAACTGCAGATTATAGGTCCATGTTGGAAAAATCAGATAAGGTAG
TTGCTGGAGTTCAAATAATTATGAAAATCCTCAATGTGGAAAAAGCATTT
GTAGGTATTGAAGATAATAAACCAGATGCCATAGAAGCTATGAAAAAAGC
TTTTGAAGGTACAAAAGTACAAGTAGTAGGCCTTCCTACTAAGTATCCTC
AGGGTGCTGAAAAAATGCTTATAAATGTTTTGACAGGTAGAGAAGTTCCA
TCAGGTGGATTGCCTGCAGATGTAGGTGCGGTTGTTCAAAATGTAGGTAC
ATGCATAGCAATAAGCGATGCAGTGGAGAGAGGAATTCCACTTATACAGA
GAGTTACAACTATAAGTGGAGGTGCTATTAAAGAGCCTAAAAATATATTA
GTTAGAATTGGAACTACATTTAAAGATGCCATTGATTTTTGTGGAGGATT
TAAGGAAGAACCAGTTAAAATAATTTCAGGTGGACCTATGATGGGATTTG
CCCAATCAAATTTGGATATTCCAATAATGAAGGGTTCATCAGGAATACTT
GGTTTAACTAAAAATGATGTAAATGATGGAAAAGAATCTTCTTGCATTAG
ATGTGGCAGATGTCTAAAAGCCTGTCCTATGCACTTGAATCCAAGTATGT
TAAGTATTCTTGGACAAAAAGATTTATATCAAGAAGCTAAGGAAGAATAT
AATCTTTTGGACTGCGTAGAATGCGGCAGCTGTGTATATACATGTCCTGC
TAAACGAAGAATTGTACAGTATATTAGATATTTAAAATCAGAAAATAGAG
CTGCAGGGGCAAGGGAAAAGGCTAAAGCAGAAAAGGCTAAAGAAAAGAAA
GAAAAAGAAGAGGTCTTAAAATAA
```

In order to create the minimum sets found in SEQ ID NOS. 1-3, the genomes of *C. ragsdahlii*, *C. ljungdahlii*, *C. autoethanogenum*, and *C. carboxydivorans* were fully sequenced. A sequence-level analysis and comparison was performed with a cutoff score of $P=1\times10^{-20}$, and function was established for the genes present. At such a level of identity, one of skill in the art recognizes that there is virtually no probability that the alignment is the result of chance. Therefore, the minimum sets found in SEQ ID NOS. 1-3 represent fully conserved sets.

At the present time, screening potential microorganisms for high ethanol titer production capability is an extended and daunting task. Function may be established, but often through costly and time-consuming bench assays. Using several embodiments of the present invention, however, a prospective microorganism may be prescreened for function, and such function may be confirmed.

To practice such embodiments, a sample is first collected that may contain anaerobic solventogenic microorganisms. The sample is amplified, and then undergoes an isolation and enrichment process that may comprise any number of steps according to techniques well-known in the art. Enrichment and isolation may include, but are not limited to, confirmation of autotrophic function, screening for syngas utilization, confirmation of the presence of an Acetyl-CoA reductase gene, or confirmation of the presence of a CODH/ACS operon. After isolating and enriching any microorganisms of interest, the microorganisms are plated for further phenotypic metagenomic analysis.

The narrowed microorganisms may then undergo a polymerase chain reaction with a sample of at least one degenerate primer that will bind to one of the essential genes for solventogenesis function. A kit with primers which will bind to all sixty-four essential metabolic genes may also be utilized. A separation is then performed based on size; in a preferred embodiment the product of the PCR will be electrophoresed. The results are then read to determine the presence or absence of each essential gene of interest. If one of the essential genes listed in Table 1 is absent, the metabolic pathway may not produce high titers of product.

In a further embodiment, to confirm de novo high ethanologenic function, the genome of the potentially ethanologenic microorganism is sequenced. A comparison is performed between the genes contained in the prospective microorganism's genome and the gene sequences of the minimum set with a cutoff score of $P=1\times10^{-20}$. If the genome of the prospective microorganism comprises at least the minimum set, then ethanologenic function via the Wood-Ljungdahl pathway is preserved, and the microorganism is likely to produce high ethanol titers when fermented with syngas.

What is claimed is:

1. An isolated and purified polynucleotide comprising at least 95% identity to SEQ ID NO. 1.

2. An isolated and purified polynucleotide comprising at least 95% identity to SEQ ID NO. 2.

* * * * *

SEQUENCE LISTING

```
<160> NUMBER OF SEQ ID NOS: 3

<210> SEQ ID NO 1
<211> LENGTH: 72785
<212> TYPE: DNA
<213> ORGANISM: AUTOTROPHIC SOLVENTOGENIC CLOSTRIDIAL SPECIES

<400> SEQUENCE: 1
cacgattctg tggaagaaat gcttaaaaga atcagggaag atggtatgtc aaacgtattt      60
gacagatggt cctctcaaga aaaaattaga tgtaagtttt gcctagaagg attaagctgt     120
caattgtgtt ctcaaggtcc ctgcagaatt aatcttaaag gagaacagaa aaaggtgttt     180
gtggtattgg cccagatgcc atggcaatgc gaaatatgtt acttaaaaac ataatgggag     240
ctggtacata tagccatcac gcatatgaag cctttagaac attaagagaa actggagaag     300
gcaagactcc atttacaatt aaagatgtgg ataaactcaa atggatgtgc cagaaagtcg     360
gaattaatac aagcggagat accaataaaa tggcagtgaa tctggcaaat tttttggaag     420
```

```
ctgagatggg taaagatgta aagaaccta gtgttatggt agatgtgttt tcaccaagaa      480
agagaaaaaa agtttggaaa gatcttggaa tttatccttc aggagtagtt cacgaagagc      540
aaaatgcagt agcaagttgt ttaacaaatg ttgatgggga ttatgtatca ttagctaaaa      600
aagcgctgcg gctaggtctg tcaactatct atacagcaca ataggactt gaaatggctc       660 aggatatact ttttggcacg cctacacccc atgaggtaaa tgtggactta ggaattatgg      720
atccagagta tataaatatt gtatttaatg gacatcaacc ttgggctggt gttgctacta      780
ttcaaaaggc aaagatgcag cagatacagg aaagagcaaa ggcagctggt gcaaagggc      840 ttagaatagt tgggtcaatt gaaacaggac aggaattatt acaaagattt gaggtagatg      900
atgtatttgt aggtttaatg ggagattggc tatctataga accacttctt gctacaggta      960
cagttgatgt tcttgcaatg gaagaaaact gttctccacc tgcaatagat cattatgctg     1020
aaaagtatca ggtaacttta gtaggtgtaa gtactattat aggtattccg gggttaaatc     1080
atatgattcc atataatcct gaaaagtgg gtgaaatggc tgataaattg attgatttgg      1140
ccattgaaaa ttttaaaaag agaaaggata acattacacc aaaggttcct aaaataacac     1200
agaaagcaat agcagggttt tctactgaag cagttttaaa agctttagga ataagcttg      1260 atccacttgt tgatgttatt aaggcaggga agattaaagg aattgtggct ttggcaaatt     1320
gttcaactct aagaaatggt cctcaagatt ggaatacagt taacctggta aaggaattga     1380
ttaaaaagga tattttagtt gtggctggtg ggtgcggcaa tcatgctctt gaagtagcag     1440
ggctgtgcaa cctagatgca ataaacatgg ctggccaagg actaaaagaa gtatgcaata     1500
tgctaaagat tcctccagtt ctaagctttg aacttgtac agatacggga agaatatcca      1560
tgcttgttac agaacttgct aattaccttg atgtagatat accagatctt cctattgctg     1620
taacggctcc tgagtggatg gaacaaaaag ctactataga tggtttattt gcagtagcct     1680
atgggacata tacacattta tctccaactc catttctaac aggcgcagaa cagcttgtaa     1740
agcttcttac tgaggatgta gagagcttaa caggaggtaa agttgcatta ggagataatc     1800
caaaagaggc agctgataat attgaagcac atatattaag taaaagaaag ggtttggagt     1860
tataacaatt attttttagt tagttgtact tgtaaataaa tagtattaat taatactatt     1920
aaactattac agttttttgat tcttagtata agtattctta gtatctttag cacttagaat     1980
acgttatcct ttaggagaat aatcctaatc agtaatttta ataatttaat agtatactta     2040
aatagtatag tttggaggtt ttattatgtc aaataacaaa atttgtaagt cagcagataa     2100
ggtacttgaa aagtttatag gttctctaga tggtgtagaa acttctcatc ataggtagaa     2160
aagccaaagt gttaaatgtg gttttggtca gctaggagtc tgctgtagac tctgtgcaaa     2220
cggtccctgc agaataacac ctaaagctcc aagaggagta tgtggtgcta gtgctgatac     2280
catggttgca agaaactttc ttagagctgt agctgccggc agtggatgtt atatccatat     2340
agtcgaaaat acagctagaa acgtaaaatc agtaggtgaa accggcgag agataaaagg     2400 aatgaatgct ctcaacaccc tagcagaaaa acttggtata acagaatctg acccacataa     2460
aaaagctgta ctagtagctg atgccgtatt aaaggactta tacaaaccaa aattcgaaaa     2520
aatggaagtt ataaataaat tagccttatgc acctagacta gaaattgga acaaattaaa     2580 tataatgcct ggcggtgcaa aatcagaagt ttttgatggt gtagtaaaaa cttctacaaa     2640
tctaaacagc gaccctgtag atatgcttct aaattgttta aaacttggaa tatccactgg     2700
gatttacgga cttaccctta caaatttatt aaatgacata attttaggtg aacctgctat     2760
```

```
aagacctgca aaagttggtt ttaaagttgt agatacggat tatataaatt tgatgataac   2820
aggccaccag cactccatga ttgcccacct tcaagaagaa cttgtaaaac ctgaagctgt   2880
aaaaaaagcc caagcagttg gtgctaaagg attcaaacta gttggatgta cctgtgtcgg   2940
acaggattta cagttaagag gtaaatacta tactgatgtt ttctccggtc atgcaggaaa   3000
taactttaca agtgaagcct aatagcaac tggaggtata gatgcaatag tatctgaatt    3060
taactgtact cttcctggca tcgagccaat agctgataag ttcatggtta aaatgatatg   3120
cctagatgac gtttctaaaa aatcaaatgc agaatatgta gaatactctt ttaaagatag   3180
agaaaaaata agcaaccatg ttatagatac ggctattgaa agttataagg aaagaagatc   3240
taaagttaca atgaatattc ctaaaaacca tggctttgat gacgtcataa caggtgtaag   3300
tgaaggttcc ttaaaatcct tcttaggcgg aagttggaaa cctcttgtag acttaattgc   3360
tgctggaaaa attaaaggtg ttgctggaat agtaggttgt tcaaacttaa ctgccaaagg   3420
tcacgatgta tttacagtag aacttacaaa agaactcata aagagaaata taattgtact   3480
ttctgcaggt tgttcaagtg gtggacttga aaatgtagga cttatgtctc caggagctgc   3540
tgaacttgca ggagatagct taaaagaagt atgtaagagc ctaggtatac cacctgtact   3600
aaattttggt ccatgtcttg ctattggaag attggaaatt gtagcaaaag aactagcaga   3660
atacctaaaa atagatattc cacagcttcc acttgtgctt tctgcacctc aatggcttga   3720
agaacaagca ttggcagatg gaagttttgg tcttgccctt ggattaccac ttcaccttgc   3780
tatatctcct ttcattggtg gaagcaaagt ggtaacaaaa gttttatgtg aagatatgga   3840
aaatctaaca ggcggcaagc ttataataga agacgatgta ataaaagctg cagataaatt   3900
agaagaaacc atacttgcaa gaaggaaaag cttaggtctt aattaaatga aaagaataat   3960
gataaataag gatttatgta ccggatgctt aaattgtact ttagcttgta tggcagaaca   4020
caatgaaaat gggaaatctt tttatgatct ggatctcagc aataaatttc ttgaaagtag   4080
aaatcatata tctaaagatg ataatggaaa caagcttcct atattttgcc gtcactgtga   4140
cgaacctgag tgcgtaatga catgtatgag cggtgccatg actaaagatc ctgaaactgg   4200
tatagtatcc tatgatgagc ataaatgtgc cagctgcttt atgtgcgtca tgtcctgtcc   4260
ttatggagta ttgaaaccag atactcagac caaaagtaaa gtagttaaat gtgacctgtg   4320
tggtgacaga gatacaccta gatgcgttga aaattgtcca acagaagcaa tttatattga   4380
aaaggaggca gatctcctat gaatgagtgg tttaacaata aaaatatttt ttcacacaaa   4440
atatgtaata ataggagcca gtgctgctgg aataaatgct gctaaaactt taagaaagtt   4500
agataaatcc tccaaaataa ctattatttc aaaggatgat gcagtttatt caagatgtat   4560
actccacaaa gtacttgagg gaagtagaaa tttagatacc ataaattttg tagattctga   4620
tttctttgaa aaaataata tagaatggat aaaagatgca gatgtaagca atattgatat   4680
tgacaagaaa aaagtcttac ttcaagacaa cagcagcttc aaatttgaca agctccttat   4740
agcttctggt gcttcctcct ttattccccc agttaaaaaa ttaagagaag ctaaaggagt   4800
gtactccctt agaaattttg aagatgtaac tgctatacaa gacaaactta aaaacgcaaa   4860
acaagtggta atacttggtg caggtcttgt aggaattgat gcacttttag gtcttatggt   4920
gaaaaatata aagatttcag ttgtagaaat gggagatagg attctccccc ttcaactgga   4980
caaaactgca tccactatat atgaaaagtt gttaaaagaa aaaggtatag atgtctttac   5040
ttcagttaaa ttggaagagg tagttttaaa taaagacgga actgtaagta agcagtact    5100
atcaaattca acttctatag attgcgatat gataatagtt gctgctggtg ttagaccaaa   5160
```

```
tgtaagcttt ataaaagaca gcaggataaa agttgaaaaa ggcattgtca tagacaaaca   5220
ttgtaaaacc actgtagata atatatatgc tgcaggagat gttactttta ctgctcctat   5280
atggcctata gctgtaaagc agggaataac tgctgcttac aacatggtag gtataaatag   5340
agaattacat gacacttttg gcatgaagaa ctcaatgaat ttatttaacc ttccatgcgt   5400
atcccttggt aatgtaaata tagcagatga aagttatgct gttgatacat tagaaggaga   5460
tggagtttat caaaaaatag ttcacaaaga tggagtaatc tacggtgcac ttctagttgg   5520
agatatatct tactgcggcg tactaggata tctcataaaa aataaagtaa atataagcaa   5580
tatccataaa aatatttttg acatagatta ttctgatttt tacaatgttg aagaagatgg   5640
acaatatagt tatcaattga ggtaattata cttaaatgga tgtttatttt ttaacatttt   5700
ttatggtaaa tatatttatt ttatgtagta aaaaggttat aattataatt gtatttatta   5760
caattaatta aaataaaaaa atagggtttt aggtaaaatt aagttatttt aagaagtaat   5820
tacaacaaaa attgaagtta tttctttaag gagggaatta ttaaaatgga agaaaaggca   5880
aagtcaattg atcaagctac tttacaatta ttggacaagg caaaaaaaga tggggttgaa   5940
actgctttag ataggaaagc agacatgaag gtacagtgtg gatttgggtc agcaggagtt   6000
tgctgtagaa attgcagcat gggtccttgt agagtaagtc cagtgccagg aaaaggcgtt   6060
gaaagaggta tatgtggtgc tacagcagat gtaattgtat ctagaaattt tgcaagaatg   6120
gttgtaggcg gagctgctgc acattcagat catggtagaa gtatagcact tagcttatac   6180
cactccagca aagatggaga tataaaagtt aaagatgaaa ataaattgaa agaagttgca   6240
aaaatatatg atgtagaaac tgaaggaaga gacatatatg atatagctca tgatgtagct   6300
aaaagaggat tagatgatta tggtagacaa atgggagaag ttaaacttcc accgtcccTT   6360
ccaccaaaga gaaaggaaat atgggataaa cttgacatag ttccaagggc aattgataga   6420
gaaatagctg cagttatgca ctcaacacat ataggatgta atgcagatgc agaagctatg   6480
attaaaatgg ctatgagatg ttcgctaggt gatggatggc taggatcata tatggctaca   6540
gaatttagag atataatgtt tggaacacct aagtcaattg agacagaagc aaatcttgga   6600
gtacttgaaa agaattctgt aaatgtagtt ttacacggac atgaacctct tctttcagat   6660
atgatagtag aagcagcatc agatccagaa ctagttgaac ttgctaaatc agtaggtgct   6720
gatggaataa acttatgcgg aatgtgctgt actggaaatg aagtttccat gatacatggc   6780
atcaaaatag caggaaactt tatgcagcag gaattggctg tagttacagg agcagtagat   6840
ggacttatag ttgatgtaca gtgtataatg ccagcattag caaaattgac taagtcatat   6900
catactaagt ttataacgac ttcaccaaag gcacatatca cagattcaac ttatattgaa   6960
tttgatgaag aacatccact tgattctgct aaacagattt taaaggaagc aatattaaat   7020
tttaaaaata gagataacag taaagtaatg attcctgaat tgaaatcaaa gggaattgta   7080
ggatatagtt ttgaagaagt aataaacaaa ttggacaaag ttgttaatac acaaatagga   7140
ccaatgcaaa ctgtaaagcc tttagcagat gttttagtat caggagtatt aagaggtgcc   7200
gcaggtgtag ttggttgtaa caatcctaaa gttactcata attctgcaca tattgaaact   7260
ataaagggat taataaagaa tgatgtaata gttgttgcta caggttgtgc agctcaagca   7320
gcagcagaat atggattaat gcaattagaa gcagcagaaa aatatgcagg accaggacta   7380
gctactgtat gtaagcttgt tggtatacca ccagtacttc atatgggttc ttgtgttgat   7440
ataagccgta tattagactt agttggtaga gtagctaatt tcttaggtac agatatgagt   7500
```

```
gatcttccag ttgtaggtgt agcacctgaa tggatgtcag aaaaagctgt ttctataggt    7560
acttatgtag taacttcagg tatagatact tggcttggag taacacctcc agtaacaggc    7620
ggtccagaag ttgtagatat tcttactaat aagatggaag actgggtagg agctaaattc    7680
tttatagaaa cagatcctca taaagcagtt gaacaaatgg ttaataggat gaatgaaaaa    7740
cgtaaaaaat taggtatcta atcaaagtga tatgaagtca agattacata tcattttgag    7800
aagaatttta atttatagat ggtataatgt agaataaaat ttataattta tctacaaata    7860
cataaattat aagggaatat atttgtagat aaaagtatat attaagtttg tattttaaat    7920
aaattatata aaatggttgt tcaaaatggg agggactaca tatgaaaatg aaaatggcta    7980
taacaggtaa aggtggtgta ggtaaaacta cattttcagc gataatgagt agaatatatg    8040
cagaagaagg atataatgtt ttagctgtgg atgcagatcc tgatcccaat ttggcattag    8100
cattaggatt tccaaaagag atagcagatg agattgttcc aatttcagaa atgaaaaagt    8160
tagtagcaga gagaacaaat tctactccag gatcctttgg aaaaatgttt aaaataaatc    8220
ctaaagttga tgatatacca gaaagatatt gcaaggaata caaggtgta agacttttaa     8280 ctatgggaac agttgataca ggcggaacag gttgtttctg cccggaaaat gttttgctta    8340
aaaaactcac gtcacattta atgctccaaa acaaagatat cgtcataatg gatatggaag    8400
caggtattga acatttggga aggggaacag cgcaaggtgt agatgtattt attgttgttg    8460
tagaacctgg aataagaagt atacagacgt tcaagcatgt taaaaaatta gctaaggata    8520
taggaataga aagatatttt gtggtagcaa ataaaattag aaataagaag gacgaagaat    8580
ttgtattgga aaatgtagat gaaaagaat gtcttggatt tatacattat agtgacacag     8640
ttggaagttc tgatagagtc aatcaatctc cttacgattc caatgaggaa actgttaagg    8700
aggtaaaaaa tataaaacaa aaattagaaa tgggggtttt ttaaatgact tataaatcag    8760
acatcgaaat agctcaagaa tgcacaatga aggacattaa ggaaattgca aagaaattaa    8820
atatttccga agatgatatt gaattgtatg gtaaatacaa agcaaaggta aattacaact    8880
tgttaaagac tacacctgga aagaatggaa aacttatatt atgtacagct ataaacccaa    8940
cacctgctgg agaaggaaaa actactacag caataggtgt agcagatgca ttaaatagaa    9000
tgggaaaatc tgttgttgtt gcacttagag aaccatctat gggacctgta tttggtataa    9060
aaggtggagc tgccggtggt ggatatgctc aagtagtacc tatggaagac ataaacctac    9120
actttacagg tgatatacat gcactcactg ctgctaacaa tttacttgca gcaatgatag    9180
ataatcatat atatcaaggc aataagctta acatagaccc aagaagaatt gcttggagaa    9240
gatgcgtaga catgaacgac agacagctca ggtttgtagt tgatggatta ggtggaaaag    9300
ccaatggtac acctagagaa gatggatttg atataacagt tgcttcagaa ataatggcta    9360
tattctgttt atcaagtgac ataattgatt tgaagaagag aattgctaaa atagttgtag    9420
gatacactag agatggccag cctgtaacag ctcatgattt gaaagctgaa ggagctatgg    9480
cagcacttct taaagatgca ttaaaaccaa atctagttca aactcttgaa ggaacaccag    9540
catttgtaca cggcggacca tttgcaaata tagctcatgg ttgtaactca ataatggcta    9600
ctagaatggc tcttcacttt ggtgattatg tagttacgga ggcaggtttc ggtgctgacc    9660
taggtgctga aaaattctta gatatcaagt gcagaatggc aggattaaaa ccagatgcag    9720
taataatagt tgctacagtt agagcattga atacaatgg cggagttcca aaggctgact    9780
taaataatga aaacttagaa gctcttgaaa aaggacttcc aaatctatta aaacatgtag    9840
agaatataac taaggtatat aaattaccag cagtagttgc attaaatgca ttccctacag    9900
```

```
atacacaggc agaattaaaa ttagtagaag ataaatgtaa agaattaggt gtaaatgtaa    9960
gattatcaga agtttgggct aaaggcggcg aaggtggact agaagttgcc aaagaagtgc   10020
ttagacttat aaaagaagag aaaaatgact tccagtttgc ttatgatgaa aaattaccaa   10080
ttagagataa aataagagca gtagctcaaa agatatatgg tgctgatgat gttactttca   10140
caagtcaggc agaaaagaa attgatgagc ttgaaaaatt aggatttggt aaaacaccag    10200
tatgtatagc aaagacccaa tactccttaa ctgatgacca gactaaactt ggaagaccaa   10260
caggatttaa tattacagta agacaggtta caatttctgc tggagcaggt tttgtagttg   10320
cagtaactgg ttcaataatg aagatgccag gtcttggaaa agttccatct gctgaaaaaa   10380
tagatgtaga tgagaatgga gtaataagcg gattattcta aatgaaatta gcagataaaa   10440
gttgcacaga ttttatagaa gttcttgcat ctaaagctgc aactcctggt ggaggcggag   10500
gatcagctat tacaggtgct ataggaatgg cacttggagg catggtatgt aaccttacaa   10560
taggaaagaa aaagtatgca cagtatgatg aaaaggtaaa aggcatactt aaaagatctg   10620
atgagcttca agcagagctt ttaaagatga tggatgcaga tgcagaatgc tttctgcctc   10680
tttcaaaggc ttatggaatg ccaaaagaca ctgaagagca gaaaaaaata aaagaagaaa   10740
ctctagaaaa gtgtctaaag caagcatgca gtgttccagt aagcattgtt aagcaagctt   10800
atgaagcaat aaaactccac gaggcacttg tagataactg ctccaaactt gcaataagtg   10860
atgttggtgt aggagttcag tgtctaagag ctgctattat tggagcacag cttaatgtca   10920
taatcaacat taattccatt aaagatcagg aatatgttaa aaaggtaaaa gcagagacgg   10980
aacctttagt tgaagaaggc attaagattg cagataaggt atatgaaaaa gtagttagtg   11040
cactttccaa ataaatgggt caaataatta aaggtaaacc agtggcagat gctataagtg   11100
aagctttaac taaagaagtt aatgatttaa aggtaaaggg tattactcca aaacttacat   11160
tagtaagagt tgggagcaaac ggaagtgacc ttgcttatga aaaaggagct ctaaaaaagt   11220
gcgaaaaaat tggaatagag gcagttgtta aagagctacc agcagatata tcacaagaca   11280
agtttattga agaattgaaa aaaataaatg cggacaagac tgtaaatgca ataatggtat   11340
tcagaccatt tcctaagcaa ttagatgaaa gcgttataaa atatataatc gcccctgaaa   11400
aagatgtaga ttgctttagt cctgtaaatg ttgctaaatt gatggaaaaa gatatgacag   11460
gatttgcacc ttgtacacca tctgctgtta tagaaatcct taagcattat aaagttccta   11520
tgaagggaaa gaatgcagtt atagtaggaa gatctatggt agttggaaaa ccagcgtgca   11580 tgctccctatt aaatgaaaat gctacagtta ccgtatgtca ttcaaaaact actgatatgc   11640
caaaggtttg ttcccaggca gacatactgg tagtaggcat aggaaaagct aaaatgatag   11700
attcaaaata tgtaaaagat ggtgccgtag ttatagatgt aggcataaat gtagatgaaa   11760
gtggaaagct atgtggagat gtagatacag aagactgtga atcaaaagct tcaatgataa   11820
cacctgttcc taaaggagta ggctctgtta catcatctat acttgcacag catattgtaa   11880
aggcctgtaa gttacaaaat aacctataaa tgattatttc agaaaaaaaa tcttttgatg   11940
aattattgga ttaccttaaa gacagtgaaa agtaataat cacaggatgt tctttatgcg    12000
caactacctg taaagtaggc gggagaagaag aagtattagc aatgaaagcc aagttagaag   12060
aacaaggcaa aaaagtttta ggctataaaa tacttgatcc ttcctgcaat cttttaaaaa   12120
caagaaaaga tttaaagtcc ttaaaagctg aattaaaaga agcagatgca gtagtatccc   12180
tagcttgtgg tgatggaact caaactgtag ccaagttagt aaagattccc gtttatccag   12240
```

```
gtaataacac tatgtttata ggcgaagtag aaagagttgg acaatatgca gaagcttgta    12300
aagcttgtgg aaattgccag cttggatgga caggggaat atgtccaatt acaatgtgtg     12360
caaagggact tttgaatgga ccttgcggtg gtgcaagaga tggtaaatgt gaagttgatc    12420
ctgaaaatga ttgtgcttgg atattaatat acaataaatt aaaagaacta ggacagctcg    12480
ataatttgac agaattaaga aagccaagag attatcaaat aagtgctcat cctagaaaaa    12540
taaatttaaa tgctaagtaa atgagcttat tgaaggaagc ttttgaaaag ggagagtttg    12600
cagttacagc tgaaatggca cctccaaagg aacggatct ttctcattta attgaatgtg     12660
ccaaaaagat aaaaggaaga gttcatggag ttaatgtaac ggattttcag tctgctacgt    12720
taaaagctac atctttagct acttgtaaag tgttaaaaga tgcaggatta gaacctgtat    12780
ttcaaataac aggaagagat agaaacagaa tagcaattca aggagaattg ttatctgcag    12840 gtgttttga aattgaaaat gttttagctc ttactggaga ttatactgct acaggagatc     12900
accctggtgc aaagccagtt tatgatctag atagtgttgg aatattacag gtggcaagca    12960
ttttaaatgg cggaaaagac atgggtggaa ctgatttaaa agggaaacca gatttctttt    13020
taggggcctg tgttacacct agatatgatc cgttagagct tcaagttata aagatgaaga    13080
agaaaattaa agctggagct aaattctttc aaactcaagc tgtttatgat atggaaactt    13140
taaagaaatt caagaagag actaaagctc aaggtgtaga tgctaaagtt atggtaggca     13200
taatcctttt aaagtcagct ggtatggcta aatacatgaa taaaaacgtg cctggtatat    13260
tcgtacctga tgaacttata gatagaatga aaaatgctga ggataaagtt caagaaggca    13320
taaagatagc aggagaattt ataaaggccg taaaagaatc aggactttgc gatggagttc    13380
atataatggc aattggtgcg gaagaaaatg tgccattaat attggacgaa gcaggattat    13440
aaatgaaatt agttgtaatt ggtggaggac caggaggata tgtagctgca ctgcaagctg    13500
caattttagg agcagatgtt actgtagttg agaagaaagc tgtaggagga acttgcttaa    13560
atgtaggatg tatacctaca aaagcactgc ttgcttccac agatgtttta agtgtaataa    13620
aaggagcatc aaaatttgga attaatgttg aaggtgaagt aaaacctgat tttgatgcaa    13680
ttatgaagag aaaagataaa gtagtagatc aacttgtaaa aggcatagaa tatatgtttg    13740
aacatagagg ggtaaagctt ataaggggaa caggaaaact tataagcaat aaagaggtag    13800
aggttacaaa gcaggatgga tctaaagaat ccataacggc agataaaatt atacttgcta    13860
ctggttctgt acctgttaca cctggagtat tcaagtatga tggtaaaaag gttataactt    13920
cagatgaagt tttgaattta gagaaacttc caaagtcaat gatactagtt ggtgaggtc     13980 ctataggatg tgaaatagga ttcttcttaa atagtatggg agtagaagtt aaggtagttg    14040
aagctcttcc acatcttgca ccacttgaag atgaagatgt tgcaaaacaa cttcagagaa    14100
ttttcaaaca gcataagatt aaatactttg taggcgatgg tataactagt gtagaagtta    14160 aggtgatac ggtaactgct acattgggaa gcggaaaagt tttagaggct gaaacacttc     14220
tcatagcagt tggaagaaga gcttatgctg aaggtttagg tttggatgat attggtatta    14280
agaaagatca aaaggaaga ataattgtaa atgaatattt agaaactaat gtagagggag     14340
tttatgcaat aggtgattta attcctactg ctgctcttgc acatgtagct gaaagagaag    14400
gtattgtagc tgttcaaaat gcagttttag ataaaaagaa gaagatgagt tacaaagcag    14460
tacctggttg tacatttgta gaaccagaaa tagcttctgt aggtatgaaa gagaaagatg    14520
ctgaaaaagc aggaatccag tacaaggttg gaaaatttga ctttaggggg cttgaaaaag    14580
ctcaagctat gggtaaatta caaggatttg taaagattat tacagacgaa aaggacgtaa    14640
```

```
taattggagc tgctattgta ggtgatagag caacagatat gatttcagaa ttaggtgttg      14700
cttgtgagct tggtttaaca gcagaacgag ttggtgaagt tattcatcca catccgactt      14760
tatctgaggc aatgatggaa gctcttcatg atgtacacaa acaatgtgtt cattctgttg      14820
attaaatggg atataaaata gctgtagcag gtaagggtgg taccggcaaa actactttga      14880
caggtctttt aatagattat ttgacaaaaa aaggttcagg acctatttta gcagtagatg      14940
ctgatgcaaa tgctaattta aatgaagtac ttggaacaga cattgaggaa actattggag      15000
aaataaaaga ggacgtaaat aaaaaatcac ttgaagggga taattttcct ggaggtatga      15060
tgaaagcaga ttatttaaag tataaattaa atgcatcagt agctgaagga gacggttatg      15120
accttattgt tatgggaaga tcccaggggc caggatgtta ttgttatgtt aatggaatac      15180
ttaaagcaca agtggattca ctttctggta attatgatta catagtagtt gataatgaag      15240
caggaatgga acacttaagt agaaaactta tagatcctat tgatactcta tttctgataa      15300
gcgattgttc cagaagaggc atacaggctg ttggaagaat aaaacggtta gttgctgaat      15360
taaagttaaa agttggccaa atctttctta tcgtaaatag agctccagaa ggtaaattga      15420
attcaggaat aaaagaagaa ataaaaaagc aagaactgga tttagtagga gttgtgccga      15480
tggaccaaat ggtctatcaa tttgattcag atggaaaagc attagtagag ctgccagagg      15540
attcttcatg cagaaaagca ttgaatgaaa tactatcaaa aattcaattt gaaaattaaa      15600
tgttcaaaaa accaacacaa aaattttcag gcaaaattgg tgaagttgaa attggaacag      15660
gagaaaaagt attaaaatta ggaggagaat cagtattacc attttacact tttgatggag      15720
atacaggaaa tagcccaaaa gtaggtatgg aaattttgga tgtatatcca gaagactgga      15780
tagatccttt aaaagacata tacaaggatg ttgcaaaaga tcctgttaaa tgggcacaat      15840
ttgtagaaga aaaatatagt ccagatttta tatgcctaag acttataagt gctgatccaa      15900
acggtacaga tgctgcacca gaagattgtg ctaaaacagc taaagcagta gttgaagcta      15960
taaaaactcc attagtagtt gcaggtacag gaaatcatga aaaagatgca aaattatttg      16020
aaaaagttgc tcaggaaact gaaggacaca atatactttt aatgtctgca gtagaagata      16080
attataagac agtaggagct gcaggcgtaa tggcttataa tgacaaagtt gtagctgaat      16140
cttcagttga tataaaccct gcaaaacaga taaatatttt aatgaatcaa cttggaatag      16200
acaatacaaa gtttgttgac aacgtaggat gtgcagcagg tggatatggt tatgaatatg      16260
ttatatcaac tttagacaga gtaaaacttg cagcacttgg tcaagatgat aaaactcttc      16320
aaattcctat aataagccct gtttctttcg aagcttgcaa agtaaaagaa gcaatggatt      16380
cagaagaaga ttcaccacaa tggggaagtc aggaagacag aacagtttcc atggaagttg      16440
caacagcatc cggagtatta gcatcaggaa cagatgctgt aatattacgt catccaaaat      16500
ctgtagaagt aattagaaat tttattaagg aattattagg ttaaatggct ttaacaggat      16560
taaatatatt taaattaaca ccaaaaaaga attgtaagga ttgtggtttt cctacttgtc      16620 tagcttttc aatgaaagta gcagcaggag ctgtggaaat aggaaaatgt cctcatatga      16680
gtgatgaggc aatggaaaaa ttagctgaag ctactgcacc aattatgaag acaataacta      16740
ttggtaaggg agataatgaa tataaattag gtggagaaac tgttttattc cgtcatgaaa      16800
aaacttttgt aaatagaaat agatttgcag ttgcattttc cgatagtatg gatgatgcag      16860
aagtagatgc taagatccaa catataaaag atgtagatta tgttagaatc ggtgaacaaa      16920
tgaaaaccga atttgctgca ataaaatatg caggaaataa agacaaatat cttgctttga      16980
```

```
taaataaaat aaaagcaagt ggagtaaaag tagcttatgc tctagtttgt gaagatgcag    17040
cagtaatgaa agaagctctt ccactagtta aagatgaaaa tccattagtt tatggagcta    17100
ataaagataa cttcaaagaa atggttgaac ttgtaaaaga agataaatta gctttaggtg    17160
taaaggcaga cggattggaa gctctttatg gtttagtaga agaaatacaa aaattaggat    17220
ataagaactt agtacttgat ccaggtggaa aatccattaa agaagctttt gaaaatacag    17280
ttcaaattag aagaataaat attgaaaatc aggatagaac ttttggatat ccttctatac    17340
tattcctaga tgaacttact aaagctgata aatttatgga agtagcttta tctacattat    17400
ttactttgaa atatggttca ttacttgttt taagtgatat ggattatgca agagcacttc    17460
ctctttatag tataagacag aatgtattta cagatccaca aaagccaatg acagttgatt    17520
tgggcataca tggaattaac aacccagatg aaaactcacc agtattatgt actgttgact    17580
ttgctcttac ttacttccta gtttcaggag aagttgaaag atctaaagtt ccagtatgga    17640
tggttatacc agatgcaggt ggatattctg ttcttacatc ttgggctgca ggtaaattta    17700
ctggtgctgc aatagctgat gaaataaaga aatgtgaaat atcagagaag actaagaaca    17760
gaactctttt aatcccagga aaggttgcag ttttgaaagg cgaattagag gaacttcttc    17820
cagactggaa tatagtaatt agtagtacag aagctatgtt tattcctaag ttattaaaag    17880
agttaactgc taagtaaatg gataaattta tgattatagg cgaaagaatt cactgcatat    17940
ctccatctat aaggaaggct attgaggaga gaaatcctga accatatttt aaaagagcaa    18000
aagaacaatt ggatgcagga gctaattatc tagattttaa tataggacca gcaagaaaag    18060
atggagaaga ataatgcag tggggtgtta aggctcttca aagtgaattt gacaatgttc    18120
cactagcact tgatacaaca aataagaagg ctatagaggc aggacttaaa gtttacaata    18180
gagaaaaagg aaaacctatc ataaattctg cagatgcagg agaaagaatt ggaaatatag    18240
atttagctgc agagtatgat gctatgagca tagctctttg tgcaaaagaa ggaataacaa    18300
aagacaatga tgaaagaata gcatattgta cagaaatgct tgaaaaaggt atgggtcttg    18360
gaatggagcc tacagattta ctgtttgatc cattattttt agtaataaag ggcatgcagg    18420
ataaacaaaa agaagtatta gaggctatta aattaataag tgatatgggt cttagaactt    18480
gctgtggatt aagcaatgtt tcaaatggag cacctaagga aataagacca ataatggatg    18540
caacttttgc agctatggca atacaatgtg gtcttacttc tgcaataatg aatccatgtg    18600
ataagagatt aatggagaca ataaagactt gtgatgttgt aaatggtgct gttttatatg    18660
cagattctta cttagagtta taaatgaatt tatttcaaac tgtattcact ggttcaaagc    18720
aggctttagc agctgctgaa ggcatagtta agcaagctgt tgacgagaag ggtagagact    18780
ataaagtagc atttcctgat actgcatatt cattattagt aattttttgca gctacaggaa    18840 aaaagataac taatgtagga gaattagaag gtgcattaga tatagtaaga agtttgatag    18900
ttgaggagga aatgcttgat aagcttttaa attcaggact tgcaacagct gttgcagcag    18960
aaattataga agctgcaaag tatgtccttt cagatgctcc ttacgcagaa ccatgtgtag    19020
gatttatctc agatccaata attagatcat ttggagtacc acttgttaca ggtgatgttc    19080
caggtgtagc agttgtactt ggagaattcc cagattctga aactgcagca aaagtaataa    19140
aggattacca atcaaaagga ttacttactt gtttggtagg caaagtaata gatcaggcta    19200
tagaaggcaa agttaagatg ggacttgacc tcagggttat tccacttgga tatgatgtta    19260
catccgtaat tcatattgta agttttgcta taagagctgc acttatgttc ggaggaatta    19320
agggcggaca gttaaatgat atattgaaat atacagcaga aagagtacct gcttttgtaa    19380
```

```
atgcatttgg accattaagc gaacttgtag tttcagcagg tgcaggagct atagcacttg    19440
gattccctgt aataactgat caggttgtac cagaagttcc tacattgttg ttaactcaaa    19500
aagattacga taaagttgtt aaaacttcat tagaagctag gaatataaag ataaagataa    19560
ctgagatccc aattccagtt gcttttgcag cagcatttga aggtgaaaga ataagaaaga    19620
atgatatgct tgcagagttt ggtggaaata agactaaagc ttgggaatta gttatgtgtg    19680
cagatcaggg agaagttgaa gatcacaaga tagaagttat aggaccagat atagatacta    19740
tagataaggc tcctggaaga atgcctcttg gaatgcttat taaagtaagt ggaacaaata    19800
tgcagaagga ttttgagcca gtgcttgaaa gaagacttca ctacttctta aactatatag    19860
aaggagtaat gcatgttggt cagagaaatc ttacttgggt aagaataggt aaggaagctt    19920
ttgaaaaagg atttagattg aaacattttg gtgaagtaat atatgctaaa atgttagatg    19980
aatttggttc agttgtagat aaatgtgaag taactataat aactgatcca gataaggctg    20040
aagaattgga aggcaaatat gctgtaccta gatattcaga aagagatgca agacttgaat    20100
cattagttga tgaaaaagtt gatactttct attcatgtaa tttgtgtcaa tcatttgcac    20160
ctgcacatgt atgtatagta actcctgaaa gacttggact ttgcggtgca gtttcatggc    20220
ttgatgctaa agctacactt gaattgaatc caacaggacc atgtcaggca gttccaaaag    20280
aaggcgtggt tgatgaaaat ttaggtattt gggaaaaagt aaatgaaact gtttcaaaaa    20340
tttctcaagg cgctgtaaag agtgttacat tatacagtat attacaagat ccaatgactt    20400
cctgtggatg ttttgagtgt attacaggta taatgccaga agcaaatggt gttgtaatgg    20460
taaacaggga atttggagca acaactcctc ttggaatgac atttggtgaa cttgcatcta    20520
tgacaggtgg tggagttcag actccaggat ttatgggaca tggaagacaa ttcatagctt    20580
caaagaagtt tatgaaaggt gaaggtggac ttggtagaat agtttggatg ccaaaagaat    20640
taaaagactt tgttgcagaa aaattaaata agacagcaaa ggaattatat aatatagata    20700
attttgcaga tatgatctgt gatgaaacta tagctacaga atctgaagaa gtattaaaat    20760
tcttggaaga aaaaggccat cctgcattaa agatggatcc aataatgtag gaattgtcac    20820
aaataaaaga gaaatatgga cctgattcta taatgggaac aggatgtgct aggggttctg    20880
gaaatgaagc aaactacgta atgcaaaagt ttatgagggc ggttattgga accaataacg    20940
tagatcactg tgccagagtt tgacatgctc cttctgtagc cggtctggct tacgttttag    21000
gaaatggtgc tatgtcaaat ggtatacatg aaatagatga tacagattta ctacttattt    21060
ttggatataa tggagcagct tcgcatccaa tagttgctaa gagaatagtt agggcaaaac    21120
aaaaaggtgc aaaggtaata gttgtagatc cacgtataac agagtctggt aggatagcag    21180
atttatggct ccctataaaa aatggaacaa atatggttct tgtaaatact tttgccaata    21240
tacttataaa caagcaattt tatgacaaac aatatgtaga agatcatact gttggttttg    21300
aagaatataa atctatagtt gaggattata cgcctgaata tgcagaaaaa gttactggta    21360
tacctgcaga ggatatagta gaagctatga aaatgtactc cagtgctaaa aatgctatga    21420
tattgtacgg tatgggagta tgtcagtttg ctcaagctgt agatgtagta aaagggttag    21480
cttcaatagc tttattaact ggtaattttg aagacctaa tgtaggcata ggacctgtaa    21540
gaggccagaa caatgtgcaa ggtgcctgcg atatgggagc acttcctaat gtatacccag    21600
gttatcaaag tgtaactgac gatgcaatta gagaaaaatt tgaaaagct tggggagtta    21660 aactttcaaa caaagttggt tatcacctga cacgagttcc tgaattaacg cttaaagagg    21720
```

```
ataaaataaa agcatattat ataatgggcg aagatccagc tcaaagtgat cctgattcta    21780
atgaaatgag ggaaacactt gataaaatgg aacttgtaat agttcaagat atatttatga    21840
ataaaactgc actccatgca gatgtaattt taccttctac gtcttgggga gaacatgaag    21900
gagtcttcag ttctgctgat agaggattcc agagatttag aaaagctgta gaacctaagg    21960
gcgatgttaa accagattgg gagataattt cagaaattgc atgtgctatg ggttatgata    22020
tgcattataa caatactgag gaaatatggg atgaacttat aaatttatgc ccaaatttca    22080
aaggagcaac ttataagaga ttggatgaat taggaggaat tcaatggcct tgtccatctg    22140
aagatcatcc aggaacttct tatctctaca aggaaataaa atttaataca cctactggaa    22200
aagcaaattt atttgcagca gaatggagac ctcctataga aagacagat gaagaatatc     22260 cacttgttct ttctacagtt agagaagtag ggcattactc cgtaagaaca atgcaggaa      22320 actgtagggc actccagcag ttagctgatg aaccaggata tgtacaaatt aatccagtgg    22380
atgcaaaggc taaaaaaata atagatggtg agcttatgag agtaagttca cgaagaggtt    22440
ctgtagttgc ccgtgcactt gttactgaaa gggcaaataa aggagcagtt tatatgacct    22500
atcaatggtg ggtaggtgca tgtaatgagc ttacagctaa taatttagat ccagtatcaa    22560
aaactcctga attaaagtat tgtgcagtga aggtagaagc tatagaagat cagaaagaag    22620
ctgaaaagtt tataaaagat caatatgctt caataaagaa aaagatgaat gtttaatatt    22680
ttgcaaagga gttcatattc atataggtaa actatgccta ttatgagtat gaacttttta    22740
tattatcaaa atattttaa tttttatttt atacaaaaaa tatataagta tattattact     22800
caagttattt ttaaagatac atagaaattt gagtgataat gattttttagt ttctaccgag   22860 ccctgaaata aaagggtga gagttatgat tacgcctatt tataaaaaag aaggagtgga    22920
attattaatg gaaaaaaagg tattaactgt atgtccttat tgcggtgctg gatgtcaact    22980
gtatctaatt gttaaagatg gacaaatagt aagagcagaa cctgctaatg aagaacaaa    23040 tgaaggaact ctttgtctta aaggacgcta tggttgggat tatctaaatg atcctcaact    23100
tctaactcca cgtataaaaa aacctatgtt aagaaaaaat ggtaaattag tagaagtaac   23160
ttgggatgaa gctattaagt ttacgtcaga aaaattaaca gaaataaaaa ataagtatgg    23220
tgctgattct ataatgacta caggctgttc tagaggtcct ggaaatgaga caaattatat    23280
aatgcaaaaa tttgcacgtg ctgtaatagg tacaaacaat gtagataact gtgctagagt    23340
ttgtcatggt ccctcagtag caggattagc tacagtactt ggaaatggtg ccatgtcaaa    23400
tactattcct gaaattgaaa atgcagattt gcttcttata tttggataca atccagcaga    23460
atctcatcct atagttgcta agaagtagt taaagcaaag gaaaaaggag caaaaattat    23520
agttgtagat cctagggtca cagaaagtgt gagaatatct gatctttggc ttcaattaaa    23580
aggtggtaca aatatggcac ttgtaaatgc atttgccaat gtactactta atgaaaattt    23640
gtataacaaa gaatatgttg ctaattatac tgaaaacttt gaagaatata atcaattat     23700 acaaaaatat aatccagaat atgcaggaa aataacaat gtccctgctg aagacataaa       23760
aaaagccatg agaatgtatg ctaacgcaaa aaatccaatg attctttatg gtatgggggt    23820
atgtcaattt ggtcaagctg tagatgtagt taaaggttta gctggcttag cgttaatgac    23880
aggaaactat ggcaggccta gcgttggtat aggtcctgta agaggacaaa ataatgttca    23940
gggcgcttgt gatatgggtg ctattcctaa ttgttaccct ggatatcaaa aggttacgga    24000 taaaatgtt agagaaaaat ttgaaaaggc ttggggagta aagcttcctg ataaagtggg    24060 atatcatttaa acagaagtgc ctgagttagt tttaaagaa aataaactga aagcttatta     24120
```

```
tataatgggc gaggattgtg ttcaaagtga cccaaatgca aacgatgtaa gaaaagcttt   24180
agataaattg gaacttgtaa tagttcaaga tatatttatg aataaaacaa ctttacatgc   24240
tgatgtaata cttccggcta ctgcttgggg agaacatgaa ggtgtataca gttctgctga   24300
tagaggtttt caaatattcc gaaaagctgt tgaaccaaag ggagatgtta aaccagattg   24360
gcagataatt tgtgagttag ctactgccat gggatatcct atgcattata ataatacaaa   24420
agaaatatgg gatgaaatga gaagtctttc tccaaaattt gctggtgcta gctatgaaag   24480
aatggaaaag ttaggaggaa taatttggcc ttgtccttct gaagatcatc ctggaactcc   24540
tgtgctttat gaaggaaaca ttttttagtac accaagtaaa aaaggtattt tatttgctgc   24600
agaatggaga cctacacaag aatctccaga taaagaatat ccattaagtt tatgtacagt   24660
tagagaaata ggtcactact ctgtaagaac aatgactggt aattgccgtg ctctcaaggc   24720
acttgaagat gaaccaggta aaattcaaat gagtttggaa gatgctgaag aacttgctat   24780
aaatgatgga gatctagtac gagtaagttc aagaagaggt tctgtaatgt caagagcctt   24840
agttacagat agagttcgta agggtaatac ttatatgact tatcaatggt ggattggagc   24900
ttgtaatgac cttactgttg ataacttaga tcctgtatca aaacacctg aatataaata   24960 ttgtgcagtt aaagtggagg caataaagga tcaagataaa gctgaaaaat gtttattaga   25020
aacatacaat gaattacgta aaaaaatggg agtaaaaaat atgtagtata aacttgttca   25080
aagatttgca aaagctgatg ctataggacc tgtatgccag ggatttgcaa aacctataaa   25140
tgatttgtca agaggatgta actccgatga tatagtaaat gtagtagctg taacagcagt   25200
tcaggcacaa gctcaaaagt aataacaaaa agcataaatg attcattttt aggaggaata   25260
ttaaacatga aaatattagt agtaaactgt ggaagttcat cttttaaaata tcaacttatt   25320 gatatgaaag atgaaagcgt tgtggcaaaa ggacttgtag aaagaatagg agcagaaggt   25380
tcagttttaa cacataaagt taacggagaa aagtttgtta cagagcagcc aatggaagat   25440
cataaagttg ctatacaatt agtattaaat gctcttgtag ataaaaaaca tggtgtaata   25500
aaagatatgt cagaaatatc tgctgtaggg catagagttt tgcatggtgg aaaaaaatat   25560
gcggcatcca ttcttattga tgacaatgta atgaaagcaa tagaagaatg tattccatta   25620
ggaccattac ataatccagc taatataatg ggaatagatg cttgtaaaaa actaatgcca   25680
aatactccaa tggtagcagt atttgataca gcatttcatc agacaatgcc agattatgct   25740
tatacttatg caatacctta tgatatatct gaaaagtatg atatcagaaa atatggtttt   25800
catgaacttt ctcatagatt cgtttcaatt gaagcagcca agttgttaaa gaaagatcca   25860
aaagatctta agctaataac ttgtcattta ggaaatggag ctagtatatg tgcagtaaac   25920
cagggaaaag cagtagatac aactatggga cttactcccc ttgcaggact tgtaatggga   25980
actagatgtg gtgatataga tccagctata ataccatttg taatgaaaag aacaggtatg   26040
tctgtagatg aaatggatac tttaatgaac aaaaagtcag gaatacttgg agtatcagga   26100
gtaagcagcg attttagaga tgtagaagaa gctgcaaatt caggaaatga tagagcaaaa   26160
cttgcattaa atatgtatta tcacaaagtt aaatctttca taggagctta tgttgcagtt   26220
ttaaatggag cagatgctat aatatttaca gcaggacttg gagaaaattc agctactagc   26280
agatctgcta tatgtaaggg attaagctat tttggaatta aaatagatga agaaaagaat   26340
aagaaaaggg gagaagcact agaaataagc acacctgatt caaagataaa agtattagta   26400
attcctacaa atgaagaact tatgatagct agggatacaa aagaaatagt tgaaaataaa   26460
```

```
taagattaaa tttttactta tttgatttac attgtataat attgagtaaa gtattgacta    26520
gtaaaatttt gtgatacttt aatctgtgaa atttcttagc aaaagttata tttttgaata    26580
atttttattg aaaatacaa ctaaaaagga ttatagtata agtgtgtgta attttgtgtt    26640
aaatttaaag ggaggaaata aacatgaaat tgatggaaaa aatttggaat aaggcaaagg    26700
aagacaaaaa aaagattgtc ttagctgaag gagaagaaga aagaactctt caagcttgtg    26760
aaaaaataat taagaaggt attgcaaatt taatccttgt agggaatgaa aaggtaatag    26820
aggagaaggc atcaaaatta ggcgtaagtt taaatggagc agaaatagta gatccagaaa    26880
cctcggataa actaaaaaaa tatgcagatg ctttttatga attgagaaag aagaagggaa    26940
taacaccaga aaaagcggat aaaatagtaa gagatccaat atattttgct acgatgatgg    27000
ttaagcttgg agatgcagat ggattggttt caggtgcagt gcatactaca ggtgatcttt    27060
tgagaccagg acttcaaata gtaaagacag ctccaggtac atcagtagtt tccagcacat    27120
ttataatgga agtaccaaat tgtgaatatg gtgacaatgg tgtacttcta tttgctgatt    27180
gtgctgtaaa tccatgccca gatagtgatc aattggcttc aattgcaata agtacagcag    27240
aaactgcaaa gaacttatgt ggaatggatc caaaagtagc aatgctttca ttttctacta    27300
agggaagtgc aaaaacacgaa ttagtagata agttagaaaa tgctgtagaa attgccaaaa    27360
aagctaaacc agatttaagt ttggacggag aattacaatt agatgcctct atcgtagaaa    27420
aggttgcaag tttaaaggct cctgaaagtg aagtagcagg aaaagcaaat gtacttgtat    27480
ttccagatct ccaagcagga aatataggtt ataaacttgt tcaaagatt gcaaaagctg    27540 atgctatagg acctgtatgc cagggatttg caaaacctat aaatgatttg tcaagaggat    27600
gtaactccga tgatatagta aatgtagtag ctgtaacagc agttcaggca caagctcaaa    27660
agtaaggaga actgtattgc ttattattta agcattttat tataaaataa aaaaacgtta    27720
ttaaattatt tactatgaat tcacttgata atcaacacat tgcatgtaat gttgattatt    27780
gagtgttttt ttgtaaccat atttggcaca atttatgctc tataacatt ctgaaataaa    27840 tatatgtata tgaggaggaa tttcaatgta tggttataat ggtaaagtat taagaattaa    27900
tttaaaagaa agaacttgca aatcagaaaa tttagattta gataaagcta aaagtttat    27960 aggctgtagg ggactaggtg ttaaaacttt atttgatgaa atagatccta aaatagatgc    28020
attatcacca gaaaataaat ttataattgt aacaggtccg ttaactggag ctccagttcc    28080
aactagtgga aggtttatgg tagttactaa agcaccgctt acaggaacta taggaatttc    28140
aaattcgggt ggaaaatggg gagtagactt gaaaaaagct ggctgggata tgataatagt    28200
agaggataag gctgattcac cagtttacat tgaaatagta gatgataaag tagaaattaa    28260
agatgcgtca cagcttggg gaaaagttac atcagaaact acaaaagagt tagaaaagat    28320
aactgagaat agatcaaagg tattatgtat aggacctgct ggtgaaagat tgtcccttat    28380
ggcagcagtt atgaatgatg tagatagaac tgcagcaaga ggcggcgttg gtgcagttat    28440
gggatctaaa aacttaaaag ctattacagt taaaggaact ggaaaaatag ctttagctga    28500
taaagaaaaa gtaaaaaag tgtccgtaga aaaaattaca acattaaaaa atgatccagt    28560
agctggtcag ggaatgccaa cttatggtac agctatactg gttaatataa taatgaaaa    28620 tggagttcat cctgtaaata ttttcaaga atcttatacg gatcaagcag ataaaataag    28680
tggagagact cttactgcta accaactagt aaggaaaaat ccttgttaca gctgtcctat    28740
aggttgtgga agatgggtta gactaaaaga tggtacagag tgcggaggac cggagtatga    28800
aacactgtgg tgtttttggct ctgactgtgg ttcatatgat ttagatgcta taaatgaagc    28860
```

```
taatatgtta tgtaatgaat atggtattga tactattacc tgtggtgcaa caattgctgc    28920
agctatggaa ctttatcaaa gaggatatgt aaaagatgaa gaaatagccg gagataacct    28980
atctctcaag tggggagata cggagtctat gattggctgg ataaagaaaa tggtatatag    29040
tgaaggcttt ggagcaaaga tgacaaatgg ttcatatagg ctttgtgaag gttatggagt    29100
acctgagtat tctatgacag ttaaaaaaca agaaattcca gcatatgatc caaggggaat    29160
acagggacat ggtattacct atgcagttaa taatagagga ggatgtcata ttaagggata    29220
tatgattaat cctgaaatat taggttatcc ggaaaaactt gatagatttg cattagatgg    29280
taaagcagcc tatgccaaaa tgatgcatga tttaactgct gtaattgatt ctttaggatt    29340
gtgcatattc actacatttg ggcttggaat acaggattat gtagatatgt ataatgcagt    29400
agtaggagaa tctacttgtg attcagattc actattagag gcaggagata gagtatggac    29460
tcttgaaaaa ttatttaatc ttgcagctgg aatagacagc agccaggata ctctaccaaa    29520
gagattgtta gaagaaccta ttccagatgg tccatcaaag ggacacgttc ataggctaga    29580
tgttcttctg ccagaatatt actcagtacg aggatggagt aaagagggta tacctacaga    29640
agaaacatta aagaaattag gattagatga atatataggg aagttctagt aaagagcaat    29700
tatgaataat aataacatag aaacaaacaa taaaagtgag aatcttgttt atccgatgac    29760
tactcgctct aatactccca cttctgcaag tgggagtaaa gagcgactac gtccctggat    29820
aacgattttt cctaaaggat aacgtcttct aagtgctgaa gcactaagaa tactgttaat    29880
aagcatcagg tggagttaaa actccatctg atgccaagaa atctgtttat atttaacagc    29940
atgaaaaata agaaagaggt gtcattaatg aaggtaacta aggtaactaa cgttgaagaa    30000
ttaatgaaaa agttagatga agtaacggct gctcaaaaaa aattctctag ttatagtcag    30060
gaacaagtgg atgagatctt taggcaggca gctatggcag ccaatagtgc tagaatagat    30120
ctagctaaaa tggcagtgga agaaagcgga atgggaattg tagaagacaa ggttattaaa    30180
aatcattttg tttcagaata tatatataac aaatataagg atgaaaagac ctgtggagtt    30240
ttagaagaag accaaggttt tggtatggtt agaattgcgg aacctgtagg ggttatagca    30300
gcagtagttc caacaactaa tccaacatcc acagcaatct ttaaatcttt aatagctttg    30360
aaaactagaa atggtatagt tttttcacca catccaagag caaaaaaatc aactattgca    30420
gcagctaaga tagtacttga tgcagcagtt aaagctggtg ctcctgaagg aattataggg    30480
tggatagatg aaccttccat tgaactctca caggtggtaa tgaaagaagc agatttaatt    30540
cttgcaactg tgggcccggg tatggttaag gctgcctatt cttcaggaaa gcctgctata    30600
ggagttggcc caggtaacac acctgctgta attgatgaaa gtgctgatat taaaatggca    30660
gtaaattcaa tactccttc aaaaactttt gataatggta tgatttgtgc ttcagagcag    30720
tcagtagtag ttgtaagctc aatatacgat gaagtcaaga agaatttgc agatagagga    30780 gcgtatatat taagtaagga tgaaacagat aaggttggaa aaacaattat gattaatggc    30840
gctctaaatg ctggcattgt agggcaaagt gcttttaaaa tagcacagat ggcaggagtg    30900
agtgtaccag aggatgctaa agtacttata ggagaagtta aatcagtaga acctgaagaa    30960
gagccctttg ctcatgaaaa gctgtctcca gttttagcta tgtacaaagc aaaagatttt    31020
gatgaagcac ttctaaaggc tggaagatta gttgaacgag gtggaattgg gcatacatct    31080
gtattatatg taaattcaat gacggaaaaa gtaaagtag aaaagttcag agaaactatg    31140
aagactggta gaacattgat aaaatatgcct tcagcacaag gtgctatagg agatatatat    31200
```

```
aactttaaac tagctccttc tttgacgcta ggatgtggtt cctggggagg aaactctgta    31260
tcagaaaatg ttggacctaa acatttatta aacataaaaa gtgttgctga gaggagagaa    31320
aatatgcttt ggtttagagt acctgaaaaa gtttatttca aatatggtag tcttggagtt    31380
gcattaaagg aattgagaac tttggagaag aaaaaggcat ttatagtaac ggataaggtt    31440
ctttatcaat taggttatgt agataaaatt acaaaaaatc tcgatgaatt aagagtttca    31500
tataaaatat ttacagatgt agaaccagat ccaaccttg ctacagctaa aaaggtgca     31560
tcagaactgc tttcctatga accagataca attatagcag ttggtggtgg ttcggcaatg    31620
gatgcagcca agatcatgtg ggtaatgtat gagcatccag aagtaagatt tgaagatttg    31680
gctatgagat ttatggatat aagaaagaga gtatatgttt ttcctaagat gggtgaaaaa    31740
gcaatgatga tttcagtagc aacatccgca ggaacaggat ctgaagttac tccatttgca    31800
gtaattacgg atgaaagaac aggagctaaa tatccactgg ctgattatga attgactcca    31860
aacatggcta taattgatgc agaacttatg atgggaatgc caaaagggct tacagcagct    31920
tcgggtatag atgcattaac ccatgcactg gaggcgtatg tatcaataat ggcttcagaa    31980
tataccaatg gattggctct tgaagcaaca agattagtat ttaaatattt gccaatagct    32040
tatacagaag gtacaactaa tgtaaaggca agagaaaaaa tggctcatgc ttcaactata    32100
gcaggtatgg cttttgccaa tgcattctta ggggtatgtc actctatggc acataaattg    32160
ggagcacagc accatatacc acatggaatt gccaatgcgc ttatgataga tgaagttata    32220
aaattcaatg ctgtagaggc tccaaggaaa caagcggcat ttccacaata taagtaccca    32280
aatgttaaaa gaagatatgc tagaatagct gattacttaa attaggagg aagcacagat    32340
gatgaaaaag tacaattgct aataaatgct atagatgact taaaaactaa gttaaatatt    32400
ccaaagacta ttaagagc aggagtttca gaagataaat tctatgctac tttagacaca    32460
atgtcagaac tggcttttga tgatcaatgt acaggagcta atccaagata tccactaata    32520
ggagaaataa acaaatgta tataaatgca tttgatacac caaaggcaac tgtggagaag    32580
aaaacaaaaa agaaaaaata atgtaaaata aaatcagaaa ttagttaaat atttaaaata    32640
aaataaaaat ttacaatg atgtatgaaa agcgatgaa gcttctaaaa gaatatttat      32700
attcttagga agctttttt atttttattgg tagctatcaa aaaattacaa aatttaatat   32760
gactaatgtg aagtttcata gatatttat taaattggag tatgattatt gtgaaaaatt    32820
ttaatgttaa accaaaggtt tattttggta ctgatgcttt aaatcatttg tgtgaattaa   32880
aatgtaagaa agctttaatc gctgcagatc catttatggt taagtcatca acggttgata   32940
aaattactga acagcttgat aaggcacata tagagtatga tatattttca gatatagtac   33000
cagatcctcc tgttgaagtt attataaaag gagtgcagga agctgttaaa tttaaacctg   33060
atgtacttat agcacttgga ggaggatcag ctattgattc tgcaaaagga ataaggtatt   33120
tttgtcagta tgtaaataat gaattgaata acgaaatgaa agagcccctg tttatagcaa   33180
ttccgacaac aagtggtaca ggctctgagg ttactaactt ttgtattgta actgataagc   33240
aaaaaggagt caaatatgct cttgttgatg acaatttgac gccggatcag gcggtacttg   33300
atattgaact tgtaaaatca gtgccaaaag ctaccacatc agaaacagga atagacgtac   33360
ttacacatgg aattgaagca tatgtttcta caaatagatc agattattct gatgcactgg   33420
cagaaaaatc aataaaaatg gtatttaaat acttgttagc cgcatatgaa aatggagatg   33480
atgaagaagc tagaacgaag atgcataatg catcctgcat agcaggtatg gcatttacaa   33540
atgcttccct tggacttaac catggcatgg ctcatgcact tggtggaaaa attcatatac   33600
```

```
cgcatggaag agcaaatgga ctacttcttc catacgtaat agagtataat gcaaacctta    33660
aaaacttaca aggaaagata aaccattcta gtgcagcata taggtatact gaaatatcaa    33720
aattcttggg acttccagca tctaaccaat ttgaaggtgt taggagtttg attgcagcag    33780
ttaagatact gatgaataaa cttaacttac ctaaatgtat taataattgt gaagttttat    33840
gtgaaaattt ggataatgag attcatgagt tatcgataac tgccctaaat gatagatgta    33900 caaaacaaa tccgagaatt cctgaaataa aggatgttga aaatttgttt aagagggttt    33960
tttctaaaga ataacataaa agaagagcat gcaattagtt ttaaattatt agatagtgta    34020
aagcgttata aacaatttct tgatacatac cctgatttgg aagaacgtgt taagcagtgt    34080
tatattgcat cctatttagg aataactcct gtgtctctta gcagaataag aagaaaatta    34140
aatcttaaca aatgataatg caataaatct ctaggtgatt tatgatgtag ttaatttta     34200 ttactggagg ttaattgtta tgaaaaatga aatagttgtt ttaattactg gatgttctac    34260
agggattgga agagagcttt gtagtatatt gtttcacaaa ggatgtacgg ttgttgcaac    34320
agcaagaaat gtagaaactt taaaagattt atctgcgtcc ttaagattac cactggatgt    34380
tacccaaaaa gagtctatta acagtacaat aaatgaagtt gtatcaaaat ttcataaaat    34440
tgatattctt ataaataacg caggctattc aattagagga gctttagaag aaattgattt    34500
aaatagtgct aaaagtatgt ttgatgtaaa tgtatttggt attattaaca tgattccaggc   34560 agttattcca gaaatgcgta aaaaacaatt tggtaagatt ataaatattg gctccatttc    34620
agggaaattt gttcaatcca tcaatggagc gtattgtgca tcaaaatttg cagttgaggc    34680
actaagtgac acacttcgtt tagaattaca cagctacaat attcagagca ccgtcattga    34740
gccaggtccc atgaaaacca actttttaa  ggcattagtg gataattcag gcgatgttat    34800
aaaaaatgaa aattcttgtt attcacattt ttataaatca gatgatgaat atagaaaaaa    34860
gcaaaaacaa gctgatccta aagtagcagc acaagctatt agtgtatataa ttttgaaaaa    34920 acgacttaat gctcgttata aagttgctgt tccatttaca tataagatgg ttacatattt    34980
tcctgatttt ctaagagaat actttatgaa aaaaagatag tagttgatat ataacttttt    35040
agtcgtacaa atacgaaata tattttatca tacttgcatg taaaatgcta tacagcttat    35100
acttctaaag tttgttttata ttagttcaca gggtttcaaa aattgtagtt tataatcaca   35160
tatattttcg aaattcatat attaaataga agtactttac aatattggag gaactactat    35220
atgtgttcaa atcatattgg atgcaaattt ccacgctttt ttccacccca acatcagcca    35280
catcaacctg gtattgaata tattatgaca cctagaccag ttttcgaacc accattatgt    35340
gcacaatatc aaacgacaaa aagattatta acaaagtag ctttaataac aggaggagac     35400
agcggtattg ggcgtgctgt agcatgtgct tatgcaaaag aaggagctga tattgccatt    35460
gtctatctaa atgaacatgt agatgcagag ggaacaaaat ctagaataaa aaaattgggg    35520
cgaagatgtt taaccattcc aattaacata ggagtcgaag agaatagtaa aattataatt    35580
caagaagtta tgaatcattt tggtaaatta gatattcttg taaataatgc tgcagtactt    35640
tattacaata attctataga agaagtatct agcaaacaat tagaatggac ttttcgtata    35700
aatgtatttt cttatttcta cttaactaaa gcagctctac cttatatgaa accaggcggt    35760
tctatcatca atacttcttc aatagttgct tttaatcctc cttatgggat atctttagat    35820
tatgaagctt caaaaggtgc cattgctaat ttcactataa atttagcccg aagtttggtt    35880
tcaagaggaa tacgtgtaaa tggtgtagct ccaggtgaaa cctggacacc tttaattcca    35940
```

```
gcaggattac ctgcagataa agttgccgtt tggggttcaa aaacaccaat gggaagagct    36000
gctcaaccat ttgaaattgc tccagcctat gtattcttag cttccaatga atcaagctat    36060
atgtcaggac aaacaatcca tatgtattct taagagtaaa agttgatgag gagagaaaat    36120
cagggtcact tctcgaaata aaacaaaaac ttgaaagaat gaaagttatt gaactcagaa    36180
atatggctag aaaaatgaat ttaagttcat tgactaagaa ggacattaaa tttggcaaga    36240
aaaagcagct gattaaagca attttagagt actatacaag gaggttaaag taaatggaaa    36300
atatagatag ggatttacaa tctatacaag atgtaaggcg gcttgttgaa aaggcaagac    36360
aagctcaaca agaatattgt aaattcagtc aggaaaagat gaataaaatt attgagcatg    36420
tagcggaatc tgctggctta caagctgaaa gattagcaaa acttgctgta gaagaaacaa    36480
cttttggaaa tttacctgat aagataatta aaaataagtt tgctagtgaa atagtgtatg    36540
aaaatataaa ggacatgaag ttagtaggta ttttaagaga tgacaaagat agaaaagtat    36600
tagagatagg ttcacctgta ggtattattg cagggcttgt accatcaact aatcctactt    36660
ctactgttat atataaaagt cttatagctt taaaatcggg aaatgcaatt gtatttagtc    36720
ctcatccaaa ggcaagacat tgcattgcag aagctataaa ggttgtaagt gatgcagctg    36780
ttgaggcagg agcaccttta ggaatggttt ccggaatgag tatacttact atggaaggaa    36840
ctcatgagct tatgaaaaac gttgatctca tactagcaac aggtggatca gctatggtaa    36900
aggcagcata cagttcagga actccggcta taggagttgg acctgaaat ggacctgctt    36960 ttattgaaaa aacagcaaat ataaaacttg cagtaaaaag aataatggat agtaaaactt    37020
ttgacaatgg ggtaatatgt gcttcagaac agtccatagt agttgaaaaa tgtataaaag    37080
atgaagttgt agatgagctt aaacgccaag gagcatactt cttatctaaa gaacaatcag    37140
aaaaagtagc aaagtttata ttgagagcaa atggtactat gaatcctcaa attgtaggaa    37200
aatcagctca gaaaatagct gaaatggcag gtataactgt agatccaaat gcaagaatat    37260
tgatttcaga gcagacgaca gttggaaaag ataaccccatt ttcaagggaa aagcttacaa    37320
cgattttagc attctactgt gaagaaaatt gggaaaaagc ttgcgagaga tgcattgagc    37380
ttttaaataa tgaaggtata ggacatactc tcataataca ttcaaataat gaagaaatag    37440
taaaagaatt tggacttaaa aaacctgtat ccagaatact tgtaaacacg ccaggatcac    37500
ttggaggaat aggagctact acaaatctag tgcctgcact tacacttgga tgcggagcag    37560
ttggaggaag tgcaacttct gataatgtag gacctaggaa tcttataaat ataagaagag    37620
ttgcctatgg agtaaaggaa atagaagata taaaaaattt tgtaagtaat tgtagtgaca    37680
gagaaacctc acacactgtt ttggatattt ctgatcagta cattgaactt ataactaaaa    37740
aaatagctga aaagcttagt ttgtaaatgg tttagaaaaa gctattgaga ttttaagtaa    37800
gtttaaggta atagagcttc gaaatctcgc tcgtaaatat aagaactttg gtatcaaagg    37860
aaggtccatt tctaaagcag acaagaagtt gctgcttata gagttcaaaa aatattatgg    37920
gcataattag ccagctataa aaattaaaat atataaataa taaacaatgg agggaacaca    37980
attggaaaat tttgataaag acttacgctc tatacaagaa gcaagagatc ttgcacgttt    38040
aggaaaaatt gcagcatgtg aaattgctga ttatactgaa gaacaaattg ataaaatcct    38100
atgtaatatg gttagggtag cagaggaaaa tgcagtttgc cttggtaaaa tggctgcaga    38160
agaaactggt tttggaaaag ctgaagataa ggcttataag aaccatatgg ctgctactac    38220
agtatataat tatatcaagg atatgaagac tattggtgtt ataaagaag ataaaagtca    38280 aggtgtaatt gaatttgctg aaccagttgg tttattaatg ggtattgtac catctacaaa    38340
```

```
tccaacatct actgttatct ataaatcaat cattgcaatt aaatcaagaa atgcaattgt   38400
attctcacca cacccagctg cattaaaatg ttcaacaaaa gcaatagaac ttatgcgtga   38460
tgcagcagta gcagcaggag ctcctgcaaa tgtaattggc ggtattgtta caccatctat   38520
acaagctaca aatgaactta tgaaagctaa agaagttgct atgataattg ccactggagg   38580
ccctggaatg gtaaaggctg cttatagttc aggaacacct gcaataggcg ttggtgctgg   38640
taactctcca tcttatatag aaagaactgc tgatgttcat caatcagtta aagatataat   38700
tgctagtaag agttttgact atggtactat ttgtgcatct gagcaatcaa taattgttga   38760
agaatgcaac catgatgaag taatagctga gttgaagaaa caaggcggat atttcatgac   38820
agctgaagaa actgcaaaag tttgcagtat acttttttaag cctggtacac acagtatgag   38880
tgctaagttt gtaggaagag ctcctcaggt tatagcagca gctgcaggtt tctcagttcc   38940
agaaggaaca aaagttttag taggagaaca aggcggagtt ggtaatggtt accctctatc   39000
ttatgagaaa cttacaacag tacttgctttt ctatacagtt aaagattggc atgaagcatg   39060
tgatcttagt ataagattac ttcaaaatgg tcttggacat actatgaaca ttcatacaaa   39120
tgacagagac ttagtaatga agtttgctaa aaaaccagca tcccgtatat tagttaatac   39180
tggtggaagc caaggaggta ctggtgcaag cacaggatta gcacctgcat ttacattagg   39240
ttgtggtaca tggggaggaa gctctgtttc cgaaaatgtt actccattac atttaatcaa   39300
tataaagaga gttgcatatg gtcttaaaga ttgttctaca ttagctgcag atgatacaac   39360
tttcaatcat cctgaacttt gtggaagcaa aaatgactta ggatgctgtg ctacaagccc   39420
tgcagaattt gcagcaaata gcaattgtgc tagcactgct gcggatacta ctgataatga   39480
taaacttgct agactcgtaa gtgaattagt agctgcaatg aagggagcta actaaaagct   39540
gtaacagata tgggcgctga agtttatagt tcagttgtta ttgcaagtcc acatccggat   39600
cttcagaaaa tcaccaaacg ttatacaatt gaaaatttac ttccttaata tgtggatgat   39660
atgataccac cacataaaat gaaaaagtac agaagtacag tacttagtta gtaaaaatga   39720
aagggagagt tagaaatgaa tattattgat aatgatttgc tctccatcca agaatcccga   39780
atccttgtgg aaaatgctgc acgagcacaa aaaatgttag caacttttcc gcaagaaaag   39840
ttagatgaga ttgttgaacg tatggctgaa gaaatcggaa aacatacccg agagcttgct   39900
gtaatgtcac aggatgaaac tggttatgga aatggcagg ataaatgcat caaaaaccga   39960
tttgcctgtg aatatttgcc agctaagctt agaggaatgc gatgtgtagg tattattaac   40020
gaaaatggtc aggataagac catggatgta ggtgtaccta tgggtgtaat tattgcatta   40080
tgtcctgcaa ctagtccggt ttctactacc atatataagg cattaattgc aattaagtct   40140
ggtaatgcaa ttatcttttc tccacatcct agagcaaagg agacaatttg taaggcgctt   40200
gacatcatga ttcgtgcagc tgaaggatat gggctgccag aaggagctct tgcatactta   40260
catactgtga cgcctagtgg aacaatcgaa ttgatgaacc atgaggcgac ttctttgatt   40320
atgaatacag gcgttccggg gatgcttaaa gcgtcatata gatctggaaa acctgtgatc   40380
tatggaggaa ctggtaatgg accagcattt attgaacgta cagctgacat caagcaggcg   40440
gtaagagata ttattgctag taagaccttt gataacggaa tagtaccatc atctgaacaa   40500
tctattgttg tagatagctg tgttgcatct gatgttaaac gtgagttgca aaatagtggt   40560
gcatatttca tgacagagga ggaagcacaa aaactgggtt ctctcttttt ccgttctgat   40620
ggtagtatgg attcagaaat ggttggcaaa tccgcacaga gattggctaa gaaagcaggt   40680
```

```
ttcagtattc ctgaaagtag cacagtgcta atttcagagc agaaatatgt ttcccaagat    40740
aatccttatt ccaaggagaa actttgtccg gtactagctt actacattga agatgattgg    40800
atgcatgcat gtgaaaagtg tattgagctg ctattaagtg agagacatgg tcacactctt    40860
gttatacatt caaagacga agatgtaatt cgccagtttg cattaaaaaa acctgtaggc    40920
aggatacttg ttaatacgcc tgcttccttt ggtagtatgg gtgctacaag taatttattt    40980
cctgctttaa ctttaggtag tggatcggca ggtaaaggta ttacctccga taatgtttca    41040
ccaatgaatc ttatttacgt ccgtaaagtc ggatatggcg tacggaatgt agaagagatt    41100
attaatacta atggattgtt tacagaagaa aaaagtgatt tgagtggtat gacaaagcag    41160
tcagactata atccagagga tatacaaatg ttgcagcata ttttgaaaaa agctatggaa    41220
aaaattaaat agaaatgaat atttattgct gcagtactat attccactgg ttgaatagtg    41280
tacttaaatg ctcctttagg tttagcaaaa atttgtgatt attatccttt agataaggaa    41340
agtatattag ttattagaag ctattgaatt agagaaaatt aattgtaatg agcaagtttt    41400
tgatgaacgg ttaagaggag atgtagtgta aattgagaga tgattatagg aatctattta    41460
aattcataat aaaggcatat tatagtggaa actttgaaga agaagtgatg tcatttttat    41520
tagagtctaa aatggataaa caggaattgt gtaagattat atctacattg tgcggtacta    41580
atgtagatta cagctctaac tttatagaaa atttaaaaaa agcaataaag tcttataaac    41640
aagatggtaa agtagtcaat aaagttaaag actgttccat ggaatgtgtg gatgaaaaag    41700
gtgagatact atgtcaaaaa acatgtcctt ttgatgcaat ttttatagac aataagaaaa    41760
attgtgctta catagataaa gaaaagtgta ccgattgtgg tttgtgtgta gatgtttgcc    41820
ctactggggg aataatggat aaagttcagt tcattcctat tttggatatt ttaaaaagta    41880
aatctccagt tgtggctata gtggctcctg ccataatagg acagtttggg gaagatgtta    41940
ctatggatca acttaggacc gctttttaaaa aactgggatt tactgatatg attgaagtgg    42000
cattttttgc agatatgctt actttaaagg aatctattga atttgacaat catgtaaaag    42060
atgaaaaaga ttttatgata acttcctgct gttgtcctat gtgggtggct atggtaaaaa    42120
aggtatacag taacttggtt aaacatgtat ctccctctgt atctccgatg gttgcaggag    42180
gaagagtact aaaaagtta agtccttact gcaaggtagt gtttataggc ccatgtattg    42240
ctaaaaaatc tgaggcaaag gaagaagata taaaaggagc aatagatttt gtacttactt    42300
ttgaagaatt aagagatata tttgatgctt ttcatatagt tccatctaaa cttgaaggag    42360
atttttcatc taaatatgct tctagaggtg gaagattata tgcccgtaca ggtggagttt    42420
ctattgcagt aagcgaagct gtggaaaaga ttttttcctga aaagcataaa ctatttagtg    42480
caattcaggc aaatggcatt agagaatgta agaaatgct taccaaggtg caaaatggag    42540
aaataaaagc taatttttatt gaaggaatgg gctgtattgg tggatgtgta ggtggtccca    42600
aagcaattgc atctaaggat gaaggtaggg atcgagtaaa taaatttgca caagattctg    42660
aaataaaagt tgctgtagat agtgaatgta tgcatggagt attacatgct ttggatatac    42720
attctataga tgattttaag gatgagaaaa aaatagaact gttagaacga gaatttttaaa    42780 taattagttc ttaattaaat aggactaaat ttatatttta attttaaat aaggtaatta    42840 aaataatttt aaattaaata tgttatatgt tttaaaatta tttcttaagc atagaggctc    42900
aaatctttga tttagagcta atatcttatt ccttctaata tttttaagggg gaaatcaatt    42960 ataatattca aatgggaggg tgaagtattt aatgttaact aaacagcaaa atgaagacct    43020
gtctggacaa gatgtaattg aaaaatatcc taaagagcag agatttactc ttgctatact    43080
```

```
acaggatata cagagaaagt acaaatatat acccagagaa gcactggaga atttagctaa    43140
gtatttggac acgcctgtaa gtagactgta tggtatggct acttttata  aggcattgag    43200
ccttactcca aaagggaaa  acataataac tgtatgtgat ggaaccgctt gccatgttgc    43260
tggttctatg gttgtaatgg atgaacttga aaaggcaata ggaattaaac caggtgaaac    43320
tacagaagat cttaaatttt caataaatac agttaactgt ataggatgct gtgcaatagc    43380
tcctgtcatg atgataaatg acaaatattt tggaaattta acacctaaac tggttgaaga    43440
aattcttagt gagtatagga gtgaaagcca tgagtgattg aagaaattct tagtgagtat    43500
aggagtgaaa gccatgagtg ataaaaaat  tgtcaatata tgttgtggaa caggttgctt    43560
agctaaaggc agcaaggaag tatatgaaga aatgaaggca caaatagcta aattaggggc    43620
aaatgcagaa gtaaatgtta aattaaaagc aacaggttgc gatggattgt gtgagaaagg    43680
tcctgtactg aaaatatatc cagatgacat tgcatatttt aaagttaaag tagaagatgt    43740
agaagacgta gtaaaaaaga cattgatgaa tggggaaata attgaaaaat tattatattt    43800
tgaaactgct acaaaacaga gattaagaaa tcataaagaa agtgaatttt gtaaaagaca    43860
atacaaaatt gctctcagaa atgttggtga aatagatcca ataagtttgg aagattatgt    43920
tgaaagaggc ggatataaag ctcttaaaaa agcaataagc agcatgaaac ctgaagatgt    43980
gcttgaagaa ataacaaaat caggtcttag aggaagaggg ggagcaggat tcccaacagg    44040
acgtaaatgg aaaactgctg cagatattga tacatcacct atatatgtag tatgcaatgg    44100
tgatgaggga gatcctggag catttatgga tagaagtata atggagggag atcctaacag    44160
tgttatagaa ggtatgacat tgtgtgccta tgcagtagga ggtacaaacg gctttgctta    44220
tataagagat gaatatggac ttgctgtaga aaatatgcag aaagctatta ataaagcaaa    44280
agatgaaaat ttattaggta ataatatatt aggaactgac ttttccttcg atatacagat    44340
agtaagaggt ggaggagctt ttgtatgtgg tgagtctact gcacttatgt catctataga    44400
aggtatggta ggagaaccta gagctaaata tatacacact acagaaaaag gattgtgggg    44460
acaacctact gttttaaata atgtagaaac ttgggccaat gtacctataa taattgaaaa    44520
aggtggagat tggtatcatg ctataggaac tatggagaag agtaagggaa caaaagtatt    44580
ctcattagtt ggaaaagtta agaatactgg acttgtagaa gtacctatgg gaactactct    44640
tagagaaata atatatgata ttggcggtgg agtattaaac gacagaaagt ttaaggcagt    44700
tcaaataggt ggaccttcag gaggatgttt accatctgaa tatttagact tgccagtaga    44760
ttatgatact ttggttaaag cggattctat gatgggttcc ggcggaatga tcgtaatgga    44820
tgatagaacc tgtatggtag atgtaactag atattacttg agtttcttag ctgaagaatc    44880
ttgtggaaag tgtgtacctt gtagagaagg cgtaaagaga atgcttgaaa tactcactga    44940
tatatgcaat ggtgatggaa agaaggaga  catagaagag cttcttgaaa tatgttccat    45000
gacaagcaag gcatctctgt gcagtcttgg taagagtgct ccaaatccag taaaagcagc    45060
tataagatat tttagagatg aatttgaaga acatataaag aataagagat gtagagcagg    45120
agtttgtaag aaacttacta catttggtat agatcaagat aaatgtaagg gatgcgatat    45180
gtgtaaaaag aattgtccag ctgattgtat aacaggggaa attaagaaac cacatacaat    45240
agatgctgat aagtgcttga gatgcggtaa ctgcatgaac atctgtaagt ttgatgctgt    45300
taaggtttta tagttgatgc tgttaaggtt ttatagggag gtgaatgtag atatgaaaat    45360
tacaatagat ggaaaagctt gtgaagctga aaaaggagaa ttcatattac aaatagcaag    45420
```

```
aagaaataat atatatatac ctacactgtg ccacagtgat gcattgcctg ggcttgctag    45480
ctgtagactg tgtatagtta aagtagtaga taggggacgt gcaaagatag taacttcctg    45540
tatattccct gtaagtaagg aagtagaagt tataactaat gacgatgaaa taaagagaat    45600
gagaaaaaac atagttatgc ttttaaaagt aagatgccct gaaaataaag aagtaaatga    45660
attagctaaa gcctttggag tagaggaaaa gagagtaaag aggttcaaat tggatccaga    45720
acaaaattgt gttttgtgcg gactttgtgc aaaagcttgc aaggaattag gtactggagc    45780
aatctcaaca gttaataggg gtatgtataa agaagtagca actccatatc acgaatcttc    45840
accagaatgt ataggatgtg cttcctgtgc aaatgtttgt ccaactaatg caataaaagt    45900
tgtggataaa gatggagaaa gagaaatatg gggcaaaaaa ttcaagatgg ttaaatgtga    45960
tttgtgcgga gaatattttg ctacagaaga acacgtaaaa tatgcttaca ataggcttgg    46020
aaaagagcag ccagaaaagc ttatgtgcag cagctgcaag aagaaagtta cagccaaaga    46080
tgtcaaaaat attttgaga acgtgtgaat gaaaccagag tttaattctt ttgtaatagc    46140
cgatcctgac aagtgcatag gctgtagatc ttgtgagatt gcctgtgctg caaaacatag    46200
agaagatact caaggaaaaa ctattggaac tatgaataat aaagttactc caaggttatt    46260
ctttgttaaa aataaaggaa atgtaatgcc ggtacaatgc agacattgtg aggatgcacc    46320
atgtctaaat gcctgcccag ttaatgctat agttgaaaaa gatggaagta tcattataaa    46380
tgaaagtgca tgtatagggt gtcagacctg tacaatagta tgtccggtag gtgctgtaag    46440
tttacttcct agaactcaag gtaaagtagt tacaggagga attcaggtta aagtaagagc    46500
agcagcttat aaatgtgatt tatgtaagga agagggagga gaacctgcct gcgtcaaaga    46560
atgtccaaaa gaggccttaa ggttagtaga tcctagagaa gataaaaaag atcgtagtgt    46620
gaaagctgct atggaactgt taaatataaa cgcaaatctc taaatgttaa atatgccaac    46680
tagtacttct atgataaata tagatgaaga attatgtaca ggctgcagac gatgtgcgga    46740
tgtctgccct gtagatgcta tagaaggtga acagggtaaa cctcagaaga taaatactga    46800
aaagtgtgtt atgtgcggac aatgcattca agtttgtaaa ggctatcaat ctgtatacga    46860
tgatattcct actccagtta gcaaaaggtt atttgataga ggattgttaa aggaagtaga    46920
tgaaccatta tttgcagcat ataataaagg tcaggcaaag agagttaaag aaattttaca    46980
aaacaaagat gtatttaaaa ttgtgcaatg tgcacctgct gtaagagttg ctataggaga    47040
ggattttgga atgcctcttg gaactttaag tgaaggaaaa atggcagctg cactcagaaa    47100
attaggattt gacaaagtat atgatacaaa ctttggtgca gatcttacta taatggaaga    47160
aggtagtgag ttactaaaaa gagtagctga aggtggagtt ttgccaatgt ttacttcttg    47220
ttgtccagca tgggtaaaat atgcagaaca aacatatcca gaactttttac ctcatctttc    47280 aagttgtaag tctccaaatc agatggctgg agctatattt aaaacttatg gagcagagat    47340
aaataaggtt aatccggcta aaatttataa tgtatctgtt atgccatgta catgcaagga    47400
atttgaaagt gaaagagaag aaatgcatga cagtggacac agagatgtag atgcagttat    47460
aactacaagg gaattagcac aactgttcaa agatgctgat atagatttta atactattga    47520
agaagaacag tttgatactc ctcttggtat gtatactggt gcaggaacta tatttggtgc    47580
tacaggtgga gttatggaag cagcacttag aactggatat gaactttata ctaaaaaact    47640
attccaagta tagatgaatt attgcacact aaatatatct caagaaaaaa ggagagttaa    47700
taaaatgaag aattgcctcg tagtagcaga tcctaataaa tgcataggat gtaggacttg    47760
tgaagcagct tgtggtattg cacattcagg agggactttt tttaatacaa atgtatccaa    47820
```

| | |
|---|---|
| aattaatttt aatcctcgct taaatgtgat aaaaactgct aaagtaagtg ctcctgttca | 47880 |
| atgcagacaa tgcgaagatg caccttgtgg taaagcttgt ccagttaacg ctatttcaaa | 47940 |
| tgaaaatggt tatgttagtg tagataaaga tgtatgtgtt ggatgtaaaa tctgcatgtt | 48000 |
| agcttgtcct tttggagcta ttgaattagc ttctcaatat aaggatggag aagttgtaga | 48060 |
| ccaaaaggga cttaagatga gtgaggaagg taatcctact gtaaatggaa aaggaagagt | 48120 |
| ggtagcaaat aagtgtgatc tttgccagga tagggatgga ggacctgctt gcatagaagt | 48180 |
| ttgtcctaca aaatctctca aattagttac ttatgatgac aataataata tagttgaaaa | 48240 |
| aaaagatgac gacgaacgtg aagtaggcta actatatgta tccataaaaa ttttcctcca | 48300 |
| ttagtcaata tattgtctaa ttatagttta atgatatttt ttatatttgt caatacattg | 48360 |
| tctattattt tatccgatga ctatataata aaaaactccc atactaccaa tactatctta | 48420 |
| agaatataaa atgaaagatg gtgaaaaaac tgcggcacag caggaaatat tatggatgta | 48480 |
| tgcaaattag ataacgaaaa actaaaagaa ctatcttcct atatagatag tttggaagaa | 48540 |
| aaagaaggtt cacttataag tgtacttcac agagctcagg atatatttgg ataccttcct | 48600 |
| gaagaattac aaacatttat tgcaaataaa cttgacatta gtgcagcaaa agtatttggc | 48660 |
| gtagttactt tctattcata ctttacaatg aagcccaaag gtaaacatgt aataagcata | 48720 |
| tgcatgggta cagcttgttt tgttaagggt gcagaaaaca ttttagaaga atttaggaat | 48780 |
| cagcttaaag taaagatgg atttaccaca gaagacggat tgttcactat agatatttta | 48840 |
| agatgtgttg gagcttgcgg ccttgcacca gtagttgtag ttgacggaac agtccatgga | 48900 |
| aaagtaaagg tcgaagatgt taaggaata ttaagtcaat ataccttaaa ataaatggat | 48960 |
| aagataaaat cctttgaaga tttaaaagct ttaagagaaa agtataaagc taagatagca | 49020 |
| aaccgtactt atgataatgc agataaaaat ataaaaaaaa ctttacttgt atgcggtgga | 49080 |
| acaggatgtc gtgcttcaag aagcttagat atagtcaata tacttaaaac tgaaattaaa | 49140 |
| aacgcaggtc tagaaaatac agttgatgtc atttctacag gatgttttgg attttgtgag | 49200 |
| aaaggaccta tcgtcaaagt tgtaccagat aatattttt atgttgaagt taataccgag | 49260 |
| agagcaaagc taattgtgta tgaacatatg gccaaaaata cagtagttga ggaagcttta | 49320 |
| tatagagatc ctatcactaa agaaaaaata tcaaatcaaa cggatattcc attttataaa | 49380 |
| aatcaaaaaa gaattgctct tagaaaactgc ggccttttaa accctgaaga tattacagaa | 49440 |
| tacatagcaa tgaatgggta cgaagcttta ggcagagttc taacacaaat gacacctgac | 49500 |
| agcacaattg atgaaattaa aaaaagcggc ctcagaggca gagggggcgg cggcttccct | 49560 |
| acaggcgtaa aatgggaaat gacaagaaaa tccaaatctg atacaaagtt tatgatctgt | 49620 |
| aatgctgatg aaggtgatcc cggtgccttt atggatagaa gcatacttga gggagatcca | 49680 |
| aattctgtac ttgaagctat ggctattgca ggttactgca taggtgcaaa taagggttat | 49740 |
| atttatatca gagctgaata tcctcttgca ataacagat taaaaattgc tttaaagcaa | 49800 |
| gcttatgatt taggtttact gggtgataat attttaggta ctgattttc ctttcatata | 49860 |
| gatttaaaat atggtgccgg agctttcatc tgtggtgagg aaactgcact cataaattcc | 49920 |
| atagaaggcg gacgtggaga gcctaccgta aaacctcctt ttccttccca aataggtctc | 49980 |
| tggaaaaaac caactaatat aaataatgta gaaactctgg caaacatccc ccctattata | 50040 |
| ttaaaaggct ctaagtggtt tagttctata ggaactgaaa agagtaaagg aaccaaagtt | 50100 |
| tttgccttag caggcaagat caataatgtt ggccttgttg aggtacctat gggtataacc | 50160 |

```
ttgcgggaaa taatatataa tttaggcgga ggtattcgcg gtggtaaaaa atttaaggct   50220
gttcaaactg gcggtccttc tggcgggtgc attcctgcag atcatttaga tactgccatt   50280
gattacgaaa gtcttactga aataggctcc atgatgggtt ctggtggaat gatagttatg   50340
gatgaagata attgtatggt gaatatagcc aaattctatc tccaatttag tgtagatgaa   50400
tcctgtggaa agtgcactgc ctgcagaatc gggaataaaa gacttttaga aattttagag   50460
gatatcacta aaggaaaagg taccatggaa catcttgaag gattaaaaga tttatcctat   50520
gtaataaagg attcagccct atgtggtctt ggtcaaacat cacctaatcc aattataagt   50580
acaatgaaat ttttttggga tgaatatata gcccacgtaa aagataaacg ctgtcctgct   50640
ggagtttgca ctgcactttt aaaatacaat ataaattctg aaaaatgtat tggctgcaca   50700
gcctgtacaa aggtatgccc taaggagct atttccggag aaataaaaaa gtcacatgta   50760
atagataagt caaaatgtat aaattgtggt gcatgtagta gtatttgtaa gttttctgct   50820
attacgaaag aataaatggt aaatttaact ataaacgata taaggtttc tgtcccagaa   50880
ggcactacaa ttttaaacgc tgcaaaaaaa gtaaacataa atatacctac tctctgctat   50940
cttgatcttc acgatataaa aatggtaaat aggacttcct cctgcagagt ctgccttgtt   51000
gaaattgaag gcaggcgaaa tcttgcacct tcatgttcta cagaagcttt cgaaggtatg   51060
atagttagaa caaatagtgc cagagctata aaagcaaggc gtactatggt agaactttta   51120
ttatcagatc atcctaccga ctgccttgta tgtgaaaaga atactcaatg tcaacttcaa   51180
ttaatcgctg ctgaattagg tataagaaaa ataagatata aaggtgctat gtctaattac   51240
aaaaaggatt catcaagtgg tgctatatat agaaatcttg ataaatgtat aatgtgcaga   51300
cgatgtgaaa ccatgtgcaa tgaagttcaa acctgtcagg tttactctgc agtagataga   51360
ggcttcgaaa ctgtagtatc ccctgcattt ggtcgtccca tggttgacac gcaatgcaca   51420
ttttgcggtc aatgtgtatc cgtatgccca actgctgcat taactcaagt tagtaatgta   51480
gctaaggtat gggaagtact aactgatcct gataaatatg tagtagttca aactgccct   51540
gctataagag ttactttagg tgaaaaattc ggtatggaac ctggaactat tgtaactggc   51600
aaaatggtat ctgctcttag aagattgggc tttgataagg tatgtgatac cgattttgca   51660
gcagatgtaa ctatttttaga agaagctcat gaatttatag atagacttca aaacggcgga   51720
agacttccaa tactcacaag ctgctgtccc agctgggtta aatttataga acatcaattt   51780
cctgatcttt tagatatacc ttcaacttgt aagtctccac acataatgtt tggtacttta   51840
gctaaaacat atatggcaga aaaattaaat attgatccat ctaaaattgt aatagtttca   51900
gttatgccat gtattgcaaa aaaatatgaa gtaagcagaa aagaacttca atatgaaggt   51960
cataaaaatg ttgatcttgt agttaccaca agagagcttg cagatatgat aatgaagca   52020
ggaatagatt ttaataaact tcctgatgaa gactttgata aaccttttgg agaatccaca   52080
ggtgcttctg taatatttgg aactaccggc ggtgtaattg aagcagctct tagaactgct   52140
tatgaatgga ttactggaga gactttaaaa gaagtagaat tcatggtgt aagaggactt   52200
gatggactta agaagccag tataaatatt ggtggtaaag aaataaacat tggcgtagct   52260
cacggtcttg gcaacgcaag aaaacttctt gaggaaatag aatctggtga atcaaaatat   52320
cacgctatag aaataatggc atgtcctgga ggatgtattg acggaggagg tcagccgtat   52380
cattttggag atttagatat tgtaaagaaa agaatggacg ctttatatag agaagataga   52440
aacaaacctc tcagaaaatc tcatgagaat cctgaagttc aagctctata taagaatttt   52500
attggagatg taggcggaaa aaaagctcat gatctccttc acactcatta tataaaaagg   52560
```

```
caaaagttat aaggtatgta taattccctt agacgtgaat ttaatatgct ataagtatac   52620
aagcttaaga agaatatatt agaaatgatt taaaagataa agctacttta aaaaataagg   52680
tggttttatt ttttttgtata aatacacgtt atattaattg tcttttaatt atataaataa   52740
tatagaaaat taaaaggcag agtgataggt aaatgaatgt tcgaaacaag ggtatatgtc   52800
ctttaatcgt agataaggaa cgcagttcaa aggcttttac tagtgaagct atagatttaa   52860
ttaaaggggg aaagacgaaa aaattaaatg ctatatggct tgaagtaaca ggatgttcag   52920
gaaatattat ttctttttta aatagtgaaa atcctggact cgattatatt ttagaaaaac   52980
tcattaattt aaaatacaac aatactctaa tgacttcaga aggtgagtat gcttttaaac   53040
aattcttaga tacattggat actgaattta tactactagt agatggagcg gtatctactg   53100
ctcaaaatgg ttttataat attgttgcca attatgaagg aaaacctgtt actgcacttg   53160
aagctgtaaa aatggcagga gaaaaagcaa agtatgttct ctgtgtagga acttgtgcat   53220
cctatggtgg aatttctgcc gccaggccaa acccatcaga aagcaaaagt gttaaagaaa   53280
tactaaatcg tgaagtcata agacttccag gctgtccatg ccatccggat tgggtagttg   53340
gaactttagc acatttagtt gcttttggca accgcaatt ggatgaagat ggaagacctc   53400
ttctttttta tggaattacc attcatgata ggtgtacaag aaggggattt tttgataaca   53460 gaattttgc aaaaaattt ggagaagatg gatgtatgtt taaacttgga tgcaggggc   53520 ctgtaactaa aacagattgt cctaggagaa agtggaatgg atatgtgaac tggcctgttg   53580
aagacaatac caactgtata ggatgtgcaa attctagatt tccagatggt atggaaccat   53640
ttgtaaggta ttagatgaaa aagaaaatta ccattgatcc aattacgaga ataagtggtt   53700
ttttggaaac taaagtgcaa gtagaaaaaa atattatagt agatgctgaa actagtggat   53760
tgctttttag aggatttgaa aaaatgttaa aaaacagaca gccgctggat gcagtatatt   53820
ttacagaaag aatttgtggg atatgttcaa cagctcatgc tgtggcagct gctacagctc   53880
ttgaagatgc tttgaagata aaaattagtg taaatgattc gtatatgcgt aatttaatac   53940
atggttttga atttatacaa aatcatataa gacattttta taatttgact ataccaagtt   54000
atgtgaagat gcccaatata aatcctctt tttcagatca atatgaagat tatagattac   54060
cttataactt aaataaaaag ataagtgaag attatattga aagtattaaa tacagtaggt   54120
tagcccatga aggattggct actcttggag gaaaggctcc ccataatcac ggaattttg   54180 ttggaggagt taccataaat atagatccat ataaacttac aaaagttaaa tctattattt   54240
ctcaaattaa tgaattcgta agtagtgtta tgttagagga catgaacata atttcaaaat   54300
actatgctga ttattttaaa atgggaaaag cctatggaaa ctttatgact tatggaatt   54360 ttgataagta tgctgatcct gagataagtt atgtaggacc ttctgtctta ataaatggac   54420
aaaagcataa ctttaatagt aataaaatta cagagaatat actttacacc tggtacatga   54480
atgatgatga aacaataaat ttatctaaag aaacaggtta cagctttata aaatcgccaa   54540
cttatgatgg ctattctatg gaagtaggac ctctagcaag attgatactt tcaggtgagt   54600
atactggtgg aagttcatgt atggacagaa atgttgccag agtacttgaa acaaaaaaga   54660
ttttagaaat tatgcaagga cttgcagata gaattaagct tattccagca gaacaaagaa   54720
tatatgaaat cccagataaa gcatttggtg caggattaat tgacacaact agaggatcct   54780
tgggacactg gataagtata gaagataaat ttataaagca ttacaatatt ataactccta   54840
cagtgtggaa catggggcca agaaatcaat caggtgcgct tggaattgga gaaaaatctt   54900
```

```
tacttggaac gaaaataaaa gatataaagc agcctataga agttgggaga attatgaggt    54960
cctttgatcc ttgtgtttcc tgtgcaactc atttgataag tgatgcatat gaaccagtgg    55020
acgtacaggt tatagtatga atgaaagcaa aagttattgc tctaggaaat atattaatgg    55080
aagacgatgg cattggaatt aagatcctgg aaaatataaa agaggaactt gcacataacc    55140
atattcaatc tataatagga gaaacagatg tggaatactg catttcccaa gtaaaagatg    55200
gtgattttat atttataata gatgcttctt ataatggaaa agttccaggt acgataacag    55260
ttgccagctt acaagattat aagtgcaaaa acaatatta tacccagcac agctatagct    55320
tcatagacat tataggagtt tactacaaat cattaactgg gtttattatt gaaattgaag    55380
cagctagtgt aagctttaaa ttgggactta gccataattt acaaagtaag cttaaggata    55440
tttcaaaaga tgtattgaaa aatattttc tgagattgaa tgatagagca gaggaggaaa    55500
aatagttgga ttttattta atgaaaaagt tgaagataat taggcgaaaa ataactttt    55560
ataaaaaaag tagtatgttt gctgtatgcc cttttataaa aagctattat ggacatctca    55620
tgaatattca ataggggaa ttagaaaaac taatgaatac aatgaacaaa gatatagtaa    55680
gacaggaaaa acaatttact ttggaagaac tttcaaaata caatggtgct ggtggctctc    55740
cggcgtatgt tgctgtaaat ggaatagtgt atgatgtgag tttgtctcct gtatggggtg    55800
gagggacgca ttttggtctg tatgctggaa aagacttaac tttacaattt agggcatgtc    55860
acagtggaga aataaagata ttaaatggtc tacctaaagt gggagagtta aaaatttaaa    55920
tgaatactgt aattatgatt ttagttgtaa tgactgttat aggtcttata tttggacttg    55980
ttttagccta tgtaaataaa agatttgcaa tggaagtaaa tccacttgtg gacttagtag    56040
aagatgtact tccaaaaggc caatgtggag ggtgtggatt tgcaggatgt aaagcttatg    56100
cagaagctgt tgtttagat gagagtgtac ctccaaatct ttgtgtacct ggaaaagcag    56160
cagttgcaga acaggtggca aagttaacgg gtaaatctgc tccaccattt gaacctagag    56220
ttgcacatgt aagatgtggt ggagattgta caaaggcagt taaaaatttt gaatatgaag    56280
gtatacatga ttgtgtagct gcaaatttac ttgaaggtgg acctaaagct tgtaaatatg    56340
gatgtctggg atttgggaca tgtgtaaaga gctgtccttt tggagctatg gcaatgggtt    56400
caaatggact tccaataatt gatacagata tatgtacagg ttgtggtacc tgtgtaagcg    56460
cgtgcccaaa acaggtactt ggatttaggc ctgtaggttc taaagtaatg gttaattgta    56520
attctaaaaa taaaggtgga gctgtacgta aggcatgtag tgtaggatgt cttggatgtg    56580
gattgtgtgc taaaaattgt ccaaatgatg ccattaaagt agagaacaat ctagcagtag    56640
tagaccaaag tatttgtgcg tcatgtagtg aagctacctg tcttgctaaa tgtcctacag    56700
gagctattaa ggctattgta agcggtacag acttacaaca gcagagcaag aatgaagctg    56760
ctgcaaattc ataaatggca tcttacctta ctctttttat aagtgcagta gttgtaaata    56820
actatgtttt aacaaggttt ttgggacttt gtatattctt tggtgttct aagaatttaa    56880
atgcttctgt aggtatgggt atggctgtta cttctgttat tactatgagt tcaatattgg    56940
cctgggtagt atatcatttt gtacttatac catttaattt aactttcttg aagacagtag    57000
tttttgtact tcttattgct agttttgtac agctttgga gactattatt aaaaagcagg    57060
caccagccct atataatatg tggggaatat accttctttt aatagctaca aactgtatag    57120
tacttgctgt acctatatta aatgctgatt ctaactttaa ttttttacag agtgttgtta    57180
atgcgatagg atctgggcta ggctttgcta tggctataat tttgatggca agccttagag    57240
aaaaattgag attagcagat gtacctaaac ctttagaagg tcttggagta gcttttattt    57300
```

```
tagcaggaat gttagccota gctttccttg gtttttcagg tatgattcct atgtagatga    57360
agaatttgtg gaatatattt aaaaaaggat tgattgcaga aaaccccata ttcgtacttg    57420
cacttagttt gtgtccagca ctggcaacta caagtacagc tgtaaatgga tttaccatgg    57480
ggctctgcgt gctatttgtt ataacttgta ataatactgt ggtttctata attaagaatt    57540
ttgtaaatcc taaggtacgt gtacctgtat atatcacttg tatagcaact atagttacag    57600
tagtggaact tgttatgcag gcttatgcac ctctattata taagcaattg ggaatttatt    57660
tagcattggt agttgtattt gctataatac ttgcccgtgc agagacattt gcatctaaaa    57720
atcctgtagt tccttctttc tttgatggac ttggaatggg atgtggattt actttggcac    57780
ttactataat aggaatgata cgtgaattat ttggatctgg agctatattt ggttttaatg    57840
tatttggggc ttcatataat ccagctttga ttatgatact tccacctgga ggattcatac    57900
ttataggata tttagttgct atagtaaaag tttataacca acatatggag aaaattaaaa    57960
tgcaaaaatt agaacaagca aatggaggtg aagcataaat ggctaaagat aaagatcaaa    58020
atagtatttt tgcaattact aagaacttaa ccattacgtg ttttatatct ggaattataa    58080
tagctgcggt ttattatgta acatcaccag tggcagcaca aaaacaagtt caaatacaaa    58140
atgataccat gaaagtttta gtcaatgatg ctgataaatt taataaagta aatggtaaaa    58200
aggattggta tgcagctcaa aaaggaaaca agacaattgc atatgttgta cctgcagaga    58260
gtaaaggtta cggtggagct atagagctat tggtagctgt tactccagat ggaaaagtaa    58320
tagatttcag cattgtatct cataatgaaa ctccaggact tggagcaaat gcttcaaagg    58380
attcttttag gggacagttt aaggataaaa aggcggatgc cttaacagtt gtaaaagata    58440
agtctaacac taaaaacatt caagctatga caggagctac aattacgtca aaagctgtaa    58500
ctaaaggagt taaagaagct gttgggcaag ttactacgtt tacgggaggt aagtaaatgg    58560
cggaagcaca gataaagaaa aatatttta ctatttcgtc atcacctcat gttcgttgtg    58620
atgaatctgt ttctaagata atgtggagtg tctgtttagc actaactcca gctgcgattt    58680
ttggcgtatt taattttgga attcatgctt tagaagtaat tataacagga attatagctg    58740
ctgtagttac agagtacctt gtagaaaaag ttagaaataa acctataact attacagatg    58800
gaagtgcttt tttaacagga ctttacttt ctatgtgttt acctcctgat attccacctt    58860
atatggtagc tataggatct tttatagcaa tagcaatagc taaacattct atgggaggac    58920
ttggtcagaa catatttaat ccagctcata ttggaagggc tgcactaatg gtttcctggc    58980
ctgtagcaat gacaacatgg tcaaaattaa gtgccagtgg tgtagatgct gtaaccacag    59040
caactcctct tggaatttta aagcttcaag gttattcaaa attacttgag acttttggag    59100
gtcaaggtgc actttacaag gcaatgttct taggtactag aaatggaagt ataggagaaa    59160
cttctacaat attacttgtt ttaggtggac tttatctaat atataaaaaa tatattaact    59220
ggcagattcc agtagtaatg atcggtactg taggaatact tacctgggct tttggaggaa    59280
ctacgggact ttttacagga gatcctgtat ttcatatgat ggcaggcgga cttgtaattg    59340
gagcttcctt tatggctact gatatggtaa caattcctat gactattaaa ggacaggtta    59400
tttttgcatt aggtgcaggt gcgcttacat cacttataag attaaaaggt ggttatccag    59460
aaggcgtatg ttattcaata ttacttatga atgcagttac tcctctaata gataagttta    59520
cacagccagt taaatttggg acaaggaggt aaaactttaa ttaataagag tatctttaa    59580 agttaactga catttaatag ataaattgtc attatatatt atttcctata gtatataatt    59640
```

```
ttataacgga ttatggaaaa ttctataatc tgttataaaa attatgttta tatttatttt    59700
gcagtttcgt ttatatacat gctgtaaaaa ttattgaaag aggtgtttaa gagtgttaaa    59760
aagttttcga ggtggagtac acccggatga tagcaaaaag tacacagcta ataaacctat    59820
agaaatagca cctataccag acaaggtgtt tattcccgtt agacagcata taggtgctcc    59880
tacatctcct gtagtacaaa aaggagatga ggtaaaaaag ggacaactta ttgcgaagag    59940
tgatgctttt gtttcagcca atatatatgc atctacttct ggaaaggttg tagatatagg    60000
agattaccca catcctggtt ttggaaagtg tcaagctata gttattgaaa aagatggaaa    60060
agatgagtgg gtagaaggaa taccaacttc acgtaattgg aaagagctaa gtgcaaaaga    60120
aatgcttgga ataataagag aagcaggcat tgtaggaatg ggaggcgcaa cttttcctgt    60180
tcatgttaaa cttgcaccac caccagataa aaaagtagat gttttttattt tgaatggtgc    60240 tgagtgtgaa ccttatttaa ctgcagatta taggtccatg ttggaaaaat cagataaggt    60300
agttgctgga gttcaaataa ttatgaaaat cctcaatgtg gaaaaagcat tgtaggtat    60360 tgaagataat aaaccagatg ccatagaagc tatgaaaaaa gcttttgaag gtacaaaagt    60420
acaagtagta ggccttccta ctaagtatcc tcagggtgct gaaaaaatgc ttataaatgt    60480
tttgacaggt agagaagttc catcaggtgg attgcctgca gatgtaggtg cggttgttca    60540
aaatgtaggt acatgcatag caataagcga tgcagtggag agaggaattc cacttataca    60600
gagagttaca actataagtg gaggtgctat taaagagcct aaaaatatat tagttagaat    60660
tggaactaca tttaaagatg ccattgattt ttgtggagga tttaaggaag aaccagttaa    60720
aataatttca ggtggaccta tgatgggatt tgcccaatca aatttggata ttccaataat    60780
gaagggttca tcaggaatac ttggtttaac taaaaatgat gtaaatgatg gaaaagaatc    60840
ttcttgcatt agatgtggca gatgtctaaa agcctgtcct atgcacttga atccaagtat    60900
gttaagtatt cttggacaaa aagatttata tcaagaagct aaggaagaat ataatctttt    60960
ggactgcgta gaatgcggca gctgtgtata tacatgtcct gctaaacgaa gaattgtaca    61020
gtatattgaa tatttaaaat cagaaaatag agctgcaggg gcaagggaaa aggctaaagc    61080
agaaaaggct aaagaaaaga aagaaaaaga agaggtctta aaataagctt tttcaccatt    61140 gttttttaata catctgggag catttcaaat tccataaact tccagtgtca ttgtacaatg    61200
ggccattatt ataattttag ctatattggc aaaatttttt acatctagta tgaaaaaata    61260
ccggataaaa aacaaagtgt tattgaaatt attgttgaag cagtaagaaa tttagttact    61320
gaaaacatgg gaaagagta tgtatcattt ataccatatg taggaacgct tgccatatac    61380 atttagtaa tgaacattgc tccagtgatg ataggagtaa gggcaccaac ggaagatcta    61440
agtgttgcag ttggattggc attaataact tttgtattag tccaatttaa ttcaattaaa    61500
aaaaatggtt tagtgcgtta ttttggagca tatactaagc cagtagtacc gctattgcca    61560
attaatatta tagaaaggct agttcttcca gtttccctaa gtctacgact ttttggtaat    61620
ttgacagcag gagctgtaat tatccggtatg gtatataaag gattaggtag tatggcatgg    61680
ttttctcaat tgttaatacc aattcctttta cacgctttct tgatttatt tgatggttca    61740 atccaaatga tagtatttgt tatgttaaca ataatgaata taaagttat agctgaagac    61800 taaatgaatt tagatgcaca ttcatttata tcaggtatgg cagcaatagg tgcaggttta    61860
gctgctatag gatgtttagg aggaggtatt ggagttggaa atgctgctgg taaggcagtt    61920
gaaggagtat caagacagcc agaagcaagt ggtaaaatac taagtacatt cttttgtaagt    61980 gcagctttat cagaggtaac agctatttac tctctattaa tagctcttat tttagtatttt   62040
```

```
aaagtttgat tggaattttaa tatgcaaatt gattggacta cagtcgttat aacaataata    62100
aattttatca tattgtatttt cattctaaag catttctttt ttaaacctgt caataacact    62160
attacaaata ggcagcaaga aattgacaat aaaataagaa ctgctgatga aaatgaaaag    62220
aagtctaaac aattagtaac tcaacatcaa gagttgttaa agaattcaaa acaagaagga    62280
aaagctattg ttgaagacta taaaaataaa gccgataaag tttccgaaaa catagtaaat    62340
gatgcccaga aagaagctca actaatatta gatagggcaa aagttgaagc tgaaagagaa    62400
agagaaaaag caaaagacga tataaaaaat caagtggtag atttagcact tttagtatca    62460
tcaaaagctt tagagggatc tattaatgag cagcagcata ggaaacttat tgaggactttt   62520 atagctaagg taggtatttta aatgcatgag tatttagata aagatatgc ccttgcactc    62580 tataaaattg gagaagaaaa aggaaaagtt aaagaatacc tagaagaatt aaggcaggtt    62640
gtagccgcta taaaaggtaa ttctaaatttt ttggaaatca tggaacatcc agaagtaagt    62700
acatcagaga agaaaaaaat gtttactgaa atctttaaag ataaggtgaa tgaagacata    62760 cttttcattct tattagttct tatagagaaa gatagaatta atgaaattga tggaaaactt    62820
agggaaatgg aaaatatata tcttgagagt aataatactg ttaaggcaaa agtaaaaaca    62880
gttattgctt tgaatgatga tgagagaaac actttaattg aaaagctaga aaagaaattt    62940
aataagaaag ttttgattga agaagaaata gatcctagta aataggtgg ggtttatgtt    63000 gaggtaaata atgaagttat tgatggtagt ataaggtcaa aactttctga atgaaaaaa    63060 ataatgctta agggagaaca gaggtgaatg aacataaaac ctgaagaaat aacttcaatt    63120
ataaaagatg aaatacagaa atatgaaaag aaaatagaaa cagttgattc aggtacaata    63180
attcaaatcg gtgatggtat tgctagagtt tatggcctta atcaatgtat ggcaaatgaa    63240
ctcttagagt ttccaaatga tgtttatggt atggctttaa accttgaaca ggataatgta    63300
ggttgtgttc ttttgggttc ccagaaggga ataaaagaag gagatacagt taaaagaaca    63360
ggtagagttg tagaagtacc agtaggtgaa gctattgttg gaagagttgt aaattcactt    63420
ggacagccta ttgatgggaa aggtcctata aagacatcag aaactaggcc tgtagatctt    63480
gtagctccag gagttataac aagacagtca gttaaagaac cactgcaaac cgggttaaag    63540
gctatagatt caatgatacc aattggaaaa ggacaaaggg aattaataat aggagacagg    63600
caaacaggta agactgctat tgccatggat actataataa atcaaaaagg aaaagatgta    63660
atatgcatat atgtagctat aggtcagaag cagtctactg tagctcatat agtaaatgac    63720
ttaacagaag caggtgctat ggactatagc ataatagtat ctgcatcagc atctgagtca    63780
gcaccacttc agtatattgc tccttatgca ggatgttcca tgggtgaata ttttatgaat    63840
aagggaaaaa atgtacttat agtgtatgat gatttatcta agcatgcggt tgcctataga    63900
gaaatgtcat tattactccg tagaccacca ggaagagaag catatcctgg agatgtattc    63960
tatctgcatt caagattact tgaaagagca gcaaagcttt ctgataagtt aggtggaggc    64020
tcacttacag cacttcctat aatagaaact atggcaggag atgttactgc atatatacca    64080
acaaatgtta tttctataac agatggtcag atattccttg aatcagagct tttctatgcg    64140
ggtcaaagac cagctataaa tgcaggtata tccgtatcca gagttggtgg taatgcacaa    64200
attaaagcaa tgaagcaggt agcaggtact cttagattgg atttagcaca gtatagagaa    64260
cttgcatcat ttgctcaatt tggatcagac cttgataaag aatctatgaa aaggcttgaa    64320
aaaggtaaga gattaacaga aatattaaaa caacctcaat acaaaccaat gcctgtagaa    64380
```

```
aatcaggtaa tgatactgtt tgcagctggt agagagtata taatggatgt accggttgaa    64440
aaagttgtag aatttgaagg agaattcctt gattatatga gtactcatca taaagaaata    64500
ggtgatgaaa taaaaaataa aaaaattata tccgatgaat taagtgataa acttggaaat    64560
gctatagagg aattcaaaaa aatattttta gcagaggcat agatggcagg ggcaggactt    64620
gttacaataa aaagaagaat tagatcaata accagtactc aaaaaataac aaatgccatg    64680
ggactcattg ccacctctaa acttagaaaa gttagaaaaa agcttgaggc aaataataaa    64740
tattgtgaac tatttagttc ccttatgaat gaatttgttt taggagcaga gggaagaaac    64800
atttatatac atggtaataa aagcaataag aaactctaca tagctttaaa ttcagataca    64860
ggattatgcg gaggctttaa tggcagtgta gtaaatgaag cagatgctgc aatgtcaaaa    64920
aataaagaaa attgcctttt gatatctgtg ggacaaaaag gaagaacgta ttttaaaagg    64980
cttaagtata gtacagaagc agaatacgtg gatatttcag atgttcctac tataaatgaa    65040
gcagatacca tagtatataa ggctctagac ctttatagaa gtggcgaggt tggagaagtt    65100
aatatagtat atactaagtt tatttcaaca gttagacaaa aagtagttgt tgaaaaatta    65160
cttccattgg aagctgataa aaaagaaaaa acaaattatc ttgttaaatt tgaaccatca    65220
atagatgaaa tgatggatga agtagtactt ttacacttaa agcaaaaagt acttaactgt    65280
atgataaatt caaaagtaag tgaacaggct tccagaatga cagcaatgga tggggcaact    65340
aaaaatgcaa atgatttact ggataaattg aatcttaaat acaatagaga gagacaatct    65400
gctattacac aggaaataac tgaaatagtt ggaggagcag aagctcttaa gtaattgatg    65460
ccaaatatag gcaaagttgt tcaggttata ggacctgtag tagatataaa gtttgataca    65520
gaaaaccttc ctaatatata taatgccata gatataaaat caggtgataa aaaaattatt    65580
acagaagttg cacaacattt gggtgatgat gtagtaagaa ctatatccat ggagagtacg    65640
gatggattaa tgagaggtat ggatgcagaa gatacaggat ctcctatatc tgtacctgta    65700
ggtgagccag ttttaggaag acttttttaat atgctaggac agccaattga tgaaaatgga    65760
gaagtaaagg cagaacaata ctatcctatt catagacagg cgccaagttt tgaagatcaa    65820
tctgttaagc ctgaaatgtt tgaaactggt attaaagtta tagatcttct tgcaccatac    65880
caaagaggcg gaaagatagg actgtttggt ggagctggtg ttggtaaaac agttcttata    65940
caggaactta taaacaatat agcaaaagaa cacggtggat tatcagtatt tacaggtgtt    66000
ggagaaagaa caagagaagg aaatgaccta tattatgaaa tgcaggaatc aggagttata    66060
aagaagactc ttttggtatt tggtcagatg aatgagccac ctggagcaag aatgagagtt    66120
gcacttacag gacttactat ggcagaatat tttagagata aaggtcagga tgtacttttta    66180 tttatagata atatattcag atttactcag gcaggatccg aagtttcagc gttacttggt    66240
agaataccta gtgctgttgg ttaccagcca actcttgcaa ctgaaatggg tgctcttcaa    66300
gaaagaataa catccacaaa acaggggtct attacatctg ttcaggcagt atatgttcca    66360
gcagatgact tgactgaccc ggcaccatct acgacattta cgcatcttga tgcaactaca    66420
gttctttcta gatctatatc agaaattggt atatatcctg ctgttgatcc actggcatcc    66480
acttcaagaa tattggatcc aaggattgta ggagaggatc attataaagt agcatcagat    66540
gttaaacata tacttgaaag atacagtgaa cttcaagata ttatagcaat acttggtgta    66600
gatgagcttt cagaagatga tagattagta gttattagag ctagaagaat tcaaagattt    66660
ttatcacaac cattttctgt tgcagaacaa tttacaggat atcagggtaa atatgttcaa    66720
ataaaggaaa ctataagagg ttttaaagaa attcttgaag gtaaatatga tgatttgcca    66780
```

```
gaaactgctt tcttatttaa aggaagtata gatgaagtgg ttgaagcagc taaaaatatg    66840
ggaaaaaatt aaatgtcaga agttttaaaa ttaactatcc ttactcccga tagagaattc    66900
tatgaaggag aagtagtaga agtaataacg gaaagtattc aaggcgacat agcaattctt    66960
ccagaccata tgcctttagt taccacttta aaacctgcag ataccgaaat cgttcaaaaa    67020
gatggcaaaa aattaaaggc atttacatca accggagtac tggaagtaat aaataatgag    67080
ctaaaaattt tatgtgattc ttgtgaatgg ccagatgaaa tagacataga tagagcaaaa    67140
gctgctaaag atagagctga aaaaagatta tctagtcaga agacggagt cgatgtaaaa     67200 agagcagaaa tggcattggc tagggcactg gcgagaatta atctgaaata aatataagag    67260
aaactatact tgcaggagct aatgctatag cttttacgcc tcctacttcg gctgaaattt    67320
taagacaaat tatgaatgaa cataggaaaa aatataaaaa tagaagacca gaataaatat    67380
ttacagtata ttatagggag aggagtaact actttatttt taattattta aaaataaagg    67440
attagattag tatgaaaggt attttatatt attttagcgg tactggaaat accaagtggg    67500
tggcggatag gtttaaggaa aaatttcagc tttataatgt agatatagac ttagcatata    67560
ttcaatctct agaagagagg aaaataaaaa aatatgattt cataatcatt ggctttcctg    67620
tccattggaa attaccacct aaaattgtaa caaatttttt aaatagactg aataatacaa    67680
aagaaaatac aagggttata gtatattcta cacaaggtgc ttcatcatct tcagcttctt    67740
gttttgttgc aggatgttta aagaagaaag gatatgtacc atctatacag attagcataa    67800
aaatgcctaa taatttttac ttctttatag gtaaaaaata taatgaaagt gaaatagaaa    67860
atttgcttgt ttctgttgat aaaaagatta caaatatagt agaaagttttt ataagggga    67920 ggattgtaaa agaatctaat tctttaataa ggcttcaatt tagtaaagta ctgaataacg    67980
tgttcaaagg tagggtacct aaattatcta gaaatatatc atcaactaaa gattgtgtta    68040
aatgtggatt atgccttaga aattgtcctc aaggtaatat aacatttgaa aatggacatg    68100 cagttttca tagcaaatgt attttatgtt tgagatgtat acatatatgt ccaataaatg    68160
caataagata tagaggtaag aaaatagatc aaactcaaaa agatattata caggtattag    68220
atctgaataa ataagaaatt gttatccagg gacatagcca ctctttgctc acacttggaa    68280
aagtgtaagt attagagtgg gtagtcatcc gataaaaaat attcgtcgca tctttgactt    68340 gttatttct ttcaaatgcc taaaattatc ttttaaaatt ataacaaatg tgataaaata    68400
caggggatga aaacattatc taaaagttaa ggaggtgtta cataagatgg catataaaat    68460
tacagaagag tgtgtaagtt gtggttcatg tgcttcagaa tgtccagctg atgctataag    68520
ccaaggagat agtcaatttg taatagatcc agaaaatgt atagaatgtg gaaactgtgc    68580
taatgtttgt ccagtaggag caccagttga agaaaactaa atatgaaagc taaaaggca    68640 gaagaataca tatcaaactc attggaatat aatgatttgc ttaataactt tataaaaaaa    68700
ttaaaataga aattaaatta ttataataag cattatttt ggaataatat aaagtgtact    68760
ttaaagtaac taattatata gcgaggagtg aaaacttgtt attaataaca ggaaaatagt    68820
atgaaagctg tagttgataa agacacttgt ataggatgtg ggttatgtcc aagtatatgt    68880
ccagaggttt tcagatgga tgatgatgaa aaagctaagg caattgaaga taatgtccca    68940
ggagaagcag aggacactgc gaaggaagca gaggacagtt gtcctgtttg tgctattaag    69000
gtaagctaag ttgaaacatt tccaatttc gaaaattgtc ctatagtgta cataaaaacc    69060
tcctaatatt tatttccttc gaagtgatta attatatttt aaactttacc ataatgtcaa    69120
```

```
agtcaataga gatagagtca aaaattgaat tatgggattt gctgggtaaa ctatgctata    69180
atttttagta gaataaaaaa tttaatttat tgctggaggt ttattctatg aaaaaagttt    69240
attttaaggc tattgattca tactccaaaa cagaagagat aagtgatgct gctggcaaac    69300
tcttaagaaa agtagtggaa gaggagcata taagtcttga aaaattcata cctctcaagg    69360
ttcattttgg agaaaagggt aataatactt ttatacaatc aaaaaatttt gttggtataa    69420
taaattattt aaaggaaaat aacatagata gtgcatttat agagacgaat gttctctata    69480
gaggtgaaag aactacaaga gaaaagcatt tgaaactagc aaaagatcat gggtttacgg    69540
aactccctat aataatagcc gatggtgaac atggagaaga ttttgaggag attgaaatca    69600
gtaaaaaaaa ttttaacaaa tgtaaggtag gaaaacaaat tgcaaacaaa aaacagctta    69660
ttgtcctaag tcactttaaa ggtcatatac ttgctggttt tggaggtgcc ataaaacaac    69720
ttggaatggg atgtgcatca agaggaggaa agcttgccca gcatgcaaat tctacaccta    69780
aaattaactt ttttaagtgt aaaggctgca gcgcttgtgc aaaaaagtgc cctcaaaatg    69840
ccataactgt aaatagaaag gcaaagatca ataaagacaa gtgtattgga tgtgcctctt    69900
gtatggcaat atgtccacag ggagctattt accacagctg gattggatct atgaccaaat    69960
cttttaatga aagacttgca gaatatgctt atgctgcagc aaaggaaaaa aataatatttt   70020 atataacctt tgcttttaat ataactaaaa attgtgactg tgaaggacac aatatgaaat    70080
caatagcaaa tgatattgga gttttttgctt caacggatcc tgtagctatt gataaagcat    70140
gccttgatgt tcttgataaa aataatgata gaattgtatt taaaggggc aggtatactc     70200 ttgattatgc agaaaaaata ggcttgggta gtaaaaaata tgaacttgtt gaaataaatt    70260
agatctgatg gctacctact gtaacactcc cacgcacaca gcgaaagcga ctatcaccaa    70320
atcaaagatt tgggatatct gcttttccca ctaagtaaga ttcgttgata taaccaaaa     70380 taataggcat aaaatttgcg gtattgatat ataccttata tatttgtata attaagatat    70440
atgtacaaag tatatataaa taatgtttaa aggggaatgt attatgaaaa aattagttgt    70500
taaagataag tctttatgta tgtcttgttt aagttgtgaa atggcttgtt ccgaggcatt    70560
ttacaaaacc tacggcaatt cttgtattaa gattgatgaa ggaaaagatg gatctgtaga    70620
tttaaaagta tgcaatcaat gtggagtgtg tgctaaaaaa tgtcctgaag aggcaattaa    70680
acaaaatgct aagggaatat atatgataga taaaaaagct tgtactggct gtggtacatg    70740
tgtagaagcc tgtccaaaag gtattattgt aaaagtagaa gacaagccta atccaagtaa    70800
gtgtatggca tgtggtattt tgtgttaaagc ttgtcctatg ggagtacttg aaattcaaga    70860
agattaaatt gttatgttgc ggttgtggat gcagataatt gtacaataag tagtagagaa    70920
ggaaacgaaa ttttcgtttc cttttctcta tttaaagaaa gatattgtta tctgttatgt    70980 actcttttaga cttagtaaca tatgttacgg attttgtgac tgcattttat tataatatag    71040
acagtaaaat aaggaggaga aaatattatg ataagaaaaa ttgttaatat aaataaagag    71100
aaatgcaatg gatgtggact ttgcgtaaat gcatgtcatg aaggtgctat tgaacttgta    71160
aagggaaaag ctgaacttat aagtgatgag tactgtgacg gacttggtga ctgtcttcct    71220
gaatgtccta caggagctat aagtataatt gaaagagaaa gcaaggatta tgatgaggaa    71280
ctagttgcta aaaaggctaa agaaaaggaa gaagttatgc cttgtggatg tccaggtaca    71340
gcagctagaa gaatagagag agcttcagat aaaaatgcgt atacagataa aaagaattcg    71400
gaagatttta gtgccgcttc tgagttaaca cagtggcctg ttcaattgag acttataaat    71460
acaaatgcac cttatcttaa gaatgcgaag ttacttgtag ctgctgattg tactgcatat    71520
```

```
gcctgtggag attttcacaa aaaatttata aggatcaca ttacagtaat agggtgtcct    71580
aagttagacg acattaaata ttatgaagat aaattaactg aaattataga aaaaaatgat    71640
ttgaaaagta taactgtagt gagaatggaa gtaccatgct gctcaggcat tgtaaatgca    71700
gtgaaaaatg caatgcttag ggcaaagaca ataattcctt atgaggaagt tataatatca    71760
atttaaaaga atggtgtttt ataatatgct taatatgctg ctggattccc tagaaggtga    71820
tatgaatggg gatgaacgaa gaaatgtggt aagatttgcg tttaaataca attatgatgg    71880
atttaaaaga ttacttacag aatacactaa gtaaaattgt gaatgggaaa agtgtagaat    71940
tacattgaaa aaggagtaaa aactttatga tgaatgtaaa tagtgaaaag tgtataggat    72000
gcggacaatg tgttaaagat tgttttgcaa gagacataga gataataaat ggtaaagcta    72060
aaattaataa tattacttgc ataaagtgcg ggcactgtat tgcagtgtgc cctaaaaatg    72120
cagtatcaac ggacgaatat aacatggaag atgtaaaaga atataataaa gaatattttt    72180
ccatagatgc tgatactta ttaaattcta ttaagtttag aagaactata aggcagttta    72240
aagacaaaga agtagagaag gaaaaactgc ttaaaattat agaagctgga aggtttactc    72300
aaacagcaag taatatgcag gatgtatctt atacagttgt aagagatgga atacaggatt    72360
taagaaaatt aataattgaa agtttaaatc aaattggaga aaaaatactt aaagatacaa    72420
atgcgaaaaa tatactttat caaagatatg ctaaaatatg gattgatatg tataaggaat    72480
ataaagaaaa ccctaaaaat gatagattgt tttttaatgc tccagtagta atagttgtta    72540
cagcaagaca ggaagtaaat ggagctttag catcttcaaa tatggaactt atgattaatt    72600
ctttaggact tggaacgttg tttagtggtt tttctgttgc ggctgcccaa atggatgaaa    72660
aaataagtaa gtttcttgga gttaagaaag gaagaaaggt tgtaactttc atgatagttg    72720
gatatcctaa tgtgaaatat ctaagaactg taccaaggag aaaagcagat atacgctgga    72780
agtaa                                                                72785
```

<210> SEQ ID NO 2
<211> LENGTH: 16166
<212> TYPE: DNA
<213> ORGANISM: AUTOTROPHIC SOLVENTOGENIC CLOSTRIDIAL SPECIES

<400> SEQUENCE: 2

```
tataaacttg ttcaaagatt tgcaaaagct gatgctatag gacctgtatg ccagggattt      60
gcaaaaccta taatgatttt gtcaagagga tgtaactccg atgatatagt aaatgtagta     120
gctgtaacag cagttcaggc acaagctcaa aagtaataac aaaaagcata aatgattcat     180
ttttaggagg aatattaaac atgaaaatat tagtagtaaa ctgtggaagt tcatctttaa     240
aatatcaact tattgatatg aaagatgaaa gcgttgtggc aaaaggactt gtagaaagaa     300
taggagcaga aggttcagtt ttaacacata aagttaacgg agaaaagttt gttacagagc     360
agccaatgga agatcataaa gttgctatac aattagtatt aaatgctctt gtagataaaa     420
aacatggtgt aataaaagat atgtcagaaa tatctgctgt agggcataga gttttgcatg     480
gtggaaaaaa atatgcggca tccattctta ttgatgacaa tgtaatgaaa gcaatagaag     540
aatgtattcc attaggacca ttacataatc cagctatat aatgggaata gatgcttgta     600
aaaaactaat gccaaatact ccaatggtag cagtatttga tacagcattt catcagacaa     660
tgccagatta tgcttatact tatgcaatac cttatgatat atctgaaaag tatgatatca     720
gaaaatatgg ttttcatgga acttctcata gattcgtttc aattgaagca gccaagttgt     780
```

-continued

```
taaagaaaga tccaaaagat cttaagctaa taacttgtca tttaggaaat ggagctagta      840
tatgtgcagt aaaccaggga aaagcagtag atacaactat gggacttact ccccttgcag      900
gacttgtaat gggaactaga tgtggtgata tagatccagc tataatacca tttgtaatga      960
aaagaacagg tatgtctgta gatgaaatgg atactttaat gaacaaaaag tcaggaatac     1020
ttggagtatc aggagtaagc agcgatttta gagatgtaga agaagctgca aattcaggaa     1080
atgatagagc aaaacttgca ttaaatatgt attatcacaa agttaaatct ttcataggag     1140
cttatgttgc agttttaaat ggagcagatg ctataatatt tacagcagga cttggagaaa     1200
attcagctac tagcagatct gctatatgta agggattaag ctattttgga attaaaatag     1260
atgaagaaaa gaataagaaa aggggagaag cactagaaat aagcacacct gattcaaaga     1320
taaaagtatt agtaattcct acaaatgaag aacttatgat agctagggat acaaaagaaa     1380
tagttgaaaa taaataagat taaatttttta cttatttgat ttacattgta taatattgag     1440
taaagtattg actagtaaaa ttttgtgata ctttaatctg tgaaatttct tagcaaaagt     1500
tatatttttg aataattttt attgaaaaat acaactaaaa aggattatag tataagtgtg     1560
tgtaattttg tgttaaattt aaagggagga aataaacatg aaattgatgg aaaaaatttg     1620
gaataaggca aaggaagaca aaaaaaagat tgtcttagct gaaggagaag aagaaagaac     1680
tcttcaagct tgtgaaaaaa taattaaaga aggtattgca aatttaatcc ttgtagggaa     1740
tgaaaaggta atagaggaga aggcatcaaa attaggcgta agtttaaatg gagcagaaat     1800
agtagatcca gaaacctcgg ataaactaaa aaaatatgca gatgcttttt atgaattgag     1860
aaagaagaag ggaataacac cagaaaaagc ggataaaata gtaagagatc caatatattt     1920
tgctacgatg atggttaagc ttggagatgc agatggattg gtttcaggtg cagtgcatac     1980
tacaggtgat ctttttgagac caggacttca aatagtaaag acagctccag gtacatcagt     2040
agtttccagc acatttataa tggaagtacc aaattgtgaa tatggtgaca atggtgtact     2100
tctatttgct gattgtgctg taaatccatg cccagatagt gatcaattgg cttcaattgc     2160
aataagtaca gcagaaactg caaagaactt atgtggaatg gatccaaaag tagcaatgct     2220
ttcattttct actaagggaa gtgcaaaaca cgaattagta gataaagtta gaaatgctgt     2280
agaaattgcc aaaaaagcta aaccagattt aagtttggac ggagaattac aattagatgc     2340
ctctatcgta gaaaaggttg caagtttaaa ggctcctgaa agtgaagtag caggaaaagc     2400
aaatgtactt gtatttccag atctccaagc aggaaatata ggttataaac ttgttcaaag     2460
atttgcaaaa gctgatgcta taggacctgt atgccaggga tttgcaaaac ctataaatga     2520
tttgtcaaga ggatgtaact ccgatgatat agtaaatgta gtagctgtaa cagcagttca     2580
ggcacaagct caaaagtaag gagaactgta ttgcttatta tttaagcatt ttattataaa     2640
ataaaaaaac gttattaaat tatttactat gaattcactt gataatcaac acattgcatg     2700
taatgttgat tattgagtgt ttttttgtaa ccatatttgg cacaatttat gctctataac     2760
atttctgaaa taaatatatg tatatgagga ggaatttcaa tgtatggtta taatggtaaa     2820
gtattaagaa ttaatttaaa agaaagaact tgcaaatcag aaaatttaga tttagataaa     2880
gctaaaaagt ttataggctg taggggacta ggtgttaaaa ctttatttga tgaaatagat     2940
cctaaaatag atgcattatc accagaaaat aaatttataa ttgtaacagg tccgttaact     3000
ggagctccag ttccaactag tggaaggttt atggtagtta ctaaagcacc gcttacagga     3060
actataggaa tttcaaattc gggtggaaaa tggggagtag acttgaaaaa agctggctgg     3120
gatatgataa tagtagagga taaggctgat tcaccagttt acattgaaat agtagatgat     3180
```

```
aaagtagaaa ttaaagatgc gtcacagctt tggggaaaag ttacatcaga aactacaaaa    3240
gagttagaaa agataactga gaatagatca aaggtattat gtataggacc tgctggtgaa    3300
agattgtccc ttatggcagc agttatgaat gatgtagata gaactgcagc aagaggcggc    3360
gttggtgcag ttatgggatc taaaaactta aaagctatta cagttaaagg aactggaaaa    3420
atagctttag ctgataaaga aaaagtaaaa aaagtgtccg tagaaaaaat tacaacatta    3480
aaaaatgatc cagtagctgg tcagggaatg ccaacttatg gtacagctat actggttaat    3540
ataataaatg aaaatggagt tcatcctgta aataattttc aagaatctta tacggatcaa    3600
gcagataaaa taagtggaga gactcttact gctaaccaac tagtaaggaa aaatccttgt    3660
tacagctgtc ctataggttg tggaagatgg gttagactaa aagatggtac agagtgcgga    3720
ggaccggagt atgaaacact gtggtgtttt ggctctgact gtggttcata tgatttagat    3780
gctataaatg aagctaatat gttatgtaat gaatatggta ttgatactat tacctgtggt    3840
gcaacaattg ctgcagctat ggaactttat caaagaggat atgtaaaaga tgaagaaata    3900
gccggagata acctatctct caagtgggga gatacggagt ctatgattgg ctggataaag    3960
aaaatggtat atagtgaagg ctttggagca aagatgacaa atggttcata taggcttttgt    4020 gaaggttatg gagtacctga gtattctatg acagttaaaa aacaagaaat tccagcatat    4080
gatccaaggg gaatacaggg acatggtatt acctatgcag ttaataatag aggaggatgt    4140
catattaagg gatatatgat taatcctgaa atattaggtt atccggaaaa acttgataga    4200
tttgcattag atggtaaagc agcctatgcc aaaatgatgc atgatttaac tgctgtaatt    4260
gattctttag gattgtgcat attcactaca tttgggcttg gaatacagga ttatgtagat    4320
atgtataatg cagtagtagg agaatctact tgtgattcag attcactatt agaggcagga    4380
gatagagtat ggactcttga aaaattattt aatcttgcag ctggaataga cagcagccag    4440
gatactctac caaagagatt gttagaagaa cctattccag atggtccatc aaagggacac    4500
gttcataggc tagatgttct tctgccagaa tattactcag tacgaggatg gagtaaagag    4560 ggtatcaccta cagaagaaac attaaagaaa ttaggattag atgaatatat aggtaagttc    4620
tagtaaagag caattatgaa taataataac atagaaacaa caataaaaag tgagaatctt    4680
gtttatccga tgactactcg ctctaatact cccacttctg caagtgggag taaagagcga    4740
ctacgtccct ggataacgat ttttcctaaa ggataacgtc ttctaagtgc tgaagcacta    4800
agaatactgt taataagcat caggtggagt taaaactcca tctgatgcca agaaatctgt    4860
ttatatttaa cagcatgaaa aataagaaag aggtgtcatt aatgaaggta actaaggtaa    4920
ctaacgttga agaattaatg aaaagttag atgaagtaac ggctgctcaa aaaaaattct    4980 ctagttatg tcaggaacaa gtggatgaga tctttaggca ggcagctatg gcagccaata    5040
gtgctagaat agatctagct aaaatggcag tggaagaaag cggaatggga attgtagaag    5100
acaaggttat taaaaatcat tttgtttcag aatatatata taacaaatat aaggatgaaa    5160
agacctgtgg agttttagaa gaagaccaag gttttggtat ggttagaatt gcggaacctg    5220 tagggttat agcagcagta gttccaacaa ctaatccaac atccacagca atctttaaat    5280
ctttaatagc tttgaaaact agaaatggta tagttttttc accacatcca agagcaaaaa    5340
aatcaactat tgcagcagct aagatagtac ttgatgcagc agttaaagct ggtgctcctg    5400
aaggaattat aggatggata gatgaacctt ccattgaact ctcacaggtg gtaatgaaag    5460
aagcagattt aattcttgca actggtggcc cgggtatggt taaggctgcc tattcttcag    5520
```

```
gaaagcctgc tataggagtt ggcccaggta acacacctgc tgtaattgat gaaagtgctg    5580
atattaaaat ggcagtaaat tcaatactcc tttcaaaaac ttttgataat ggtatgattt    5640
gtgcttcaga gcagtcagta gtagttgtaa gctcaatata cgatgaagtc aagaaagaat    5700
ttgcagatag aggagcgtat atattaagta aggatgaaac agataaggtt ggaaaaacaa    5760
ttatgattaa tggcgctcta aatgctggca ttgtagggca aagtgctttt aaaatagcac    5820
agatggcagg agtgagtgta ccagaggatg ctaaagtact tataggagaa gttaaatcag    5880
tagaacctga agaagagccc tttgctcatg aaaagctgtc tccagtttta gctatgtaca    5940
aagcaaaaga ttttgatgaa gcacttctaa aggctggaag attagttgaa cgaggtggaa    6000
ttgggcatac atctgtatta tatgtaaatt caatgacgga aaaagtaaaa gtagaaaagt    6060
tcagagaaac tatgaagact ggtagaacat tgataaatat gccttcagca caaggtgcta    6120
taggagatat atataacttt aaactagctc cttctttgac gctaggatgt ggttcctggg    6180
gaggaaactc tgtatcagaa aatgttggac ctaaacattt attaaacata aaaagtgttg    6240
ctgagaggag agaaaatatg ctttggttta gagtacctga aaaagtttat ttcaaatatg    6300
gtagtcttgg agttgcatta aaggaattga gaactttgga gaagaaaaag gcatttatag    6360
taacggataa ggttctttat caattaggtt atgtagataa aattacaaaa aatctcgatg    6420
aattaagagt ttcatataaa atatttacag atgtagaacc agatccaacc cttgctacag    6480
ctaaaaaagg tgcatcagaa ctgctttcct atgaaccaga tacaattata gcagttggtg    6540
gtggttcggc aatggatgca gccaagatca tgtgggtaat gtatgagcat ccagaagtaa    6600
gatttgaaga tttggctatg agatttatgg atataagaaa gagagtatat gttttttccta    6660 agatgggtga aaaagcaatg atgatttcag tagcaacatc cgcaggaaca ggatctgaag    6720
ttactccatt tgcagtaatt acggatgaaa gaacaggagc taaatatcca ctggctgatt    6780
atgaattgac tccaaacatg gctataattg atgcagaact tatgatggga atgccaaaag    6840
ggcttacagc agcttcgggt atagatgcat taacccatgc actggaggcg tatgtatcaa    6900
taatggcttc agaatatacc aatggattgg ctcttgaagc aacaagatta gtatttaaat    6960
atttgccaat agcttataca gaaggtacaa ctaatgtaaa ggcaagagaa aaaatggctc    7020
atgcttcaac tatagcaggt atggcttttg ccaatgcatt cttaggggta tgtcactcta    7080
tggcacataa attgggagca cagcaccata taccacatgg aattgccaat gcgcttatga    7140
tagatgaagt tataaaattc aatgctgtag aggctccaag gaaacaagcg gcatttccac    7200
aatataagta cccaaatgtt aaagaagat atgctgaaat agctgattac ttaaatttag    7260
gaggaagcac agatgatgaa aaagtacaat tgctaataaa tgctatagat gacttaaaaa    7320
ctaagttaaa tattccaaag actattaaag aggcaggagt tcagaagat aaattctatg    7380 ctactttaga cacaatgtca gaactggctt ttgatgatca atgtacagga gctaatccaa    7440
gatatccact aataggagaa ataaaacaaa tgtatataaa tgcatttgat acaccaaagg    7500
caactgtgga gaagaaaaca aaaaagaaaa aataatgtaa aataaaatca gaattagtt    7560 aaatatttaa aataaaataa aaatttatac aatgatgtat gaaaaagcga tgaagcttct    7620
aaaagaatat ttatattctt aggaagcttt ttttattttta ttggtagcta tcaaaaaatt    7680
acaaaattta atatgactaa tgtgaagttt catagatatt ttattaaatt ggagtatgat    7740
tattgtgaaa aattttaatg ttaaaccaaa ggtttatttt ggtactgatg ctttaaatca    7800
tttgtgtgaa ttaaaatgta agaaagcttt aatcgctgca gatccattta tggttaagtc    7860
atcaacggtt gataaaatta ctgaacagct tgataaggca catatagagt atgatatatt    7920
```

```
ttcagatata gtaccagatc ctcctgttga agttattata aaaggagtgc aggaagctgt    7980
taaatttaaa cctgatgtac ttatagcact tggaggagga tcagctattg attctgcaaa    8040
aggaataagg tattttttgtc agtatgtaaa taatgaattg aataacgaaa tgaaagagcc    8100
cctgttata gcaattccga caacaagtgg tacaggctct gaggttacta acttttgtat    8160
tgtaactgat aagcaaaaag gagtcaaata tgctcttgtt gatgacaatt tgacgccgga    8220
tcaggcggta cttgatattg aacttgtaaa atcagtgcca aaagctacca catcagaaac    8280
aggaatagac gtacttacac atggaattga agcatatgtt tctacaaata gatcagatta    8340
ttctgatgca ctggcagaaa atcaataaa atggtatttt aaatacttgt tagccgcata    8400
tgaaaatgga gatgatgaag aagctagaac gaagatgcat aatgcatcct gcatagcagg    8460
tatggcattt acaaatgctt cccttggact taaccatggc atggctcatg cacttggtgg    8520
aaaaattcat ataccgcatg gaagagcaaa tggactactt cttccatacg taatagagta    8580
taatgcaaac cttaaaaact tacaaggaaa gataaaccat tctagtgcag catataggta    8640
tactgaaata tcaaaattct tgggacttcc agcatctaac caatttgaag gtgttaggag    8700
tttgattgca gcagttaaga tactgatgaa taaacttaac ttacctaaat gtattaataa    8760
ttgtgaagtt ttatgtgaaa atttggataa tgagattcat gagttatcga taactgccct    8820
aaatgataga tgtacaaaaa caaatccgag aattcctgaa ataaaggatg ttgaaaattt    8880
gtttaagagg gttttttcta aagaataaca taaaagaaga gcatgcaatt agttttaaat    8940
tattagatag tgtaaagcgt tataaacaat ttcttgatac ataccctgat ttggaagaac    9000
gtgttaagca gtgttatatt gcatcctatt taggaataac tcctgtgtct cttagcagaa    9060
taagaagaaa attaaatctt aacaaatgat aatgcaataa atctctaggt gatttatgat    9120
gtagttaatt tttattactg gaggttaatt gttatgaaaa atgaaatagt tgttttaatt    9180
actggatgtt ctacagggat tggaagagag ctttgtagta tattgtttca caaaggatgt    9240
acggttgttg caacagcaag aaatgtagaa actttaaaag atttatctgc gtccttaaga    9300
ttaccactgg atgttaccca aaaagagtct attaacagta caataaatga agttgtatca    9360
aaatttcata aaattgatat tcttataaat aacgcaggct attcaattag aggagcttta    9420
gaagaaattg atttaaatag tgctaaaagt atgtttgatg taaatgtatt tggtattatt    9480
aacatgattc aggcagttat tccagaaatg cgtaaaaaac aatttggtaa gattataaat    9540
attggctcca tttcagggaa atttgttcaa tccatcaatg gagcgtattg tgcatcaaaa    9600
tttgcagttg aggcactaag tgacacactt cgtttagaat tacacagcta caatattcag    9660
agcaccgtca ttgagccagg tcccatgaaa accaactttt ttaaggcatt agtggataat    9720
tcaggcgatg ttataaaaaa tgaaaattct tgttattcac attttataa atcagatgat    9780
gaatatagaa aaaagcaaaa acaagctgat cctaaagtag cagcacaagc tattagtgat    9840
ataattttga aaaaacgact taatgctcgt tataaagttg ctgttccatt tacatataag    9900
atggttacat atttttcctga ttttctaaga gaatacttta tgaaaaaaag atagtagttg    9960
atatataact ttttagtcgt acaaatacga aatatatttt atcatacttg catgtaaaat   10020
gctatacagc ttatacttct aaagtttgtt tatattagtt cacagggttt caaaaattgt   10080
agtttataat cacatatatt ttcgaaattc atatattaaa tagaagtact ttacaatatt   10140
ggaggaacta ctatatgtgt tcaaatcata ttggatgcaa atttccacgc ttttttccac   10200
cccaacatca gccacatcaa cctggtattg aatatattat gacacctaga ccagttttcg   10260
```

```
aaccaccatt atgtgcacaa tatcaaacga caaaaagatt attaaacaaa gtagctttaa    10320
taacaggagg agacagcggt attgggcgtg ctgtagcatg tgcttatgca aaagaaggag    10380
ctgatattgc cattgtctat ctaaatgaac atgtagatgc agagggaaca aaatctagaa    10440
taaaaaaatt ggggcgaaga tgtttaacca ttccaattaa cataggagtc gaagagaata    10500
gtaaaattat aattcaagaa gttatgaatc attttggtaa attagatatt cttgtaaata    10560
atgctgcagt actttattac aataattcta tagaagaagt atctagcaaa caattagaat    10620
ggacttttcg tataaatgta ttttcttatt tctacttaac taaagcagct ctaccttata    10680
tgaaaccagg cggttctatc atcaatactt cttcaatagt tgcttttaat cctccttatg    10740
ggatatcttt agattatgaa gcttcaaaag gtgccattgc taatttcact ataaatttag    10800
cccgaagttt ggtttcaaga ggaatacgtg taaatggtgt agctccaggt gaaacctgga    10860 caccttttaat tccagcagga ttacctgcag ataaagttgc cgtttggggt tcaaaaacac    10920
caatgggaag agctgctcaa ccatttgaaa ttgctccagc ctatgtattc ttagcttcca    10980
atgaatcaag ctatatgtca ggacaaacaa tccatatgta ttcttaagag taaaagttga    11040
tgaggagaga aaatcagggt cacttctcga aataaaacaa aaacttgaaa gaatgaaagt    11100
tattgaactc agaaatatgg ctagaaaaat gaatttaagt tcattgacta agaaggacat    11160
taaatttggc aagaaaaagc agctgattaa agcaatttta gagtactata caaggaggtt    11220
aaagtaaatg gaaaatatag atagggattt acaatctata caagatgtaa ggcggcttgt    11280
tgaaaaggca agacaagctc aacaagaata ttgtaaattc agtcaggaaa agatgaataa    11340
aattattgag catgtagcgg aatctgctgg cttacaagct gaaagattag caaaacttgc    11400
tgtagaagaa caacttttg gaaatttacc tgataagata attaaaaata gtttgctag    11460 tgaaatagtg tatgaaaata taaggacat gaagttagta ggtatttaa gagatgacaa    11520 agatagaaaa gtattagaga taggttcacc tgtaggtatt attgcagggc ttgtaccatc    11580
aactaatcct acttctactg ttatatataa aagtcttata gctttaaaat cgggaaatgc    11640 aattgtatt agtcctcatc caaaggcaag acattgcatt gcagaagcta taaaggttgt    11700
aagtgatgca gctgttgagg caggagcacc tttaggaatg gtttccggaa tgagtatact    11760
tactatggaa ggaactcatg agcttatgaa aaacgttgat ctcatactag caacaggtgg    11820
atcagctatg gtaaaggcag catacagttc aggaactccg gctataggag ttggacctgg    11880
aaatggacct gcttttattg aaaaaacagc aaatataaaa cttgcagtaa aagaataat    11940 ggatagtaaa acttttgaca atggggtaat atgtgcttca gaacagtcca tagtagttga    12000
aaaatgtata aaagatgaag ttgtagatga gcttaaacgc caaggagcat acttcttatc    12060
taaagaacaa tcagaaaaag tagcaaagtt tatattgaga gcaaatggta ctatgaatcc    12120
tcaaattgta ggaaaatcag ctcagaaaat agctgaaatg gcaggtataa ctgtagatcc    12180
aaatgcaaga atattgattt cagagcgagac gacagtggga aaagataacc cattttcaag    12240
ggaaaagctt acaacgattt tagcattcta ctgtgaagaa aattgggaaa agcttgcga    12300 gagatgcatt gagctttaa ataatgaagg tataggacat actctcataa tacattcaaa    12360
taatgaagaa atagtaaaag aatttggact taaaaaccct gtatccagaa tacttgtaaa    12420
cacgccagga tcacttggag gaataggagc tactacaaat ctagtgcctg cacttacact    12480
tggatgcgga gcagttggag gaagtgcaac ttctgataat gtaggaccta ggaatcttat    12540
aaatataaga agagttgcct atggagtaaa ggaaatagaa gatataaaaa attttgtaag    12600
taattgtagt gacagagaaa cctcacacac tgttttggat atttctgatc agtacattga    12660
```

```
acttataact aaaaaaatag ctgaaaagct tagtttgtaa atggtttaga aaaagctatt    12720
gagattttaa gtaagtttaa ggtaatagag cttcgaaatc tcgctcgtaa atataagaac    12780
tttggtatca aaggaaggtc catttctaaa gcagacaaga agttgctgct tatagagttc    12840
aaaaaatatt atgggcataa ttagccagct ataaaaatta aatatataaa ataataaaca    12900
atggagggaa cacaattgga aaattttgat aaagacttac gctctataca agaagcaaga    12960
gatcttgcac gtttaggaaa aattgcagca tgtgaaattg ctgattatac tgaagaacaa    13020
attgataaaa tcctatgtaa tatggttagg gtagcagagg aaaatgcagt ttgccttggt    13080
aaaatggctg cagaagaaac tggttttgga aaagctgaag ataaggctta taagaaccat    13140
atggctgcta ctacagtata taattatatc aaggatatga agactattgg tgttataaaa    13200
gaagataaaa gtcaaggtgt aattgaattt gctgaaccag ttggtttatt aatgggtatt    13260
gtaccatcta caaatccaac atctactgtt atctataaat caatcattgc aattaaatca    13320
agaaatgcaa ttgtattctc accacaccca gctgcattaa aatgttcaac aaaagcaata    13380
gaacttatgc gtgatgcagc agtagcagca ggagctcctg caaatgtaat tggcggtatt    13440
gttacaccat ctatacaagc tacaaatgaa cttatgaaag ctaaagaagt tgctatgata    13500
attgccactg gaggccctgg aatggtaaag gctgcttata gttcaggaac acctgcaata    13560
ggcgttggtg ctggtaactc tccatcttat atagaaagaa ctgctgatgt tcatcaatca    13620
gttaaagata taattgctag taagagtttt gactatggta ctatttgtgc atctgagcaa    13680
tcaataattg ttgaagaatg caaccatgat gaagtaatag ctgagttgaa gaaacaaggc    13740
ggatatttca tgacagctga agaaactgca aaagtttgca gtatactttt taagcctggt    13800
acacacagta tgagtgctaa gtttgtagga agagctcctc aggttatagc agcagctgca    13860
ggtttctcag ttccagaagg aacaaaagtt ttagtaggag aacaaggcgg agttggtaat    13920
ggttaccctc tatcttatga gaaacttaca acagtacttg ctttctatac agttaaagat    13980
tggcatgaag catgtgatct tagtataaga ttacttcaaa atggtcttgg acatactatg    14040
aacattcata caaatgacag agacttagta atgaagtttg ctaaaaaacc agcatcccgt    14100
atattagtta atactggtgg aagccaagga ggtactggtg caagcacagg attagcacct    14160
gcatttacat taggttgtgg tacatgggga ggaagctctg tttccgaaaa tgttactcca    14220
ttacatttaa tcaatataaa gagagttgca tatggtctta agattgttc tacattagct    14280 gcagatgata caacttttcaa tcatcctgaa cttttgtggaa gcaaaaatga cttaggatgc    14340
tgtgctacaa gccctgcaga atttgcagca aatagcaatt gtgctagcac tgctgcggat    14400
actactgata atgataaact tgctagactc gtaagtgaat tagtagctgc aatgaaggga    14460
gctaactaaa agctgtaaca gatatgggcg ctgaagttta tagttcagtt gttattgcaa    14520
gtccacatcc ggatcttcag aaaatcacca aacgttatac aattgaaaat ttacttcctt    14580
aatatgtgga tgatatgata ccaccacata aaatgaaaaa gtacagaagt acagtactta    14640
gttagtaaaa atgaaaggga gagttagaaa tgaatattat tgataatgat ttgctctcca    14700
tccaagaatc ccgaatcctt gtggaaaatg ctgcacgagc acaaaaaatg ttagcaactt    14760
ttccgcaaga aaagttagat gagattgttg aacgtatggc tgaagaaatc ggaaaacata    14820
cccgagagct tgctgtaatg tcacaggatg aaactggtta tggaaaatgg caggataaat    14880
gcatcaaaaa ccgatttgcc tgtgaatatt tgccagctaa gcttagagga atgcgatgtg    14940
taggtattat taacgaaaat ggtcaggata agaccatgga tgtaggtgta cctatgggtg    15000
```

-continued

| | |
|---|---|
| taattattgc attatgtcct gcaactagtc cggtttctac taccatatat aaggcattaa | 15060 |
| ttgcaattaa gtctggtaat gcaattatct tttctccaca tcctagagca aaggagacaa | 15120 |
| tttgtaaggc gcttgacatc atgattcgtg cagctgaagg atatgggctg ccagaaggag | 15180 |
| ctcttgcata cttacatact gtgacgccta gtggaacaat cgaattgatg aaccatgagg | 15240 |
| cgacttcttt gattatgaat acaggcgttc ccgggatgct taaagcgtca tatagatctg | 15300 |
| gaaaacctgt gatctatgga ggaactggta atggaccagc atttattgaa cgtacagctg | 15360 |
| acatcaagca ggcggtaaga gatattattg ctagtaagac ctttgataac ggaatagtac | 15420 |
| catcatctga acaatctatt gttgtagata gctgtgttgc atctgatgtt aaacgtgagt | 15480 |
| tgcaaaatag tggtgcatat ttcatgacag aggaggaagc acaaaaactg ggttctctct | 15540 |
| ttttccgttc tgatggtagt atggattcag aaatggttgg caaatccgca cagagattgg | 15600 |
| ctaagaaagc aggtttcagt attcctgaaa gtagcacagt gctaatttca gagcagaaat | 15660 |
| atgtttccca agataatcct tattccaagg agaaactttg tccggtacta gcttactaca | 15720 |
| ttgaagatga ttggatgcat gcatgtgaaa agtgtattga gctgctatta agtgagagac | 15780 |
| atggtcacac tcttgttata cattcaaaag acgaagatgt aattcgccag tttgcattaa | 15840 |
| aaaaacctgt aggcaggata cttgttaata cgcctgcttc ctttggtagt atgggtgcta | 15900 |
| caagtaattt atttcctgct ttaactttag gtagtggatc ggcaggtaaa ggtattacct | 15960 |
| ccgataatgt ttcaccaatg aatcttattt acgtccgtaa agtcggatat ggcgtacgga | 16020 |
| atgtagaaga gattattaat actaatggat tgtttacaga agaaaaaagt gatttgagtg | 16080 |
| gtatgacaaa gcagtcagac tataatccag aggatataca aatgttgcag catattttga | 16140 |
| aaaaagctat ggaaaaaatt aaatag | 16166 |

<210> SEQ ID NO 3
<211> LENGTH: 5207
<212> TYPE: DNA
<213> ORGANISM: AUTOTROPHIC SOLVENTOGENIC CLOSTRIDIAL SPECIES

<400> SEQUENCE: 3

| | |
|---|---|
| atgaatactg taattatgat tttagttgta atgactgtta taggtcttat atttggactt | 60 |
| gttttagcct atgtaaataa aagatttgca atggaagtaa atccacttgt ggacttagta | 120 |
| gaagatgtac ttccaaaagg ccaatgtgga gggtgtggat ttgcaggatg taaagcttat | 180 |
| gcagaagctg ttgttttaga tgagagtgta cctccaaatc tttgtgtacc tggaaaagca | 240 |
| gcagttgcag aacaggtggc aaagttaacg ggtaaatctg ctccaccttat tgaacctaga | 300 |
| gttgcacatg taagatgtgg tggagattgt acaaaggcag ttaaaaattt tgaatatgaa | 360 |
| ggtatacatg attgtgtagc tgcaaattta cttgaaggtg gacctaaagc ttgtaaaatat | 420 |
| ggatgtctgg gatttgggac atgtgtaaag agctgtcctt ttggagctat ggcaatgggt | 480 |
| tcaaatggac ttccaataat tgatacagat atatgtacag gttgtggtac ctgtgtaagc | 540 |
| gcgtgcccaa acaggtact tggatttagg cctgtaggtt ctaaagtaat ggttaattgt | 600 |
| aattctaaaa ataaaggtgg agctgtacgt aaggcatgta gtgtaggatg tcttggatgt | 660 |
| ggattgtgtg ctaaaaattg tccaaatgat gccattaaag tagagaacaa tctagcagta | 720 |
| gtagaccaaa gtatttgtgc gtcatgtagt gaagctacct gtcttgctaa atgtcctaca | 780 |
| ggagctatta aggctattgt aagcggtaca gacttacaac agcagagcaa gaatgaagct | 840 |
| gctgcaaatt cataaatggc atcttacctt actctttta taagtgcagt agttgtaaat | 900 |
| aactatgttt taacaaggtt tttgggactt tgtatattct ttggtgtttc taagaattta | 960 |

```
aatgcttctg taggtatggg tatggctgtt acttctgtta ttactatgag ttcaatattg    1020
gcctgggtag tatatcattt tgtacttata ccatttaatt taactttctt gaagacagta    1080 gttttttgtac ttcttattgc tagttttgta cagcttttgg agactattat taaaaagcag   1140
gcaccagccc tatataatat gtggggaata taccttcttt taatagctac aaactgtata    1200
gtacttgctg tacctatatt aaatgctgat tctaacttta attttttaca gagtgttgtt    1260
aatgcgatag gatctgggct aggctttgct atggctataa ttttgatggc aagcttaga    1320 gaaaaattga gattagcaga tgtacctaaa cctttagaag gtcttggagt agcttttatt    1380
ttagcaggaa tgttagccct agcttttcctt ggttttttcag gtatgatttc tatgtagatg  1440
aagaatttgt ggaatatatt taaaaaagga ttgattgcag aaaacccat attcgtactt     1500 gcacttagtt tgtgtccagc actggcaact acaagtacag ctgtaaatgg atttaccatg    1560
gggctctgcg tgctatttgt tataacttgt aataatactg tggtttctat aattaagaat    1620
tttgtaaatc ctaaggtacg tgtacctgta tatatcactt gtatagcaac tatagttaca    1680
gtagtggaac ttgttatgca ggcttatgca cctctattat ataagcaatt gggaatttat    1740
ttagcattgg tagttgtatt tgctataata cttgcccgtg cagagacatt tgcatctaaa    1800
aatcctgtag ttccttcttt ctttgatgga cttggaatgg gatgtggatt tactttggca    1860
cttactataa taggaatgat acgtgaatta tttggatctg gagctatatt tggttttaat    1920
gtatttgggg cttcatataa tccagctttg attatgatac ttccacctgg aggattcata   1980
cttataggat atttagttgc tatagtaaaa gtttataacc aacatatgga gaaaattaaa    2040
atgcaaaaat tagaacaagc aaatggaggt gaagcataaa tggctaaaga taaagatcaa    2100
aatagtattt ttgcaattac taagaactta accattacgt gttttatatc tggaattata    2160
atagctgcgg tttattatgt aacatcacca gtggcagcac aaaaacaagt tcaaatacaa    2220
aatgatacca tgaaagtttt agtcaatgat gctgataaat ttaataaagt aaatggtaaa    2280
aaggattggt atgcagctca aaaaggaaac aagacaattg catatgttgt acctgcagag    2340
agtaaaggtt acggtggagc tatagagcta ttggtagctg ttactccaga tggaaaagta    2400
atagatttca gcattgtatc tcataatgaa actccaggac ttggagcaaa tgcttcaaag    2460
gattctttta ggggacagtt taaggataaa aaggcggatg ccttaacagt tgtaaaagat    2520
aagtctaaca ctaaaaacat tcaagctatg acaggagcta caattacgtc aaaagctgta    2580
actaaaggag ttaaagaagc tgttgggcaa gttactacgt ttacgggagg taagtaaatg    2640
gcggaagcac agataaagaa aaatattttt actatttcgt catcacctca tgttcgttgt    2700
gatgaatctg tttctaagat aatgtggagt gtctgtttag cactaactcc agctgcgatt    2760
tttggcgtat ttaattttgg aattcatgct ttagaagtaa ttataacagg aattatagct    2820
gctgtagtta cagagtacct tgtagaaaaa gttagaaata aacctataac tattacagat    2880
ggaagtgctt ttttaacagg acttttactt tctatgtgtt tacctcctga tattccacct    2940
tatatggtag ctataggatc ttttatagca atagcaatag ctaaacattc tatgggagga    3000
cttggtcaga acatatttaa tccagctcat attggaaggg ctgcactaat ggtttcctgg    3060
cctgtagcaa tgacaacatg gtcaaaatta agtgccagtg gtgtagatgc tgtaaccaca    3120
gcaactcctc ttggaatttt aaagcttcaa ggttattcaa aattacttga gacttttgga    3180
ggtcaaggtg cactttacaa ggcaatgttc ttaggtacta gaaatggaag tataggagaa    3240
acttctacaa tattacttgt tttaggtgga ctttatctaa tatataaaaa atatattaac    3300
```

```
tggcagattc cagtagtaat gatcggtact gtaggaatac ttacctgggc ttttggagga    3360
actacgggac ttttacagg agatcctgta tttcatatga tggcaggcgg acttgtaatt     3420
ggagctttct ttatggctac tgatatggta acaattccta tgactattaa aggacaggtt   3480
atttttgcat taggtgcagg tgcgcttaca tcacttataa gattaaaagg tggttatcca   3540
gaaggcgtat gttattcaat attacttatg aatgcagtta ctcctctaat agataagttt   3600
acacagccag ttaaatttgg gacaaggagg taaaacttta attaataaga gtatctttta   3660
aagttaactg acatttaata gataaattgt cattatatat tatttcctat agtatataat   3720
tttataacgg attatggaaa attctataat ctgttataaa aattatgttt atatttattt   3780
tgcagtttcg tttatataca tgctgtaaaa attattgaaa gaggtgttta agagtgttaa   3840
aaagttttcg aggtggagta cacccggatg atagcaaaaa gtacacagct aataaaccta   3900
tagaaatagc acctatacca gacaaggtgt ttattcccgt tagacagcat ataggtgctc   3960
ctacatctcc tgtagtacaa aaaggagatg aggtaaaaaa gggacaactt attgcgaaga   4020
gtgatgcttt tgtttcagcc aatatatatg catctacttc tggaaaggtt gtagatatag   4080
gagattaccc acatcctggt tttggaaagt gtcaagctat agttattgaa aaagatggaa   4140
aagatgagtg ggtagaagga ataccaactt cacgtaattg gaaagagcta agtgcaaaag   4200
aaatgcttgg aataataaga gaagcaggca ttgtaggaat gggaggcgca acttttcctg   4260
ttcatgttaa acttgcacca ccaccagata aaaaagtaga tgtttttatt ttgaatggtg   4320
ctgagtgtga accttattta actgcagatt ataggtccat gttggaaaaa tcagataagg   4380
tagttgctgg agttcaaata attatgaaaa tcctcaatgt ggaaaaagca tttgtaggta   4440
ttgaagataa taaaccagat gccatagaag ctatgaaaaa agcttttgaa ggtacaaaag   4500
tacaagtagt aggccttcct actaagtatc ctcagggtgc tgaaaaaatg cttataaatg   4560
ttttgacagg tagagaagtt ccatcaggtg gattgcctgc agatgtaggt gcggttgttc   4620
aaaatgtagg tacatgcata gcaataagcg atgcagtgga gagaggaatt ccacttatac   4680
agagagttac aactataagt ggaggtgcta ttaaagagcc taaaaatata ttagttagaa   4740
ttggaactac atttaaagat gccattgatt tttgtggagg attttaaggaa gaaccagtta   4800
aaataatttc aggtggacct atgatgggat ttgcccaatc aaatttggat attccaataa   4860
tgaagggttc atcaggaata cttggtttaa ctaaaaatga tgtaaatgat ggaaaagaat   4920
cttcttgcat tagatgtggc agatgtctaa aagcctgtcc tatgcacttg aatccaagta   4980
tgttaagtat tcttggacaa aaagatttat atcaagaagc taaggaagaa tataatctttt  5040
tggactgcgt agaatgcggc agctgtgtat atacatgtcc tgctaaacga agaattgtac   5100
agtatattag atatttaaaa tcagaaaata gagctgcagg ggcaagggaa aaggctaaag   5160
cagaaaaggc taaagaaaag aaagaaaaag aagaggtctt aaaataa                  5207
```